(12) United States Patent
Dillon et al.

(10) Patent No.: US 9,115,332 B2
(45) Date of Patent: *Aug. 25, 2015

(54) FRACTIONATION OF OIL-BEARING MICROBIAL BIOMASS

(71) Applicant: Solazyme, Inc., South San Francisco, CA (US)

(72) Inventors: Harrison F. Dillon, San Mateo, CA (US); Dan Elefant, Pacifica, CA (US); Anthony G. Day, San Francisco, CA (US); Scott Franklin, La Jolla, CA (US); Jon Wittenberg, San Mateo, CA (US)

(73) Assignee: Solazyme, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/055,763

(22) Filed: Oct. 16, 2013

(65) Prior Publication Data

US 2014/0093945 A1    Apr. 3, 2014

Related U.S. Application Data

(63) Continuation of application No. 13/322,435, filed as application No. PCT/US2010/036238 on May 26, 2010, now Pat. No. 8,580,540.

(60) Provisional application No. 61/181,252, filed on May 26, 2009.

(51) Int. Cl.
   *C11B 1/10*    (2006.01)
   *C10L 1/02*    (2006.01)
   (Continued)

(52) U.S. Cl.
   CPC . *C11B 1/10* (2013.01); *C10L 1/026* (2013.01); *C11B 1/106* (2013.01); *C11C 3/003* (2013.01); *C12P 7/649* (2013.01); *C12P 7/6463* (2013.01); *Y02E 50/13* (2013.01); *Y02T 50/678* (2013.01)

(58) Field of Classification Search
   CPC ...... C12P 7/6463; C12P 7/649; C12P 7/6409; C12P 7/6436; C11B 11/10; C12N 9/16; C12N 9/20; C12N 9/2408; C12N 9/88
   See application file for complete search history.

(56) References Cited

U.S. PATENT DOCUMENTS

3,983,008 A    9/1976    Shinozaki et al.
4,373,434 A    2/1983    Alexander et al.
(Continued)

FOREIGN PATENT DOCUMENTS

CN          1304986 A      7/2001
WO    WO 2008/113041 A2    9/2008
(Continued)

OTHER PUBLICATIONS

Casaregola et al., "T7 end of clone AWOAA009C11 of library AWOAA from strain CLIB 89 of *Yarrowia lipolytica*, genomic survey sequence," Genebank Accession AL411154, [online], (2001). [Retrieved from the internet Sep. 28, 2010: <URL: http://www.ncbi.nlm.nih.gov/nucgss/12180296>].

El-Sheekh et al., "Variation of Some Nutritional Constituents and Fatty Acid Profiles of *Chlorella vulgaris* Beijerinck Grown under Auto and Heterotrophic Conditions," International Journal of Botany, 5 (2):153-159, (2009).

International Search Report for PCT/US2010/031108 mailed Oct. 1, 2010.

International Search Report for PCT/US2010/036238 mailed Oct. 29, 2010.

PCT International Preliminary Report on Patentability (Chapter I) of Jan. 18, 2012 for application PCT/US10/031108.

PCT International Preliminary Report on Patentability (Chapter I) of Jan. 17, 2012 for application PCT/US10/036238.

(Continued)

*Primary Examiner* — Alexander Kim
(74) *Attorney, Agent, or Firm* — Alston & Bird LLP

(57) ABSTRACT

The invention generally relates to the production of hydrocarbon compositions, such as a lipid, in microorganisms. In particular, the invention provides methods for extracting, recovering, isolating and obtaining a lipid from a microorganism and compositions comprising the lipid. The invention also discloses methods for producing hydrocarbon compositions for use as biodiesel, renewable diesel, jet fuel, and other materials.

20 Claims, 8 Drawing Sheets

(51) Int. Cl.
*C12P 7/64* (2006.01)
*C11C 3/00* (2006.01)

(56) References Cited

U.S. PATENT DOCUMENTS

| | | | |
|---|---|---|---|
| 4,901,635 | A | 2/1990 | Williams |
| 5,338,673 | A | 8/1994 | Thepenier et al. |
| 5,680,812 | A | 10/1997 | Linsgeseder |
| 5,685,218 | A | 11/1997 | Kemper |
| 5,826,500 | A | 10/1998 | Kemper |
| 6,166,231 | A | 12/2000 | Hoeksema |
| 6,176,176 | B1 | 1/2001 | Dale et al. |
| 6,750,048 | B2 | 6/2004 | Ruecker et al. |
| 7,351,558 | B2 | 4/2008 | Ruecker et al. |
| 7,662,598 | B2 | 2/2010 | Ruecker et al. |
| 7,678,931 | B2 | 3/2010 | Fichtali et al. |
| 7,781,193 | B2 | 8/2010 | Ruecker et al. |
| 8,580,540 | B2 | 11/2013 | Dillon et al. |
| 2004/0049062 | A1 | 3/2004 | Bijl et al. |
| 2006/0122410 | A1 | 6/2006 | Fichtali et al. |
| 2007/0113467 | A1 | 5/2007 | Abou-Nemeh |
| 2008/0060257 | A1 | 3/2008 | Duyvesteyn |
| 2008/0155888 | A1 | 7/2008 | Vick et al. |
| 2008/0179434 | A1 | 7/2008 | Palm |
| 2008/0233175 | A1 | 9/2008 | Steer et al. |
| 2009/0061493 | A1 | 3/2009 | Trimbur et al. |
| 2012/0130099 | A1 | 5/2012 | Wittenberg et al. |

FOREIGN PATENT DOCUMENTS

| | | |
|---|---|---|
| WO | WO 2010/138620 A1 | 9/2008 |
| WO | WO 2008/151149 A2 | 12/2008 |
| WO | WO 2010/120939 A2 | 10/2010 |

OTHER PUBLICATIONS

Turmel et al., "Prototheca wickerharnii large subunit ribosomal RNA (rrnL) gene, partial sequence; chloroplast gene for chloroplast product," Genebank Accession L42851, [online], (2001). [Retrieved from the internet Sep. 28, 2010: <URL: http://www.ncbi.nlm.nih.gov/nuccore/17028073>].

U.S. Appl. No. 13/322,435, Non-Final Office Action mailed Aug. 5, 2013.

U.S. Appl. No. 13/322,435, Notice of Allowance mailed Sep. 27, 2013.

U.S. Appl. No. 13/322,435, Requirement for Restriction/Election mailed Jun. 19, 2013.

Written Opinion of the International Searching Authority for PCT/US10/031108 mailed Oct. 1, 2010.

Written Opinion of the International Searching Authority for PCT/US2010/036238 mailed Oct. 29, 2010.

SEQUENCE LISTING

<160> NUMBER OF SEQ ID NOS: 96

<210> SEQ ID NO 1
<211> LENGTH: 1187
<212> TYPE: DNA
<213> ORGANISM: Chlorella sp.

<400> SEQUENCE: 1

```
gatcagacgg gcctgacctg cgagataatc aagtgctcgt aggcaaccaa ctcagcagct      60
gcttggtgtt gggtctgcag gatagtgttg cagggcccca aggacagcag gggaacttac     120
accttgtccc cgacccagtt ttatggagtg cattgcctca agagcctagc cggagcgcta     180
ggctacatac ttgccgcacc ggtatgaggg gatatagtac tcgcactgcg ctgtctagtg     240
agatgggcag tgctgcccat aaacaactgg ctgctcagcc atttgttggc ggaccattct     300
gggggggcca gcaatgcctg actttcgggt agggtgaaaa ctgaacaaag actaccaaaa     360
cagaatttct tcctccttgg aggtaagcgc aggccggccc gcctgcgccc acatggcgct     420
ccgaacacct ccatagctgt aagggcgcaa acatggccgg actgttgtca gcactctttc     480
atggccatac aaggtcatgt cgagattagt gctgagtaag acactatcac cccatgttcg     540
attgaagccg tgacttcatg ccaacctgcc cctgggcgta gcagacgtat gccatcatga     600
ccactagccg acatgcgctg tcttttgcca ccaaaacaac tggtacaccg ctcgaagtcg     660
tgccgcacac ctccgggagt gagtccggcg actcctcccc ggcgggccgc ggccctacct     720
gggtagggtc gccatacgcc cacgaccaaa cgacgcagga ggggattggg gtagggaatc     780
ccaaccagcc taaccaagac ggcacctata ataataggtg gggggactaa cagccctata     840
tcgcaagctt tgggtgccta tcttgagaag cacgagttgg agtggctgtg tacggtcgac     900
cctaaggtgg gtgtgccgca gcctgaaaca aagcgtctag cagctgcttc tataatgtgt     960
cagccgttgt gtttcagtta tattgtatgc tattgtttgt tcgtgctagg gtggcgcagg    1020
cccacctact gtggcgggcc attggttggt gcttgaattg cctcaccatc taaggtctga    1080
acgctcactc aaacgccttt gtacaactgc agaactttcc ttggcgctgc aactacagtg    1140
tgcaaaccag cacatagcac tcccttacat cacccagcag tacaaca                  1187
```

<210> SEQ ID NO 2
<211> LENGTH: 1414
<212> TYPE: DNA
<213> ORGANISM: Chlorella ellipsoidea

<400> SEQUENCE: 2

| | | | | | |
|---|---|---|---|---|---|
| cgctgcgcac | cagggccgcc | agctcgctga | tgtcgctcca | aatgcggtcc | cccgattttt | 60 |
| tgttcttcat | cttctccacc | ttggtggcct | tcttggccag | ggccttcagc | tgcatgcgca | 120 |
| cagaccgttg | agctcctgat | cagcatcctc | aggaggccct | tgacaagca | agcccctgtg | 180 |
| caagcccatt | cacggggtac | cagtggtgct | gaggtagatg | ggtttgaaaa | ggattgctcg | 240 |
| gtcgattgct | gctcatggaa | ttggcatgtg | catgcatgtt | cacaatatgc | caccaggctt | 300 |
| tggagcaaga | gagcatgaat | gccttcaggc | aggttgaaag | ttcctggggg | tgaagaggca | 360 |
| gggccgagga | ttggaggagg | aaagcatcaa | gtcgtcgctc | atgctcatgt | tttcagtcag | 420 |
| agtttgccaa | gctcacagga | gcagagacaa | gactggctgc | tcaggtgttg | catcgtgtgt | 480 |
| gtggtggggg | ggggggggtt | aatacggtac | gaaatgcact | tggaattccc | acctcatgcc | 540 |
| agcggaccca | catgcttgaa | ttcgaggcct | gtggggtgag | aaatgctcac | tctgccctcg | 600 |
| ttgctgaggt | acttcaggcc | gctgagctca | agtcgatgc | cctgctcgtc | tatcagggcc | 660 |
| tgcacctctg | ggctgaccgg | ctcagcctcc | ttcgcgggca | tggagtaggc | gccggcagcg | 720 |
| ttcatgtccg | ggcccagggc | agcggtggtg | ccataaatgt | cggtgatggt | ggggaggggg | 780 |
| gccgtcgcca | caccattgcc | gttgctggct | gacgcatgca | catgtggcct | ggctggcacc | 840 |
| ggcagcactg | gtctccagcc | agccagcaag | tggctgttca | ggaaagcggc | catgttgttg | 900 |
| gtccctgcgc | atgtaattcc | ccagatcaaa | ggagggaaca | gcttggattt | gatgtagtgc | 960 |
| ccaaccggac | tgaatgtgcg | atggcaggtc | cctttgagtc | tcccgaatta | ctagcagggc | 1020 |
| actgtgacct | aacgcagcat | gccaaccgca | aaaaatgat | tgacagaaaa | tgaagcggtg | 1080 |
| tgtcaatatt | tgctgtattt | attcgtttta | atcagcaacc | aagttcgaaa | cgcaactatc | 1140 |
| gtggtgatca | agtgaacctc | atcagactta | cctcgttcgg | caaggaaacg | gaggcaccaa | 1200 |
| attccaattt | gatattatcg | cttgccaagc | tagagctgat | ctttgggaaa | ccaactgcca | 1260 |
| gacagtggac | tgtgatggag | tgccccgagt | ggtggagcct | cttcgattcg | gttagtcatt | 1320 |
| actaacgtga | accctcagtg | aagggaccat | cagaccagaa | agaccagatc | tcctcctcga | 1380 |
| caccgagaga | gtgttgcggc | agtaggacga | caag | | | 1414 |

<210> SEQ ID NO 3
<211> LENGTH: 1113
<212> TYPE: DNA
<213> ORGANISM: Botryococcus braunii

<400> SEQUENCE: 3

| | | | | | |
|---|---|---|---|---|---|
| aattggaaac | cccgcgcaag | accgggttgt | ttggccgcct | gaccggaaag | gggggggcctg | 60 |
| tcccgaaggg | ggtctatctc | ttgggggatg | tcgggcgcgg | aaagtcgatg | ttgatggacc | 120 |
| tcttcttcga | ccatgtcggg | gtcgaggcca | agagccgcgt | ccatttcgcc | gagttcatga | 180 |
| tggaggtgaa | tgaccgcatc | gccaccgaac | gcgccaagaa | gcgggcgacc | gatcgccccc | 240 |
| gtcgctgcag | cccttgccga | ggaagtccgg | ctgctggcgt | tcgacgagat | gatggtgacg | 300 |
| aacagcccgg | acgcgatgat | cctgtcgcgg | ctgttcaccg | cgctgatcga | ggcggggtg | 360 |
| acgatcgtca | ccacctccaa | ccggccgccc | agggatctct | ataagaacgg | gctcaaccgc | 420 |

```
gagcatttcc tgcccttcat cgcgctgatc gaggcgcggc tggacgtgct ggcgctgaac    480
ggcccgaccg actatcggcg cgaccggctg gggcggctgg acacgtggtt ggtgcccaat    540
ggccccaagg cgacgattac cttgtcggcg gcgttcttcc gcctgaccga ctatccggtc    600
gaggatgccg cgcatgtgcc ctctgaggac ctgaaggtgg gcgggcgcgt gctgaatgtc    660
cccaaggcgc tgaagggcgt cgcggtcttc tcgttcaagc ggttgtgcgg cgaagcgcgg    720
ggggcggcgg actatctggc ggtcgcgcgg ggcttccaca ccgtcatcct ggtcggaatc    780
cccaagctgg gggcggagaa ccgcaacgag gcggggcgct tcgtccagct gatcgacgcg    840
ctctacgaac ataaggtcaa gctgctcgcc cagccgatg  ccagcccgcc gaactctatg    900
aaaccggcga cggccggttc gagtttgagc gcagatcagc cggttggaag agatgcgctc    960
cgaggattat ctggcccaag gccatggctc ggaggggcct tgatcaggcc ttaatgcact   1020
tcgcaaccat tatcgtttaa aatcttaaac tctgtggaat aacggttccc cgacgccgca   1080
atacacgtac gtccactacg gagtaggatt gga                                1113

<210> SEQ ID NO 4
<211> LENGTH: 253
<212> TYPE: DNA
<213> ORGANISM: Chlamydomonas reinhardtii

<400> SEQUENCE: 4
cgcttagaag atttcgataa ggcgccagaa ggagcgcagc caaaccagga tgatgtttga     60
tggggtattt gagcacttgc aacccttatc cggaagcccc ctggcccaca aaggctaggc    120
gccaatgcaa gcagttcgca tgcagcccct ggagcggtgc cctcctgata aaccggccag    180
ggggcctatg ttctttactt ttttacaaga gaagtcactc aacatcttaa acggtcttaa    240
gaagtctatc cgg                                                      253

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgttgaagaa tgagccggcg ac                                             22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagtgagcta ttacgcactc                                                20

<210> SEQ ID NO 7
<211> LENGTH: 565
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
```

| | |
|---|---|
| tgttgaagaa tgagccggcg acttagaaaa agtggcgtgg ttaaggaaaa attccgaagc | 60 |
| cttagcgaaa gcgagtctga atagggcgat caaatatttt aatatttaca atttagtcat | 120 |
| tttttctaga cccgaacccg ggtgatctaa ccatgaccag gatgaaactt gggtgatacc | 180 |
| aagtgaaggt ccgaaccgac cgatgttgaa aaatcggcgg atgagttgtg gttagcggtg | 240 |
| aaataccagt cgaacccgga gctagctggt tctccccgaa atgcgttgag cgcagcagt | 300 |
| acatctagtc tatctagggg taaagcactg tttcggtgcg ggctgtgaaa acggtaccaa | 360 |
| atcgtggcaa actctgaata ctagaaatga cggtgtagta gtgagactgt ggggataag | 420 |
| ctccattgtc aagagggaaa cagcccagac caccagctaa ggccccaaaa tgtaatgta | 480 |
| gtgacaaagg aggtgaaaat gcaaacacaa ccaggaggtt ggcttagaag cagccatcct | 540 |
| ttaaagagtg cgtaatagct cactg | 565 |

```
<210> SEQ ID NO 8
<211> LENGTH: 546
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
```

| | |
|---|---|
| tgttgaagaa tgagccggcg acttagaaaa cgtggcaagg ttaaggaaac gtatccggag | 60 |
| ccgaagcgaa agcaagtctg aacagggcga ttaagtcatt ttttctagac ccgaacccgg | 120 |
| gtgatctaac catgaccagg atgaagcttg ggtgacacca agtgaaggtc cgaaccgacc | 180 |
| gatgttgaaa aatcggcgga tgagttgtgg ttagcggtga ataccagtc gaactcggag | 240 |
| ctagctggtt ctccccgaaa tgcgttgagg cgcagcggtt cataaggctg tctagggta | 300 |
| aagcactgtt tcggtgcggg ctgcgaaagc ggtaccaaat cgtggcaaac tctgaatact | 360 |
| agatatgcta tttatgggcc agtgagacgg tgggggataa gcttcatcgt cgagagggaa | 420 |
| acagcccaga tcactagcta aggccccaaa atgatcgtta agtgacaaag gaggtgagaa | 480 |
| tgcagaaaca accaggaggt ttgcttagaa gcagccaccc tttaaagagt gcgtaatagc | 540 |
| tcactg | 546 |

```
<210> SEQ ID NO 9
<211> LENGTH: 565
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
```

| | |
|---|---|
| tgttgaagaa tgagccggcg acttagaaaa agtggcgtgg ttaaggaaaa attccgaagc | 60 |
| cttagcgaaa gcgagtctga atagggcgat caaatatttt aatatttaca atttagtcat | 120 |
| tttttctaga cccgaacccg ggtgatctaa ccatgaccag gatgaaactt gggtgatacc | 180 |
| aagtgaaggt ccgaaccgac cgatgttgaa aaatcggcgg atgagttgtg gttagcggtg | 240 |
| aaataccagt cgaacccgga gctagctggt tctccccgaa atgcgttgag cgcagcagt | 300 |
| acatctagtc tatctagggg taaagcactg tttcggtgcg ggctgtgaaa acggtaccaa | 360 |
| atcgtggcaa actctgaata ctagaaatga cggtgtagta gtgagactgt ggggataag | 420 |
| ctccattgtc aagagggaaa cagcccagac caccagctaa ggccccaaaa tgtaatgta | 480 |
| gtgacaaagg aggtgaaaat gcaaacacaa ccaggaggtt ggcttagaag cagccatcct | 540 |

```
ttaaagagtg cgtaatagct cactg                                         565

<210> SEQ ID NO 10
<211> LENGTH: 565
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
tgttgaagaa tgagccggcg acttagaaaa agtggcgtgg ttaaggaaaa attccgaagc     60
cttagcgaaa gcgagtctga atagggcgat caaatatttt aatatttaca atttagtcat    120
tttttctaga cccgaacccg ggtgatctaa ccatgaccag gatgaaactt gggtgatacc    180
aagtgaaggt ccgaaccgac cgatgttgaa aaatcggcgg atgagttgtg gttagcggtg    240
aaataccagt cgaacccgga gctagctggt tctccccgaa atgcgttgag gcgcagcagt    300
acatctagtc tatctagggg taaagcactg tttcggtgcg ggctgtgaaa acggtaccaa    360
atcgtggcaa actctgaata ctagaaatga cggtgtagta gtgagactgt ggggataag     420 ctccattgtc aagagggaaa cagcccagac caccagctaa ggcccaaaa tggtaatgta     480 gtgacaaagg aggtgaaaat gcaaacacaa ccaggaggtt ggcttagaag cagccatcct    540
ttaaagagtg cgtaatagct cactg                                         565

<210> SEQ ID NO 11
<211> LENGTH: 548
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
tgttgaagaa tgagccggcg acttagaaga agtggcttgg ttaaggataa ctatccggag     60
ccagagcgaa agcaagtctg aatagggcgc ttaaaggtca ctttttctag acccgaaccc    120
gggtgatcta accatgacca ggatgaagct tgggtaacac cacgtgaagg tccgaaccga    180
ccgatgttga aaaatcggcg gatgagttgt ggttagcggt gaaataccaa tcgaactcgg    240
agctagctgg ttctccccga atgcgttga ggcgcagcgg tttatgaggc tgtctagggg     300
taaagcactg tttcggtgcg ggctgcgaaa gcggtaccaa atcgtggcaa actctgaata    360
ctagatatgc tattcatgag ccagtgagac ggtggggat aagcttcatc gtcaagaggg     420
aaacagccca gatcaccagc taaggcccca aaatggtcgt taagtggcaa aggaggtgag    480
aatgctgaaa caaccaggag gtttgcttag aagcagccac cctttaaaga gtgcgtaata    540
gctcactg                                                            548

<210> SEQ ID NO 12
<211> LENGTH: 548
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
tgttgaagaa tgagccggcg acttagaaga agtggcttgg ttaaggataa ctatccggag     60
ccagagcgaa agcaagtctg aatagggcgc ttaaaggtca ctttttctag acccgaaccc    120
```

```
gggtgatcta accatgacca ggatgaagct tgggtaacac cacgtgaagg tccgaaccga      180
ccgatgttga aaatcggcg gatgagttgt ggttagcggt gaaataccaa tcgaactcgg       240
agctagctgg ttctccccga aatgcgttga ggcgcagcgg tttatgaggc tgtctagggg      300
taaagcactg tttcggtgcg ggctgcgaaa gcggtaccaa atcgtggcaa actctgaata      360
ctagatatgc tattcatgag ccagtgagac ggtgggggat aagcttcatc gtcaagaggg      420
aaacagccca gatcaccagc taaggcccca aaatggtcgt taagtggcaa aggaggtgag      480
aatgctgaaa caaccaggag gtttgcttag aagcagccac cctttaaaga gtgcgtaata      540
gctcactg                                                               548

<210> SEQ ID NO 13
<211> LENGTH: 548
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
tgttgaagaa tgagccggcg acttagaaga agtggcttgg ttaaggataa ctatccggag       60
ccagagcgaa agcaagtctg aatagggcgc ttaaaggtca ctttttctag acccgaaccc      120
gggtgatcta accatgacca ggatgaagct tgggtaacac cacgtgaagg tccgaaccga      180
ccgatgttga aaatcggcg gatgagttgt ggttagcggt gaaataccaa tcgaactcgg       240
agctagctgg ttctccccga aatgcgttga ggcgcagcgg tttatgaggc tgtctagggg      300
taaagcactg tttcggtgcg ggctgcgaaa gcggtaccaa atcgtggcaa actctgaata      360
ctagatatgc tattcatgag ccagtgagac ggtgggggat aagcttcatc gtcaagaggg      420
aaacagccca gatcaccagc taaggcccca aaatggtcgt taagtggcaa aggaggtgag      480
aatgctgaaa caaccaggag gtttgcttag aagcagccac cctttaaaga gtgcgtaata      540
gctcactg                                                               548

<210> SEQ ID NO 14
<211> LENGTH: 548
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
tgttgaagaa tgagccggcg acttagaaga agtggcttgg ttaaggataa ctatccggag       60
ccagagcgaa agcaagtctg aatagggcgc ttaaaggtca ctttttctag acccgaaccc      120
gggtgatcta accatgacca ggatgaagct tgggtaacac cacgtgaagg tccgaaccga      180
ccgatgttga aaatcggcg gatgagttgt ggttagcggt gaaataccaa tcgaactcgg       240
agctagctgg ttctccccga aatgcgttga ggcgcagcgg tttatgaggc tgtctagggg      300
taaagcactg tttcggtgcg ggctgcgaaa gcggtaccaa atcgtggcaa actctgaata      360
ctagatatgc tattcatgag ccagtgagac ggtgggggat aagcttcatc gtcaagaggg      420
aaacagccca gatcaccagc taaggcccca aaatggtcgt taagtggcaa aggaggtgag      480
aatgctgaaa caaccaggag gtttgcttag aagcagccac cctttaaaga gtgcgtaata      540
gctcactg                                                               548
```

<210> SEQ ID NO 15
<211> LENGTH: 565
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 15

```
tgttgaagaa tgagccggcg acttagaaaa agtggcgtgg ttaaggaaaa attccgaagc      60
cttagcgaaa gcgagtctga atagggcgat caaatatttt aatatttaca atttagtcat     120
tttttctaga cccgaacccg ggtgatctaa ccatgaccag gatgaaactt gggtgatacc     180
aagtgaaggt ccgaaccgac cgatgttgaa aaatcggcgg atgagttgtg gttagcggtg     240
aaataccagt cgaacccgga gctagctggt tctccccgaa atgcgttgag cgcagcagt     300 acatctagtc tatctagggg taaagcactg tttcggtgcg ggctgtgaaa acggtaccaa     360
atcgtggcaa actctgaata ctagaaatga cggtgtagta gtgagactgt ggggataag     420 ctccattgtc aagagggaaa cagcccagac caccagctaa ggccccaaaa tggtaatgta     480
gtgacaaagg aggtgaaaat gcaaacacaa ccaggaggtt ggcttagaag cagccatcct     540
ttaaagagtg cgtaatagct cactg                                          565
```

<210> SEQ ID NO 16
<211> LENGTH: 541
<212> TYPE: DNA
<213> ORGANISM: Prototheca stagnora

<400> SEQUENCE: 16

```
tgttgaagaa tgagccggcg agttaaaaaa aatggcatgg ttaaagatat ttctctgaag      60
ccatagcgaa agcaagtttt acaagctata gtcattttt ttagacccga aaccgagtga     120
tctacccatg atcagggtga agtgttggtc aaataacatg gaggcccgaa ccgactaatg     180
gtgaaaaatt agcggatgaa ttgtgggtag gggcgaaaaa ccaatcgaac tcggagttag     240
ctggttctcc ccgaaatgcg tttaggcgca gcagtagcaa cacaaataga ggggtaaagc     300
actgtttctt ttgtgggctt cgaaagttgt acctcaaagt ggcaaactct gaatactcta     360
tttagatatc tactagtgag accttggggg ataagctcct tggtcaaaag ggaaacagcc     420
cagatcacca gttaaggccc caaaatgaaa atgatagtga ctaaggacgt gagtatgtca     480
aaacctccag caggttagct tagaagcagc aatcctttca agagtgcgta atagctcact     540
g                                                                    541
```

<210> SEQ ID NO 17
<211> LENGTH: 573
<212> TYPE: DNA
<213> ORGANISM: Prototheca moriformis

<400> SEQUENCE: 17

```
tgttgaagaa tgagccggcg acttaaaata aatggcaggc taagagaatt aataactcga      60
aacctaagcg aaagcaagtc ttaatagggc gctaatttaa caaaacatta aataaaatct     120
aaagtcattt attttagacc cgaacctgag tgatctaacc atggtcagga tgaaacttgg     180
gtgacaccaa gtggaagtcc gaaccgaccg atgttgaaaa atcggcggat gaactgtggt     240
tagtggtgaa ataccagtcg aactcagagc tagctggttc tccccgaaat gcgttgaggc     300
gcagcaatat atctcgtcta tctaggggta aagcactgtt tcggtgcggg ctatgaaaat     360
```

```
ggtaccaaat cgtggcaaac tctgaatact agaaatgacg atatattagt gagactatgg    420
gggataagct ccatagtcga gagggaaaca gcccagacca ccagttaagg ccccaaaatg    480
ataatgaagt ggtaaaggag gtgaaaatgc aaatacaacc aggaggttgg cttagaagca    540
gccatccttt aaagagtgcg taatagctca ctg                                 573
```

<210> SEQ ID NO 18
<211> LENGTH: 573
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
tgttgaagaa tgagccggcg acttaaaata aatggcaggc taagagaatt aataactcga     60
aacctaagcg aaagcaagtc ttaatagggc gctaatttaa caaaacatta ataaaatct    120 aaagtcattt attttagacc cgaacctgag tgatctaacc atggtcagga tgaaacttgg    180
gtgacaccaa gtggaagtcc gaaccgaccg atgttgaaaa atcggcggat gaactgtggt    240
tagtggtgaa ataccagtcg aactcagagc tagctggttc tccccgaaat gcgttgaggc    300
gcagcaatat atctcgtcta tctaggggta aagcactgtt tcggtgcggg ctatgaaaat    360
ggtaccaaat cgtggcaaac tctgaatact agaaatgacg atatattagt gagactatgg    420
gggataagct ccatagtcga gagggaaaca gcccagacca ccagttaagg ccccaaaatg    480
ataatgaagt ggtaaaggag gtgaaaatgc aaatacaacc aggaggttgg cttagaagca    540
gccatccttt aaagagtgcg taatagctca ctg                                 573
```

<210> SEQ ID NO 19
<211> LENGTH: 565
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
tgttgaagaa tgagccggcg acttagaaaa agtggcgtgg ttaaggaaaa attccgaagc     60
cttagcgaaa gcgagtctga atagggcgat caaatatttt aatatttaca atttagtcat    120
tttttctaga cccgaacccg ggtgatctaa ccatgaccag gatgaaactt gggtgatacc    180
aagtgaaggt ccgaaccgac cgatgttgaa aaatcggcgg atgagttgtg gttagcggtg    240
aaataccagt cgaacccgga gctagctggt tctccccgaa atgcgttgag gcgcagcagt    300
acatctagtc tatctagggg taaagcactg tttcggtgcg ggctgtgaaa acggtaccaa    360
atcgtggcaa actctgaata ctagaaatga cggtgtagta gtgagactgt ggggataag    420 ctccattgtc aagagggaaa cagcccgac caccagctaa ggccccaaaa tggtaatgta    480
gtgacaaagg aggtgaaaat gcaaacacaa ccaggaggtt ggcttagaag cagccatcct    540
ttaaagagtg cgtaatagct cactg                                          565
```

<210> SEQ ID NO 20
<211> LENGTH: 565
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
tgttgaagaa tgagccggcg acttagaaaa agtggcgtgg ttaaggaaaa attccgaagc    60
cttagcgaaa gcgagtctga atagggcgat caaatatttt aatatttaca atttagtcat   120
tttttctaga cccgaacccg ggtgatctaa ccatgaccag gatgaaactt gggtgatacc   180
aagtgaaggt ccgaaccgac cgatgttgaa aaatcggcgg atgagttgtg gttagcggtg   240
aaataccagt cgaacccgga gctagctggt tctccccgaa atgcgttgag gcgcagcagt   300
acatctagtc tatctagggg taaagcactg tttcggtgcg ggctgtgaaa acggtaccaa   360
atcgtggcaa actctgaata ctagaaatga cggtgtagta gtgagactgt gggggataag   420
ctccattgtc aagagggaaa cagcccagac caccagctaa ggccccaaaa tggtaatgta   480
gtgacaaagg aggtgaaaat gcaaacacaa ccaggaggtt ggcttagaag cagccatcct   540
ttaaagagtg cgtaatagct cactg                                         565
```

<210> SEQ ID NO 21
<211> LENGTH: 546
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 21

```
tgttgaagaa tgagccggcg acttagaaaa cgtggcaagg ttaaggacat gtatccggag    60
ccgaagcgaa agcaagtctg aatagggcgc ctaagtcatt ttttctagac ccgaacccgg   120
gtgatctaac catgaccagg atgaagcttg ggtgacacca agtgaaggtc cgaaccgacc   180
gatgttgaaa aatcggcgga tgagttgtgg ttagcggtga ataccagtcg aactcggag    240
ctagctggtt ctccccgaaa tgcgttgagg cgcagcggtt cataaggctg tctagggta    300
aagcactgtt tcggtgcggg ctgcgaaagc ggtaccaaat cgtggcaaac tctgaatact   360
agatatgcta tttatgagcc agtgagacgg tgggggataa gcttcatcgt cgagagggaa   420
acagcccaga tcactagcta aggcccctaa atgatcgtta agtgacaaag gaggtgagaa   480
tgcagaaaca accaggaggt tgcttagaa gcagccaccc tttaaagagt gcgtaatagc   540
tcactg                                                              546
```

<210> SEQ ID NO 22
<211> LENGTH: 550
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 22

```
tgttgaagaa tgagccggcg acttatagga agtggcaggg ttaaggaaga atctccggag    60
cccaagcgaa agcgagtctg aaaagggcga tttggtcact tcttatggac ccgaacctgg   120
atgatctaat catggccaag ttgaagcatg gtaacacta tgtcgaggac tgaacccacc   180
gatgttgaaa aatcggggga tgagctgtga ttagcggtga aattccaatc gaattcagag   240
ctagctggat ctccccgaaa tgcgttgagg cgcagcggcg acgatgtcct gtctaagggt   300
agagcgactg tttcggtgcg ggctgcgaaa gcggtaccaa gtcgtggcaa actccgaata   360
ttaggcaaag gattccgtga gccagtgaga ctgtggggga taagcttcat agtcaagagg   420
gaaacagccc agaccatcag ctaaggcccc taaatggctg ctaagtggaa aaggatgtga   480
```

```
gaatgctgaa acaaccagga ggttcgctta gaagcagcta ttccttgaaa gagtgcgtaa      540
tagctcactg                                                            550
```

\<210\> SEQ ID NO 23
\<211\> LENGTH: 548
\<212\> TYPE: DNA
\<213\> ORGANISM: Artificial Sequence
\<220\> FEATURE:
\<223\> OTHER INFORMATION: Description of Artificial Sequence: Synthetic
      polynucleotide

\<400\> SEQUENCE: 23

```
tgttgaagaa tgagccggcg acttagaaga agtggcttgg ttaaggataa ctatccggag       60
ccagagcgaa agcaagtctg aatagggcgc ttaaaggtca cttttctag acccgaaccc      120 gggtgatcta accatgacca ggatgaagct tgggtaacac cacgtgaagg tccgaaccga     180
ccgatgttga aaaatcggcg gatgagttgt ggttagcggt gaaataccaa tcgaactcgg     240
agctagctgg ttctccccga aatgcgttga ggcgcagcgg tttatgaggc tgtctagggg    300
taaagcactg tttcggtgcg ggctgcgaaa gcggtaccaa atcgtggcaa actctgaata    360
ctagatatgc tattcatgag ccagtgagac ggtggggat aagcttcatc gtcaagaggg     420
aaacagccca gatcaccagc taaggcccca aaatggtcgt taagtggcaa aggaggtgag    480
aatgctgaaa caaccaggag gtttgcttag aagcagccac cctttaaaga gtgcgtaata    540
gctcactg                                                              548
```

\<210\> SEQ ID NO 24
\<211\> LENGTH: 556
\<212\> TYPE: DNA
\<213\> ORGANISM: Artificial Sequence
\<220\> FEATURE:
\<223\> OTHER INFORMATION: Description of Artificial Sequence: Synthetic
      polynucleotide

\<400\> SEQUENCE: 24

```
tgttgaagaa tgagccggcg acttataggg ggtggcgtgg ttaaggaagt aatccgaagc      60
caaagcgaaa gcaagttttc aatagagcga ttttgtcacc ccttatggac ccgaacccgg    120
gtgatctaac cttgaccagg atgaagcttg gtaacacca agtgaaggtc cgaactcatc     180
gatcttgaaa atcgtggga tgagttgggg ttagttggtt aaatgctaat cgaactcgga     240
gctagctggt tctccccgaa atgtgttgag gcgcagcgat taacgaaata ttttgtacgg    300 tttagggta aagcactgtt tcggtgcggg ctgcgaaagc ggtaccaaat cgtggcaaac    360
tctgaatact aagcctgtat accgttagtc agtgagagta taggggataa gctctatact    420
caagagggaa acagcccaga tcaccagcta aggccccaaa atgacagcta agtggcaaag    480
gaggtgaaag tgcagaaaca accaggaggt tcgcttagaa gcagcaaccc tttaaagagt    540
gcgtaatagc tcactg                                                     556
```

\<210\> SEQ ID NO 25
\<211\> LENGTH: 548
\<212\> TYPE: DNA
\<213\> ORGANISM: Artificial Sequence
\<220\> FEATURE:
\<223\> OTHER INFORMATION: Description of Artificial Sequence: Synthetic
      polynucleotide

\<400\> SEQUENCE: 25

```
tgttgaagaa tgagccggcg acttagaaga agtggcttgg ttaaggataa ctatccggag       60
```

```
ccagagcgaa agcaagtctg aatagggcgc ttaaaggtca cttttctag acccgaaccc    120 gggtgatcta accatgacca ggatgaagct tgggtaacac cacgtgaagg tccgaaccga    180
ccgatgttga aaatcggcg  gatgagttgt ggttagcggt gaaataccaa tcgaactcgg    240
agctagctgg ttctccccga aatgcgttga ggcgcagcgg tttatgaggc tgtctagggg    300
taaagcactg tttcggtgcg ggctgcgaaa gcggtaccaa atcgtggcaa actctgaata    360
ctagatatgc tattcatgag ccagtgagac ggtgggggat aagcttcatc gtcaagaggg    420
aaacagccca gatcaccagc taaggcccca aaatggtcgt taagtggcaa aggaggtgag    480
aatgctgaaa caaccaggag gtttgcttag aagcagccac cctttaaaga gtgcgtaata    540
gctcactg                                                             548

<210> SEQ ID NO 26
<211> LENGTH: 565
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
tgttgaagaa tgagccggcg acttagaaaa agtggcgtgg ttaaggaaaa attccgaagc     60
cttagcgaaa gcgagtctga atagggcgat caaatatttt aatatttaca atttagtcat    120
tttttctaga cccgaacccg ggtgatctaa ccatgaccag gatgaaactt gggtgatacc    180
aagtgaaggt ccgaaccgac cgatgttgaa aaatcggcgg atgagttgtg gttagcggtg    240
aaataccagt cgaacccgga gctagctggt ctccccgaa atgcgttgag gcgcagcagt    300
acatctagtc tatctagggg taaagcactg tttcggtgcg ggctgtgaaa acggtaccaa    360
atcgtggcaa actctgaata ctagaaatga cggtgtagta gtgagactgt ggggataag    420 ctccattgtc aagagggaaa cagcccagac caccagctaa ggcccaaaa tggtaatgta    480 gtgacaaagg aggtgaaaat gcaaacacaa ccaggaggtt ggcttagaag cagccatcct    540
ttaaagagtg cgtaatagct cactg                                          565

<210> SEQ ID NO 27
<211> LENGTH: 573
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
tgttgaagaa tgagccggcg acttataggg ggtggcttgg ttaaggacta caatccgaag     60
cccaagcgaa agcaagtttg aagtgtacac acattgtgtg tctagagcga ttttgtcact    120
ccttatggac ccgaacccgg gtgatctatt catggccagg atgaagcttg ggtaacacca    180
agtgaaggtc cgaactcatc gatgttgaaa aatcgtggga tgagttgtga ataggggtga    240
aatgccaatc gaactcggag ctagctggtt ctccccgaaa tgtgttgagg cgcagcgatt    300
cacgatctaa agtacggttt aggggtaaag cactgtttcg gtgcgggctg ttaacgcggt    360
accaaatcgt ggcaaactaa gaatactaaa cttgtatgcc gtgaatcagt gagactaaga    420
gggataagct tcttagtcaa gagggaaaca gcccagatca ccagctaagg ccccaaaatg    480
acagctaagt ggcaaaggag gtgagagtgc agaaacaacc aggaggtttg cttagaagca    540
```

```
gccatccttt aaagagtgcg taatagctca ctg                              573
```

<210> SEQ ID NO 28
<211> LENGTH: 573
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
tgttgaagaa tgagccggcg acttataggg ggtggcttgg ttaaggacta caatccgaag    60
cccaagcgaa agcaagtttg aagtgtacac acgttgtgtg tctagagcga ttttgtcact   120
ccttatggac ccgaacccgg gtgatctatt catggccagg atgaagcttg ggtaacacca   180
agtgaaggtc cgaactcatc gatgttgaaa atcgtgggga tgagttgtga ataggggtga   240
aatgccaatc gaactcggag ctagctggtt ctccccgaaa tgtgttgagg cgcagcgatt   300
cacgatctaa agtacggttt aggggtaaag cactgtttcg gtgcgggctg ttaacgcggt   360
accaaatcgt ggcaaactaa gaatactaaa cttgtatgcc gtgaatcagt gagactaaga   420
gggataagct tcttagtcaa gagggaaaca gcccagatca ccagctaagg ccccaaaatg   480
acagctaagt ggcaaaggag gtgagagtgc agaaacaacc aggaggtttg cttagaagca   540
gccatccttt aaagagtgcg taatagctca ctg                              573
```

<210> SEQ ID NO 29
<211> LENGTH: 573
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
tgttgaagaa tgagccggcg acttataggg ggtggcttgg ttaaggacta caatccgaag    60
cccaagcgaa agcaagtttg aagtgtacac acattgtgtg tctagagcga ttttgtcact   120
ccttatggac ccgaacccgg gtgatctatt catggccagg atgaagcttg ggtaacacca   180
agtgaaggtc cgaactcatc gatgttgaaa atcgtgggga tgagttgtga ataggggtga   240
aatgccaatc gaactcggag ctagctggtt ctccccgaaa tgtgttgagg cgcagcgatt   300
cacgatctaa agtacggttt aggggtaaag cactgtttcg gtgcgggctg ttaacgcggt   360
accaaatcgt ggcaaactaa gaatactaaa cttgtatgcc gtgaatcagt gagactaaga   420
gggataagct tcttagtcaa gagggaaaca gcccagatca ccagctaagg ccccaaaatg   480
acagctaagt ggcaaaggag gtgagagtgc agaaacaacc aggaggtttg cttagaagca   540
gccatccttt aaagagtgcg taatagctca ctg                              573
```

<210> SEQ ID NO 30
<211> LENGTH: 546
<212> TYPE: DNA
<213> ORGANISM: Chlorella protothecoides

<400> SEQUENCE: 30

```
tgttgaagaa tgagccggcg acttagaaaa cgtggcaagg ttaaggaaac gtatccggag    60
ccgaagcgaa agcaagtctg aacagggcga ttaagtcatt ttttctagac ccgaacccgg   120
gtgatctaac catgaccagg atgaagcttg ggtgacacca agtgaaggtc cgaaccgacc   180
gatgttgaaa atcggcgga tgagttgtgg ttagcggtga ataccagtc gaactcggag    240
```

```
ctagctggtt ctccccgaaa tgcgttgagg cgcagcggtt cataaggctg tctagggta      300 aagcactgtt tcggtgcggg ctgcgaaagc ggtaccaaat cgtggcaaac tctgaatact    360
agatatgcta tttatgggcc agtgagacgg tgggggataa gcttcatcgt cgagagggaa    420
acagcccaga tcactagcta aggccccaaa atgatcgtta agtgacaaag gaggtgagaa    480
tgcagaaaca accaggaggt ttgcttagaa gcagccaccc tttaaagagt gcgtaatagc    540
tcactg                                                               546
```

<210> SEQ ID NO 31
<211> LENGTH: 565
<212> TYPE: DNA
<213> ORGANISM: Chlorella protothecoides

<400> SEQUENCE: 31

```
tgttgaagaa tgagccggcg acttagaaaa agtggcgtgg ttaaggaaaa attccgaagc     60
cttagcgaaa gcgagtctga atagggcgat caaatatttt aatatttaca atttagtcat    120
tttttctaga cccgaacccg ggtgatctaa ccatgaccag gatgaaactt gggtgatacc    180
aagtgaaggt ccgaaccgac cgatgttgaa aaatcggcgg atgagttgtg gttagcggtg    240
aaataccagt cgaacccgga gctagctggt tctccccgaa atgcgttgag gcgcagcagt    300
acatctagtc tatctagggg taaagcactg tttcggtgcg ggctgtgaaa acggtaccaa    360
atcgtggcaa actctgaata ctagaaatga cggtgtagta gtgagactgt gggggataag    420
ctccattgtc aagagggaaa cagcccgac caccagctaa ggccccaaaa tggtaatgta     480
gtgacaaagg aggtgaaaat gcaaacacaa ccaggaggtt ggcttagaag cagccatcct    540
ttaaagagtg cgtaatagct cactg                                          565
```

<210> SEQ ID NO 32
<211> LENGTH: 565
<212> TYPE: DNA
<213> ORGANISM: Prototheca moriformis

<400> SEQUENCE: 32

```
tgttgaagaa tgagccggcg acttagaaaa ggtggcatgg ttaaggaaat attccgaagc     60
cgtagcaaaa gcgagtctga atagggcgat aaaatatatt aatatttaga atctagtcat    120
tttttctaga cccgaacccg ggtgatctaa ccatgaccag gatgaagctt gggtgatacc    180
aagtgaaggt ccgaaccgac cgatgttgaa aaatcggcgg atgagttgtg gttagcggtg    240
aaataccagt cgaacccgga gctagctggt tctccccgaa atgcgttgag gcgcagcagt    300
acatctagtc tatctagggg taaagcactg tttcggtgcg ggctgtgaga acggtaccaa    360
atcgtggcaa actctgaata ctagaaatga cgatgtagta gtgagactgt gggggataag    420
ctccattgtc aagagggaaa cagcccagac caccagctaa ggccccaaaa tggtaatgta    480
gtgacaaagg aggtgaaaat gcaaatacaa ccaggaggtt ggcttagaag cagccatcct    540
ttaaagagtg cgtaatagct cactg                                          565
```

<210> SEQ ID NO 33
<211> LENGTH: 573
<212> TYPE: DNA
<213> ORGANISM: Prototheca moriformis

<400> SEQUENCE: 33

```
tgttgaagaa tgagccggcg acttaaaata aatggcaggc taagagaatt aataactcga     60
```

```
aacctaagcg aaagcaagtc ttaatagggc gctaatttaa caaaacatta aataaaatct    120
aaagtcattt attttagacc cgaacctgag tgatctaacc atggtcagga tgaaacttgg    180
gtgacaccaa gtggaagtcc gaaccgaccg atgttgaaaa atcggcggat gaactgtggt    240
tagtggtgaa ataccagtcg aactcagagc tagctggttc tccccgaaat gcgttgaggc    300
gcagcaatat atctcgtcta tctaggggta agcactgttt cggtgcgggg ctatgaaaat    360
ggtaccaaat cgtggcaaac tctgaatact agaaatgacg atatattagt gagactatgg    420
gggataagct ccatagtcga gagggaaaca gcccagacca ccagttaagg ccccaaaatg    480
ataatgaagt ggtaaaggag gtgaaaatgc aaatacaacc aggaggttgg cttagaagca    540
gccatccttt aaagagtgcg taatagctca ctg                                 573

<210> SEQ ID NO 34
<211> LENGTH: 541
<212> TYPE: DNA
<213> ORGANISM: Prototheca kruegani

<400> SEQUENCE: 34
tgttgaagaa tgagccggcg agttaaaaag agtggcatgg ttaaagaaaa tactctggag     60
ccatagcgaa agcaagttta gtaagcttag gtcattcttt ttagacccga aaccgagtga    120
tctacccatg atcagggtga agtgttagta aaataacatg gaggcccgaa ccgactaatg    180
ttgaaaaatt agcggatgaa ttgtgggtag ggcgaaaaa ccaatcgaac tcggagttag     240
ctggttctcc ccgaaatgcg tttaggcgca gcagtagcag tacaaataga ggggtaaagc    300
actgtttctt ttgtgggctt cgaaagttgt acctcaaagt ggcaaactct gaatactcta    360
tttagatatc tactagtgag accttgggg ataagctcct tggtcaaaag ggaaacagcc     420
cagatcacca gttaaggccc caaaatgaaa atgatagtga ctaaggatgt gggtatgtca    480
aaacctccag caggttagct tagaagcagc aatccttca agagtgcgta atagctcact    540
g                                                                    541

<210> SEQ ID NO 35
<211> LENGTH: 573
<212> TYPE: DNA
<213> ORGANISM: Prototheca wickerhamii

<400> SEQUENCE: 35
tgttgaagaa tgagccggcg acttaaaata aatggcaggc taagagattt aataactcga     60
aacctaagcg aaagcaagtc ttaatagggc gtcaatttaa caaaacttta aataaaattat    120 aaagtcattt attttagacc cgaacctgag tgatctaacc atggtcagga tgaaacttgg    180
gtgacaccaa gtggaagtcc gaaccgaccg atgttgaaaa atcggcggat gaactgtggt    240
tagtggtgaa ataccagtcg aactcagagc tagctggttc tccccgaaat gcgttgaggc    300
gcagcaatat atctcgtcta tctaggggta agcactgttt cggtgcgggg ctatgaaaat    360
ggtaccaaat cgtggcaaac tctgaatact agaaatgacg atatattagt gagactatgg    420
gggataagct ccatagtcga gagggaaaca gcccagacca ccagttaagg ccccaaaatg    480
ataatgaagt ggtaaaggag gtgaaaatgc aaatacaacc aggaggttgg cttagaagca    540
gccatccttt aaagagtgcg taatagctca ctg                                 573

<210> SEQ ID NO 36
<211> LENGTH: 541
<212> TYPE: DNA
<213> ORGANISM: Prototheca moriformis
```

<400> SEQUENCE: 36

```
tgttgaagaa tgagccggcg agttaaaaag agtggcatgg ttaaagataa ttctctggag      60
ccatagcgaa agcaagttta acaagctaaa gtcacccttt ttagacccga aaccgagtga     120
tctacccatg atcagggtga agtgttggta aaataacatg gaggcccgaa ccgactaatg     180
gtgaaaaatt agcggatgaa ttgtgggtag gggcgaaaaa ccaatcgaac tcggagttag     240
ctggttctcc ccgaaatgcg tttaggcgca gcagtagcaa cacaaataga ggggtaaagc     300
actgtttctt ttgtgggctt cgaaagttgt acctcaaagt ggcaaactct gaatactcta     360
tttagatatc tactagtgag accttggggg ataagctcct tggtcaaaag ggaaacagcc     420
cagatcacca gttaaggccc caaaatgaaa atgatagtga ctaaggatgt gggtatgtta     480
aaacctccag caggttagct tagaagcagc aatcctttca agagtgcgta atagctcact     540
g                                                                     541
```

<210> SEQ ID NO 37
<211> LENGTH: 573
<212> TYPE: DNA
<213> ORGANISM: Prototheca wickerhamii

<400> SEQUENCE: 37

```
tgttgaagaa tgagccgtcg acttaaaata aatggcaggc taagagaatt aataactcga      60
aacctaagcg aaagcaagtc ttaatagggc gctaatttaa caaaacatta ataaaaatct     120
aaagtcattt attttagacc cgaacctgag tgatctaacc atggtcagga tgaaacttgg     180
gtgacaccaa gtggaagtcc gaaccgaccg atgttgaaaa atcggcggat gaactgtggt     240
tagtggtgaa ataccagtcg aactcagagc tagctggttc tccccgaaat gcgttgaggc     300
gcagcaatat atctcgtcta tctaggggta aagcactgtt tcggtgcggg ctatgaaaat     360
ggtaccaaat cgtggcaaac tctgaatact agaaatgacg atatattagt gagactatgg     420
gggataagct ccatagtcga gagggaaaca gcccagacca ccagttaagg ccccaaaatg     480
ataatgaagt ggtaaaggag gtgaaaatgc aaatacaacc aggaggttgg cttagaagca     540
gccatccttt aaagagtgcg taatagctca ctg                                   573
```

<210> SEQ ID NO 38
<211> LENGTH: 541
<212> TYPE: DNA
<213> ORGANISM: Prototheca moriformis

<400> SEQUENCE: 38

```
tgttgaagaa tgagccggcg agttaaaaag agtggcgtgg ttaaagaaaa ttctctggaa      60
ccatagcgaa agcaagttta acaagcttaa gtcactttt ttagacccga aaccgagtga     120
tctacccatg atcagggtga agtgttggta aaataacatg gaggcccgaa ccgactaatg     180
gtgaaaaatt agcggatgaa ttgtgggtag gggcgaaaaa ccaatcgaac tcggagttag     240
ctggttctcc ccgaaatgcg tttaggcgca gcagtagcaa cacaaataga ggggtaaagc     300
actgtttctt ttgtgggctc cgaaagttgt acctcaaagt ggcaaactct gaatactcta     360
tttagatatc tactagtgag accttggggg ataagctcct tggtcaaaag ggaaacagcc     420
cagatcacca gttaaggccc caaaatgaaa atgatagtga ctaaggatgt gagtatgtca     480
aaacctccag caggttagct tagaagcagc aatcctttca agagtgcgta atagctcact     540
g                                                                     541
```

<210> SEQ ID NO 39
<211> LENGTH: 541
<212> TYPE: DNA
<213> ORGANISM: Prototheca zopfii

<400> SEQUENCE: 39

```
tgttgaagaa tgagccggcg agttaaaaag agtggcatgg ttaaagaaaa ttctctggag      60
ccatagcgaa agcaagttta acaagcttaa gtcactttt ttagacccga aaccgagtga     120
tctacccatg atcagggtga agtgttggta aaataacatg gaggcccgaa ccgactaatg     180
gtgaaaaatt agcggatgaa ttgtgggtag gggcgaaaaa ccaatcgaac tcggagttag     240
ctggttctcc ccgaaatgcg tttaggcgca gcagtagcaa cacaaataga ggggtaaagc     300
actgtttctt tcgtgggctt cgaaagttgt acctcaaagt ggcaaactct gaatactcta     360
tttagatatc tactagtgag accttggggg ataagctcct tggtcaaaag ggaaacagcc     420
cagatcacca gttaaggccc caaaatgaaa atgatagtga ctaaggatgt gagtatgtca     480
aaacctccag caggttagct tagaagcagc aatcctttca agagtgcgta atagctcact     540
g                                                                    541
```

<210> SEQ ID NO 40
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Met Thr Phe Gly Val Ala Leu Pro Ala Met Gly Arg Gly Val Ser Leu
1               5                   10                  15

Pro Arg Pro Arg Val Ala Val Arg Ala Gln Ser Ala Ser Gln Val Leu
            20                  25                  30

Glu Ser Gly Arg Ala Gln Leu
        35
```

<210> SEQ ID NO 41
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Met Ala Ile Lys Thr Asn Arg Gln Pro Val Glu Lys Pro Pro Phe Thr
1               5                   10                  15

Ile Gly Thr Leu Arg Lys Ala Ile Pro Ala His Cys Phe Glu Arg Ser
            20                  25                  30

Ala Leu Arg Gly Arg Ala Gln Leu
        35                  40
```

<210> SEQ ID NO 42
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Arg Ala
        35

<210> SEQ ID NO 43
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Gln Leu
        35                  40

<210> SEQ ID NO 44
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Val Ala Ala Ala Ser Ser Ala Phe Phe Pro Val Pro Ala Pro
1               5                   10                  15

Gly Ala Ser Pro Lys Pro Gly Lys Phe Gly Asn Trp Pro Ser Ser Leu
            20                  25                  30

Ser Pro Ser Phe Lys Pro Lys Ser Ile Pro Asn Gly Gly Phe Gln Val
        35                  40                  45

Lys Ala Asn Asp Ser Ala His Pro Lys Ala Asn Gly Ser Ala Val Ser
50                  55                  60

Leu Lys Ser Gly Ser Leu Asn Thr Gln Glu Asp Thr Ser Ser Ser Pro
65                  70                  75                  80

Pro Pro Arg Thr Phe Leu His
                85

<210> SEQ ID NO 45
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu
```

<210> SEQ ID NO 46
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

Met Ala Thr Thr Ser Leu Ala Ser Ala Phe Cys Ser Met Lys Ala Val
1               5                   10                  15
Met Leu Ala Arg Asp Gly Arg Gly Met Lys Pro Arg Ser Ser Asp Leu
            20                  25                  30
Gln Leu Arg Ala Gly Asn Ala Gln Thr Ser Leu Lys Met Ile Asn Gly
        35                  40                  45
Thr Lys Phe Ser Tyr Thr Glu Ser Leu Lys Lys Leu
    50                  55                  60

<210> SEQ ID NO 47
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
tgacctaggt gattaattaa ctcgaggcag cagcagctcg gatagtatcg          50

<210> SEQ ID NO 48
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
ctacgagctc aagctttcca tttgtgttcc catcccacta cttcc               45

<210> SEQ ID NO 49
<211> LENGTH: 1568
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49
gaattccttt cttgcgctat gacacttcca gcaaaaggta gggcgggctg cgagacggct    60
tcccggcgct gcatgcaaca ccgatgatgc ttcgaccccc cgaagctcct tcggggctgc   120
atgggcgctc cgatgccgct ccagggcgag cgctgtttaa atagccaggc ccccgattgc   180
aaagacatta tagcgagcta ccaaagccat attcaaacac ctagatcact accacttcta   240
cacaggccac tcgagcttgt gatcgcactc cgctaagggg gcgcctcttc ctcttcgttt   300
cagtcacaac ccgcaaacgg cgcgccatat caatgattga acaagatgga ttgcacgcag   360
gttctccggc cgcttgggtg gagaggctat tcggctatga ctgggcacaa cagacaatcg   420
gctgctctga tgccgccgtg ttccggctgt cagcgcaggg gcgcccggtt ctttttgtca   480
agaccgacct gtccggtgcc ctgaatgaac tgcaggacga ggcagcgcgg ctatcgtggc   540

```
tggccacgac gggcgttcct tgcgcagctg tgctcgacgt tgtcactgaa gcgggaaggg    600
actggctgct attgggcgaa gtgccggggc aggatctcct gtcatctcac cttgctcctg    660
ccgagaaagt atccatcatg gctgatgcaa tgcggcggct gcatacgctt gatccggcta    720
cctgcccatt cgaccaccaa gcgaaacatc gcatcgagcg agcacgtact cggatggaag    780
ccggtcttgt cgatcaggat gatctggacg aagagcatca ggggctcgcg ccagccgaac    840
tgttcgccag gctcaaggcg cgcatgcccg acggcgagga tctcgtcgtg acccatggcg    900
atgcctgctt gccgaatatc atggtggaaa atggccgctt ttctggattc atcgactgtg    960
gccggctggg tgtggcggac cgctatcagg acatagcgtt ggctacccgt gatattgctg   1020
aagagcttgg cggcgaatgg gctgaccgct tcctcgtgct ttacggtatc gccgctcccg   1080
attcgcagcg catcgccttc tatcgccttc ttgacgagtt cttctaagat ctgtcgatcg   1140
acaagtgact cgaggcagca gcagctcgga tagtatcgac acactctgga cgctggtcgt   1200
gtgatggact gttgccgcca cacttgctgc cttgacctgt gaatatccct gccgcttttta  1260 tcaaacagcc tcagtgtgtt tgatcttgtg tgtacgcgct tttgcgagtt gctagctgct   1320
tgtgctattt gcgaatacca cccccagcat ccccttccct cgtttcatat cgcttgcatc   1380
ccaaccgcaa cttatctacg ctgtcctgct atccctcagc gctgctcctg ctcctgctca   1440
ctgcccctcg cacagccttg gtttgggctc cgcctgtatt ctcctggtac tgcaacctgt   1500
aaaccagcac tgcaatgctg atgcacggga agtagtggga tgggaacaca aatggaaagc   1560
ttgagctc                                                            1568

<210> SEQ ID NO 50
<211> LENGTH: 2571
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (997)..(999)
<223> OTHER INFORMATION: a, c, t, g, unknown or other

<400> SEQUENCE: 50
gaattccgcc tgcaacgcaa gggcagccac agccgctccc acccgccgct gaaccgacac     60
gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggacgtg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg ggcatgccac agcacgggca ccggggagtg    420
gaatggcacc accaagtgtg tgcgagccag catcgccgcc tggctgtttc agctacaacg    480
gcaggagtca tccaactaac catagctgat caacactgca atcatcggcg gctgatgcaa    540
gcatcctgca agacacatgc tgtgcgatgc tgcgctgctg cctgctgcgc acgccgttga    600
gttggcagca gctcagccat gcactggatc aggctgggct gccactgcaa tgtggtggat    660
aggatgcaag tggagcgaat accaaaccct ctggctgctt gctgggttgc atggcatcgc    720
accatcagca ggagcgcatg cgaagggact ggccccatgc acgccatgcc aaaccggagc    780
gcaccgagtg tccacactgt caccaggccc gcaagctttg cagaaccatg ctcatggacg    840
```

```
catgtagcgc tgacgtccct tgacggcgct cctctcgggt gtgggaaacg caatgcagca    900
caggcagcag aggcggcggc agcagagcgg cggcagcagc ggcggggggcc acccttcttg    960 cggggtcgcg ccccagccag cggtgatgcg ctgatcnnnc caaacgagtt cacattcatt   1020
tgcagcctgg agaagcgagg ctgggcctt tgggctggtg cagcccgcaa tggaatgcgg   1080
gaccgccagg ctagcagcaa aggcgcctcc cctactccgc atcgatgttc catagtgcat   1140
tggactgcat ttgggtgggg cggccggctg tttctttcgt gttgcaaaac gcgccacgtc   1200
agcaacctgt cccgtgggtc ccccgtgccg atgaaatcgt gtgcacgccg atcagctgat   1260
tgcccggctc gcgaagtagg cgccctcttt ctgctcgccc tctctccgtc ccgccactag   1320
tggcgcgcca tatcaatgat tgaacaagat ggattgcacg caggttctcc ggccgcttgg   1380
gtggagaggc tattcggcta tgactgggca acagacaa tcggctgctc tgatgccgcc    1440
gtgttccggc tgtcagcgca ggggcgcccg gttctttttg tcaagaccga cctgtccggt   1500
gccctgaatg aactgcagga cgaggcagcg cggctatcgt ggctggccac gacgggcgtt   1560
ccttgcgcag ctgtgctcga cgttgtcact gaagcgggaa gggactggct gctattgggc   1620
gaagtgccgg gcaggatct cctgtcatct caccttgctc ctgccgagaa agtatccatc   1680
atggctgatg caatgcggcg gctgcatacg cttgatccgg ctacctgccc attcgaccac   1740
caagcgaaac atcgcatcga gcgagcacgt actcggatgg aagccggtct tgtcgatcag   1800
gatgatctgg acgaagagca tcaggggctc gcgccagccg aactgttcgc caggctcaag   1860
gcgcgcatgc ccgacggcga ggatctcgtc gtgacccatg gcgatgcctg cttgccgaat   1920
atcatggtgg aaaatggccg cttttctgga ttcatcgact gtggccggct gggtgtggcg   1980
gaccgctatc aggacatagc gttggctacc cgtgatattg ctgaagagct tggcggcgaa   2040
tgggctgacc gcttcctcgt gctttacggt atcgccgctc ccgattcgca gcgcatcgcc   2100
ttctatcgcc ttcttgacga gttcttctaa gatctgtcga tcgacaagtg actcgaggca   2160
gcagcagctc ggatagtatc gacacactct ggacgctggt cgtgtgatgg actgttgccg   2220
ccacacttgc tgccttgacc tgtgaatatc cctgccgctt ttatcaaaca gcctcagtgt   2280
gtttgatctt gtgtgtacgc gcttttgcga gttgctagct gcttgtgcta tttgcgaata   2340 ccaccccccag catcccccttc cctcgtttca tatcgcttgc atcccaaccg caacttatct   2400
acgctgtcct gctatccctc agcgctgctc ctgctcctgc tcactgcccc tcgcacagcc   2460
ttggtttggg ctccgcctgt attctcctgg tactgcaacc tgtaaaccag cactgcaatg   2520
ctgatgcacg ggaagtagtg ggatgggaac acaaatggaa agcttgagct c           2571
```

<210> SEQ ID NO 51
<211> LENGTH: 2550
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (997)..(999)
<223> OTHER INFORMATION: a, c, t, g, unknown or other

<400> SEQUENCE: 51

```
gaattccgcc tgcaacgcaa gggcagccac agccgctccc accgccgct gaaccgacac       60 gtgcttgggc gcctgccgcc tgcctgccgc atgcttgtgc tggtgaggct gggcagtgct      120
gccatgctga ttgaggcttg gttcatcggg tggaagctta tgtgtgtgct gggcttgcat      180
```

```
gccgggcaat gcgcatggtg gcaagagggc ggcagcactt gctggacgtg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg ggcatgccac agcacgggca ccggggagtg    420
gaatggcacc accaagtgtg tgcgagccag catcgccgcc tggctgtttc agctacaacg    480
gcaggagtca tccaactaac catagctgat caacactgca atcatcggcg gctgatgcaa    540
gcatcctgca agacacatgc tgtgcgatgc tgcgctgctg cctgctgcgc acgccgttga    600
gttggcagca gctcagccat gcactggatc aggctgggct gccactgcaa tgtggtggat    660
aggatgcaag tggagcgaat accaaaccct ctggctgctt gctgggttgc atggcatcgc    720
accatcagca ggagcgcatg cgaagggact ggccccatgc acgccatgcc aaaccggagc    780
gcaccgagtg tccacactgt caccaggccc gcaagctttg cagaaccatg ctcatggacg    840
catgtagcgc tgacgtccct tgacggcgct cctctcgggt gtgggaaacg caatgcagca    900
caggcagcag aggcggcggc agcagagcgg cggcagcagc ggcgggggcc acccttcttg    960
cggggtcgcg ccccagccag cggtgatgcg ctgatcnnnc aaacgagtt cacattcatt    1020 tgcagcctgg agaagcgagg ctggggcctt tgggctggtg cagcccgcaa tggaatgcgg    1080
gaccgccagg ctagcagcaa aggcgcctcc cctactccgc atcgatgttc catagtgcat    1140
tggactgcat ttgggtgggg cggccggctg tttctttcgt gttgcaaaac gcgccacgtc    1200
agcaacctgt cccgtgggtc ccccgtgccg atgaaatcgt gtgcacgccg atcagctgat    1260
tgcccggctc gcgaagtagg cgccctcttt ctgctcgccc tctctccgtc ccgccactag    1320
tggcgcgcca tatcaatgat cgagcaggac ggcctccacg ccggctcccc cgccgcctgg    1380
gtggagcgcc tgttcggcta cgactgggcc cagcagacca tcggctgctc cgacgccgcc    1440
gtgttccgcc tgtccgccca gggccgcccc gtgctgttcg tgaagaccga cctgtccggc    1500
gccctgaacg agctgcagga cgaggccgcc cgcctgtcct ggctggccac caccggcgtg    1560
ccctgcgccg ccgtgctgga cgtggtgacc gaggccggcc gcgactggct gctgctgggc    1620
gaggtgcccg gccaggacct gctgtcctcc cacctggccc ccgccgagaa ggtgtccatc    1680
atggccgacg ccatgcgccg cctgcacacc ctggaccccg ccacctgccc cttcgaccac    1740
caggccaagc accgcatcga gcgcgcccgc acccgcatgg aggccggcct ggtggaccag    1800
gacgacctgg acgaggagca ccagggcctg gccccgccg agctgttcgc ccgcctgaag    1860 gccccgcatgc ccgacggcga ggacctggtg gtgacccacg cgacgcctg cctgcccaac    1920 atcatggtgg agaacggccg cttctccggc ttcatcgact gcggccgcct gggcgtggcc    1980
gaccgctacc aggacatcgc cctggccacc cgcgacatcg ccgaggagct gggcggcgag    2040
tgggccgacc gcttcctggt gctgtacggc atcgccgccc ccgactccca gcgcatcgcc    2100
ttctaccgct gctgacga gttcttctga ctcgaggcag cagcagctcg atagtatcg    2160 acacactctg gacgctggtc gtgtgatgga ctgttgccgc cacacttgct gccttgacct    2220
gtgaatatcc ctgccgcttt tatcaaacag cctcagtgtg tttgatcttg tgtgtacgcg    2280
cttttgcgag ttgctagctg cttgtgctat ttgcgaatac caccccagc atccccttcc    2340 ctcgtttcat atcgcttgca tcccaaccgc aacttatcta cgctgtcctg ctatccctca    2400
gcgctgctcc tgctcctgct cactgcccct cgcacagcct tggtttgggc tccgcctgta    2460
ttctcctggt actgcaacct gtaaaccagc actgcaatgc tgatgcacgg gaagtagtgg    2520
```

```
gatgggaaca caaatggaaa gcttgagctc                                    2550
```

<210> SEQ ID NO 52
<211> LENGTH: 1547
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
gaattccttt cttgcgctat gacacttcca gcaaaaggta gggcgggctg cgagacggct     60
tcccggcgct gcatgcaaca ccgatgatgc ttcgaccccc cgaagctcct tcggggctgc    120
atgggcgctc cgatgccgct ccagggcgag cgctgtttaa atagccaggc ccccgattgc    180
aaagacatta tagcgagcta ccaaagccat attcaaacac ctagatcact accacttcta    240
cacaggccac tcgagcttgt gatcgcactc cgctaagggg gcgcctcttc ctcttcgttt    300
cagtcacaac ccgcaaacgg cgcgccatat caatgatcga gcaggacggc ctccacgccg    360
gctcccccgc cgcctgggtg gagcgcctgt tcggctacga ctgggcccag cagaccatcg    420
gctgctccga cgccgccgtg ttccgcctgt ccgcccaggg ccgccccgtg ctgttcgtga    480
agaccgacct gtccggcgcc ctgaacgagc tgcaggacga ggccgcccgc ctgtcctggc    540
tggccaccac cggcgtgccc tgcgccgccg tgctggacgt ggtgaccgag gccggccgcg    600
actggctgct gctgggcgag gtgcccggcc aggacctgct gtcctccac ctggcccccg    660
ccgagaaggt gtccatcatg gccgacgcca tgcgccgcct gcacaccctg daccccgcca    720
cctgccccct cgaccaccag gccaagcacc gcatcgagcg cgcccgcacc cgcatggagg    780
ccggcctggt ggaccaggac gacctggacg aggagcacca gggcctggcc ccgccgagc    840
tgttcgcccg cctgaaggcc cgcatgcccg acggcgagga cctggtggtg acccacggcg    900
acgcctgcct gcccaacatc atggtggaga acggccgctt ctccggcttc atcgactgcg    960
gccgcctggg cgtggccgac cgctaccagg acatcgccct ggccaccgcgc acatcgccg   1020
aggagctggg cggcgagtgg gccgaccgct tcctggtgct gtacggcatc gccgcccccg   1080
actcccagcg catcgccttc taccgcctgc tggacgagtt cttctgactc gaggcagcag   1140
cagctcggat agtatcgaca cactctggac gctggtcgtg tgatggactg ttgccgccac   1200
acttgctgcc ttgacctgtg aatatccctg ccgcttttat caaacagcct cagtgtgttt   1260
gatcttgtgt gtacgcgctt ttgcgagttg ctagctgctt gtgctatttg cgaataccac   1320
ccccagcatc cccttccctc gtttcatatc gcttgcatcc caaccgcaac ttatctacgc   1380
tgtcctgcta tccctcagcg ctgctcctgc tcctgctcac tgcccctcgc acagccttgg   1440
tttgggctcc gcctgtattc tcctggtact gcaacctgta aaccagcact gcaatgctga   1500
tgcacgggaa gtagtgggat gggaacacaa atggaaagct tgagctc                 1547
```

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53

```
gccgcgactg gctgctgctg g                                              21
```

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
aggtcctcgc cgtcgggcat g                                       21

<210> SEQ ID NO 55
<211> LENGTH: 2357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

| | | | | | |
|---|---|---|---|---|---|
| ctttcttgcg | ctatgacact | tccagcaaaa | ggtagggcgg | gctgcgagac | ggcttcccgg | 60 |
| cgctgcatgc | aacaccgatg | atgcttcgac | ccccgaagc | tccttcgggg | ctgcatgggc | 120 |
| gctccgatgc | cgctccaggg | cgagcgctgt | ttaaatagcc | aggcccccga | ttgcaaagac | 180 |
| attatagcga | gctaccaaag | ccatattcaa | acacctagat | cactaccact | tctacacagg | 240 |
| ccactcgagc | ttgtgatcgc | actccgctaa | ggggcgcct | cttcctcttc | gtttcagtca | 300 |
| caacccgcaa | acggcgcgcc | atatcaatgc | ttcttcaggc | cttttctttt | cttcttgctg | 360 |
| gttttgctgc | caagatcagc | gcctctatga | cgaacgaaac | ctcggataga | ccacttgtgc | 420 |
| actttacacc | aaacaagggc | tggatgaatg | accccaatgg | actgtggtac | gacgaaaaag | 480 |
| atgccaagtg | gcatctgtac | tttcaataca | acccgaacga | tactgtctgg | gggacgccat | 540 |
| tgttttgggg | ccacgccacg | tccgacgacc | tgaccaattg | ggaggaccaa | ccaatagcta | 600 |
| tcgctccgaa | gaggaacgac | tccggagcat | tctcgggttc | catggtggtt | gactacaaca | 660 |
| atacttccgg | cttttttcaac | gataccattg | acccgagaca | acgctgcgtg | gccatatgga | 720 |
| cttacaacac | accggagtcc | gaggagcagt | acatctcgta | tagcctggac | ggtggataca | 780 |
| cttttacaga | gtatcagaag | aaccctgtgc | ttgctgcaaa | ttcgactcag | ttccgagatc | 840 |
| cgaaggtctt | ttggtacgag | ccctcgcaga | agtggatcat | gacagcggca | aagtcacagg | 900 |
| actacaagat | cgaaatttac | tcgtctgacg | accttaaatc | ctggaagctc | gaatccgcgt | 960 |
| tcgcaaacga | gggctttctc | ggctaccaat | acgaatgccc | aggcctgata | gaggtcccaa | 1020 |
| cagagcaaga | tccagcaag | tcctactggg | tgatgtttat | ttccattaat | ccaggagcac | 1080 |
| cggcaggagg | ttcttttaat | cagtacttcg | tcggaagctt | taacggaact | catttcgagg | 1140 |
| catttgataa | ccaatcaaga | gtagttgatt | ttggaaagga | ctactatgcc | ctgcagactt | 1200 |
| tcttcaatac | tgacccgacc | tatgggagcg | ctcttggcat | tgcgtgggct | tctaactggg | 1260 |
| agtattccgc | attcgttcct | acaaacccctt | ggaggtcctc | catgtcgctc | gtgaggaaat | 1320 |
| tctctctcaa | cactgagtac | caggccaacc | cggaaaccga | actcataaac | ctgaaagccg | 1380 |
| aaccgatcct | gaacattagc | aacgctggcc | cctggagccg | gtttgcaacc | aacaccacgt | 1440 |
| tgacgaaagc | caacagctac | aacgtcgatc | tttcgaatag | caccggtaca | cttgaatttg | 1500 |
| aactggtgta | tgccgtcaat | accacccaaa | cgatctcgaa | gtcggtgttc | gcggacctct | 1560 |
| ccctctggtt | taaaggcctg | gaagacccg | aggagtacct | cagaatgggt | ttcgaggttt | 1620 |
| ctgcgtcctc | cttcttcctt | gatcgcggga | acagcaaagt | aaaatttgtt | aaggagaacc | 1680 |

```
catatttttac caacaggatg agcgttaaca accaaccatt caagagcgaa aacgacctgt    1740
cgtactacaa agtgtatggt ttgcttgatc aaaatatcct ggaactctac ttcaacgatg    1800
gtgatgtcgt gtccaccaac acatacttca tgacaaccgg gaacgcactg ggctccgtga    1860
acatgacgac gggtgtggat aacctgttct acatcgacaa attccaggtg agggaagtca    1920
agtgagatct gtcgatcgac aagctcgagg cagcagcagc tcggatagta tcgacacact    1980
ctggacgctg gtcgtgtgat ggactgttgc cgccacactt gctgccttga cctgtgaata    2040
tccctgccgc ttttatcaaa cagcctcagt gtgtttgatc ttgtgtgtac gcgcttttgc    2100
gagttgctag ctgcttgtgc tatttgcgaa taccacccccc agcatcccct tccctcgttt    2160
catatcgctt gcatcccaac cgcaacttat ctacgctgtc ctgctatccc tcagcgctgc    2220
tcctgctcct gctcactgcc cctcgcacag ccttggtttg ggctccgcct gtattctcct    2280
ggtactgcaa cctgtaaacc agcactgcaa tgctgatgca cgggaagtag tgggatggga    2340
acacaaatgg aaagctt                                                   2357

<210> SEQ ID NO 56
<211> LENGTH: 2335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
ctttcttgcg ctatgacact tccagcaaaa ggtagggcgg gctgcgagac ggcttcccgg      60
cgctgcatgc aacaccgatg atgcttcgac cccccgaagc tccttcgggg ctgcatgggc     120
gctccgatgc cgctccaggg cgagcgctgt ttaaatagcc aggccccccga ttgcaaagac     180 attatagcga gctaccaaag ccatattcaa acacctagat cactaccact tctacacagg     240
ccactcgagc ttgtgatcgc actccgctaa gggggcgcct cttcctcttc gtttcagtca     300
caacccgcaa acggcgcgcc atgctgctgc aggccttcct gttcctgctg gccggcttcg     360
ccgccaagat cagcgcctcc atgacgaacg agacgtccga ccgcccctg gtgcacttca     420 ccccccaacaa gggctggatg aacgaccccca acggcctgtg gtacgacgag aaggacgcca     480
agtggcacct gtacttccag tacaacccga cgacaccgt ctgggggacg cccttgttct     540
ggggccacgc cacgtccgac gacctgacca actgggagga ccagcccatc gccatcgccc     600
cgaagcgcaa cgactccggc gccttctccg gctccatggt ggtggactac aacaacacct     660
ccggcttctt caacgacacc atcgaccgc gccagcgctg cgtggccatc tggacctaca     720
acaccccgga gtccgaggag cagtacatct cctacagcct ggacggcggc tacaccttca     780
ccgagtacca gaagaacccc gtgctggccg ccaactccac ccagttccgc gacccgaagg     840
tcttctggta cgagccctcc cagaagtgga tcatgaccgc ggccaagtcc caggactaca     900
agatcgagat ctactcctcc gacgacctga agtcctggaa gctggagtcc gcgttcgcca     960
acgagggctt cctcggctac cagtacgagt gccccggcct gatcgaggtc cccaccgagc    1020
aggaccccag caagtcctac tgggtgatgt tcatctccat caaccccggc gccccggccg    1080
gcggctcctt caaccagtac ttcgtcggca gcttcaacgg cacccacttc gaggccttcg    1140
acaaccagtc ccgcgtggtg gacttcggca aggactacta cgccctgcag accttcttca    1200
acaccgaccc gacctacggg agcgccctgg gcatcgcgtg ggcctccaac tgggagtact    1260
ccgccttcgt gcccaccaac ccctggcgct cctccatgtc cctcgtgcgc aagttctccc    1320
```

```
tcaacaccga gtaccaggcc aacccggaga cggagctgat caacctgaag gccgagccga      1380
tcctgaacat cagcaacgcc ggcccctgga gccggttcgc caccaacacc acgttgacga      1440
aggccaacag ctacaacgtc gacctgtcca acagcaccgg caccctggag ttcgagctgg      1500
tgtacgccgt caacaccacc cagacgatct ccaagtccgt gttcgcggac ctctccctct      1560
ggttcaaggg cctggaggac cccgaggagt acctccgcat gggcttcgag gtgtccgcgt      1620
cctccttctt cctggaccgc gggaacagca aggtgaagtt cgtgaaggag aaccnctact      1680
tcaccaaccg catgagcgtg aacaaccagc ccttcaagag cgagaacgac ctgtcctact      1740
acaaggtgta cggcttgctg gaccagaaca tcctggagct gtacttcaac gacggcgacg      1800
tcgtgtccac caacacctac ttcatgacca ccgggaacgc cctgggctcc gtgaacatga      1860 cgacggggt ggacaacctg ttctacatcg acaagttcca ggtgcgcgag gtcaagtgat      1920
taattaactc gaggcagcag cagctcggat agtatcgaca cactctggac gctggtcgtg      1980
tgatggactt ttgccgccac acttgctgcc ttgacctgtg aatatccctg ccgcttttat      2040
caaacagcct cagtgtgttt gatcttgtgt gtacgcgctt ttgcgagttg ctagctgctt      2100
gtgctatttg cgaataccac ccccagcatc cccttccctc gtttcatatc gcttgcatcc      2160
caaccgcaac ttatctacgc tgtcctgcta tccctcagcg ctgctcctgc tcctgctcac      2220
tgcccctcgc acagccttgg tttgggctcc gcctgtattc tcctggtact gcaacctgta      2280
aaccagcact gcaatgctga tgcacgggaa gtagtgggat gggaacacaa atgga          2335
```

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ccgccgtgct ggacgtggtg                                                   20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggtggcgggg tccagggtgt                                                   20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cggccggcgg ctccttcaac                                                   20

<210> SEQ ID NO 60
<211> LENGTH: 20
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 60
ggcgctcccg taggtcgggt                                                  20

<210> SEQ ID NO 61
<211> LENGTH: 1335
<212> TYPE: DNA
<213> ORGANISM: Chlorella sorokiniana

<400> SEQUENCE: 61

```
cgcctgcaac gcaagggcag ccacagccgc tcccacccgc cgctgaaccg acacgtgctt      60
gggcgcctgc cgcctgcctg ccgcatgctt gtgctggtga ggctgggcag tgctgccatg     120
ctgattgagg cttggttcat cgggtggaag cttatgtgtg tgctgggctt gcatgccggg     180
caatgcgcat ggtggcaaga gggcggcagc acttgctgga gctgccgcgg tgcctccagg     240
tggttcaatc gcggcagcca gagggatttc agatgatcgc gcgtacaggt tgagcagcag     300
tgtcagcaaa ggtagcagtt tgccagaatg atcggttcag ctgttaatca atgccagcaa     360
gagaaggggt caagtgcaaa cacgggcatg ccacagcacg ggcaccgggg agtggaatgg     420
caccaccaag tgtgtgcgag ccagcatcgc cgcctggctg tttcagctac aacggcagga     480
gtcatccaac gtaaccatga gctgatcaac actgcaatca tcgggcgggc gtgatgcaag     540
catgcctggc gaagacacat ggtgtgcgga tgctgccggc tgctgcctgc tgcgcacgcc     600
gttgagttgg cagcaggctc agccatgcac tggatggcag ctgggctgcc actgcaatgt     660
ggtggatagg atgcaagtgg agcgaatacc aaaccctctg gctgcttgct gggttgcatg     720
gcatcgcacc atcagcagga gcgcatgcga agggactggc cccatgcacg ccatgccaaa     780
ccggagcgca ccgagtgtcc acactgtcac caggcccgca agctttgcag aaccatgctc     840
atggacgcat gtagcgctga cgtcccttga cggcgctcct ctcgggtgtg gaaacgcaa      900
tgcagcacag gcagcagagg cggcggcagc agagcggcgg cagcagcggc ggggggccacc    960
cttcttgcgg ggtcgcgccc cagccagcgg tgatgcgctg atcccaaacg agttcacatt    1020
catttgcatg cctggagaag cgaggctggg gcctttgggc tggtgcagcc cgcaatggaa    1080
tgcgggaccg ccaggctagc agcaaaggcg cctcccctac tccgcatcga tgttccatag    1140
tgcattggac tgcatttggg tggggcggcc ggctgtttct ttcgtgttgc aaaacgcgcc    1200
agctcagcaa cctgtcccgt gggtcccccg tgccgatgaa atcgtgtgca cgccgatcag    1260
ctgattgccc ggctcgcgaa gtaggcgccc tcctttctgc tcgccctctc tccgtcccgc    1320
cactagtggc gcgcc                                                     1335
```

<210> SEQ ID NO 62
<211> LENGTH: 1146
<212> TYPE: DNA
<213> ORGANISM: Umbellularia californica

<400> SEQUENCE: 62

```
atggccacca ccagcctggc ctccgccttc tgctccatga aggccgtgat gctggcccgc      60
gacgccgcg gcatgaagcc ccgcagctcc gacctgcagc tgcgcgccgg caacgccccc     120
acctccctga agatgatcaa cggcaccaag ttcagctaca ccgagagcct gaagcgcctg     180
cccgactggt ccatgctgtt cgccgtgatc accaccatct tcagcgccgc cgagaagcag     240
tggaccaacc tggagtggaa gcccaagccc aagctgcccc agctgctgga cgaccacttc     300
```

```
ggcctgcacg gcctggtgtt ccgccgcacc ttcgccatcc gctcctacga ggtgggcccc      360
gaccgcagca cctccatcct ggccgtgatg aaccacatgc aggaggccac cctgaaccac      420
gccaagagcg tgggcatcct gggcgacggc ttcggcacca ccctggagat gtccaagcgc      480
gacctgatgt gggtggtgcg ccgcacccac gtggccgtgg agcgctaccc cacctggggc      540
gacaccgtgg aggtggagtg ctggatcggc gccagcggca caacggcat gcgccgcgac      600 ttcctggtgc gcgactgcaa gaccggcgag atcctgaccc gctgcacctc cctgagcgtg      660
ctgatgaaca cccgcacccg ccgcctgagc accatccccg acgaggtgcg cggcgagatc      720
ggccccgcct tcatcgacaa cgtggccgtg aaggacgacg agatcaagaa gctgcagaag      780
ctgaacgact ccaccgccga ctacatccag ggcggcctga ccccgctg aacgacctg       840 gacgtgaacc agcacgtgaa caacctgaag tacgtggcct gggtgttcga gaccgtgccc      900
gacagcatct tcgagtccca ccacatcagc tccttcaccc tggagtaccg ccgcgagtgc      960
acccgcgact ccgtgctgcg cagcctgacc accgtgagcg cggcagctc cgaggccggc     1020 ctggtgtgcg accacctgct gcagctggag ggcggcagcg aggtgctgcg cgcccgcacc     1080
gagtggcgcc ccaagctgac cgactccttc cgcggcatca gcgtgatccc cgccgagccc     1140
cgcgtg                                                               1146

<210> SEQ ID NO 63
<211> LENGTH: 1146
<212> TYPE: DNA
<213> ORGANISM: Cinnamomum camphora

<400> SEQUENCE: 63
atggccacca cctccctggc ctccgccttc tgcagcatga aggccgtgat gctggcccgc       60
gacggccgcg gcatgaagcc ccgctccagc gacctgcagc tgcgcgccgg caacgcccag      120
acctccctga agatgatcaa cggcaccaag ttctcctaca ccgagagcct gaagaagctg      180
cccgactggt ccatgctgtt cgccgtgatc accaccatct ctccgccgc cgagaagcag      240 tggaccaacc tggagtggaa gcccaagccc aaccccccc agctgctgga cgaccacttc      300
ggcccccacg gcctggtgtt ccgccgcacc ttcgccatcc gcagctacga ggtgggcccc      360
gaccgctcca ccagcatcgt ggccgtgatg aaccacctgc aggaggccgc cctgaaccac      420
gccaagtccg tgggcatcct gggcgacggc ttcggcacca ccctggagat gtccaagcgc      480
gacctgatct gggtggtgaa gcgcacccac gtggccgtgg agcgctaccc cgcctggggc      540
gacaccgtgg aggtggagtg ctgggtgggc gcctccggca caacggccg ccgccacgac      600 ttcctggtgc gcgactgcaa gaccggcgag atcctgaccc gctgcacctc cctgagcgtg      660
atgatgaaca cccgcacccg ccgcctgagc aagatccccg aggaggtgcg cggcgagatc      720
ggccccgcct tcatcgacaa cgtggccgtg aaggacgagg agatcaagaa gccccagaag      780
ctgaacgact ccaccgccga ctacatccag ggcggcctga ccccgctg aacgacctg       840 gacatcaacc agcacgtgaa caacatcaag tacgtggact ggatcctgga ccgtgccc       900 gacagcatct tcgagagcca ccacatctcc tccttcacca tcgagtaccg ccgcgagtgc      960
accatggaca gcgtgctgca gtccctgacc accgtgagcg cggctcctc cgaggccggc     1020 ctggtgtgcg agcacctgct gcagctggag ggcggcagcg aggtgctgcg cgccaagacc     1080
gagtggcgcc ccaagctgac cgactccttc cgcggcatca gcgtgatccc cgccgagtcc     1140
agcgtg                                                               1146
```

-continued

```
<210> SEQ ID NO 64
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
atggactaca aggaccacga cggcgactac aaggaccacg acatcgacta caaggacgac      60
gacgacaagt ga                                                          72

<210> SEQ ID NO 65
<211> LENGTH: 408
<212> TYPE: DNA
<213> ORGANISM: Chlorella vulgaris

<400> SEQUENCE: 65
ctcgaggcag cagcagctcg gatagtatcg acacactctg gacgctggtc gtgtgatgga      60
ctgttgccgc cacacttgct gccttgacct gtgaatatcc ctgccgcttt tatcaaacag     120
cctcagtgtg tttgatcttg tgtgtacgcg cttttgcgag ttgctagctg cttgtgctat     180
ttgcgaatac caccccccagc atccccttcc ctcgtttcat atcgcttgca tcccaaccgc    240
aacttatcta cgctgtcctg ctatccctca gcgctgctcc tgctcctgct cactgcccct     300
cgcacagcct tggtttgggc tccgcctgta ttctcctggt actgcaacct gtaaaccagc     360
actgcaatgc tgatgcacgg gaagtagtgg gatgggaaca caaatgga                  408

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ctgggcgacg gcttcggcac                                                  20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
aagtcgcggc gcatgccgtt                                                  20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
taccccgcct ggggcgacac                                                  20

<210> SEQ ID NO 69
<211> LENGTH: 20
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 69

```
cttgctcagg cggcgggtgc                                              20
```

<210> SEQ ID NO 70
<211> LENGTH: 1317
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70

```
atggtggccg ccgccgcctc cagcgccttc ttccccgtgc ccgcccccgg cgcctccccc      60
aagcccggca agttcggcaa ctggccctcc agcctgagcc cctccttcaa gcccaagtcc     120
atccccaacg gcggcttcca ggtgaaggcc aacgacagcg cccaccccaa ggccaacggc     180
tccgccgtga gcctgaagag cggcagcctg aacacccagg aggacacctc ctccagcccc     240
ccccccgca ccttcctgca ccagctgccc gactggagcc gctgctgac cgccatcacc       300
accgtgttcg tgaagtccaa cgcccccgac atgcacgacc gcaagtccaa cgcccccgac     360
atgctggtgg acagcttcgg cctggagtcc accgtgcagg acggcctggt gttccgccag     420
tccttctcca tccgctccta cgagatcggc accgaccgca ccgccagcat cgagaccctg     480
atgaaccacc tgcaggagac ctccctgaac cactgcaaga gcaccggcat cctgctggac     540
ggcttcggcc gcaccctgga gatgtgcaag cgcgacctga tctgggtggt gatcaagatg     600
cagatcaagg tgaaccgcta ccccgcctgg ggcgacaccg tggagatcaa cacccgcttc     660
agccgcctgg gcaagatcgg catgggccgc gactggctga tctccgactg caacaccggc     720
gagatcctgt gcgcgccac cagcgcctac gccatgatga accagaagac ccgccgcctg     780
tccaagctgc cctacgaggt gcaccaggag atcgtgcccc tgttcgtgga cagccccgtg     840
atcgaggact ccgacctgaa ggtgcacaag ttcaaggtga agaccggcga cagcatccag     900
aagggcctga ccccggctg aacgacctg gacgtgaacc agcacgtgtc caacgtgaag     960
tacatcggct ggatcctgga gagcatgccc accgaggtgc tggagaccca ggagctgtgc    1020
tccctggccc tggagtaccg ccgcgagtgc ggccgcgact ccgtgctgga gagcgtgacc    1080
gccatggacc ccagcaaggt gggcgtgcgc tcccagtacc agcacctgct cgcctggag    1140
gacggcaccg ccatcgtgaa cggcgccacc gagtggcgcc caagaacgc cggcgccaac    1200
ggcgccatct ccaccggcaa gaccagcaac ggcaactccg tgtccatgga ctacaaggac    1260
cacgacggcg actacaagga ccacgacatc gactacaagg acgacgacga caagtga       1317
```

<210> SEQ ID NO 71
<211> LENGTH: 1170
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
atggccaccg catccacttt tctcggcgttc aatgcccgct gcggcgacct gcgtcgctcg      60
gcgggctccg ggccccggcg cccagcgagg cccctccccg tgcgcgggcg cgcccagctg     120
```

```
cccgactgga gccgcctgct gaccgccatc accaccgtgt tcgtgaagtc caagcgcccc      180
gacatgcacg accgcaagtc caagcgcccc gacatgctgg tggacagctt cggcctggag      240
tccaccgtgc aggacggcct ggtgttccgc cagtccttct ccatccgctc ctacgagatc      300
ggcaccgacc gcaccgccag catcgagacc ctgatgaacc acctgcagga gacctccctg      360
aaccactgca gagcaccgg catcctgctg gacggcttcg gccgcaccct ggagatgtgc       420
aagcgcgacc tgatctgggt ggtgatcaag atgcagatca aggtgaaccg ctaccccgcc      480
tggggcgaca ccgtggagat caacacccgc ttcagccgcc tgggcaagat cggcatgggc      540
cgcgactggc tgatctccga ctgcaacacc ggcgagatcc tggtgcgcgc caccagcgcc      600
tacgccatga tgaaccagaa gacccgccgc ctgtccaagc tgccctacga ggtgcaccag      660
gagatcgtgc ccctgttcgt ggacagcccc gtgatcgagg actccgacct gaaggtgcac      720
aagttcaagg tgaagaccgg cgacagcatc cagaagggcc tgaccccgg ctggaacgac      780 ctggacgtga accagcacgt gtccaacgtg aagtacatcg gctggatcct ggagagcatg      840
cccaccgagg tgctggagac ccaggagctg tgctccctgg ccctggagta ccgccgcgag      900
tgcggccgcg actccgtgct ggagagcgtg accgccatgg accccagcaa ggtgggcgtg      960
cgctcccagt accagcacct gctgcgcctg gaggacggca ccgccatcgt gaacggcgcc     1020
accgagtggc gccccaagaa cgccggcgcc aacggcgcca tctccaccgg caagaccagc     1080
aacggcaact ccgtgtccat ggactacaag gaccacgacg gcgactacaa ggaccacgac     1140
atcgactaca aggacgacga cgacaagtga                                      1170
```

<210> SEQ ID NO 72
<211> LENGTH: 1170
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
atggctatca agacgaacag gcagcctgtg gagaagcctc cgttcacgat cgggacgctg       60
cgcaaggcca tccccgcgca ctgtttcgag cgctcggcgc ttcgtgggcg cgcccagctg      120
cccgactgga gccgcctgct gaccgccatc accaccgtgt tcgtgaagtc caagcgcccc      180
gacatgcacg accgcaagtc caagcgcccc gacatgctgg tggacagctt cggcctggag      240
tccaccgtgc aggacggcct ggtgttccgc cagtccttct ccatccgctc ctacgagatc      300
ggcaccgacc gcaccgccag catcgagacc ctgatgaacc acctgcagga gacctccctg      360
aaccactgca gagcaccgg catcctgctg gacggcttcg gccgcaccct ggagatgtgc       420
aagcgcgacc tgatctgggt ggtgatcaag atgcagatca aggtgaaccg ctaccccgcc      480
tggggcgaca ccgtggagat caacacccgc ttcagccgcc tgggcaagat cggcatgggc      540
cgcgactggc tgatctccga ctgcaacacc ggcgagatcc tggtgcgcgc caccagcgcc      600
tacgccatga tgaaccagaa gacccgccgc ctgtccaagc tgccctacga ggtgcaccag      660
gagatcgtgc ccctgttcgt ggacagcccc gtgatcgagg actccgacct gaaggtgcac      720
aagttcaagg tgaagaccgg cgacagcatc cagaagggcc tgaccccgg ctggaacgac      780 ctggacgtga accagcacgt gtccaacgtg aagtacatcg gctggatcct ggagagcatg      840
cccaccgagg tgctggagac ccaggagctg tgctccctgg ccctggagta ccgccgcgag      900
tgcggccgcg actccgtgct ggagagcgtg accgccatgg accccagcaa ggtgggcgtg      960
```

```
cgctcccagt accagcacct gctgcgcctg gaggacggca ccgccatcgt gaacggcgcc    1020
accgagtggc gccccaagaa cgccggcgcc aacggcgcca tctccaccgg caagaccagc    1080
aacggcaact ccgtgtccat ggactacaag gaccacgacg gcgactacaa ggaccacgac    1140
atcgactaca aggacgacga cgacaagtga                                     1170

<210> SEQ ID NO 73
<211> LENGTH: 1167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
atgacgttcg gggtcgccct cccggccatg ggccgcggtg tctcccttcc ccggcccagg      60
gtcgcggtgc gcgcccagtc ggcgagtcag gttttggaga gcgggcgcgc ccagctgccc     120
gactggagcc gcctgctgac cgccatcacc accgtgttcg tgaagtccaa cgcccccgac     180
atgcacgacc gcaagtccaa cgcccccgac atgctggtgg acagcttcgg cctggagtcc     240
accgtgcagg acggcctggt gttccgccag tccttctcca tccgctccta cgagatcggc     300
accgaccgca ccgccagcat cgagaccctg atgaaccacc tgcaggagac ctccctgaac     360
cactgcaaga gcaccggcat cctgctggac ggcttcggcc gcaccctgga gatgtgcaag     420
cgcgacctga tctgggtggt gatcaagatg cagatcaagg tgaaccgcta ccccgcctgg     480
ggcgacaccg tggagatcaa caccccgcttc agccgcctgg gcaagatcgg catgggccgc     540
gactggctga tctccgactg caacaccggc gagatcctgg tgcgcgccac cagcgcctac     600
gccatgatga accagaagac ccgccgcctg tccaagctgc cctacgaggt gcaccaggag     660
atcgtgcccc tgttcgtgga cagccccgtg atcgaggact ccgacctgaa ggtgcacaag     720
ttcaaggtga agaccggcga cagcatccag aagggcctga ccccggctg gaacgacctg     780 gacgtgaacc agcacgtgtc caacgtgaag tacatcggct ggatcctgga gagcatgccc     840
accgaggtgc tggagaccca ggagctgtgc tccctggccc tggagtaccg ccgcgagtgc     900
ggccgcgact ccgtgctgga gagcgtgacc gccatggacc ccagcaaggt gggcgtgcgc     960
tcccagtacc agcacctgct gcgcctggag acggcaccg ccatcgtgaa cggcgccacc    1020
gagtggcgcc ccaagaacgc cggcgccaac ggcgccatct ccaccggcaa gaccagcaac    1080
ggcaactccg tgtccatgga ctacaaggac cacgacggcg actacaagga ccacgacatc    1140
gactacaagg acgacgacga caagtga                                       1167

<210> SEQ ID NO 74
<211> LENGTH: 1149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
atgacgttcg gggtcgccct cccggccatg ggccgcggtg tctcccttcc ccggcccagg      60
gtcgcggtgc gcgcccagtc ggcgagtcag gttttggaga gcgggcgcgc ccccgactgg     120
tccatgctgt tcgccgtgat caccaccatc ttcagcgccg ccgagaagca gtggaccaac     180
ctggagtgga agcccaagcc caagctgccc agctgctgg acgaccactt cggcctgcac     240
ggcctggtgt tccgccgcac cttcgccatc cgctcctacg aggtgggccc cgaccgcagc     300
```

```
acctccatcc tggccgtgat gaaccacatg caggaggcca ccctgaacca cgccaagagc    360
gtgggcatct tgggcgacgg cttcggcacc accctggaga tgtccaagcg cgacctgatg    420
tgggtggtgc gccgcaccca cgtggccgtg gagcgctacc ccacctgggg cgacaccgtg    480
gaggtggagt gctggatcgg cgccagcggc aacaacggca tgcgccgcga cttcctggtg    540
cgcgactgca agaccggcga gatcctgacc cgctgcacct ccctgagcgt gctgatgaac    600
acccgcaccc gccgcctgag caccatcccc gacgaggtgc gcggcgagat cggccccgcc    660
ttcatcgaca acgtggccgt gaaggacgac gagatcaaga agctgcagaa gctgaacgac    720
tccaccgccg actacatcca gggcggcctg accccccgct ggaacgacct ggacgtgaac    780
cagcacgtga acaacctgaa gtacgtggcc tgggtgttcg agaccgtgcc cgacagcatc    840
ttcgagtccc accacatcag ctccttcacc ctggagtacc gccgcgagtg cacccgcgac    900
tccgtgctgc gcagcctgac caccgtgagc ggcggcagct ccgaggccgg cctggtgtgc    960
gaccacctgc tgcagctgga gggcggcagc gaggtgctgc gcgcccgcac cgagtggcgc    1020
cccaagctga ccgactcctt ccgcggcatc agcgtgatcc ccgccgagcc ccgcgtgatg    1080
gactacaagg accacgacgg cgactacaag gaccacgaca tcgactacaa ggacgacgac    1140
gacaagtga                                                           1149
```

<210> SEQ ID NO 75
<211> LENGTH: 1146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
atggcttccg cggcattcac catgtcggcg tgccccgcga tgactggcag ggcccctggg    60
gcacgtcgct ccggacggcc agtcgccacc cgcctgaggg ggcgcgcccc cgactggtcc    120
atgctgttcg ccgtgatcac caccatcttc agcgccgccg agaagcagtg gaccaacctg    180
gagtggaagc ccaagcccaa gctgccccag ctgctggacg accacttcgg cctgcacggc    240
ctggtgttcc gccgcacctt cgccatccgc tcctacgagg tgggccccga ccgcagcacc    300
tccatcctgg ccgtgatgaa ccacatgcag gaggccaccc tgaaccacgc caagagcgtg    360
ggcatcctgg gcgacggctt cggcaccacc ctggagatgt ccaagcgcga cctgatgtgg    420
gtggtgcgcc gcacccacgt ggccgtggag cgctacccca cctggggcga caccgtggag    480
gtggagtgct ggatcggcgc cagcggcaac aacggcatgc gccgcgactt cctggtgcgc    540
gactgcaaga ccggcgagat cctgacccgc tgcacctccc tgagcgtgct gatgaacacc    600
cgcacccgcc gcctgagcac catccccgac gaggtgcgcg gcgagatcgg ccccgccttc    660
atcgacaacg tggccgtgaa ggacgacgag atcaagaagc tgcagaagct gaacgactcc    720
accgccgact acatccaggg cggcctgacc cccgctgga cgacctggac gtgaaccag    780 cacgtgaaca acctgaagta cgtggcctgg gtgttcgaga ccgtgcccga cagcatcttc    840
gagtcccacc acatcagctc cttcaccctg gagtaccgcc gcgagtgcac ccgcgactcc    900
gtgctgcgca gcctgaccac cgtgagcggc ggcagctccg aggccggcct ggtgtgcgac    960
cacctgctgc agctggaggg cggcagcgag gtgctgcgcg cccgcaccga gtggcgcccc    1020
aagctgaccg actccttccg cggcatcagc gtgatccccg ccgagcccg cgtgatggac    1080 tacaaggacc acgacggcga ctacaaggac cacgacatcg actacaagga cgacgacgac    1140
```

```
                                                                aagtga                                                                  1146

<210> SEQ ID NO 76
<211> LENGTH: 1155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
atggccaccg catccacttt ctcggcgttc aatgcccgct gcggcgacct gcgtcgctcg      60
gcgggctccg ggccccggcg cccagcgagg cccctccccg tgcgcgggcg cgccccccgac   120
tggtccatgc tgttcgccgt gatcaccacc atcttcagcg ccgccgagaa gcagtggacc     180
aacctggagt ggaagcccaa gcccaagctg ccccagctgc tggacgacca cttcggcctg    240
cacggcctgg tgttccgccg caccttcgcc atccgctcct acgaggtggg ccccgaccgc    300
agcacctcca tcctggccgt gatgaaccac atgcaggagg ccaccctgaa ccacgccaag   360
agcgtgggca tcctgggcga cggcttcggc accaccctgg agatgtccaa gcgcgacctg    420
atgtgggtgg tgcgccgcac ccacgtggcc gtggagcgct accccacctg ggcgacacc     480
gtggaggtgg agtgctggat cggcgccagc ggcaacaacg gcatgcgccg cgacttcctg   540
gtgcgcgact gcaagaccgg cgagatcctg acccgctgca cctccctgag cgtgctgatg   600
aacacccgca cccgccgcct gagcaccatc cccgacgagg tgcgcggcga gatcggcccc    660
gccttcatcg acaacgtggc cgtgaaggac gacgagatca agaagctgca gaagctgaac   720
gactccaccg ccgactacat ccagggcggc ctgaccccc gctggaacga cctggacgtg    780
aaccagcacg tgaacaacct gaagtacgtg gcctgggtgt cgagaccgt gcccgacagc    840
atcttcgagt cccaccacat cagctccttc accctggagt accgccgcga gtgcacccgc   900
gactccgtgc tgcgcagcct gaccaccgtg agcggcggca gctccgaggc cggcctggtg   960
tgcgaccacc tgctgcagct ggagggcggc agcgaggtgc tgcgcgcccg caccgagtgg  1020
cgccccaagc tgaccgactc cttccgcggc atcagcgtga tccccgccga gccccgcgtg  1080
atggactaca aggaccacga cggcgactac aaggaccacg acatcgacta caaggacgac   1140
gacgacaagt gatga                                                   1155

<210> SEQ ID NO 77
<211> LENGTH: 1152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
atggctatca agacgaacag gcagcctgtg gagaagcctc cgttcacgat cgggacgctg      60
cgcaaggcca tccccgcgca ctgtttcgag cgctcggcgc ttcgtgggcg cgccccgac    120
tggtccatgc tgttcgccgt gatcaccacc atcttcagcg ccgccgagaa gcagtggacc     180
aacctggagt ggaagcccaa gcccaagctg ccccagctgc tggacgacca cttcggcctg    240
cacggcctgg tgttccgccg caccttcgcc atccgctcct acgaggtggg ccccgaccgc    300
agcacctcca tcctggccgt gatgaaccac atgcaggagg ccaccctgaa ccacgccaag   360
agcgtgggca tcctgggcga cggcttcggc accaccctgg agatgtccaa gcgcgacctg    420
```

| | |
|---|---|
| atgtgggtgg tgcgccgcac ccacgtggcc gtggagcgct accccacctg ggcgacacc | 480 |
| gtggaggtgg agtgctggat cggcgccagc ggcaacaacg gcatgcgccg cgacttcctg | 540 |
| gtgcgcgact gcaagaccgg cgagatcctg acccgctgca cctccctgag cgtgctgatg | 600 |
| aacacccgca cccgccgcct gagcaccatc cccgacgagg tgcgcggcga gatcggcccc | 660 |
| gccttcatcg acaacgtggc cgtgaaggac gacgagatca agaagctgca gaagctgaac | 720 |
| gactccaccg ccgactacat ccagggcggc ctgaccccccc gctggaacga cctggacgtg | 780 |
| aaccagcacg tgaacaacct gaagtacgtg gcctgggtgt cgagaccgt gcccgacagc | 840 |
| atcttcgagt cccaccacat cagctccttc accctggagt accgccgcga gtgcacccgc | 900 |
| gactccgtgc tgcgcagcct gaccaccgtg agcggcggca gctccgaggc cggcctggtg | 960 |
| tgcgaccacc tgctgcagct ggagggcggc agcgaggtgc tgcgcgcccg caccgagtgg | 1020 |
| cgccccaagc tgaccgactc cttccgcggc atcagcgtga tccccgccga gccccgcgtg | 1080 |
| atggactaca aggaccacga cggcgactac aaggaccacg acatcgacta caaggacgac | 1140 |
| gacgacaagt ga | 1152 |

<210> SEQ ID NO 78
<211> LENGTH: 1155
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 78

| | |
|---|---|
| atggccaccg catccacttt ctcggcgttc aatgcccgct gcggcgacct gcgtcgctcg | 60 |
| gcgggctccg ggccccggcg cccagcgagg cccctccccg tgcgcgggcg cgcccccgac | 120 |
| tggtccatgc tgttcgccgt gatcaccacc atcttctccg ccgccgagaa gcagtggacc | 180 |
| aacctggagt ggaagcccaa gcccaacccc ccccagctgc tggacgacca cttcggcccc | 240 |
| cacggcctgg tgttccgccg caccttcgcc atccgcagct acgaggtggg ccccgaccgc | 300 |
| tccaccagca tcgtggccgt gatgaaccac ctgcaggagg ccgccctgaa ccacgccaag | 360 |
| tccgtgggca tcctgggcga cggcttcggc accaccctgg agatgtccaa gcgcgacctg | 420 |
| atctgggtgg tgaagcgcac ccacgtggcc gtggagcgct accccgcctg ggcgacacc | 480 |
| gtggaggtgg agtgctgggt gggcgccctcc ggcaacaacg gccgccgcca cgacttcctg | 540 |
| gtgcgcgact gcaagaccgg cgagatcctg acccgctgca cctccctgag cgtgatgatg | 600 |
| aacacccgca cccgccgcct gagcaagatc cccgaggagg tgcgcggcga gatcggcccc | 660 |
| gccttcatcg acaacgtggc cgtgaaggac gaggagatca agaagcccca gaagctgaac | 720 |
| gactccaccg ccgactacat ccagggcggc ctgaccccccc gctggaacga cctggacatc | 780 |
| aaccagcacg tgaacaacat caagtacgtg gactggatcc tggagaccgt gcccgacagc | 840 |
| atcttcgaga ccaccacat ctcctccttc accatcgagt accgccgcga gtgcaccatg | 900 |
| gacagcgtgc tgcagtccct gaccaccgtg agcggcggct cctccgaggc cggcctggtg | 960 |
| tgcgagcacc tgctgcagct ggagggcggc agcgaggtgc tgcgcgccaa gaccgagtgg | 1020 |
| cgccccaagc tgaccgactc cttccgcggc atcagcgtga tccccgccga gtccagcgtg | 1080 |
| atggactaca aggaccacga cggcgactac aaggaccacg acatcgacta caaggacgac | 1140 |
| gacgacaagt gatga | 1155 |

<210> SEQ ID NO 79

<211> LENGTH: 4817
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

| | | | | | |
|---|---|---|---|---|---|
| ggtacccgcc | tgcaacgcaa | gggcagccac | agccgctccc | acccgccgct | gaaccgacac | 60 |
| gtgcttgggc | gcctgccgcc | tgcctgccgc | atgcttgtgc | tggtgaggct | gggcagtgct | 120 |
| gccatgctga | ttgaggcttg | gttcatcggg | tggaagctta | tgtgtgtgct | gggcttgcat | 180 |
| gccgggcaat | gcgcatggtg | gcaagagggc | ggcagcactt | gctggagctg | ccgcggtgcc | 240 |
| tccaggtggt | tcaatcgcgg | cagccagagg | gatttcagat | gatcgcgcgt | acaggttgag | 300 |
| cagcagtgtc | agcaaaggta | gcagtttgcc | agaatgatcg | gttcagctgt | taatcaatgc | 360 |
| cagcaagaga | aggggtcaag | tgcaaacacg | gcatgccac | agcacgggca | ccggggagtg | 420 |
| gaatggcacc | accaagtgtg | tgcgagccag | catcgccgcc | tggctgtttc | agctacaacg | 480 |
| gcaggagtca | tccaacgtaa | ccatgagctg | atcaacactg | caatcatcgg | gcgggcgtga | 540 |
| tgcaagcatg | cctggcgaag | acacatggtg | tgcggatgct | gccggctgct | gcctgctgcg | 600 |
| cacgccgttg | agttggcagc | aggctcagcc | atgcactgga | tggcagctgg | gctgccactg | 660 |
| caatgtggtg | gataggatgc | aagtggagcg | aataccaaac | cctctggctg | cttgctgggt | 720 |
| tgcatggcat | cgcaccatca | gcaggagcgc | atgcgaaggg | actggcccca | tgcacgccat | 780 |
| gccaaaccgg | agcgcaccga | gtgtccacac | tgtcaccagg | cccgcaagct | ttgcagaacc | 840 |
| atgctcatgg | acgcatgtag | cgctgacgtc | ccttgacggc | gctcctctcg | ggtgtgggaa | 900 |
| acgcaatgca | gcacaggcag | cagaggcggc | ggcagcagag | cggcggcagc | agcggcgggg | 960 |
| gccacccttc | ttgcggggtc | gcgccccagc | cagcggtgat | gcgctgatcc | caaacgagtt | 1020 |
| cacattcatt | tgcatgcctg | gagaagcgag | gctggggcct | ttgggctggt | gcagcccgca | 1080 |
| atggaatgcg | ggaccgccag | gctagcagca | aaggcgcctc | ccctactccg | catcgatgtt | 1140 |
| ccatagtgca | ttggactgca | tttgggtggg | gcggccggct | gtttcttcg | tgttgcaaaa | 1200 |
| cgcgccagct | cagcaacctg | tcccgtgggt | ccccgtgcc | gatgaaatcg | tgtgcacgcc | 1260 |
| gatcagctga | ttgcccggct | cgcgaagtag | gcgccctcct | ttctgctcgc | cctctctccg | 1320 |
| tcccgcctct | agaatatcaa | tgatcgagca | ggacggcctc | cacgccggct | ccccgccgc | 1380 |
| ctgggtggag | cgcctgttcg | gctacgactg | ggcccagcag | accatcggct | gctccgacgc | 1440 |
| cgccgtgttc | cgcctgtccg | cccagggccg | ccccgtgctg | ttcgtgaaga | ccgacctgtc | 1500 |
| cggcgccctg | aacgagctgc | aggacgaggc | cgcccgcctg | tcctggctgg | ccaccaccgg | 1560 |
| cgtgccctgc | gccgccgtgc | tggacgtggt | gaccgaggcc | ggccgcgact | ggctgctgct | 1620 |
| gggcgaggtg | cccggccagg | acctgctgtc | ctcccacctg | gcccccgccg | agaaggtgtc | 1680 |
| catcatggcc | gacgccatgc | gccgcctgca | caccctggac | cccgccacct | gccccttcga | 1740 |
| ccaccaggcc | aagcaccgca | tcgagcgcgc | ccgcacccgc | atggaggccg | gcctggtgga | 1800 |
| ccaggacgac | ctggacgagg | agcaccaggg | cctggcccc | gccgagctgt | tcgcccgcct | 1860 |
| gaaggcccgc | atgcccgacg | gcgaggacct | ggtggtgacc | cacggcgacg | cctgcctgcc | 1920 |
| caacatcatg | gtggagaacg | gccgcttctc | cggcttcatc | gactgcggcc | gctgggcgt | 1980 |
| ggccgaccgc | taccaggaca | tcgccctggc | cacccgcgac | atcgccgagg | agctgggcgg | 2040 |
| cgagtgggcc | gaccgcttcc | tggtgctgta | cggcatcgcc | gcccccgact | cccagcgcat | 2100 |

-continued

```
cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg cttttatcaa acagcctcag tgtgtttgat cttgtgtgta    2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgaccccc cgaagctcct tcggggctgc    2880
atgggcgctc cgatgccgct ccagggcgag cgctgtttaa atagccaggc ccccgattgc    2940
aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacgg cgcgccatgg tggccgccgc cgcctccagc gccttcttcc    3120
ccgtgcccgc ccccggcgcc tccccaagc ccggcaagtt cggcaactgg ccctccagcc    3180
tgagcccctc cttcaagccc aagtccatcc caacggcgg cttccaggtg aaggccaacg    3240
acagcgccca ccccaaggcc aacggctccg ccgtgagcct gaagagcggc agcctgaaca    3300
cccaggagga cacctcctcc agccccccc cccgcacctt cctgcaccag ctgcccgact    3360
ggagccgcct gctgaccgcc atcaccaccg tgttcgtgaa gtccaagcgc cccgacatgc    3420
acgaccgcaa gtccaagcgc cccgacatgc tggtggacag cttcggcctg gagtccaccg    3480
tgcaggacgg cctggtgttc cgccagtcct tctccatccg ctcctacgag atcggcaccg    3540
accgcaccgc cagcatcgag accctgatga accaccgtgca ggagacctcc ctgaaccact    3600
gcaagagcac cggcatcctg ctggacggct tcggccgcac cctggagatg tgcaagcgcg    3660
acctgatctg ggtggtgatc aagatgcaga tcaaggtgaa ccgctacccc gcctggggcg    3720
acaccgtgga gatcaacacc cgcttcagcc gcctgggcaa gatcggcatg gccgcgact    3780
ggctgatctc cgactgcaac accggcgaga tcctggtgcg cgccaccagc gcctacgcca    3840
tgatgaacca gaagacccgc cgcctgtcca agctgcccta cgaggtgcac caggagatcg    3900
tgccctgtt cgtggacagc cccgtgatcg aggactccga cctgaaggtg cacaagttca    3960
aggtgaagac cggcgacagc atccagaagg gcctgacccc cggctggaac gacctggacg    4020
tgaaccagca cgtgtccaac gtgaagtaca tcggctggat cctggagagc atgcccaccg    4080
aggtgctgga cacccaggag ctgtgctccc tggccctgga gtaccgccgc gagtgcggcc    4140
gcgactccgt gctggagagc gtgaccgcca tggacccag caaggtgggc gtgcgctccc    4200
agtaccagca cctgctgcgc ctggaggacg gcaccgccat cgtgaacggc gccaccgagt    4260
ggcgccccaa gaacgccggc gccaacggcg ccatctccac cggcaagacc agcaacggca    4320
actccgtgtc catggactac aaggaccacg acggcgacta caaggaccac gacatcgact    4380
acaaggacga cgacgacaag tgactcgagg cagcagcagc tcggatagta tcgacacact    4440
ctggacgctg gtcgtgtgat ggactgttgc cgccacactt gctgccttga cctgtgaata    4500
```

```
tccctgccgc ttttatcaaa cagcctcagt gtgtttgatc ttgtgtgtac gcgcttttgc    4560
gagttgctag ctgcttgtgc tatttgcgaa taccaccccc agcatcccct tccctcgttt    4620
catatcgctt gcatcccaac cgcaacttat ctacgctgtc ctgctatccc tcagcgctgc    4680
tcctgctcct gctcactgcc cctcgcacag ccttggtttg ggctccgcct gtattctcct    4740
ggtactgcaa cctgtaaacc agcactgcaa tgctgatgca cgggaagtag tgggatggga    4800
acacaaatgg aaagctt                                                  4817
```

<210> SEQ ID NO 80
<211> LENGTH: 4665
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 80

```
ggtacccgcc tgcaacgcaa gggcagccac agccgctccc accgccgct gaaccgacac      60 gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg gcatgccac agcacgggca ccggggagtg     420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct tgcagaacc    840 atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
gccacccttc ttgcggggtc gcgccccagc cagcggtgat gcgctgatcc caaacgagtt   1020
cacattcatt tgcatgcctg gagaagcgag gctggggcct ttgggctggt gcagcccgca   1080
atggaatgcg ggaccgccag gctagcagca aaggcgcctc ccctactccg catcgatgtt   1140
ccatagtgca ttggactgca tttgggtggg gcggccggct gtttcttcg tgttgcaaaa    1200 cgcgccagct cagcaacctg tcccgtgggt ccccgtgcc gatgaaatcg tgtgcacgcc    1260
gatcagctga ttgcccggct cgcgaagtag gcgccctcct ttctgctcgc cctctctccg    1320
tcccgcctct agaatatcaa tgatcgagca ggacggcctc cacgccggct cccccgccgc    1380
ctgggtggag cgcctgttcg gctacgactg ggcccagcag accatcggct gctccgacgc    1440
cgccgtgttc cgcctgtccg cccagggccg cccgtgctg ttcgtgaaga ccgacctgtc    1500
cggcgccctg aacgagctgc aggacgaggc cgcccgcctg tcctggctgg ccaccaccgg   1560
cgtgccctgc gccgccgtgc tggacgtggt gaccgaggcc ggccgcgact ggctgctgct    1620
gggcgaggtg cccggccagg acctgctgtc ctcccacctg gcccccgccg agaaggtgtc    1680
```

-continued

```
catcatggcc gacgccatgc gccgcctgca cacccctggac cccgccacct gcccctttcga    1740
ccaccaggcc aagcaccgca tcgagcgcgc ccgcacccgc atggaggccg gcctggtgga    1800
ccaggacgac ctggacgagg agcaccaggg cctggccccc gccgagctgt tcgcccgcct    1860
gaaggcccgc atgcccgacg cgaggacct ggtggtgacc cacggcgacg cctgcctgcc    1920
caacatcatg gtggagaacg gccgcttctc cggcttcatc gactgcggcc gctgggcgt    1980
ggccgaccgc taccaggaca tcgccctggc caccgcgac atcgccgagg agctgggcgg    2040
cgagtgggcc gaccgcttcc tggtgctgta cggcatcgcc gcccccgact cccagcgcat    2100
cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg cttttatcaa acagcctcag tgtgtttgat cttgtgtgta    2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgaccccc cgaagctcct tcggggctgc    2880
atgggcgctc cgatgccgct ccagggcgag cgctgtttaa atagccaggc ccccgattgc    2940
aaagacatta tagcgagcta ccaaaagccat attcaaacac ctagatcact accacttcta    3000
cacaggccac tcgagcttgt gatcgcactc cgctaagggg gcgcctcttc ctcttcgttt    3060
cagtcacaac ccgcaaacac tagtatgacg ttcggggtcg ccctcccggc catgggccgc    3120
ggtgtctccc ttccccggcc cagggtcgcg gtgcgcgccc agtcggcgag tcaggttttg    3180
gagagcgggc gcgcccagct gcccgactgg agccgcctgc tgaccgccat caccaccgtg    3240
ttcgtgaagt ccaagcgccc cgacatgcac gaccgcaagt ccaagcgccc cgacatgctg    3300
gtggacagct tcggcctgga gtccaccgtg caggacggcc tggtgttccg ccagtccttc    3360
tccatccgct cctacgagat cggcaccgac cgcaccgcca gcatcgagac cctgatgaac    3420
cacctgcagg agacctccct gaaccactgc aagagcaccg gcatcctgct ggacggcttc    3480
ggccgcaccc tggagatgtg caagcgcgac ctgatctggg tggtgatcaa gatgcagatc    3540
aaggtgaacc gctaccccgc ctggggcgac accgtggaga tcaacacccg cttcagccgc    3600
ctgggcaaga tcggcatggg ccgcgactgg ctgatctccg actgcaacac cggcgagatc    3660
ctggtgcgcg ccaccagcgc ctacgccatg atgaaccaga agacccgccg cctgtccaag    3720
ctgccctacg aggtgcacca ggagatcgtg cccctgttcg tggacagccc cgtgatcgag    3780
gactccgacc tgaaggtgca caagttcaag gtgaagaccg cgacagcat ccagaagggc    3840
ctgacccccg gctggaacga cctggacgtg aaccagcacg tgtccaacgt gaagtacatc    3900
ggctggatcc tggagagcat gcccaccgag gtgctggaga cccaggagct gtgctccctg    3960
gccctggagt accgccgcga gtgcggccgc gactccgtgc tggagagcgt gaccgccatg    4020
```

```
gaccccagca aggtgggcgt gcgctcccag taccagcacc tgctgcgcct ggaggacggc    4080
accgccatcg tgaacggcgc caccgagtgg cgccccaaga acgccggcgc caacggcgcc    4140
atctccaccg gcaagaccag caacggcaac tccgtgtcca tggactacaa ggaccacgac    4200
ggcgactaca aggaccacga catcgactac aaggacgacg acgacaagtg actcgaggca    4260
gcagcagctc ggatagtatc gacacactct ggacgctggt cgtgtgatgg actgttgccg    4320
ccacacttgc tgccttgacc tgtgaatatc cctgccgctt ttatcaaaca gcctcagtgt    4380
gtttgatctt gtgtgtacgc gcttttgcga gttgctagct gcttgtgcta tttgcgaata    4440 ccaccccag catcccctc cctcgtttca tatcgcttgc atcccaaccg caacttatct    4500
acgctgtcct gctatccctc agcgctgctc ctgctcctgc tcactgcccc tcgcacagcc    4560
ttggtttggg ctccgcctgt attctcctgg tactgcaacc tgtaaaccag cactgcaatg    4620
ctgatgcacg ggaagtagtg ggatgggaac acaaatggaa agctt                   4665
```

<210> SEQ ID NO 81
<211> LENGTH: 4668
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81

```
ggtacccgcc tgcaacgcaa gggcagccac agccgctccc accgccgct gaaccgacac      60 gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg gcatgccac agcacgggca ccggggagtg    420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtt gcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct tgcagaacc    840 atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960 gccaccette ttgcggggtc gcgccccagc cagcggtgat gcgctgatcc caaacgagtt   1020
cacattcatt tgcatgcctg gagaagcgag gctggggcct ttgggctggt gcagcccgca   1080
atggaatgcg ggaccgccag gctagcagca aaggcgcctc ccctactccg catcgatgtt   1140
ccatagtgca ttggactgca tttggtgggg cggccggct gtttctttcg tgttgcaaaa    1200
cgcgccagct cagcaacctg tcccgtgggt ccccgtgcc gatgaaatcg tgtgcacgcc    1260
gatcagctga ttgcccggct cgcgaagtag gcgccctcct ttctgctcgc cctctctccg    1320
tcccgcctct agaatatcaa tgatcgagca ggacggcctc cacgcggct cccccgccgc    1380
```

```
ctgggtggag cgcctgttcg gctacgactg ggcccagcag accatcggct gctccgacgc    1440
cgccgtgttc cgcctgtccg ccccaggccg ccccgtgctg ttcgtgaaga ccgacctgtc    1500
cggcgccctg aacgagctgc aggacgaggc cgcccgcctg tcctggctgg ccaccaccgg    1560
cgtgccctgc gccgccgtgc tggacgtggt gaccgaggcc ggccgcgact ggctgctgct    1620
gggcgaggtg cccggccagg acctgctgtc ctcccacctg gcccccgccg agaaggtgtc    1680
catcatggcc gacgccatgc gccgcctgca caccctggac cccgccacct gcccttcga    1740 ccaccaggcc aagcaccgca tcgagcgcgc ccgcacccgc atggaggccg gcctggtgga    1800
ccaggacgac ctggacgagg agcaccaggg cctggccccc gccgagctgt cgcccgcct    1860 gaaggcccgc atgcccgacg gcgaggacct ggtggtgacc cacggcgacg cctgcctgcc    1920
caacatcatg gtggagaacg gccgcttctc cggcttcatc gactgcggcc gcctgggcgt    1980
ggccgaccgc taccaggaca tcgccctggc cacccgcgac atcgccgagg agctgggcgg    2040
cgagtgggcc gaccgcttcc tggtgctgta cggcatcgcc gccccgact cccagcgcat    2100 cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg cttttatcaa acagcctcag tgtgtttgat cttgtgtgta    2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gcttggtttt gggctccgcc    2460
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgaccccc cgaagctcct cggggctgc    2880 atgggcgctc cgatgccgct ccagggcgag cgctgtttaa atagccaggc cccgattgc    2940 aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacac tagtatggct atcaagacga acaggcagcc tgtggagaag    3120
cctccgttca cgatcgggac gctgcgcaag gccatccccg cgcactgttt cgagcgctcg    3180
gcgcttcgtg ggcgcgccca gctgcccgac tggagccgcc tgctgaccgc catcaccacc    3240
gtgttcgtga agtccaagcg ccccgacatg cacgaccgca gtccaagcg ccccgacatg    3300 ctggtggaca gcttcggcct ggagtccacc gtgcaggacg gcctggtgtt ccgccagtcc    3360
ttctccatcc gctcctacga gatcggcacc gaccgcaccg ccagcatcga cccctgatg    3420 aaccacctgc aggagaccct cctgaaccac tgcaagagca ccggcatcct gctggacggc    3480
ttcggccgca ccctggagat gtgcaagcgc gacctgatct gggtggtgat caagatgcag    3540
atcaaggtga accgctaccc cgcctggggc gacaccgtgg agatcaacac ccgcttcagc    3600
cgcctgggca agatcggcat gggccgcgac tggctgatct ccgactgcaa caccggcgag    3660
atcctggtgc gcgccaccag cgcctacgcc atgatgaacc agaagacccg ccgcctgtcc    3720
aagctgccct acgaggtgca ccaggagatc gtgcccctgt tcgtggacag ccccgtgatc    3780
```

```
gaggactccg acctgaaggt gcacaagttc aaggtgaaga ccggcgacag catccagaag    3840
ggcctgaccc ccggctggaa cgacctggac gtgaaccagc acgtgtccaa cgtgaagtac    3900
atcggctgga tcctggagag catgcccacc gaggtgctgg agacccagga gctgtgctcc    3960
ctggccctgg agtaccgccg cgagtgcggc cgcgactccg tgctggagag cgtgaccgcc    4020
atggacccca gcaaggtggg cgtgcgctcc cagtaccagc acctgctgcg cctggaggac    4080
ggcaccgcca tcgtgaacgg cgccaccgag tggcgcccca gaacgccgg cgccaacggc     4140 gccatctcca ccggcaagac cagcaacggc aactccgtgt ccatggacta caaggaccac    4200
gacggcgact acaaggacca cgacatcgac tacaaggacg acgacgacaa gtgactcgag    4260
gcagcagcag ctcggatagt atcgacacac tctggacgct ggtcgtgtga tggactgttg    4320
ccgccacact tgctgccttg acctgtgaat atccctgccg cttttatcaa acagcctcag    4380
tgtgtttgat cttgtgtgta cgcgcttttg cgagttgcta gctgcttgtg ctatttgcga    4440
ataccacccc cagcatcccc ttccctcgtt tcatatcgct tgcatcccaa ccgcaactta    4500
tctacgctgt cctgctatcc ctcagcgctg ctcctgctcc tgctcactgc ccctcgcaca    4560
gccttggttt gggctccgcc tgtattctcc tggtactgca acctgtaaac cagcactgca    4620
atgctgatgc acgggaagta gtgggatggg aacacaaatg gaaagctt                 4668
```

<210> SEQ ID NO 82
<211> LENGTH: 4668
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82

```
ggtacccgcc tgcaacgcaa gggcagccac agccgctccc accgccgct gaaccgacac      60 gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg ggcatgccac agcacgggca ccggggagtg    420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct tgcagaacc    840 atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg   960
gccacccttc ttgcggggtc gcgccccagc cagcggtgat gcgctgatcc caaacgagtt    1020
cacattcatt tgcatgcctg gagaagcgag gctgggcct ttgggctggt gcagcccgca     1080
atggaatgcg ggaccgccag gctagcagca aggcgcctc ccctactccg catcgatgtt    1140
```

```
ccatagtgca ttggactgca tttgggtggg gcggccggct gtttctttcg tgttgcaaaa    1200
cgcgccagct cagcaacctg tcccgtgggt cccccgtgcc gatgaaatcg tgtgcacgcc    1260
gatcagctga ttgcccggct cgcgaagtag gcgccctcct ttctgctcgc cctctctccg    1320
tcccgcctct agaatatcaa tgatcgagca ggacggcctc cacgccggct cccccgccgc    1380
ctgggtggag cgcctgttcg gctacgactg ggcccagcag accatcggct gctccgacgc    1440
cgccgtgttc cgcctgtccg cccagggccg ccccgtgctg ttcgtgaaga ccgacctgtc    1500
cggcgccctg aacgagctgc aggacgaggc cgcccgcctg tcctggctgg ccaccaccgg    1560
cgtgccctgc gccgccgtgc tggacgtggt gaccgaggcc ggccgcgact ggctgctgct    1620
gggcgaggtg cccggccagg acctgctgtc ctcccacctg gccccgccg agaaggtgtc    1680
catcatggcc gacgccatgc gccgcctgca caccctggac cccgccacct gcccccttcga   1740
ccaccaggcc aagcaccgca tcgagcgcgc ccgcacccgc atggaggccg gcctggtgga    1800
ccaggacgac ctggacgagg agcaccaggg cctggccccc gccgagctgt cgcccgcct    1860
gaaggcccgc atgcccgacg gcgaggacct ggtggtgacc cacggcgacg cctgcctgcc    1920
caacatcatg gtggagaacg gccgcttctc cggcttcatc gactgcggcc gcctgggcgt    1980
ggccgaccgc taccaggaca tcgccctggc caccgcgac atcgccgagg agctgggcgg    2040
cgagtgggcc gaccgcttcc tggtgctgta cggcatcgcc gccccgact cccagcgcat    2100
cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg cttttatcaa acagcctcag tgtgtttgat cttgtgtgta    2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgaccccc cgaagctcct tcggggctgc    2880
atgggcgctc cgatgccgct ccagggcgag cgctgtttaa atagccaggc ccccgattgc    2940
aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacac tagtatggcc accgcatcca cttttctcggc gttcaatgcc    3120
cgctgcggcg acctgcgtcg ctcggcgggc tccgggcccc ggcgcccagc gaggcccctc    3180
cccgtgcgcg ggcgcgccca gctgcccgac tggagccgcc tgctgaccgc catcaccacc    3240
gtgttcgtga agtccaagcg cccccgacatg cacgaccgca agtccaagcg ccccgacatg    3300
ctggtggaca gcttcggcct ggagtccacc gtgcaggacg gcctggtgtt ccgccagtcc    3360
ttctccatcc gctcctacga gatcggcacc gaccgcaccg ccagcatcga gaccctgatg    3420
aaccacctgc aggagacctc cctgaaccac tgcaagagca ccggcatcct gctggacggc    3480
```

```
ttcggccgca ccctggagat gtgcaagcgc gacctgatct gggtggtgat caagatgcag    3540
atcaaggtga accgctaccc cgcctggggc gacaccgtgg agatcaacac ccgcttcagc    3600
cgcctgggca agatcggcat gggccgcgac tggctgatct ccgactgcaa caccggcgag    3660
atcctggtgc gcgccaccag cgcctacgcc atgatgaacc agaagacccg ccgcctgtcc    3720
aagctgccct acgaggtgca ccaggagatc gtgccctgt tcgtggacag ccccgtgatc    3780
gaggactccg acctgaaggt gcacaagttc aaggtgaaga ccggcgacag catccagaag    3840
ggcctgaccc ccggctggaa cgacctggac gtgaaccagc acgtgtccaa cgtgaagtac    3900
atcggctgga tcctggagag catgcccacc gaggtgctgg agacccagga gctgtgctcc    3960
ctggccctgg agtaccgccg cgagtgcggc cgcgactccg tgctggagag cgtgaccgcc    4020
atggacccca gcaaggtggg cgtgcgctcc cagtaccagc acctgctgcg cctggaggac    4080
ggcaccgcca tcgtgaacgg cgccaccgag tggcgcccca gaacgccgg cgccaacggc    4140 gccatctcca ccggcaagac cagcaacggc aactccgtgt ccatggacta caaggaccac    4200
gacggcgact acaaggacca cgacatcgac tacaaggacg acgacgacaa gtgactcgag    4260
gcagcagcag ctcggatagt atcgacacac tctggacgct ggtcgtgtga tggactgttg    4320
ccgccacact tgctgccttg acctgtgaat atccctgccg cttttatcaa acagcctcag    4380
tgtgtttgat cttgtgtgta cgcgcttttg cgagttgcta gctgcttgtg ctatttgcga    4440
ataccacccc cagcatcccc ttccctcgtt tcatatcgct tgcatcccaa ccgcaactta    4500
tctacgctgt cctgctatcc ctcagcgctg ctcctgctcc tgctcactgc ccctcgcaca    4560
gccttggttt gggctccgcc tgtattctcc tggtactgca acctgtaaac cagcactgca    4620
atgctgatgc acgggaagta gtgggatggg aacacaaatg gaaagctt              4668
```

<210> SEQ ID NO 83
<211> LENGTH: 4656
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 83

```
ggtacccgcc tgcaacgcaa gggcagccac agccgctccc accgccgct gaaccgacac      60 gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg gcatgccac agcacgggca ccggggagtg    420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct ttgcagaacc    840
```

```
atgctcatgg acgcatgtag cgctgacgtc ccttgacggc gctcctctcg ggtgtgggaa      900
acgcaatgca gcacaggcag cagaggcggc ggcagcagag cggcggcagc agcggcgggg      960
gccaccccttc ttgcggggtc gcgccccagc cagcggtgat gcgctgatcc caaacgagtt   1020
cacattcatt tgcatgcctg gagaagcgag gctggggcct ttgggctggt gcagcccgca    1080
atggaatgcg ggaccgccag gctagcagca aaggcgcctc ccctactccg catcgatgtt    1140
ccatagtgca ttggactgca tttgggtggg gcggccggct gttctttcg tgttgcaaaa     1200
cgcgccagct cagcaacctg tcccgtgggt cccccgtgcc gatgaaatcg tgtgcacgcc    1260
gatcagctga ttgcccggct cgcgaagtag gcgccctcct ttctgctcgc cctctctccg    1320
tcccgcctct agaatatcaa tgatcgagca ggacggcctc cacgccggct cccccgccgc    1380
ctgggtggag cgcctgttcg gctacgactg ggcccagcag accatcggct gctccgacgc    1440
cgccgtgttc cgcctgtccg cccagggccg ccccgtgctg ttcgtgaaga ccgacctgtc    1500
cggcgccctg aacgagctgc aggacgaggc cgcccgcctg tcctggctgg ccaccaccgg    1560
cgtgccctgc gccgccgtgc tggacgtggt gaccgaggcc ggccgcgact ggctgctgct    1620
gggcgaggtg cccggccagg acctgctgtc ctcccacctg gccccgccg agaaggtgtc     1680
catcatggcc gacgccatgc gccgcctgca caccctggac cccgccacct gccccttcga    1740
ccaccaggcc aagcaccgca tcgagcgcgc ccgcacccgc atggaggccg gcctggtgga    1800
ccaggacgac ctggacgagg agcaccaggg cctggccccc gccgagctgt cgcccgcct    1860
gaaggcccgc atgcccgacg gcgaggacct ggtggtgacc cacggcgacg cctgcctgcc    1920
caacatcatg gtggagaacg gccgcttctc cggcttcatc gactgcggcc gctgggcgt     1980
ggccgaccgc taccaggaca tcgccctggc cacccgcgac atcgccgagg agctgggcgg    2040
cgagtgggcc gaccgcttcc tggtgctgta cggcatcgcc gccccgact cccagcgcat     2100
cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg ctttttatcaa acagcctcag tgtgtttgat cttgtgtgta   2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgaccccc cgaagctcct tcggggctgc    2880
atgggcgctc cgatgccgct ccagggcgag cgctgtttaa atagccaggc ccccgattgc    2940
aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacac tagtatggct tccgcggcat tcaccatgtc ggcgtgcccc    3120
gcgatgactg gcagggcccc tggggcacgt cgctccggac ggccagtcgc cacccgcctg    3180
agggggcgcg ccccccgactg gagccgcctg ctgaccgcca tcaccaccgt gttcgtgaag    3240
```

```
tccaagcgcc ccgacatgca cgaccgcaag tccaagcgcc ccgacatgct ggtggacagc    3300
ttcggcctgg agtccaccgt gcaggacggc ctggtgttcc gccagtcctt ctccatccgc    3360
tcctacgaga tcggcaccga ccgcaccgcc agcatcgaga ccctgatgaa ccacctgcag    3420
gagacctccc tgaaccactg caagagcacc ggcatcctgc tggacggctt cggccgcacc    3480
ctggagatgt gcaagcgcga cctgatctgg gtggtgatca agatgcagat caaggtgaac    3540
cgctaccccg cctggggcga caccgtggag atcaacaccc gcttcagccg cctgggcaag    3600
atcggcatgg ccgcgactg gctgatctcc gactgcaaca ccggcgagat cctggtgcgc    3660
gccaccagcg cctacgccat gatgaaccag aagacccgcc gcctgtccaa gctgccctac    3720
gaggtgcacc aggagatcgt gcccctgttc gtggacagcc ccgtgatcga ggactccgac    3780
ctgaaggtgc acaagttcaa ggtgaagacc ggcgacagca tccagaaggg cctgaccccc    3840
ggctggaacg acctggacgt gaaccagcac gtgtccaacg tgaagtacat cggctggatc    3900
ctggagagca tgcccaccga ggtgctggag acccaggagc tgtgctccct ggccctggag    3960
taccgccgcg agtgcggccg cgactccgtg ctggagagcg tgaccgccat ggaccccagc    4020 aaggtggggcg tgcgctccca gtaccagcac ctgctgcgcc tggaggacgg caccgccatc    4080
gtgaacggcg ccaccgagtg gcgccccaag aacgccggcg ccaacggcgc catctccacc    4140
ggcaagacca gcaacggcaa ctccgtgtcc atggactaca aggaccacga cggcgactac    4200
aaggaccacg acatcgacta caaggacgac gacgacaagt gactcgaggc agcagcagct    4260
cggatagtat cgacacactc tggacgctgg tcgtgtgatg gactgttgcc gccacacttg    4320
ctgccttgac ctgtgaatat ccctgccgct tttatcaaac agcctcagtg tgtttgatct    4380
tgtgtgtacg cgcttttgcg agttgctagc tgcttgtgct atttgcgaat accacccca     4440 gcatcccctt ccctcgtttc atatcgcttg catcccaacc gcaacttatc tacgctgtcc    4500
tgctatccct cagcgctgct cctgctcctg ctcactgccc ctcgcacagc cttggtttgg    4560
gctccgcctg tattctcctg gtactgcaac ctgtaaacca gcactgcaat gctgatgcac    4620
gggaagtagt gggatgggaa cacaaatgga aagctt                              4656
```

<210> SEQ ID NO 84
<211> LENGTH: 4721
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84

```
ggtacccgcc tgcaacgcaa gggcagccac agccgctccc accgccgct gaaccgacac      60 gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg gcatgccac agcacgggca ccggggagtg     420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
```

```
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct ttgcagaacc    840
atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
gccacccttc ttgcggggtc gcgcccagc cagcggtgat gcgctgatcc caaacgagtt   1020
cacattcatt tgcatgcctg gagaagcgag gctggggcct ttgggctggt gcagcccgca   1080
atggaatgcg ggaccgccag gctagcagca aaggcgcctc ccctactccg catcgatgtt   1140
ccatagtgca ttggactgca tttgggtggg gcggccggct gtttcttccg tgttgcaaaa   1200
cgcgccagct cagcaacctg tcccgtgggt cccccgtgcc gatgaaatcg tgtgcacgcc   1260
gatcagctga ttgcccggct cgcgaagtag gcgccctcct ttctgctcgc cctctctccg   1320
tcccgcctct agaatatcaa tgatcgagca ggacggcctc cacgccggct ccccccgccgc  1380 ctgggtggag cgcctgttcg gctacgactg ggcccagcag accatcggct gctccgacgc   1440
cgccgtgttc cgcctgtccg cccagggccg ccccgtgctg ttcgtgaaga ccgacctgtc   1500
cggcgccctg aacgagctgc aggacgaggc cgcccgcctg tcctggctgg ccaccaccgg   1560
cgtgccctgc gccgccgtgc tggacgtggt gaccgaggcc ggccgcgact ggctgctgct   1620
gggcgaggtg cccggccagg acctgctgtc ctcccacctg gcccccgccg agaaggtgtc   1680
catcatggcc gacgccatgc gccgcctgca caccctggac cccgccacct gccccttcga   1740
ccaccaggcc aagcaccgca tcgagcgcgc ccgcacccgc atggaggccg gcctggtgga   1800
ccaggacgac ctggacgagg agcaccaggg cctggccccc gccgagctgt tcgcccgcct   1860
gaaggcccgc atgcccgacg cgaggacct ggtggtgacc cacggcgacg cctgcctgcc   1920
caacatcatg gtggagaacg gccgcttctc cggcttcatc gactgcggcc gctgggcgt   1980 ggccgaccgc taccaggaca tcgccctggc caccccgcgac atcgcgagg agctgggcgg   2040 cgagtgggcc gaccgcttcc tggtgctgta cggcatcgcc gccccgact cccagcgcat   2100 cgccttctac cgcctgctgg acgagttctt ctgacaattg gcagcagcag ctcggatagt   2160
atcgacacac tctggacgct ggtcgtgtga tggactgttg ccgccacact tgctgccttg   2220
acctgtgaat atccctgccg cttttatcaa acagcctcag tgtgtttgat cttgtgtgta   2280
cgcgcttttg cgagttgcta gctgcttgtg ctatttgcga ataccacccc cagcatcccc   2340
ttccctcgtt tcatatcgct tgcatcccaa ccgcaactta tctacgctgt cctgctatcc   2400
ctcagcgctg ctcctgctcc tgctcactgc ccctcgcaca gccttggttt gggctccgcc   2460
tgtattctcc tggtactgca acctgtaaac cagcactgca atgctgatgc acgggaagta   2520
gtgggatggg aacacaaatg gaggatcccg cgtctcgaac agagcgcgca gaggaacgct   2580
gaaggtctcg cctctgtcgc acctcagcgc ggcatacacc acaataacca cctgacgaat   2640
gcgcttggtt cttcgtccat tagcgaagcg tccggttcac acacgtgcca cgttggcgag   2700
gtggcaggtg acaatgatcg gtggagctga tggtcgaaac gttcacagcc tagggatatc   2760
gaattccttt cttgcgctat gacacttcca gcaaaggta gggcgggctg cgagacggct   2820
tcccggcgct gcatgcaaca ccgatgatgc ttcgaccccc cgaagctcct tcggggctgc   2880
atgggcgctc cgatgccgct ccagggcgag cgctgtttaa atagccaggc ccccgattgc   2940
```

| | |
|---|---|
| aaagacatta tagcgagcta ccaaagccat attcaaacac ctagatcact accacttcta | 3000 |
| cacaggccac tcgagcttgt gatcgcactc cgctaagggg gcgcctcttc ctcttcgttt | 3060 |
| cagtcacaac ccgcaaacgg cgcgccatgg ccaccaccag cctggcctcc gccttctgct | 3120 |
| ccatgaaggc cgtgatgctg gcccgcgacg gccgcggcat gaagcccgc agctccgacc | 3180 |
| tgcagctgcg cgccggcaac gcccccacct ccctgaagat gatcaacggc accaagttca | 3240 |
| gctacaccga gagcctgaag cgcctgcccg actggtccat gctgttcgcc gtgatcacca | 3300 |
| ccatcttcag cgccgccgag aagcagtgga ccaacctgga gtggaagccc aagcccaagc | 3360 |
| tgccccagct gctggacgac cacttcggcc tgcacggcct ggtgttccgc cgcaccttcg | 3420 |
| ccatccgctc ctacgaggtg gccccgacc gcagcaccc catcctggcc gtgatgaacc | 3480 |
| acatgcagga ggccaccctg aaccacgcca gagcgtggg catcctgggc gacggcttcg | 3540 |
| gcaccaccct ggagatgtcc aagcgcgacc tgatgtgggt ggtgcgccgc acccacgtgg | 3600 |
| ccgtggagcg ctaccccacc tggggcgaca ccgtggaggt ggagtgctgg atcggcgcca | 3660 |
| gcggcaacaa cggcatgcgc cgcgacttcc tggtgcgcga ctgcaagacc ggcgagatcc | 3720 |
| tgacccgctg cacctccctg agcgtgctga tgaacacccg caccgccgc ctgagcacca | 3780 |
| tccccgacga ggtgcgcggc gagatcggcc ccgccttcat cgacaacgtg gccgtgaagg | 3840 |
| acgacgagat caagaagctg cagaagctga acgactccac cgccgactac atccagggcg | 3900 |
| gcctgacccc ccgctggaac gacctggacg tgaaccagca cgtgaacaac ctgaagtacg | 3960 |
| tggcctgggt gttcgagacc gtgcccgaca gcatcttcga gtcccaccac atcagctcct | 4020 |
| tcaccctgga gtaccgccgc gagtgcaccc gcgactccgt gctgcgcagc ctgaccaccg | 4080 |
| tgagcggcgg cagctccgag gccggcctgg tgtgcgacca cctgctgcag ctggagggcg | 4140 |
| gcagcgaggt gctgcgcgcc cgcaccgagt ggcgcccaa gctgaccgac tccttccgcg | 4200 |
| gcatcagcgt gatccccgcc gagccccgcg tgatggacta caaggaccac gacggcgact | 4260 |
| acaaggacca cgacatcgac tacaaggacg acgacgacaa gtgatgactc gaggcagcag | 4320 |
| cagctcggat agtatcgaca cactctggac gctggtcgtg tgatggactg ttgccgccac | 4380 |
| acttgctgcc ttgacctgtg aatatccctg ccgcttttat caaacagcct cagtgtgttt | 4440 |
| gatcttgtgt gtacgcgctt ttgcgagttg ctagctgctt gtgctatttg cgaataccac | 4500 |
| ccccagcatc cccttccctc gtttcatatc gcttgcatcc caaccgcaac ttatctacgc | 4560 |
| tgtcctgcta tccctcagcg ctgctcctgc tcctgctcac tgcccctcgc acagccttgg | 4620 |
| tttgggctcc gcctgtattc tcctggtact gcaacctgta aaccagcact gcaatgctga | 4680 |
| tgcacgggaa gtagtgggat gggaacacaa atggaaagct t | 4721 |

<210> SEQ ID NO 85
<211> LENGTH: 4650
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 85

| | |
|---|---|
| ggtacccgcc tgcaacgcaa gggcagccac agccgctccc acccgccgct gaaccgacac | 60 |
| gtgcttgggc gcctgccgcc tgcctgccgc atgcttgtgc tggtgaggct gggcagtgct | 120 |
| gccatgctga ttgaggcttg gttcatcggg tggaagctta tgtgtgtgct gggcttgcat | 180 |
| gccgggcaat gcgcatggtg gcaagagggc ggcagcactt gctggagctg ccgcggtgcc | 240 |

-continued

```
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg ggcatgccac agcacgggca ccggggagtg    420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct ttgcagaacc    840
atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
gccacccttc ttgcggggtc gcgccccagc cagcggtgat gcgctgatcc caaacgagtt   1020
cacattcatt tgcatgcctg gagaagcgag gctgggccct ttgggctggt gcagcccgca   1080
atggaatgcg ggaccgccag gctagcagca aaggcgcctc ccctactccg catcgatgtt   1140
ccatagtgca ttggactgca tttgggtggg gcggccggct gtttctttcg tgttgcaaaa   1200
cgcgccagct cagcaacctg tcccgtgggt ccccgtgcc gatgaaatcg tgtgcacgcc    1260
gatcagctga ttgcccggct cgcgaagtag gcgccctcct ttctgctcgc cctctctccg   1320
tcccgcctct agaatatcaa tgatcgagca ggacggcctc cacgccggct ccccgccgc    1380 ctgggtggag cgcctgttcg gctacgactg ggcccagcag accatcggct gctccgacgc   1440
cgccgtgttc cgcctgtccg cccagggccg cccgtgctg ttcgtgaaga ccgacctgtc    1500
cggcgccctg aacgagctgc aggacgaggc cgcccgcctg tcctggctgg ccaccaccgg   1560
cgtgccctgc gccgccgtgc tggacgtggt gaccgaggcc ggccgcgact ggctgctgct   1620
gggcgaggtg cccggccagg acctgctgtc ctcccacctg gcccccgccg agaaggtgtc   1680
catcatggcc gacgccatgc gccgcctgca cccctggac cccgccacct gcccccttcga   1740 ccaccaggcc aagcaccgca tcgagcgcgc ccgcacccgc atggaggccg gcctggtgga   1800
ccaggacgac ctggacgagg agcaccaggg cctggccccc gccgagctgt cgcccgcct    1860 gaaggcccgc atgcccgacg gcgaggacct ggtggtgacc cacggcgacg cctgcctgcc   1920
caacatcatg gtggagaacg gccgcttctc cggcttcatc gactgcggcc gcctgggcgt   1980
ggccgaccgc taccaggaca tcgccctggc cacccgcgac atcgccgagg agctgggcgg   2040
cgagtgggcc gaccgcttcc tggtgctgta cggcatcgcc gccccgact cccagcgcat    2100 cgccttctac cgcctgctgg acgagttctt ctgacaattg gcagcagcag ctcggatagt   2160
atcgacacac tctggacgct ggtcgtgtga tggactgttg ccgccacact tgctgccttg   2220
acctgtgaat atccctgccg cttttatcaa acagcctcag tgtgtttgat cttgtgtgta   2280
cgcgcttttg cgagttgcta gctgcttgtg ctatttgcga ataccacccc cagcatcccc   2340
ttccctcgtt tcatatcgct tgcatcccaa ccgcaactta tctacgctgt cctgctatcc   2400
ctcagcgctg ctcctgctcc tgctcactgc ccctcgcaca gccttggttt gggctccgcc   2460
tgtattctcc tggtactgca acctgtaaac cagcactgca atgctgatgc acgggaagta   2520
gtgggatggg aacacaaatg gaggatcccg cgtctcgaac agagcgcgca gaggaacgct   2580
gaaggtctcg cctctgtcgc acctcagcgc ggcatacacc acaataacca cctgacgaat   2640
```

```
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgaccccc cgaagctcct tcggggctgc    2880
atgggcgctc cgatgccgct ccagggcgag cgctgtttaa atagccaggc ccccgattgc    2940
aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacac tagtatgacg ttcggggtcg ccctcccggc catgggccgc    3120
ggtgtctccc ttccccggcc cagggtcgcg gtgcgcgccc agtcggcgag tcaggttttg    3180
gagagcgggc gcgcccccga ctggtccatg ctgttcgccg tgatcaccac catcttcagc    3240
gccgccgaga agcagtggac caacctggag tggaagccca gcccaagct gccccagctg    3300 ctggacgacc acttcggcct gcacggcctg tgttccgcc gcaccttcgc catccgctcc    3360
tacgaggtgg gccccgaccg cagcacctcc atcctggccg tgatgaacca catgcaggag    3420
gccaccctga accacgccaa gagcgtgggc atcctgggcg acggcttcgg caccaccctg    3480
gagatgtcca gcgcgacct gatgtgggtg gtgcgccgca cccacgtggc cgtggagcgc    3540
taccccacct ggggcgacac cgtggaggtg gagtgctgga tcggcgccag cggcaacaac    3600
ggcatgcgcc gcgacttcct ggtgcgcgac tgcaagaccg gcgagatcct gacccgctgc    3660
acctccctga gcgtgctgat gaacacccgc acccgccgcc tgagcaccat ccccgacgag    3720
gtgcgcggcg agatcggccc cgccttcatc gacaacgtgg ccgtgaagga cgacgagatc    3780
aagaagctgc agaagctgaa cgactccacc gccgactaca tccagggcgg cctgacccc    3840 cgctggaacg acctggacgt gaaccagcac gtgaacaacc tgaagtacgt ggcctgggtg    3900
ttcgagaccg tgcccgacag catcttcgag tcccaccaca tcagctcctt caccctggag    3960
taccgccgcg agtgcacccg cgactccgtg ctgcgcagcc tgaccaccgt gagcggcggc    4020
agctccgagg ccggcctggt gtgcgaccac ctgctgcagc tggagggcgg cagcgaggtg    4080
ctgcgcgccc gcaccgagtg gcgccccaag ctgaccgact ccttccgcgg catcagcgtg    4140
atccccgccg agccccgcgt gatggactac aaggaccacg acggcgacta caaggaccac    4200
gacatcgact acaaggacga cgacgacaag tgatgactcg aggcagcagc agctcggata    4260
gtatcgacac actctggacg ctggtcgtgt gatggactgt tgccgccaca cttgctgcct    4320
tgacctgtga atatccctgc cgcttttatc aaacagcctc agtgtgtttg atcttgtgtg    4380
tacgcgcttt tgcgagttgc tagctgcttg tgctatttgc gaataccacc cccagcatcc    4440
ccttccctcg tttcatatcg cttgcatccc aaccgcaact tatctacgct gtcctgctat    4500
ccctcagcgc tgctcctgct cctgctcact gccctcgca cagccttggt ttgggctccg    4560
cctgtattct cctggtactg caacctgtaa accagcactg caatgctgat gcacgggaag    4620
tagtgggatg ggaacacaaa tggaaagctt                                     4650
```

<210> SEQ ID NO 86
<211> LENGTH: 4653
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 86

-continued

```
ggtacccgcc tgcaacgcaa gggcagccac agccgctccc acccgccgct gaaccgacac      60
gtgcttgggc gcctgccgcc tgcctgccgc atgcttgtgc tggtgaggct gggcagtgct     120
gccatgctga ttgaggcttg gttcatcggg tggaagctta tgtgtgtgct gggcttgcat     180
gccgggcaat gcgcatggtg gcaagagggc ggcagcactt gctggagctg ccgcggtgcc     240
tccaggtggt tcaatcgcgg cagccagagg gatttcagat gatcgcgcgt acaggttgag     300
cagcagtgtc agcaaaggta gcagtttgcc agaatgatcg gttcagctgt taatcaatgc     360
cagcaagaga aggggtcaag tgcaaacacg gcatgccac agcacgggca ccggggagtg     420
gaatggcacc accaagtgtg tgcgagccag catcgccgcc tggctgtttc agctacaacg     480
gcaggagtca tccaacgtaa ccatgagctg atcaacactg caatcatcgg gcgggcgtga     540
tgcaagcatg cctggcgaag acacatggtg tgcggatgct gccggctgct gcctgctgcg     600
cacgccgttg agttggcagc aggctcagcc atgcactgga tggcagctgg gctgccactg     660
caatgtggtg gataggatgc aagtggagcg aataccaaac cctctggctg cttgctgggt     720
tgcatggcat cgcaccatca gcaggagcgc atgcgaaggg actggcccca tgcacgccat     780
gccaaaccgg agcgcaccga gtgtccacac tgtcaccagg cccgcaagct ttgcagaacc     840
atgctcatgg acgcatgtag cgctgacgtc ccttgacggc gctcctctcg ggtgtgggaa     900
acgcaatgca gcacaggcag cagaggcggc ggcagcagag cggcggcagc agcggcgggg     960
gccacccttc ttgcggggtc gcgccccagc cagcggtgat gcgctgatcc caaacgagtt    1020
cacattcatt tgcatgcctg gagaagcgag gctggggcct ttgggctggt gcagcccgca    1080
atggaatgcg ggaccgccag gctagcagca aaggcgcctc ccctactccg catcgatgtt    1140
ccatagtgca ttggactgca tttgggtggg gcggccggct gtttcttccg tgttgcaaaa    1200
cgcgccagct cagcaacctg tcccgtgggt cccccgtgcc gatgaaatcg tgtgcacgcc    1260
gatcagctga ttgcccggct cgcgaagtag gcgccctcct ttctgctcgc cctctctccg    1320
tcccgcctct agaatatcaa tgatcgagca ggacggcctc cacgccggct cccccgccgc    1380
ctgggtggag cgcctgttcg gctacgactg ggcccagcag accatcggct gctccgacgc    1440
cgccgtgttc cgcctgtccg cccagggccg cccccgtgctg ttcgtgaaga ccgacctgtc    1500
cggcgccctg aacgagctgc aggacgaggc cgcccgcctg tcctggctgg ccaccaccgg    1560
cgtgccctgc gccgccgtgc tggacgtggt gaccgaggcc ggccgcgact ggctgctgct    1620
gggcgaggtg cccggccagg acctgctgtc ctcccacctg ccccccgccg agaaggtgtc    1680
catcatggcc gacgccatgc gccgcctgca caccctggac cccgccacct gccccttcga    1740
ccaccaggcc aagcaccgca tcgagcgcgc ccgcacccgc atggaggccg gcctggtgga    1800
ccaggacgac ctgacgagg agcaccaggg cctggccccc gccgagctgt tcgcccgcct    1860
gaaggcccgc atgcccgacg gcgaggacct ggtggtgacc cacggcgacg cctgcctgcc    1920
caacatcatg gtggagaacg gccgcttctc cggcttcatc gactgcggcc gctgggcgt    1980 ggccgaccgc taccaggaca tcgccctggc cacccgcgac atcgccgagg agctgggcgg    2040
cgagtgggcc gaccgcttcc tggtgctgta cggcatcgcc gccccgact cccagcgcat    2100 cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg cttttatcaa acagcctcag tgtgtttgat cttgtgtgta    2280
cgcgcttttg cgagttgcta gctgcttgtg ctatttgcga ataccacccc cagcatcccc    2340
```

-continued

| | |
|---|---|
| ttccctcgtt tcatatcgct tgcatcccaa ccgcaactta tctacgctgt cctgctatcc | 2400 |
| ctcagcgctg ctcctgctcc tgctcactgc ccctcgcaca gccttggttt gggctccgcc | 2460 |
| tgtattctcc tggtactgca acctgtaaac cagcactgca atgctgatgc acgggaagta | 2520 |
| gtgggatggg aacacaaatg gaggatcccg cgtctcgaac agagcgcgca gaggaacgct | 2580 |
| gaaggtctcg cctctgtcgc acctcagcgc ggcatacacc acaataacca cctgacgaat | 2640 |
| gcgcttggtt cttcgtccat tagcgaagcg tccggttcac acacgtgcca cgttggcgag | 2700 |
| gtggcaggtg acaatgatcg gtggagctga tggtcgaaac gttcacagcc tagggatatc | 2760 |
| gaattccttt cttgcgctat gacacttcca gcaaaaggta gggcgggctg cgagacggct | 2820 |
| tcccggcgct gcatgcaaca ccgatgatgc ttcgaccccc cgaagctcct tcggggctgc | 2880 |
| atgggcgctc cgatgccgct ccagggcgag cgctgtttaa atagccaggc ccccgattgc | 2940 |
| aaagacatta tagcgagcta ccaaagccat attcaaacac ctagatcact accacttcta | 3000 |
| cacaggccac tcgagcttgt gatcgcactc cgctaagggg gcgcctcttc ctcttcgttt | 3060 |
| cagtcacaac ccgcaaacac tagtatggct atcaagacga acaggcagcc tgtggagaag | 3120 |
| cctccgttca cgatcgggac gctgcgcaag gccatccccg cgcactgttt cgagcgctcg | 3180 |
| gcgcttcgtg ggcgcgcccc cgactggtcc atgctgttcg ccgtgatcac caccatcttc | 3240 |
| agcgccgccg agaagcagtg gaccaacctg gagtggaagc ccaagcccaa gctgccccag | 3300 |
| ctgctggacg accacttcgg cctgcacggc ctggtgttcc gccgcacctt cgccatccgc | 3360 |
| tcctacgagg tgggccccga ccgcagcacc tccatcctgg ccgtgatgaa ccacatgcag | 3420 |
| gaggccaccc tgaaccacgc caagagcgtg gcatcctgg gcgacggctt cggcaccacc | 3480 |
| ctggagatgt ccaagcgcga cctgatgtgg gtggtgcgcc gcacccacgt ggccgtggag | 3540 |
| cgctacccca cctggggcga caccgtggag gtggagtgct ggatcggcgc cagcggcaac | 3600 |
| aacggcatgc gccgcgactt cctggtgcgc gactgcaaga ccggcgagat cctgacccgc | 3660 |
| tgcacctccc tgagcgtgct gatgaacacc cgcaccgcc gcctgagcac catccccgac | 3720 |
| gaggtgcgcg gcgagatcgg ccccgccttc atcgacaacg tggccgtgaa ggacgacgag | 3780 |
| atcaagaagc tgcagaagct gaacgactcc accgccgact acatccaggg cggcctgacc | 3840 |
| ccccgctgga acgacctgga cgtgaaccag cacgtgaaca acctgaagta cgtggcctgg | 3900 |
| gtgttcgaga ccgtgcccga cagcatcttc gagtcccacc acatcagctc cttcacctg | 3960 |
| gagtaccgcc gcgagtgcac ccgcgactcc gtgctgcgca gcctgaccac cgtgagcggc | 4020 |
| ggcagctccg aggccggcct ggtgtgcgac cacctgctgc agctggaggg cggcagcgag | 4080 |
| gtgctgcgcg cccgcaccga gtggcgcccc aagctgaccg actccttccg cggcatcagc | 4140 |
| gtgatccccg ccgagcccg cgtgatggac tacaaggacc acgacggcga ctacaaggac | 4200 |
| cacgacatcg actacaagga cgacgacgac aagtgatgac tcgaggcagc agcagctcgg | 4260 |
| atagtatcga cacactctgg acgctggtcg tgtgatggac tgttgccgcc acacttgctg | 4320 |
| ccttgacctg tgaatatccc tgccgctttt atcaaacagc ctcagtgtgt ttgatcttgt | 4380 |
| gtgtacgcgc ttttgcgagt tgctagctgc ttgtgctatt tgcgaatacc accccagca | 4440 |
| tccccttccc tcgtttcata tcgcttgcat cccaaccgca acttatctac gctgtcctgc | 4500 |
| tatccctcag cgctgctcct gctcctgctc actgcccctc gcacagcctt ggtttgggct | 4560 |
| ccgcctgtat tctcctggta ctgcaacctg taaaccagca ctgcaatgct gatgcacggg | 4620 |
| aagtagtggg atgggaacac aaatggaaag ctt | 4653 |

<210> SEQ ID NO 87
<211> LENGTH: 4653
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

```
ggtacccgcc tgcaacgcaa gggcagccac agccgctccc acccgccgct gaaccgacac      60
gtgcttgggc gcctgccgcc tgcctgccgc atgcttgtgc tggtgaggct gggcagtgct     120
gccatgctga ttgaggcttg gttcatcggg tggaagctta tgtgtgtgct gggcttgcat     180
gccgggcaat gcgcatggtg gcaagagggc ggcagcactt gctggagctg ccgcggtgcc     240
tccaggtggt tcaatcgcgg cagccagagg gatttcagat gatcgcgcgt acaggttgag     300
cagcagtgtc agcaaaggta gcagtttgcc agaatgatcg gttcagctgt taatcaatgc     360
cagcaagaga aggggtcaag tgcaaacacg gcatgccac agcacgggca ccggggagtg      420
gaatggcacc accaagtgtg tgcgagccag catcgccgcc tggctgtttc agctacaacg     480
gcaggagtca tccaacgtaa ccatgagctg atcaacactg caatcatcgg gcgggcgtga     540
tgcaagcatg cctggcgaag acacatggtg tgcggatgct gccggctgct gcctgctgcg     600
cacgccgttg agttggcagc aggctcagcc atgcactgga tggcagctgg gctgccactg     660
caatgtggtg gataggatgc aagtggacg aataccaaac cctctggctg cttgctgggt      720
tgcatggcat cgcaccatca gcaggagcgc atgcgaaggg actggcccca tgcacgccat     780
gccaaaccgg agcgcaccga gtgtccacac tgtcaccagg cccgcaagct ttgcagaacc     840
atgctcatgg acgcatgtag cgctgacgtc ccttgacggc gctcctctcg ggtgtgggaa     900
acgcaatgca gcacaggcag cagaggcggc ggcagcagag cggcggcagc agcggcgggg     960
gccacccttc ttgcggggtc gcgccccagc cagcggtgat gcgctgatcc caaacgagtt    1020
cacattcatt tgcatgcctg gagaagcgag gctggggcct ttgggctggt gcagcccgca    1080
atggaatgcg ggaccgccag gctagcagca aaggcgcctc ccctactccg catcgatgtt    1140
ccatagtgca ttggactgca tttggtgggg cggccggct gttctttcg tgttgcaaaa       1200
cgcgccagct cagcaacctg tcccgtgggt cccccgtgcc gatgaaatcg tgtgcacgcc    1260
gatcagctga ttgcccggct cgcgaagtag gcgcccctcct ttctgctcgc cctctctccg   1320
tcccgcctct agaatatcaa tgatcgagca ggacggcctc cacgccggct cccccgccgc    1380
ctgggtggag cgcctgttcg gctacgactg ggcccagcag accatcggct gctccgacgc    1440
cgccgtgttc cgcctgtccg cccagggccg cccccgtgctg ttcgtgaaga ccgacctgtc    1500
cggcgccctg aacgagctgc aggacgaggc cgcccgcctg tcctggctgg ccaccaccgg    1560
cgtgccctgc gccgccgtgc tggacgtggt gaccgaggcc ggccgcgact ggctgctgct    1620
gggcgaggtg cccggccagg acctgctgtc ctcccacctg gccccgccg agaaggtgtc     1680
catcatggcc gacgccatgc gccgcctgca cacctggac cccgccacct gccccttcga     1740
ccaccaggcc aagcaccgca tcgagcgcgc ccgcacccgc atggaggccg gctggtgga    1800
ccaggacgac ctggacgagg agcaccaggg cctggcccc gccgagctgt cgcccgcct     1860
gaaggcccgc atgcccgacg gcgaggacct ggtggtgacc cacggcgacg cctgcctgcc    1920
caacatcatg gtggagaacg gccgcttctc cggcttcatc gactgcgcc gcctgggcgt     1980
ggccgaccgc taccaggaca tcgccctggc cacccgcgac atcgccgagg agctgggcgg    2040
cgagtgggcc gaccgcttcc tggtgctgta cggcatcgcc gccccgact cccagcgcat     2100
```

```
cgccttctac cgcctgctgg acgagttctt ctgacaattg gcagcagcag ctcggatagt   2160
atcgacacac tctggacgct ggtcgtgtga tggactgttg ccgccacact tgctgccttg   2220
acctgtgaat atccctgccg cttttatcaa acagcctcag tgtgtttgat cttgtgtgta   2280
cgcgcttttg cgagttgcta gctgcttgtg ctatttgcga ataccacccc cagcatcccc   2340
ttccctcgtt tcatatcgct tgcatcccaa ccgcaactta tctacgctgt cctgctatcc   2400
ctcagcgctg ctcctgctcc tgctcactgc ccctcgcaca gccttggttt gggctccgcc   2460
tgtattctcc tggtactgca acctgtaaac cagcactgca atgctgatgc acgggaagta   2520
gtgggatggg aacacaaatg gaggatcccg cgtctcgaac agagcgcgca gaggaacgct   2580
gaaggtctcg cctctgtcgc acctcagcgc ggcatacacc acaataacca cctgacgaat   2640
gcgcttggtt cttcgtccat tagcgaagcg tccggttcac acacgtgcca cgttggcgag   2700
gtggcaggtg acaatgatcg gtggagctga tggtcgaaac gttcacagcc tagggatatc   2760
gaattccttt cttgcgctat gacacttcca gcaaaaggta gggcgggctg cgagacggct   2820
tcccggcgct gcatgcaaca ccgatgatgc ttcgaccccc cgaagctcct tcggggctgc   2880
atgggcgctc cgatgccgct ccagggcgag cgctgtttaa atagccaggc ccccgattgc   2940
aaagacatta tagcgagcta ccaaagccat attcaaacac ctagatcact accacttcta   3000
cacaggccac tcgagcttgt gatcgcactc cgctaagggg gcgcctcttc ctcttcgttt   3060
cagtcacaac ccgcaaacac tagtatggcc accgcatcca ctttctcggc gttcaatgcc   3120
cgctgcggcg acctgcgtcg ctcggcgggc tccgggcccc ggcgcccagc gaggcccctc   3180
cccgtgcgcg ggcgcgcccc cgactggtcc atgctgttcg ccgtgatcac caccatcttc   3240
agcgccgccg agaagcagtg gaccaacctg gagtggaagc ccaagcccaa gctgccccag   3300
ctgctggacg accacttcgg cctgcacggc ctggtgttcc gccgcacctt cgccatccgc   3360
tcctacgagg tgggccccga ccgcagcacc tccatcctgg ccgtgatgaa ccacatgcag   3420
gaggccaccc tgaaccacgc caagagcgtg gcatcctgg gcgacggctt cggcaccacc   3480
ctggagatgt ccaagcgcga cctgatgtgg gtggtgcgcc gcacccacgt ggccgtggag   3540 cgctaccccca cctggggcga caccgtggag gtggagtgct ggatcggcgc cagcggcaac   3600
aacggcatgc gccgcgactt cctggtgcgc gactgcaaga ccggcgagat cctgacccgc   3660
tgcacctccc tgagcgtgct gatgaacacc cgcacccgcc gctgagcac catccccgac   3720 gaggtgcgcg gcgagatcgg ccccgccttc atcgacaacg tggccgtgaa ggacgacgag   3780
atcaagaagc tgcagaagct gaacgactcc accgccgact acatccaggg cggcctgacc   3840
ccccgctgga cgacctgga cgtgaaccag cacgtgaaca acctgaagta cgtggcctgg   3900
gtgttcgaga ccgtgcccga cagcatcttc gagtcccacc acatcagctc cttcacccta   3960
gagtaccgcc gcgagtgcac ccgcgactcc gtgctgcgca gcctgaccac cgtgagcggc   4020
ggcagctccg aggccggcct ggtgtgcgac cacctgctgc agctggaggg cggcagcgag   4080
gtgctgcgcg cccgcaccga gtggcgccc aagctgaccg actccttccg cggcatcagc   4140
gtgatccccg ccgagcccg cgtgatggac tacaaggacc acgacggcga ctacaaggac   4200
cacgacatcg actacaagga cgacgacgac aagtgatgac tcgaggcagc agcagctcgg   4260
atagtatcga cacactctgg acgctggtcg tgtgatggac tgttgccgcc acacttgctg   4320
ccttgacctg tgaatatccc tgccgctttt atcaaacagc tcagtgtgt ttgatcttgt   4380 gtgtacgcgc ttttgcgagt tgctagctgc ttgtgctatt tgcgaatacc acccccagca   4440
```

-continued

| | |
|---|---|
| tcccccttccc tcgtttcata tcgcttgcat cccaaccgca acttatctac gctgtcctgc | 4500 |
| tatccctcag cgctgctcct gctcctgctc actgcccctc gcacagcctt ggtttgggct | 4560 |
| ccgcctgtat tctcctggta ctgcaacctg taaaccagca ctgcaatgct gatgcacggg | 4620 |
| aagtagtggg atgggaacac aaatggaaag ctt | 4653 |

<210> SEQ ID NO 88
<211> LENGTH: 4647
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 88

| | |
|---|---|
| ggtacccgcc tgcaacgcaa gggcagccac agccgctccc acccgccgct gaaccgacac | 60 |
| gtgcttgggc gcctgccgcc tgcctgccgc atgcttgtgc tggtgaggct gggcagtgct | 120 |
| gccatgctga ttgaggcttg gttcatcggg tggaagctta tgtgtgtgct gggcttgcat | 180 |
| gccgggcaat gcgcatggtg gcaagagggc ggcagcactt gctggagctg ccgcggtgcc | 240 |
| tccaggtggt tcaatcgcgg cagccagagg gatttcagat gatcgcgcgt acaggttgag | 300 |
| cagcagtgtc agcaaaggta gcagtttgcc agaatgatcg gttcagctgt taatcaatgc | 360 |
| cagcaagaga aggggtcaag tgcaaacacg gcatgccac agcacgggca ccggggagtg | 420 |
| gaatggcacc accaagtgtg tgcgagccag catcgccgcc tggctgtttc agctacaacg | 480 |
| gcaggagtca tccaacgtaa ccatgagctg atcaacactg caatcatcgg gcgggcgtga | 540 |
| tgcaagcatg cctggcgaag acacatggtg tgcggatgct gccggctgct gctgctgcg | 600 |
| cacgccgttg agttggcagc aggctcagcc atgcactgga tggcagctgg gctgccactg | 660 |
| caatgtggtg gataggatgc aagtggagcg aataccaaac cctctggctg cttgctgggt | 720 |
| tgcatggcat cgcaccatca gcaggagcgc atgcgaaggg actggcccca tgcacgccat | 780 |
| gccaaaccgg agcgcaccga gtgtccacac tgtcaccagg cccgcaagct ttgcagaacc | 840 |
| atgctcatgg acgcatgtag cgctgacgtc ccttgacggc gctcctctcg ggtgtgggaa | 900 |
| acgcaatgca gcacaggcag cagaggcggc ggcagcagag cggcggcagc agcggcgggg | 960 |
| gccacccttc ttgcggggtc gcgccccagc cagcggtgat gcgctgatcc caaacgagtt | 1020 |
| cacattcatt tgcatgcctg gagaagcgag gctggggcct ttgggctggt gcagcccgca | 1080 |
| atggaatgcg ggaccgccag gctagcagca aaggcgcctc ccctactccg catcgatgtt | 1140 |
| ccatagtgca ttggactgca tttgggtggg gcggccggct gtttctttcg tgttgcaaaa | 1200 |
| cgcgccagct cagcaacctg tcccgtgggt ccccgtgcc gatgaaatcg tgtgcacgcc | 1260 |
| gatcagctga ttgcccggct cgcgaagtag gcgccctcct ttctgctcgc cctctctccg | 1320 |
| tcccgcctct agaatatcaa tgatcgagca ggacggcctc cacgccggct ccccgccgc | 1380 |
| ctgggtggag cgcctgttcg gctacgactg ggcccagcag accatcggct gctccgacgc | 1440 |
| cgccgtgttc cgcctgtccg cccagggccg cccgtgctg ttcgtgaaga ccgacctgtc | 1500 |
| cggcgccctg aacgagctgc aggacgaggc cgcccgcctg tcctggctgg ccaccaccgg | 1560 |
| cgtgccctgc gccgccgtgc tggacgtggt gaccgaggcc ggccgcgact ggctgctgct | 1620 |
| gggcgaggtg cccggccagg acctgctgtc ctcccacctg gccccgccg agaaggtgtc | 1680 |
| catcatggcc gacgccatgc gccgcctgca cacccctggac cccgccacct gccccttcga | 1740 |
| ccaccaggcc aagcaccgca tcgagcgcgc ccgcacccgc atggaggccg gctggtggga | 1800 |

```
ccaggacgac ctggacgagg agcaccaggg cctggccccc gccgagctgt tcgcccgcct    1860
gaaggcccgc atgcccgacg gcgaggacct ggtggtgacc cacggcgacg cctgcctgcc    1920
caacatcatg gtggagaacg gccgcttctc cggcttcatc gactgcggcc gcctgggcgt    1980
ggccgaccgc taccaggaca tcgccctggc cacccgcgac atcgccgagg agctgggcgg    2040
cgagtgggcc gaccgcttcc tggtgctgta cggcatcgcc gcccccgact cccagcgcat    2100
cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg cttttatcaa acagcctcag tgtgtttgat cttgtgtgta    2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgacccccc gaagctcct tcggggctgc    2880
atgggcgctc cgatgccgct ccagggcgag cgctgtttaa atagccaggc ccccgattgc    2940
aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacac tagtatggct tccgcggcat tcaccatgtc ggcgtgcccc    3120
gcgatgactg gcagggcccc tggggcacgt cgctccggac ggccagtcgc cacccgcctg    3180
agggggcgcg ccccgactg gtccatgctg ttcgccgtga tcaccaccat cttcagcgcc    3240
gccgagaagc agtggaccaa cctggagtgg aagcccaagc caagctgcc ccagctgctg    3300
gacgaccact tcggcctgca cggcctggtg ttccgccgca ccttcgccat ccgctcctac    3360
gaggtgggcc ccgaccgcag cacctccatc ctggccgtga tgaaccacat gcaggaggcc    3420
accctgaacc acgccaagag cgtgggcatc ctgggcgacg gcttcggcac caccctggag    3480
atgtccaagc gcgacctgat gtgggtggtg cgccgcaccc acgtggccgt ggagcgctac    3540
cccacctggg gcgacaccgt ggaggtggag tgctggatcg gcgccagcgg caacaacggc    3600
atgcgccgcg acttcctggt gcgcgactgc aagaccggcg agatcctgac cgctgcacc    3660
tccctgagcg tgctgatgaa caccgcacc cgccgcctga gcaccatccc cgacgaggtg    3720
cgcggcgaga tcggcccgc cttcatcgac aacgtggccg tgaaggacga cgagatcaag    3780
aagctgcaga agctgaacga ctccaccgcc gactacatcc agggcggcct gacccccgc    3840
tggaacgacc tggacgtgaa ccagcacgtg aacaacctga agtacgtggc ctgggtgttc    3900
gagaccgtgc ccgacagcat cttcgagtcc caccacatca gctccttcac cctggagtac    3960
cgccgcgagt gcacccgcga ctccgtgctg cgcagcctga ccaccgtgag cggcggcagc    4020
tccgaggccg gctggtgtg cgaccacctg ctgcagctgg agggcggcag cgaggtgctg    4080
cgcgcccgca ccgagtggcg ccccaagctg accgactcct tccgcggcat cagcgtgatc    4140
cccgccgagc cccgcgtgat ggactacaag gaccacgacg gcgactacaa ggaccacgac    4200
```

```
atcgactaca aggacgacga cgacaagtga tgactcgagg cagcagcagc tcggatagta    4260
tcgacacact ctggacgctg gtcgtgtgat ggactgttgc cgccacactt gctgccttga    4320
cctgtgaata tccctgccgc ttttatcaaa cagcctcagt gtgtttgatc ttgtgtgtac    4380
gcgcttttgc gagttgctag ctgcttgtgc tatttgcgaa taccacccc agcatccct    4440 tccctcgttt catatcgctt gcatcccaac cgcaacttat ctacgctgtc ctgctatccc    4500
tcagcgctgc tcctgctcct gctcactgcc cctcgcacag ccttggtttg gctccgcct    4560 gtattctcct ggtactgcaa cctgtaaacc agcactgcaa tgctgatgca cgggaagtag    4620
tgggatggga acacaaatgg aaagctt                                          4647
```

<210> SEQ ID NO 89
<211> LENGTH: 4721
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

```
ggtacccgcc tgcaacgcaa gggcagccac agccgctccc accgccgct gaaccgacac     60 gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga agggtcaag tgcaaacacg gcatgccac agcacgggca ccggggagtg     420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct tgcagaacc    840 atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960 gccaccttc ttgcggggtc gcgccccagc cagcggtgat gcgctgatcc caaacgagtt   1020
cacattcatt tgcatgcctg gagaagcgag gctggggcct ttgggctggt gcagcccgca   1080
atggaatgcg ggaccgccag gctagcagca aaggcgcctc ccctactccg catcgatgtt   1140
ccatagtgca ttgactgca tttgggtggg gcggccggct gtttctttcg tgttgcaaaa    1200
cgcgccagct cagcaacctg tcccgtgggt ccccgtgcc gatgaaatcg tgtgcacgcc   1260
gatcagctga ttgcccggct cgcgaagtag gcgccctcct ttctgctcgc cctctctccg   1320
tcccgcctct agaatatcaa tgatcgagca ggacggcctc cacgccggct cccccgccgc   1380
ctgggtggag cgcctgttcg gctacgactg ggcccagcag accatcggct gctccgacgc   1440
cgccgtgttc cgcctgtccg cccagggccg cccgtgctc ttcgtgaaga ccgacctgtc   1500
cggcgccctg aacgagctgc aggacgaggc cgcccgcctg tcctggctgg ccaccaccgg   1560
```

```
cgtgccctgc gccgccgtgc tggacgtggt gaccgaggcc ggccgcgact ggctgctgct    1620
gggcgaggtg cccggccagg acctgctgtc ctcccacctg gccccgccg agaaggtgtc     1680 catcatggcc gacgccatgc gccgcctgca cccctggac cccgccacct gccccttcga     1740
ccaccaggcc aagcaccgca tcgagcgcgc ccgcacccgc atggaggccg gcctggtgga    1800
ccaggacgac ctggacgagg agcaccaggg cctggccccc gccgagctgt cgcccgcct    1860 gaaggcccgc atgcccgacg cgaggacct ggtggtgacc cacggcgacg cctgcctgcc     1920
caacatcatg gtggagaacg ccgcttctc cggcttcatc gactgcggcc gctgggcgt     1980 ggccgaccgc taccaggaca tcgccctggc acccgcgac atcgccgagg agctgggcgg    2040
cgagtgggcc gaccgcttcc tggtgctgta cggcatcgcc gccccgact cccagcgcat     2100 cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg cttttatcaa acagcctcag tgtgtttgat cttgtgtgta    2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acggaagta    2520 gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgaccccc cgaagctcct tcggggctgc    2880
atgggcgctc cgatgccgct ccagggcgag cgctgtttaa atagccaggc ccccgattgc    2940
aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacgg cgcgccatgg ccaccacctc cctggcctcc gcttctgca    3120 gcatgaaggc cgtgatgctg gcccgcgacg gccgcggcat gaagcccgc tccagcgacc     3180 tgcagctgcg cgccggcaac gcccagacct ccctgaagat gatcaacggc accaagttct    3240
cctacaccga gagcctgaag aagctgcccg actggtccat gctgttcgcc gtgatcacca    3300
ccatcttctc cgccgccgag aagcagtgga ccaacctgga gtggaagccc aagcccaacc    3360 cccccagct gctggacgac cacttcggcc ccacgcct ggtgttccgc cgcaccttcg      3420
ccatccgcag ctacgaggtg gccccgacc gctccaccag catcgtggcc gtgatgaacc    3480
acctgcagga ggccgccctg aaccacgcca agtccgtggg catcctgggc gacggcttcg    3540
gcaccaccct ggagatgtcc aagcgcgacc tgatctgggt ggtgaagcgc acccacgtgg    3600
ccgtggagcg ctaccccgcc tggggcgaca ccgtggaggt ggagtgctgg gtgggcgcct    3660
ccggcaacaa cggccgccgc cacgacttcc tggtgcgcga ctgcaagacc ggcgagatcc    3720
tgacccgctg cacctccctg agcgtgatga tgaacacccg cacccgccgc ctgagcaaga    3780
tccccgagga ggtgcgcggc gagatcggcc ccgccttcat cgacaacgtg gccgtgaagg    3840
acgaggagat caagaagccc cagaagctga acgactccac cgccgactac atccagggcg    3900
```

| | |
|---|---:|
| gcctgacccc ccgctggaac gacctggaca tcaaccagca cgtgaacaac atcaagtacg | 3960 |
| tggactggat cctggagacc gtgcccgaca gcatcttcga gagccaccac atctcctcct | 4020 |
| tcaccatcga gtaccgccgc gagtgcacca tggacagcgt gctgcagtcc ctgaccaccg | 4080 |
| tgagcggcgg ctcctccgag gccggcctgg tgtgcgagca cctgctgcag ctggagggcg | 4140 |
| gcagcgaggt gctgcgcgcc aagaccgagt ggcgccccaa gctgaccgac tccttccgcg | 4200 |
| gcatcagcgt gatccccgcc gagtccagcg tgatggacta caaggaccac gacgcgact | 4260 |
| acaaggacca cgacatcgac tacaaggacg acgacgacaa gtgatgactc gaggcagcag | 4320 |
| cagctcggat agtatcgaca cactctggac gctggtcgtg tgatggactg ttgccgccac | 4380 |
| acttgctgcc ttgacctgtg aatatccctg ccgcttttat caaacagcct cagtgtgttt | 4440 |
| gatcttgtgt gtacgcgctt ttgcgagttg ctagctgctt gtgctatttg cgaataccac | 4500 |
| ccccagcatc cccttccctc gtttcatatc gcttgcatcc caaccgcaac ttatctacgc | 4560 |
| tgtcctgcta tccctcagcg ctgctcctgc tcctgctcac tgcccctcgc acagccttgg | 4620 |
| tttgggctcc gcctgtattc tcctggtact gcaacctgta aaccagcact gcaatgctga | 4680 |
| tgcacgggaa gtagtgggat gggaacacaa atggaaagct t | 4721 |

<210> SEQ ID NO 90
<211> LENGTH: 4650
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

| | |
|---|---:|
| ggtacccgcc tgcaacgcaa gggcagccac agccgctccc accgccgct gaaccgacac | 60 |
| gtgcttgggc gcctgccgcc tgcctgccgc atgcttgtgc tggtgaggct gggcagtgct | 120 |
| gccatgctga ttgaggcttg gttcatcggg tggaagctta tgtgtgtgct gggcttgcat | 180 |
| gccgggcaat gcgcatggtg gcaagagggc ggcagcactt gctggagctg ccgcggtgcc | 240 |
| tccaggtggt tcaatcgcgg cagccagagg gatttcagat gatcgcgcgt acaggttgag | 300 |
| cagcagtgtc agcaaaggta gcagtttgcc agaatgatcg gttcagctgt taatcaatgc | 360 |
| cagcaagaga aggggtcaag tgcaaacacg ggcatgccac agcacgggca ccggggagtg | 420 |
| gaatggcacc accaagtgtg tgcgagccag catcgccgcc tggctgtttc agctacaacg | 480 |
| gcaggagtca tccaacgtaa ccatgagctg atcaacactg caatcatcgg gcgggcgtga | 540 |
| tgcaagcatg cctggcgaag acacatggtg tgcggatgct gccggctgct gcctgctgcg | 600 |
| cacgccgttg agttggcagc aggctcagcc atgcactgga tggcagctgg gctgccactg | 660 |
| caatgtggtg gataggatgc aagtggacg aataccaaac cctctggctg cttgctgggt | 720 |
| tgcatggcat cgcaccatca gcaggagcgc atgcgaaggg actggcccca tgcacgccat | 780 |
| gccaaaccgg agcgcaccga gtgtccacac tgtcaccagg cccgcaagct tgcagaacc | 840 |
| atgctcatgg acgcatgtag cgctgacgtc ccttgacggc gctcctctcg ggtgtgggaa | 900 |
| acgcaatgca gcacaggcag cagaggcggc ggcagcagag cggcggcagc agcggcgggg | 960 |
| gccacccttc ttgcggggtc gcgccccagc cagcggtgat gcgctgatcc caaacgagtt | 1020 |
| cacattcatt tgcatgcctg gagaagcgag gctggggcct ttgggctggt gcagccgca | 1080 |
| atggaatgcg ggaccgccag gctagcagca aaggcgcctc ccctactccg catcgatgtt | 1140 |
| ccatagtgca ttggactgca tttgggtggg gcggccggct gtttctttcg tgttgcaaaa | 1200 |

```
cgcgccagct cagcaacctg tcccgtgggt cccccgtgcc gatgaaatcg tgtgcacgcc    1260
gatcagctga ttgcccggct cgcgaagtag gcgccctcct ttctgctcgc cctctctccg    1320
tcccgcctct agaatatcaa tgatcgagca ggacggcctc cacgccggct ccccgccgc     1380
ctgggtggag cgcctgttcg gctacgactg ggcccagcag accatcggct gctccgacgc    1440
cgccgtgttc cgcctgtccg cccagggccg ccccgtgctg ttcgtgaaga ccgacctgtc    1500
cggcgccctg aacgagctgc aggacgaggc cgcccgcctg tcctggctgg ccaccaccgg    1560
cgtgccctgc gccgccgtgc tggacgtggt gaccgaggcc ggccgcgact ggctgctgct    1620
gggcgaggtg cccggccagg acctgctgtc ctcccacctg gccccgccg agaaggtgtc     1680
catcatggcc gacgccatgc gccgcctgca caccctggac cccgccacct gcccttcga    1740
ccaccaggcc aagcaccgca tcgagcgcgc ccgcacccgc atggaggccg gcctggtgga    1800
ccaggacgac ctggacgagg agcaccaggg cctggccccc gccgagctgt cgcccgcct    1860
gaaggcccgc atgcccgacg cgaggacct ggtggtgacc cacggcgacg cctgcctgcc     1920
caacatcatg gtggagaacg gccgcttctc cggcttcatc gactgcggcc gctgggcgt    1980
ggccgaccgc taccaggaca tcgccctggc caccgcgac atcgccgagg agctgggcgg    2040
cgagtgggcc gaccgcttcc tggtgctgta cggcatcgcc gccccgact cccagcgcat    2100
cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg ctttatcaa acagcctcag tgtgtttgat cttgtgtgta     2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgacccc cgaagctcct tcggggctgc     2880
atgggcgctc cgatgccgct ccagggcgag cgctgtttaa atagccaggc ccccgattgc    2940
aaagacatta tagcgagcta ccaaagccat attcaaacac ctagatcact accacttcta    3000
cacaggccac tcgagcttgt gatcgcactc cgctaagggg cgcctcttc ctcttcgttt     3060
cagtcacaac ccgcaaacac tagtatgacg ttcggggtcg ccctcccggc catgggccgc    3120
ggtgtctccc ttccccggcc cagggtcgcg gtgcgcgccc agtcggcgag tcaggttttg    3180
gagagcgggc gcgcccccga ctggtccatg ctgttcgccg tgatcaccac catcttctcc    3240
gccgccgaga agcagtggac caacctggag tggaagccca gcccaacccc ccccagctg     3300
ctggacgacc acttcggccc ccacggcctg gtgttccgcc gcaccttcgc catccgcagc    3360
tacgaggtgg ccccgaccg ctccaccagc atcgtggccg tgatgaacca cctgcaggag     3420
gccgccctga accacgccaa gtccgtgggc atcctgggcg acggcttcgg caccaccctg    3480
gagatgtcca gcgcgacct gatctgggtg gtgaagcgca cccacgtggc cgtggagcgc    3540
tacccccgcct ggggcgacac cgtggaggtg gagtgctggg tgggcgcctc cggcaacaac    3600
```

```
ggccgccgcc acgacttcct ggtgcgcgac tgcaagaccg gcgagatcct gaccgctgc    3660 acctccctga gcgtgatgat gaacacccgc accgccgcc tgagcaagat ccccgaggag    3720
gtgcgcggcg agatcggccc cgccttcatc gacaacgtgg ccgtgaagga cgaggagatc    3780
aagaagcccc agaagctgaa cgactccacc gccgactaca tccagggcgg cctgaccccc    3840
cgctggaacg acctggacat caaccagcac gtgaacaaca tcaagtacgt ggactggatc    3900
ctggagaccg tgcccgacag catcttcgag agccaccaca tctcctcctt caccatcgag    3960
taccgccgcg agtgcaccat ggacagcgtg ctgcagtccc tgaccaccgt gagcggcggc    4020
tcctccgagg ccgccctggt gtgcgagcac ctgctgcagc tggagggcgg cagcgaggtg    4080
ctgcgcgcca agaccgagtg gcgccccaag ctgaccgact ccttccgcgg catcagcgtg    4140
atccccgccg agtccagcgt gatggactac aaggaccacg acggcgacta caaggaccac    4200
gacatcgact acaaggacga cgacgacaag tgatgactcg aggcagcagc agctcggata    4260
gtatcgacac actctggacg ctggtcgtgt gatggactgt tgccgccaca cttgctgcct    4320
tgacctgtga atatccctgc cgcttttatc aaacagcctc agtgtgtttg atcttgtgtg    4380
tacgcgcttt tgcgagttgc tagctgcttg tgctatttgc gaataccacc cccagcatcc    4440
ccttccctcg tttcatatcg cttgcatccc aaccgcaact tatctacgct gtcctgctat    4500
ccctcagcgc tgctcctgct cctgctcact gcccctcgca cagccttggt ttgggctccg    4560
cctgtattct cctggtactg caacctgtaa accagcactg caatgctgat gcacgggaag    4620
tagtgggatg ggaacacaaa tggaaagctt                                    4650
```

<210> SEQ ID NO 91
<211> LENGTH: 4653
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91

```
ggtacccgcc tgcaacgcaa gggcagccac agccgctccc accgccgct gaaccgacac     60 gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg gcatgccac agcacgggca ccggggagtg    420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggacg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct ttgcagaacc    840
atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
```

```
gccacccttc ttgcggggtc gcgcccagc cagcggtgat gcgctgatcc caaacgagtt    1020
cacattcatt tgcatgcctg gagaagcgag gctgggcct ttgggctggt gcagcccgca    1080
atggaatgcg ggaccgccag gctagcagca aggcgcctc ccctactccg catcgatgtt    1140
ccatagtgca ttggactgca tttgggtggg gcggccggct gtttctttcg tgttgcaaaa    1200
cgcgccagct cagcaacctg tcccgtgggt ccccgtgcc gatgaaatcg tgtgcacgcc    1260
gatcagctga ttgcccggct cgcgaagtag gcgcctcct ttctgctcgc cctctctccg    1320
tcccgcctct agaatatcaa tgatcgagca ggacggcctc cacgccggct ccccgccgc    1380 ctgggtggag cgcctgttcg gctacgactg gcccagcag accatcggct gctccgacgc    1440
cgccgtgttc cgcctgtccg cccagggccg ccccgtgctg ttcgtgaaga ccgacctgtc    1500
cggcgccctg aacgagctgc aggacgaggc cgcccgcctg tcctggctgg ccaccaccgg    1560
cgtgccctgc gccgccgtgc tggacgtggt gaccgaggcc ggccgcgact ggctgctgct    1620
gggcgaggtg cccggccagg acctgctgtc ctcccacctg gccccgccg agaaggtgtc    1680 catcatggcc gacgccatgc gccgcctgca caccctggac ccgccacct gccccttcga    1740 ccaccaggcc aagcaccgca tcgagcgcgc ccgcacccgc atggaggccg gcctggtgga    1800
ccaggacgac ctggacgagg agcaccaggg cctggccccc gccgagctgt tcgcccgcct    1860
gaaggcccgc atgcccgacg gcgaggacct ggtggtgacc cacggcgacg cctgcctgcc    1920
caacatcatg gtggagaacg gccgcttctc cggcttcatc gactgcggcc gctgggcgt    1980 ggccgaccgc taccaggaca tcgccctggc caccccgcgac atcgcgagg agctgggcgg    2040 cgagtgggcc gaccgcttcc tggtgctgta cggcatcgcc gccccgact cccagcgcat    2100 cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg cttttatcaa acagcctcag tgtgtttgat cttgtgtgta    2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaggta gggcgggctg cgagacggct    2820
tcccggcgct gcatgcaaca ccgatgatgc ttcgaccccc cgaagctcct tcggggctgc    2880
atgggcgctc cgatgccgct ccagggcgag cgctgtttaa atagccaggc cccgattgc    2940 aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacac tagtatggct atcaagacga acaggcagcc tgtggagaag    3120
cctccgttca cgatcgggac gctgcgcaag gccatccccg cgcactgttt cgagcgctcg    3180
gcgcttcgtg ggcgcgcccc cgactggtcc atgctgttcg ccgtgatcac caccatcttc    3240
tccgccgccg agaagcagtg gaccaacctg gagtggaagc ccaagcccaa cccccccag    3300
```

```
ctgctggacg accacttcgg cccccacggc ctggtgttcc gccgcacctt cgccatccgc    3360
agctacgagg tgggccccga ccgctccacc agcatcgtgg ccgtgatgaa ccacctgcag    3420
gaggccgccc tgaaccacgc caagtccgtg gcatcctgg gcgacggctt cggcaccacc     3480
ctggagatgt ccaagcgcga cctgatctgg gtggtgaagc gcacccacgt ggccgtggag    3540
cgctaccccg cctggggcga caccgtggag gtggagtgct gggtgggcgc ctccggcaac    3600
aacggccgcc gccacgactt cctggtgcgc gactgcaaga ccggcgagat cctgacccgc    3660
tgcacctccc tgagcgtgat gatgaacacc cgcacccgcc gcctgagcaa gatccccgag    3720
gaggtgcgcg cgagatcgg ccccgccttc atcgacaacg tggccgtgaa ggacgaggag     3780
atcaagaagc cccagaagct gaacgactcc accgccgact acatccaggg cggcctgacc    3840
ccccgctgga cgacctgga catcaaccag cacgtgaaca catcaagta cgtggactgg      3900 atcctggaga ccgtgcccga cagcatcttc gagagccacc acatctcctc cttcaccatc    3960
gagtaccgcc gcgagtgcac catggacagc gtgctgcagt ccctgaccac cgtgagcggc    4020
ggctcctccg aggccggcct ggtgtgcgag cacctgctgc agctggaggg cggcagcgag    4080
gtgctgcgcg ccaagaccga gtggcgcccc aagctgaccg actccttccg cggcatcagc    4140
gtgatccccg ccgagtccag cgtgatggac tacaaggacc acgacggcga ctacaaggac    4200
cacgacatcg actacaagga cgacgacgac aagtgatgac tcgaggcagc agcagctcgg    4260
atagtatcga cacactctgg acgctggtcg tgtgatggac tgttgccgcc acacttgctg    4320
ccttgacctg tgaatatccc tgccgctttt atcaaacagc ctcagtgtgt ttgatcttgt    4380
gtgtacgcgc ttttgcgagt tgctagctgc ttgtgctatt tgcgaatacc acccccagca    4440
tccccttccc tcgtttcata tcgcttgcat cccaaccgca acttatctac gctgtcctgc    4500
tatccctcag cgctgctcct gctcctgctc actgcccctc gcacagcctt ggtttgggct    4560
ccgcctgtat tctcctggta ctgcaacctg taaaccagca ctgcaatgct gatgcacggg    4620
aagtagtggg atgggaacac aaatggaaag ctt                                 4653
```

<210> SEQ ID NO 92
<211> LENGTH: 1893
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

```
gaattccttt cttgcgctat gacacttcca gcaaaaggta gggcgggctg cgagacggct      60
tcccggcgct gcatgcaaca ccgatgatgc ttcgaccccc gaagctcct tcggggctgc      120 atgggcgctc cgatgccgct ccagggcgag cgctgtttaa atagccaggc ccccgattgc     180
aaagacatta tagcgagcta ccaaagccat attcaaacac ctagatcact accacttcta     240
cacaggccac tcgagcttgt gatcgcactc cgctaagggg cgcctcttc ctcttcgttt      300 cagtcacaac ccgcaaacac tagtatggcc accgcatcca ctttctcggc gttcaatgcc     360
cgctgcggcg acctgcgtcg ctcggcgggc tccgggcccc ggcgcccagc gaggcccctc     420
cccgtgcgcg ggcgcgcccc cgactggtcc atgctgttcg ccgtgatcac caccatcttc    480
tccgccgccg agaagcagtg gaccaacctg gagtggaagc caagcccaa cccccccag      540 ctgctggacg accacttcgg cccccacggc ctggtgttcc gccgcacctt cgccatccgc    600
agctacgagg tgggccccga ccgctccacc agcatcgtgg ccgtgatgaa ccacctgcag    660
```

```
gaggccgccc tgaaccacgc caagtccgtg ggcatcctgg gcgacggctt cggcaccacc    720
ctggagatgt ccaagcgcga cctgatctgg gtggtgaagc gcacccacgt ggccgtggag    780
cgctaccccg cctggggcga caccgtggag gtggagtgct gggtgggcgc ctccggcaac    840
aacggccgcc gccacgactt cctggtgcgc gactgcaaga ccggcgagat cctgacccgc    900
tgcacctccc tgagcgtgat gatgaacacc cgcacccgcc gcctgagcaa gatccccgag    960
gaggtgcgcg cgagatcgg ccccgccttc atcgacaacg tggccgtgaa ggacgaggag    1020
atcaagaagc cccagaagct gaacgactcc accgccgact acatccaggg cggcctgacc    1080
ccccgctgga cgacctgga catcaaccag cacgtgaaca acatcaagta cgtggactgg    1140
atcctggaga ccgtgcccga cagcatcttc gagagccacc acatctcctc cttcaccatc    1200
gagtaccgcc gcgagtgcac catggacagc gtgctgcagt ccctgaccac cgtgagcggc    1260
ggctcctccg aggccggcct ggtgtgcgag cacctgctgc agctggaggg cggcagcgag    1320
gtgctgcgcg ccaagaccga gtggcgcccc aagctgaccg actccttccg cggcatcagc    1380
gtgatccccg ccgagtccag cgtgatggac tacaaggacc acgacggcga ctacaaggac    1440
cacgacatcg actacaagga cgacgacgac aagtgatgac tcgaggcagc agcagctcgg    1500
atagtatcga cacactctgg acgctggtcg tgtgatggac tgttgccgcc acacttgctg    1560
ccttgacctg tgaatatccc tgccgctttt atcaaacagc ctcagtgtgt ttgatcttgt    1620
gtgtacgcgc ttttgcgagt tgctagctgc ttgtgctatt tgcgaatacc accccagca    1680 tccccttccc tcgtttcata tcgcttgcat cccaaccgca acttatctac gctgtcctgc    1740
tatccctcag cgctgctcct gctcctgctc actgccctc gcacagcctt ggtttgggct    1800
ccgcctgtat tctcctggta ctgcaacctg taaaccagca ctgcaatgct gatgcacggg    1860
aagtagtggg atgggaacac aaatggaaag ctt                                1893
```

<210> SEQ ID NO 93
<211> LENGTH: 1887
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

```
gaattccttt cttgcgctat gacacttcca gcaaaaggta gggcgggctg cgagacggct     60
tcccggcgct gcatgcaaca ccgatgatgc ttcgaccccc cgaagctcct tcggggctgc    120
atgggcgctc cgatgccgct ccagggcgag cgctgtttaa atagccaggc ccccgattgc    180
aaagacatta tagcgagcta ccaaagccat attcaaacac ctagatcact accacttcta    240
cacaggccac tcgagcttgt gatcgcactc cgctaagggg gcgcctcttc ctcttcgttt    300
cagtcacaac ccgcaaacac tagtatggct tccgcggcat tcaccatgtc ggcgtgcccc    360
gcgatgactg gcagggcccc tggggcacgt cgctccggac ggccagtcgc cacccgcctg    420
agggggcgcg ccccgactg gtccatgctg ttcgccgtga tcaccaccat cttctccgcc    480
gccgagaagc agtggaccaa cctggagtgg aagcccaagc caacccccc ccagctgctg    540 gacgaccact tcgcccccca cggcctggtg ttccgccgca ccttcgccat ccgcagctac    600
gaggtgggcc ccgaccgctc caccagcatc gtggccgtga tgaaccacct gcaggaggcc    660
gccctgaacc acgccaagtc cgtgggcatc ctgggcgacg gcttcggcac caccctggag    720
atgtccaagc gcgacctgat ctgggtggtg aagcgcaccc acgtggccgt ggagcgctac    780
```

```
cccgcctggg gcgacaccgt ggaggtggag tgctgggtgg gcgcctccgg caacaacggc      840
cgccgccacg acttcctggt gcgcgactgc aagaccggcg agatcctgac ccgctgcacc      900
tccctgagcg tgatgatgaa cacccgcacc cgccgcctga gcaagatccc cgaggaggtg      960
cgcggcgaga tcggcccccgc cttcatcgac aacgtggccg tgaaggacga ggagatcaag     1020
aagccccaga agctgaacga ctccaccgcc gactacatcc agggcggcct gaccccccgc      1080
tggaacgacc tggacatcaa ccagcacgtg aacaacatca agtacgtgga ctggatcctg      1140
gagaccgtgc ccgacagcat cttcgagagc caccacatct cctccttcac catcgagtac      1200
cgccgcgagt gcaccatgga cagcgtgctg cagtccctga ccaccgtgag cggcggctcc      1260
tccgaggccg gcctggtgtg cgagcacctg ctgcagctgg agggcggcag cgaggtgctg      1320
cgcgccaaga ccgagtggcg ccccaagctg accgactcct tccgcggcat cagcgtgatc      1380
cccgccgagt ccagcgtgat ggactacaag gaccacgacg gcgactacaa ggaccacgac      1440
atcgactaca aggacgacga cgacaagtga tgactcgagg cagcagcagc tcggatagta      1500
tcgacacact ctggacgctg gtcgtgtgat ggactgttgc cgccacactt gctgccttga      1560
cctgtgaata tccctgccgc ttttatcaaa cagcctcagt gtgtttgatc ttgtgtgtac      1620
gcgcttttgc gagttgctag ctgcttgtgc tatttgcgaa taccacccccc agcatcccct     1680 tccctcgttt catatcgctt gcatcccaac cgcaacttat ctacgctgtc ctgctatccc      1740
tcagcgctgc tcctgctcct gctcactgcc cctcgcacag ccttggtttg ggctccgcct      1800
gtattctcct ggtactgcaa cctgtaaacc agcactgcaa tgctgatgca cgggaagtag      1860
tgggatggga acacaaatgg aaagctt                                          1887
```

<210> SEQ ID NO 94
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gatcagaatt ccgcctgcaa cgcaagggca gc                                    32

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gcatactagt ggcgggacgg agagagggcg                                       30

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Lys Asp Glu Leu
1

FRACTIONATION OF OIL-BEARING MICROBIAL BIOMASS

This application is a continuation of US Application Ser. No. 13/322,435, filed Feb. 14, 2012, now US Pat. No. 8,580,540, which is a US National Stage Application of PCT/US2010/036238, filed May 26, 2010, which claims the benefit under 35 U.S.C. 119(e) of US Provisional Application No. 61/181,252, filed May 26, 2009, each of which is incorporated herein by reference in its entirety for all purposes.

REFERENCE TO A SEQUENCE LISTING

This application includes an electronic sequence listing in a file named "438565-Sequence.txt", created on Oct. 16, 2013 and containing 170,488 bytes, which is hereby incorporated by reference in its entirety for all purposes.

FIELD OF THE INVENTION

The invention generally relates to the production of oil compositions, such as a lipid, in microorganisms. In particular, the invention provides methods for extracting, recovering, isolating and obtaining a lipid from a microorganism and compositions comprising the lipid. The invention also discloses methods for producing hydrocarbon or lipid compositions for production of biodiesel, renewable diesel, jet fuel, and lipid surfactants having various carbon chain lengths, including C8, C10, C12 and C14.

BACKGROUND OF THE INVENTION

Fossil fuel is a general term for buried combustible geologic deposits of organic materials, formed from decayed plants and animals that have been converted to crude oil, coal, natural gas, or heavy oils by exposure to heat and pressure in the earth's crust over hundreds of millions of years.

Fossil fuels are a finite, non-renewable resource. With global modernization in the 20th and 21st centuries, the thirst for energy from fossil fuels, especially gasoline derived from oil, is one of the causes of major regional and global conflicts. Increased demand for energy by the global economy has also placed increasing pressure on the cost of hydrocarbons. Aside from energy, many industries, including plastics and chemical manufacturers, rely heavily on the availability of hydrocarbons as a feedstock for their manufacturing processes. Alternatives to current sources of supply could help mitigate the upward pressure on these raw material costs.

Lipids for use in biofuels can be produced in microorganisms, such as algae, fungi, and bacteria. Typically, manufacturing a lipid in a microorganism involves growing microorganisms, such as algae, fungi, or bacteria, which are capable of producing a desired lipid in a fermentor or bioreactor, isolating the microbial biomass, drying it, and extracting the intracellular lipids.

There is a need for a process for extracting lipids from microorganism which solves the above problems of low efficiency and high cost of lipid extraction from microorganism. The present invention provides a solution to these prior art problems.

BRIEF SUMMARY OF THE INVENTION

In one aspect, the present invention is directed to a method of extracting a lipid from a microorganism. In one embodiment, the method comprises lysing a cultured microorganism that has not been subjected to a drying step between culturing and lysing, and which contains a lipid, to produce a lysate, treating the lysate with an organic solvent for a period of time sufficient to allow the lipid from the microorganism to become solubilized in the organic solvent, and separating the lysate into layers comprising a lipid:organic solvent layer and an aqueous layer, whereby the lipid is extracted from the microorganism.

In another aspect, the present invention is directed to a composition comprising a lipid isolated from a microorganism, and an oil obtained from a source other than the microorganism. In some cases, the ratio of the lipid to the oil is between 1 and 100. In other cases, the ratio of the lipid to the oil is between 1 and 10. In some embodiments, the lipid comprises at least 50% of a C18:1 lipid, or at least 10% of a C12 and C14 lipid combined.

In another aspect, the present invention is directed to a method of producing biodiesel. In one embodiment, the method comprises lysing a lipid-containing microorganism to produce a lysate, treating the lysate with an organic solvent for a period of time sufficient to allow the lipid from the microorganism to become solubilized in the organic solvent, separating the lysate into a lipid:organic solvent composition and an aqueous composition and, optionally, an emulsified composition and/or cell pellet composition, removing the lipid:organic solvent composition from the aqueous composition, emulsion composition, or cell pellet composition, and transesterifying the lipid:organic solvent composition to produce biodiesel. In some cases, the biodiesel meets or exceeds the ASTM D6751 biodiesel standard and/or the EN 14214 biodiesel standard. In one embodiment, the microorganism is not subjected to a drying step.

In some embodiments of the biodiesel production method at least 20% w/v of total lipid from the microorganism is C18:1. In one embodiment, the layers further comprise a lipid:aqueous emulsion layer and/or a cell pellet. Transesterification of the lipid:organic solvent can be performed without substantially separating the lipid from the organic solvent.

In still another aspect, the present invention is directed to a method of producing renewable diesel. In one embodiment, the method comprises lysing a lipid-containing microorganism to produce a lysate, treating the lysate with an organic solvent for a period of time sufficient to allow the lipid from the microorganism to become solubilized in the organic solvent, separating the lysate into a lipid:organic solvent composition and an aqueous composition and, optionally, an emulsified composition and/or cell pellet composition, removing the lipid:organic solvent composition from the aqueous composition, emulsion composition, or cell pellet composition, and treating the lipid:organic solvent composition to produce a straight chain alkane renewable diesel product. In some cases, the renewable diesel meets or exceeds the ASTM D 975 standard.

In various embodiments of the renewable diesel production method, the microorganism has not been subjected to a drying step. In some cases, treating the lipid:organic solvent composition is performed without substantially separating the lipid from the organic solvent. In some embodiments, treating the lipid:organic solvent composition comprises hydrotreating, hydroprocessing, or indirect liquefaction.

In another aspect, the present invention is directed to a method of producing a jet fuel. In one embodiment, the method comprises lysing a lipid-containing microorganism to produce a lysate, treating the lysate with an organic solvent for a period of time sufficient to allow the lipid from the microorganism to become solubilized in the organic solvent, separating the lysate into a lipid:organic solvent composition and an aqueous composition and, optionally, an emulsified composition or cell pellet composition, removing the lipid:organic solvent composition from the aqueous composition, emulsion composition, or cell pellet composition, treating the lipid:organic solvent composition to produce a straight chain alkane, and cracking the straight chain alkane to produce the jet fuel product.

In various embodiments of the jet fuel production method, the microorganism has not been subjected to a drying step. In some cases, treating the lipid:organic solvent composition is performed without substantially separating the lipid from the organic solvent. In some embodiments, treating the lipid:organic solvent composition is performed by flowing the lipid:organic solvent composition to a fluid catalytic cracking zone, and can further comprise contacting the lipid:organic solvent composition with a catalyst at cracking conditions. In one embodiment, treating the lipid:organic solvent composition is performed by hydrodeoxygenating the lipid:organic solvent composition. In some cases, the method further comprises subjecting the hydrodeoxygenated lipid:organic solvent composition to isomerization.

In another aspect, the present invention is directed to a method of extracting lipid from a microorganism by contacting a microorganism containing a lipid with an acid to produce a lysate, separating the lysate into layers comprising an aqueous layer and a lipid:aqueous emulsion layer, and extracting lipid from the emulsion layer.

In various embodiments of the method of extracting lipid from a microorganism, the microorgansism is contacted with the acid to produce an acid concentration of 5-200 mN, and contacting the microorganism can be performed above 25° C. In various embodiments, an organic solvent is added to the microorganism or lysate before, simultaneously with, or after contacting the microorganism with the acid. In some cases, the microorganism is contacted with an acid at a pH of no more than 4, at a pH of no more than 3, or at a pH of no more than 2. In some embodiments, in addition to contacting the microorganism with the acid, one or more additional methods of lysing the microorganism is also utilized. In some cases, contacting the microorganism with the acid is performed at a temperature of 50-160° C. In other cases, the step of contacting the microorganism with the acid is performed at a temperature of 20-65° C. In one embodiment, the lipid is extracted from the emulsion by contacting the emulsion with an organic solvent, whereby the lipid partitions from the emulsion into the organic solvent. In some cases, separation of the lysate is performed by cooling the emulsion below 25° C., below 10° C., or to a temperature at or below 0° C., whereby a lipid layer separates from the emulsion layer. In one embodiment, the method further comprises centrifuging the emulsion after the cooling to separate the lipid layer. In some embodiments, the method further comprises separating the emulsion from the aqueous layer before separating the lipid from the emulsion. In one embodiment, the lipid is extracted from the lipid:aqueous emulsion without use of an organic solvent.

In another aspect, the present invention is directed to a method of extracting lipid from a microorganism by lysing a microorganism containing a lipid to produce a lysate comprising a lipid:aqueous emulsion, and cooling the emulsion below 25° C. to separate the lipid from the emulsion.

In another aspect, the present invention is directed to a method of extracting lipid from microbial biomass generated by culturing a microorganism that produces a lipid. Extraction comprises lysing the microorganisms in the biomass to produce a lysate comprising a lipid:aqueous emulsion. In some cases, separation of a lipid layer from the emulsion comprises destabilizing the emulsion with the addition of a surfactant to the emulsion. In some cases, the lysate can be treated with an organic solvent for a period of time sufficient to allow the lipid from the microorganism to become solubilized in the organic solvent, and the lysate can be separated into two or more layers, including a lipid:organic solvent layer and at least one aqueous layer. In some cases, the method can further include removing the lipid:organic solvent composition from the other layer(s). Optionally, removing the lipid:organic solvent composition from the other layer(s) can be performed without substantially separating the lipid from the organic solvent. In some cases, the method can further include transesterifying the lipid:organic solvent composition to produce a fatty acid alkyl ester, or treating the lipid:organic solvent composition to produce a straight chain alkane. In the latter case, the method can further include cracking the straight chain alkane.

In another aspect, the present invention is directed to a composition of fatty acid esters comprising esters derived from a microorganism, and esters derived from a nonmicrobial oil. In some embodiments, no more than 20%, no more than 10%, or no more than 6%, of the esters in the composition are derived from a nonmicrobial oil. In some cases, the esters are selected from the group consisting of methyl, ethyl and alkyl esters. In some embodiments, the cultured microorganism has not been separated from liquid medium used to culture the microorganism, and/or is present at a ratio of less than 1:1 v/v of cultured microorganism to extracellular liquid media.

In various embodiments of the method of extracting lipid from a microorganism, the emulsion is cooled below 10° C., or to a temperature at or below 0° C. In one embodiment, the method further comprises centrifuging the lysate to produce layers comprising the emulsion and an aqueous layer. In some cases, the method further comprises separating the emulsion from the aqueous layer. In one embodiment, the lipid is extracted from the lipid:aqueous emulsion without use of an organic solvent. In some cases, the method further comprises treating the lysate with an organic solvent for a period of time sufficient to allow the lipid from the microorganism to become solubilized in the organic solvent.

Microorganisms useful in accordance with the present invention can be selected from the group of microorganisms consisting of a bacterium, a cyanobacterium, a eukaryotic microalgae, an oleaginous yeast, and a fungus. In some cases, the microorganisms can be selected from Tables 1, 2 or 3. Such microorganisms include microorganisms of the genus *Chlorella*. In one embodiment, the microorganism is *Chlorella protothecoides*. In some cases, the microorganisms of the present invention produce a lipid that comprises at least 10% w/v of total cellular lipid as C18 triacylglycerols, or at least 10% w/v of total cellular lipid as C16 triacylglycerols. In some cases, the microorganisms produce a lipid that comprises at least 10% w/v of total cellular lipid as C14 triacylglycerols, at least 10% w/v of total cellular lipid as C12 triacylglycerols, or at least 10% w/v of total cellular lipid as C10 triacylglycerols. In some cases, the microorganisms of the present invention have at least 85% 23S rRNA genomic sequence identity to one or more sequences selected from the group consisting of SEQ ID NOs:7-33.

In some cases, the microorganism is of the genus *Prototheca*. In one embodiment, the microorganism is *Prototheca moriformis*. In some cases, the microorganisms of the present invention have at least 75% sequence identity to one or more sequences selected from the group consisting of SEQ ID NOs: 33, 34, 35, 16, 36, 17, 37, 38, 39, and 32.

In various embodiments in accordance with the present invention, lysing the cultured microorganisms is performed at an acidic pH, at a pH of no more than 5, at a pH of no more than 4, at a pH of no more than 3, or at a pH of no more than 2. In some embodiments, lysing the cultured microorganisms is performed at a pH of at least 9. In some cases, lysing the cultured microorganism comprises one or more methods of lysing selected from the list consisting of heating, sonication, mechanical lysis, osmotic shock, pressure oscillation, expression of an autolysis gene, exposure to pH above 8, exposure to pH below 6, and digestion with an enzyme. In some cases, lysing the microorganism comprises acidic lysis and heating. In one embodiment, the microorganism is lysed by digestion with a polysaccharide-degrading enzyme, which can be a polysaccharide-degrading enzyme from *Chlorella* or a *Chlorella* virus. In some cases, the microorganism is lysed by digestion with a protease. In other cases, the microorganism is digested with a combination of at least one protease and at least one polysaccharide-degrading enzyme. In some cases, the protease is alcalase and/or the polysaccharide-degrading enzyme is mannaway. In some cases, other combinations of the foregoing are used, for example, contacting the biomass with a protease and a polysaccharide-degrading enzymes in combination with heating the biomass to a temperature of at least 30 degrees Celsius.

In various embodiments in accordance with the present invention, treating the lysate comprises treating with more than about 5% v/v of an organic solvent to the lysate. In other cases, the treating step comprises treating with more than about 6% v/v of an organic solvent to the lysate, or with more than about 7% v/v of an organic solvent to the lysate. In still other cases, the v/v of the organic solvent to the lysate is between greater than about 5% and greater than about 25%. In one embodiment, treatment of the lysate can be facilitated by agitating the lysate.

In embodiments of the present invention the organic solvent can comprise an oil. The oil can be selected from the group consisting of oil from soy, rapeseed, canola, palm, palm kernel, coconut, corn, waste vegetable, Chinese tallow, olive, sunflower, cotton seed, chicken fat, beef tallow, porcine tallow, microalgae, macroalgae, *Cuphea*, flax, peanut, choice white grease, lard, *Camelina sativa*, mustard seed cashew nut, oats, lupine, kenaf, *calendula*, hemp, coffee, linseed, hazelnut, *euphorbia*, pumpkin seed, coriander, camellia, sesame, safflower, rice, tung oil tree, cocoa, copra, pium poppy, castor beans, pecan, jojoba, jatropha, *macadamia*, Brazil nuts, avocado, a fossil oil, or a distillate fraction thereof. In some cases the oil is soy oil. In some cases the oil is palm oil. In other cases the oil is coconut oil. In still other cases the oil is canola oil. In yet other cases the oil is jatropha oil. In one embodiment, the time sufficient to allow the lipid from the microorganism to become solubilized in the organic solvent is between 0.1 and 30 minutes.

In various embodiments in accordance with the present invention, separating the lysate comprises centrifugation of the treated lysate, whereby the lysate is separated into a light layer comprising the lipid:organic solvent composition and a heavy layer comprising the aqueous composition and, optionally, an emulsified composition and/or cell pellet composition. In some cases, separating the lysate comprises settling of the treated lysate, whereby the lysate is separated into a light layer comprising the lipid:organic solvent composition and a heavy layer comprising the aqueous composition and, optionally, an emulsified composition and/or cell pellet composition. Separation of the lysate can include reducing the temperature of the mixture below 25° C., below 10° C., or to a temperature at or below 0° C. In some aspects of the invention, the layers further comprise a lipid:aqueous emulsion layer and/or a cell pellet.

In some cases, methods of the invention further comprise removing the lipid:organic solvent composition from the other layer(s). In one embodiment, removal is performed without substantially separating the lipid from the organic solvent.

In some methods of the invention, the microorganism is produced in a culturing process and then optionally stored for a period of time between termination of the culturing process and undertaking additional steps to lyse the microorganism. In some cases, lysing the microorganisms in the biomass produces a lysate comprising a lipid:aqueous emulsion. In some cases, the microorganism is stored for at least one hour between termination of the culturing process and undertaking additional steps to lyse the cultured microorganism. In some cases, the microorganism is stored for at least twenty-four hours between termination of the culturing process and undertaking additional steps to lyse the cultured microorganism. In some cases, the microorganism is stored for at least forty-eight hours between termination of the culturing process and undertaking additional steps to lyse the cultured microorganism. In other cases, the fermentation broth is stored. In some cases, the fermentation broth is concentrated, for example, by centrifugation or filtration, and the cells are resuspended in an aqueous media before storage. In some cases the aqueous media is deionized or distilled water.

In some embodiments of the present invention, microorganisms (biomass) prepared in a culture process are optionally stored at a temperature below 15 degrees Celsius between termination of the culturing process and undertaking additional steps to lyse the cultured microorganism. In some cases, the biomass is stored at a temperature below 5 degrees Celsius between termination of the culturing process and undertaking additional steps to lyse the cultured microorganisms. In some cases, the microorganism is stored at a temperature above 30 degrees Celsius between termination of the culturing process and undertaking additional steps to lyse the cultured microorganism. In some cases, the microorganism is stored at a temperature above 40 degrees Celsius between termination of the culturing process and undertaking additional steps to lyse the cultured microorganism. In some cases, the microorganism is subjected to agitation during storage.

DETAILED DESCRIPTION OF THE INVENTION

Definitions

Figure 1:
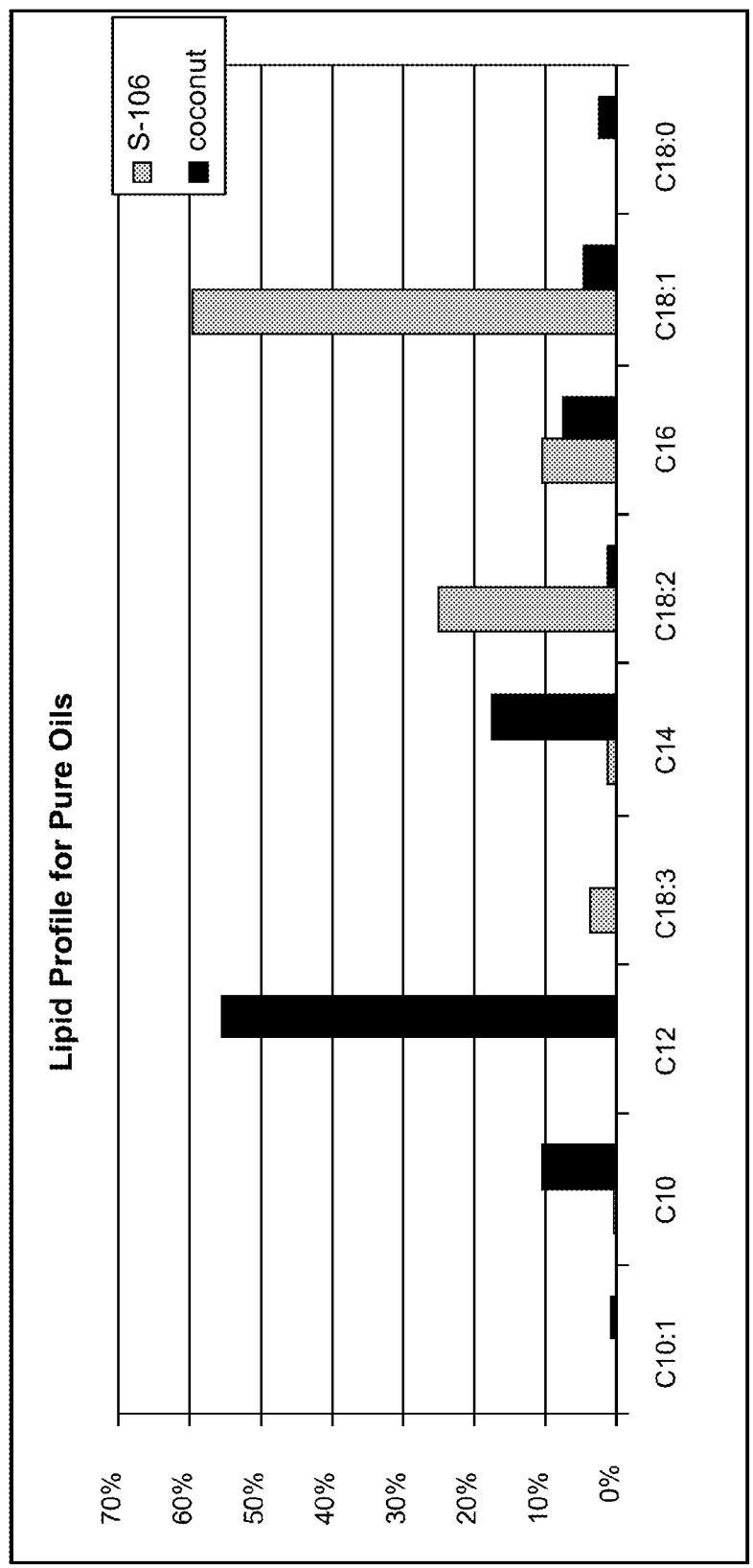
FIG. 1 depicts two lipid profiles for pure oils prepared according to the method of the present invention. Fatty acids C10:1, C10, C12, C18:3, C14, C18:2, C166, C18:1, and C18:0 of pure *Chlorella* oil (light-shaded bars) and coconut oil (dark-shaded bars) are shown. The majority of pure *Chlorella* oil comprises C18:1 fatty acids (59%), while the majority of pure coconut oil comprises C12 fatty acids (54%). Details are described in Example 6.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology* and *Molecular Biology* (2nd ed. 1994); The Cambridge Dictionary of Science and Technology (Walker ed., 1988); *The Glossary of Genetics*, 5th Ed., *R. Rieger* et al. (eds.), Springer Verlag (1991); and Hale & Marham, *The Harper Collins Dictionary of Biology* (1991). As used herein, the following terms have the meanings ascribed to them unless specified otherwise.

As used with reference to a nucleic acid, the phrase "active in microalgae" refers to a nucleic acid that is functional in microalgae. For example, a promoter that has been used to drive an antibiotic resistance gene to impart antibiotic resistance to a transgenic microalgae is active in microalgae. Examples of promoters active in microalgae are promoters endogenous to certain algae species and promoters found in plant viruses.

As used herein, an "acyl carrier protein" or "ACP" is a protein which binds a growing acyl chain during fatty acid synthesis as a thiol ester at the distal thiol of the 4'-phosphopantetheine moiety and comprises a component of the fatty acid synthase complex.

An "acyl-CoA molecule" or "acyl-CoA" is a molecule comprising an acyl moiety covalently attached to coenzyme A through a thiol ester linkage at the distal thiol of the 4'-phosphopantetheine moiety of coenzyme A.

As used herein, the term "alkyl" refers to a straight or branched chain hydrocarbon radical, and can include di- and multivalent radicals, having the number of carbon atoms designated (i.e. C1-C10 means one to ten carbons). Examples of saturated hydrocarbon radicals include groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

As used herein, the term "alkenyl" refers to an unsaturated alkyl group one having one or more double bonds. Examples of alkenyl groups include vinyl, 2-propenyl, crotyl, 2-isopentenyl, 2-(butadienyl), 2,4-pentadienyl and 3-(1,4-pentadienyl), and the higher homologs and isomers.

As used herein, the term "alkynyl" refers to an unsaturated alkyl group one having one or more triple bonds. Examples of alkynyl groups include ethynyl (acetylenyl), 1-propynyl, 1- and 2-butynyl, and the higher homologs and isomers.

As used herein, the phrase "aqueous or emulsified composition" refers to microbial biomass that contains lipid.

As used herein, the phrase "area percent" refers to the area of peaks observed using FAME GC/FID detection methods in which every fatty acid in the sample is converted into a fatty acid methyl ester (FAME) prior to detection. For examples, a separate peak is observed for a fatty acid of 14 carbon atoms with no unsaturation (C14:0) compared to any other fatty acid such as a C14:1. The peak area for each class of FAME is directly proportional to its percent composition in the mixture and is calculated based on the sum of all peaks present in the sample (i.e., [area under specific peak/total area of all measured peaks]×100). When referring to lipid profiles of oils and cells of the invention, "at least 4% C8-C14," for example, means that at least 4% of the total fatty acids in the cell or in the extracted glycerolipid composition have a chain length that includes 8, 10, 12, or 14 carbon atoms.

As used herein, the term "aryl" refers to a polyunsaturated, aromatic, hydrocarbon substituent having 5-12 ring members, which can be a single ring or multiple rings (up to three rings) which are fused together or linked covalently. Non-limiting examples of aryl groups include phenyl, 1-naphthyl, 2-naphthyl, 4-biphenyl, and benzyl. Other aryl groups are also useful in the present invention.

As used herein, the term "axenic" refers to a culture of an organism that is free from contamination by other living organisms.

As used herein, the term "base" refers to any compound whose pKa is greater than that of water.

As used herein, the term "biodiesel" refers to a fatty acid ester produced from transesterification of a lipid.

As used herein, the term "biomass" refers to material produced by growth and/or propagation of cells. Biomass may contain cells and/or intracellular contents as well as extracellular material. Extracellular material includes, but is not limited to, compounds secreted by a cell.

As used herein, the term "bioreactor" refers to an enclosure or partial enclosure in which cells, e.g., microorganisms, are cultured, optionally in suspension.

As used herein, the term "catalyst" refers to an agent, such as a molecule or macromolecular complex, capable of facilitating or promoting a chemical reaction of a reactant to a product without becoming a part of the product. A catalyst thus increases the rate of a reaction, after which, the catalyst may act on another reactant to form the product. A catalyst generally lowers the overall activation energy required for the reaction such that it proceeds more quickly or at a lower temperature. Thus a reaction equilibrium may be more quickly attained. Examples of catalysts include enzymes, which are biological catalysts, and heat, which is a non-biological catalyst.

As used herein, the term "cellulosic material" means the products of digestion of cellulose, such as glucose, xylose, arabinose, disaccharides, oligosaccharides, lignin, furfurals, and other molecules.

As used herein, the term "co-culture" and variants thereof, such as "co-cultivate," refer to the presence of two or more types of cells in the same bioreactor. The two or more types of cells may both be microorganisms, such as microalgae, or may be a microalgal cell cultured with a different cell type. The culture conditions may be those that foster growth and/or propagation of the two or more cell types or those that facilitate growth and/or proliferation of one, or a subset, of the two or more cells while maintaining cellular growth for the remainder.

As used herein, the term "cofactor" refers to any molecule, other than the substrate, that is required for an enzyme to carry out its enzymatic activity.

A "constitutive" promoter is a promoter that is active under most environmental and developmental conditions.

As used herein, the term "cultivated" and variants thereof, refer to the intentional fostering of growth (increases in cell size, cellular contents, and/or cellular activity) and/or propagation (increases in cell numbers via mitosis) of one or more cells by use of intended culture conditions. The combination of both growth and propagation may be termed proliferation. The one or more cells may be those of a microorganism, such as microalgae. Examples of intended conditions include the use of a defined medium (with known characteristics such as pH, ionic strength, and carbon source), specified temperature, oxygen tension, carbon dioxide levels, and growth in a bioreactor. The term does not refer to the growth or propagation of microorganisms in nature or otherwise without direct human intervention, such as natural growth of an organism that ultimately becomes fossilized to produce geological crude oil.

As used herein, the term "cycloalkyl" refers to a saturated cyclic hydrocarbon having 3 to 15 carbons, and 1 to 3 rings that can be fused or linked covalently. Cycloalkyl groups useful in the present invention include, but are not limited to, cyclopentyl, cyclohexyl, cycloheptyl and cyclooctyl. Bicycloalkyl groups useful in the present invention include, but are not limited to, [3.3.0]bicyclooctanyl, [2.2.2]bicyclooctanyl, [4.3.0]bicyclononane, [4.4.0]bicyclodecane (decalin), spiro[3.4]octanyl, spiro[2.5]octanyl, and so forth.

As used herein, the term "cycloalkenyl" refers to an unsaturated cyclic hydrocarbon having 3 to 15 carbons, and 1 to 3 rings that can be fused or linked covalently. Cycloalkenyl groups useful in the present invention include, but are not limited to, cyclopentenyl, cyclohexenyl, cycloheptenyl and cyclooctenyl. Bicycloalkenyl groups are also useful in the present invention.

As used herein, the term "cytolysis" refers to the lysis of cells in a hypotonic environment. Cytolysis is caused by excessive osmosis, or movement of water, towards the inside of a cell (hyperhydration). The cell membrane cannot withstand the osmotic pressure of the water inside, and so it explodes.

As used herein, the term "exogenous gene" refers to a nucleic acid transformed into a cell. A transformed cell may be referred to as a recombinant cell, into which additional exogenous gene(s) may be introduced. The exogenous gene may be from a different species (and so heterologous), or from the same species (and so homologous) relative to the cell being transformed. In the case of a homologous gene, it occupies a different location in the genome of the cell relative to the endogenous copy of the gene. The exogenous gene may be present in more than one copy in the cell. The exogenous gene may be maintained in a cell as an insertion into the genome or as an episomal molecule.

As used herein, the term "exogenously provided" in the context of culturing a cell, refers to a molecule provided to a culture media of a cell culture.

As used herein, the terms "expression vector" or "expression construct" refer to a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

As used herein, a "fatty acyl-ACP thioesterase" is an enzyme that catalyzes the cleavage of a fatty acid from an acyl carrier protein (ACP) during lipid synthesis.

As used herein, a "fatty acyl-CoA/aldehyde reductase" is an enzyme that catalyzes the reduction of an acyl-CoA molecule to a primary alcohol.

As used herein, a "fatty acyl-CoA reductase" is an enzyme that catalyzes the reduction of an acyl-CoA molecule to an aldehyde.

As used herein, a "fatty aldehyde decarbonylase" is an enzyme that catalyzes the conversion of a fatty aldehyde to an alkane.

As used herein, a "fatty aldehyde reductase" is an enzyme that catalyzes the reduction of an aldehyde to a primary alcohol.

As used herein, the term "fixed carbon source" means molecule(s) containing carbon, preferably organic, that are present at ambient temperature and pressure in solid or liquid form.

As used herein, the term "fungus," means heterotrophic organisms characterized by a chitinous cell wall from the kingdom of fungi.

As used herein, the term "heteroaryl" refers to a polyunsaturated, aromatic, hydrocarbon substituent having 5-12 ring members, which can be a single ring or multiple rings (up to three rings) which are fused together or linked covalently, and which has at least one heteroatom in the ring, such as N, O, or S. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Additional heteroaryl groups useful in the present invention include pyridyl N-oxide, tetrazolyl, benzofuranyl, benzothienyl, indazolyl, or any of the radicals substituted, especially mono- or di-substituted.

As used herein, the term "heteroatom" means any atom that is not carbon or hydrogen. Examples of heteroatoms include magnesium, calcium, potassium, sodium, sulfur, phosphorus, iron and copper.

As used herein, the term "heterocycloalkyl" refers to a saturated cyclic hydrocarbon having 3 to 15 ring members, and 1 to 3 rings that can be fused or linked covalently, and which has at least one heteroatom in the ring, such as N, O, or S. Additionally, a heteroatom can occupy the position at which the heterocycle is attached to the remainder of the molecule. Examples of heterocycloalkyl include 1 (1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

As used herein, in the context of biomass, the term "homogenate" means biomass that has been physically disrupted.

As used herein, "hydrocarbon" refers to: (a) a molecule containing only hydrogen and carbon atoms wherein the carbon atoms are covalently linked to form a linear, branched, cyclic, or partially cyclic backbone to which the hydrogen atoms are attached; or (b) a molecule that only primarily contains hydrogen and carbon atoms and that can be converted to contain only hydrogen and carbon atoms by one to four chemical reactions. Nonlimiting examples of the latter include hydrocarbons containing an oxygen atom between one carbon and one hydrogen atom to form an alcohol molecule, as well as aldehydes containing a single oxygen atom. Methods for the reduction of alcohols to hydrocarbons containing only carbon and hydrogen atoms are well known. Another example of a hydrocarbon is an ester, in which an organic group replaces a hydrogen atom (or more than one) in an oxygen acid. The molecular structure of hydrocarbon compounds varies from the simplest, in the form of methane (CH4), which is a constituent of natural gas, to the very heavy and very complex, such as some molecules such as asphaltenes found in crude oil, petroleum, and bitumens. Hydrocarbons may be in gaseous, liquid, or solid form, or any combination of these forms, and may have one or more double or triple bonds between adjacent carbon atoms in the backbone. Accordingly, the term includes linear, branched, cyclic, or partially cyclic alkanes, alkenes, lipids, and paraffin. Examples include propane, butane, pentane, hexane, octane, squalene and carotenoids.

As used herein, the term "hydrocarbon modification enzyme" refers to an enzyme that alters the covalent structure of a hydrocarbon. Examples of hydrocarbon modification enzymes include a lipase, a fatty acyl-ACP thioesterase, a fatty acyl-CoA/aldehyde reductase, a fatty acyl-CoA reductase, a fatty aldehyde reductase, and a fatty aldehyde decarbonylase.

As used herein, the term "hydrogen:carbon ratio" refers to the ratio of hydrogen atoms to carbon atoms in a molecule on an atom-to-atom basis. The ratio may be used to refer to the number of carbon and hydrogen atoms in a hydrocarbon molecule. For example, the hydrocarbon with the highest ratio is methane $CH_4$ (4:1).

As used herein, the term "hydrophobic fraction" refers to a portion, or fraction, of a material that is more soluble in a hydrophobic phase in comparison to an aqueous phase. A hydrophobic fraction is substantially insoluble in water and usually non-polar.

As used herein, the phrase "increase lipid yield" refers to an increase in the productivity of a microbial culture by, for example, increasing dry weight of cells per liter of culture, increasing the percentage of cells that constitute lipid, or increasing the overall amount of lipid per liter of culture volume per unit time.

An "inducible promoter" is one that mediates transcription of an operably linked gene in response to a particular stimulus.

As used herein, the term "in situ" means "in place" or "in its original position." For example, a culture may contain a first microalgae secreting a catalyst and a second microorganism secreting a substrate, wherein the first and second cell types produce the components necessary for a particular chemical reaction to occur in situ in the co-culture without requiring further separation or processing of the materials.

As used herein, the term "isomers" refers to compounds of the present invention that possess asymmetric carbon atoms (optical centers) or double bonds. The racemates, diastereomers, geometric isomers and individual isomers are all intended to be encompassed within the scope of the present invention.

As used herein, the phrase "limiting concentration of a nutrient" refers to a concentration in a culture that limits the propagation of a cultured organism. A "non-limiting concentration of a nutrient" is a concentration that supports maximal propagation during a given culture period. Thus, the number of cells produced during a given culture period is lower in the presence of a limiting concentration of a nutrient than when the nutrient is non-limiting. A nutrient is said to be "in excess" in a culture, when the nutrient is present at a concentration greater than that which supports maximal propagation.

As used herein, a "lipase" is an enzyme that catalyzes the hydrolysis of ester bonds in water-insoluble, lipid substrates. Lipases catalyze the hydrolysis of lipids into glycerols and fatty acids.

"Lipids" are a class of molecules that are soluble in nonpolar solvents (such as ether and chloroform) and are relatively or completely insoluble in water. Lipid molecules have these properties because they consist largely of long hydrocarbon tails that are hydrophobic in nature. Examples of lipids include fatty acids (saturated and unsaturated); glycerides or glycerolipids (such as monoglycerides, diglycerides, triglyceries or neutral fats and phosophoglycerides or glycerophospholipids); nonglycerides (sphingolipids, sterol lipids including cholesterol and steroid hormones, prenol lipids including terpenoids, fatty alcohols, waxes and polyketides); and complex lipid derivatives (sugar-linked lipids, or glycolipids, and protein-linked lipids). "Fats" are a subgroup of lipids called "triacylglycerides".

As used herein, the phrase "lipid:organic solvent composition" refers to a mixture of lipid and organic solvent.

As used herein, a "lipid pathway enzyme" is any enzyme that plays a role in lipid metabolism, i.e., either lipid synthesis, modification, or degradation. This term encompasses proteins that chemically modify lipids, as well as carrier proteins.

As used herein, the term "lysate" refers to a solution containing the contents of lysed cells.

As used herein, the term "lysis" refers to the breakage of the plasma membrane and optionally the cell wall of a biological organism sufficient to release at least some intracellular content, often by mechanical, viral or osmotic mechanisms that compromise its integrity.

As used herein, the term "lysing" refers to disrupting the cellular membrane and optionally the cell wall of a biological organism or cell sufficient to release at least some intracellular content.

As used herein, the term "microalgae" means a microbial organism that is either (a) eukaryotic and contains a chloroplast or chloroplast remnant, or (b) is a cyanobacteria. Microalgae include obligate photoautotrophs, which cannot metabolize a fixed carbon source as energy, as well as heterotrophs, which can live solely off of a fixed carbon source. Microalgae can refer to unicellular organisms that separate from sister cells shortly after cell division, such as *Chlamydomonas*, and can also refer to microbes such as, for example, *Volvox*, which is a simple multicellular photosynthetic microbe of two distinct cell types. "Microalgae" can also refer to cells such as *Chlorella* and *Dunaliella*. "Microalgae" also includes other microbial photosynthetic organisms that exhibit cell-cell adhesion, such as *Agmenellum, Anabaena*, and *Pyrobotrys*, as well as organisms that contain chloroplast-like structures that are no longer capable of performing photosynthesis, such as microalgae of the genus *Prototheca* and some dinoflagellates. "Microalgae" also includes obligate heterotrophic micoorganisms that have lost the ability to perform photosynthesis, such as certain dinoflagellate species.

The terms "microorganism" and "microbe" are used interchangeably herein to refer to microscopic unicellular organisms.

As used herein, the term "oil" means a hydrophobic, lipophilic, nonpolar carbon-containing substance including but not limited to geologically-derived crude oil, distillate fractions of geologically-derived crude oil, vegetable oil, algal oil, and microbial lipids.

As used herein, the term "oleaginous yeast," means yeast that can accumulate more than 10% of its dry cell weight as lipid. Oleaginous yeast includes organisms such as *Yarrowia lipolytica*, as well as engineered strains of yeast such as *Saccharomyces cerevisiae* that have been engineered to accumulate more than 10% of the dry cell weight as lipid.

As used herein, the terms "operably linked," "in operable linkage," or grammatical equivalents thereof refer to a functional linkage between two sequences, such a control sequence (typically a promoter) and the linked sequence. A promoter is in operable linkage with an exogenous gene if it can mediate transcription of the gene.

As used herein, the term "organic solvent" refers to a carbon-containing material that dissolves a solid, liquid, or gaseous solute, resulting in a solution.

As used herein, the term "osmotic shock" refers to the rupture of bacterial, algal, or other cells in a solution following a sudden reduction in osmotic pressure. Osmotic shock is sometimes induced to release cellular components of such cells into a solution.

As used herein, the term "photobioreactor" refers to a container, at least part of which is at least partially transparent or partially open, thereby allowing light to pass through, in which, e.g., one or more microalgae cells are cultured. Photobioreactors may be closed, as in the instance of a polyethylene bag or Erlenmeyer flask, or may be open to the environment, as in the instance of an outdoor pond.

As used herein, the term "polysaccharide" (also called "glycan") refers to carbohydrate made up of monosaccharides joined together by glycosidic linkages. Cellulose is an example of a polysaccharide that makes up certain plant cell walls. Cellulose can be depolymerized by enzymes to yield monosaccharides such as xylose and glucose, as well as larger disaccharides and oligosaccharides.

As used herein, the term "polysaccharide-degrading enzyme" refers to any enzyme capable of catalyzing the hydrolysis, or depolymerization, of any polysaccharide. For example, cellulase catalyzes the hydrolysis of cellulose.

As used herein, the term "port," in the context of a bioreactor, refers to an opening in the bioreactor that allows influx or efflux of materials such as gases, liquids, and cells. Ports are usually connected to tubing leading from the photobioreactor.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

As used herein, the term "renewable diesel" refers to a mixture of alkanes (such as C10:0, C12:0, C14:0, C16:0 and C18:0) produced through hydrogenation and deoxygenation of lipids. Renewable diesel also includes diesel fuel derived from biomass as defined in Section 45K(c)(3), using the process of thermal depolymerization (EPAct 2005).

As used herein, the term "sonication" refers to a process of disrupting biologic materials, such as a cell, by use of sound wave energy.

As used herein, the term "wastewater" refers to a watery waste which typically contains washing water, laundry waste, faeces, urine, and other liquid or semi-liquid wastes. It includes some forms of municipal waste as well as secondarily treated sewage.

II. General

U.S. Patent application Nos. 60/941,581; 60/959,174; 60/968,291; and 61/024,069 are hereby incorporated by reference in their entirety for all purposes.

The invention generally relates to the production of hydrocarbon compositions, such as a lipid, in microorganisms. In particular, the invention provides methods for extracting, recovering, isolating and obtaining a lipid from a microorganism and compositions comprising the lipid. The invention also discloses methods for producing hydrocarbon compositions for use as biodiesel, renewable diesel, jet fuel, and for producing a lipid surfactant having a carbon chain length of C12 and C14.

The invention is premised in part on the insight that certain microorganisms can be used to produce hydrocarbon compositions economically and in large quantities for use in the transportation fuel and petrochemical industry among other applications. Suitable microorganisms include microalgae, oleaginous yeast, and fungi. A preferred genus of microalgae for use in the invention is the lipid-producing microalgae *Chlorella*. Acidic transesterification of lipids yields long-chain fatty acid esters useful as biodiesel. Other enzymatic processes can be tailored to yield fatty acids, aldehydes, alcohols, and alkanes. The present application describes methods for genetic modification of multiple species and strains of microorganisms, including *Chlorella* and similar microbes to provide organisms having characteristics that facilitate the production of lipids suitable for conversion into biodiesel or other hydrocarbon compounds. The present application also describes methods of cultivating microalgae for increased productivity and increased lipid yield.

Microorganisms useful in the invention produce lipids or hydrocarbons suitable for biodiesel production or as feedstock for industrial applications. Suitable hydrocarbons for biodiesel production include triacylglycerides (TAGs) containing long-chain fatty acid molecules. Suitable hydrocarbons for industrial applications, such as surfactant manufacturing, include fatty acids, aldehydes, alcohols, and alkanes. In some embodiments, suitable fatty acids, or the corresponding primary alcohols, aldehydes, or alkanes, generated by the methods described herein, contain at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, or at least 35 carbon atoms or more. Preferred long-chain fatty acids for biodiesel generally contain at least 14 carbon atoms or more.

Preferred fatty acids, or the corresponding primary alcohols, aldehydes, and alkanes, for industrial applications contain at least 8 carbon atoms or more. In certain embodiments, the above fatty acids, as well as the other corresponding hydrocarbon molecules, are saturated (with no carbon-carbon double or triple bonds); mono unsaturated (single double bond); poly unsaturated (two or more double bonds); are linear (not cyclic); and/or have little or no branching in their structures.

Triacylglycerols containing carbon chain lengths in the C8 to C22 range are preferred. Preferred for surfactants are C10-C14. Preferred for biodiesel or renewable diesel are C16 to C18. Preferred for jet fuel are C8-C10. Preferred for nutrition are C22 polyunsaturated fatty acids (such as DHA) and carotenoids (such as astaxanthin).

III. Microorganisms Useful for Producing Lipids

Any species of organism that produces suitable lipid or hydrocarbon can be used, although microorganisms that naturally produce high levels of suitable lipid or hydrocarbon are preferred. Production of hydrocarbons by microorganisms is reviewed by Metzger et al. *Appl Microbiol Biotechnol* (2005) 66: 486-496 and A Look Back at the U.S. Department of Energy's Aquatic Species Program: Biodiesel from Algae, NREL/TP-580-24190, John Sheehan, Terri Dunahay, John Benemann and Paul Roessler (1998).

Considerations affecting the selection of a microorganism for use in the invention include, in addition to production of suitable hydrocarbons for biodiesel or for industrial applications: (1) high lipid content as a percentage of cell weight; (2) ease of growth; (3) ease of genetic engineering; and (3) ease of processing. In particular embodiments, the wild-type or genetically engineered microorganism yields cells that are at least: about 40%, about 45%, about 50%, about 55%, about 60%, about 65%, or about 70% or more lipid. Preferred organisms grow heterotrophically (on sugar in the absence of light) or can be engineered to do so using, for example, methods disclosed in commonly-owned U.S. Patent Application Nos. 60/837,839 and 60/968,291, which are incorporated herein by reference in their entireties. The ease of transformation and availability of selectable markers and promoters, constitutive and/or inducible, that are functional in the microorganism affect the ease of genetic engineering. Processing considerations can include, for example, the availability of effective means for lysing the cells.

A. Algae

In a preferred embodiment of the present invention, a microorganism producing a lipid or a microorganism from which a lipid can be extracted, recovered, or obtained, is an algae.

Examples of algae that can be used to practice the present invention include, but are not limited to the following algae listed in Table 1.

TABLE 1

Examples of algae.

*Achnanthes orientalis, Agmenellum, Amphiprora hyaline, Amphora coffeiformis, Amphora coffeiformis linea, Amphora coffeiformis punctata, Amphora coffeiformis taylori, Amphora coffeiformis tenuis, Amphora delicatissima, Amphora delicatissima capitata, Amphora sp., Anabaena, Ankistrodesmus, Ankistrodesmus falcatus, Boekelovia hooglandii, Borodinella sp., Botryococcus braunii, Botryococcus sudeticus, Carteria, Chaetoceros gracilis, Chaetoceros muelleri, Chaetoceros muelleri subsalsum, Chaetoceros sp., Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca var. vacuolata, Chlorella glucotropha, Chlorella infusionum, Chlorella infusionum var. actophila, Chlorella infusionum var. auxenophila, Chlorella kessleri, Chlorella lobophora (strain SAG 37.88), Chlorella luteoviridis, Chlorella luteoviridis var. aureoviridis, Chlorella luteoviridis var. lutescens, Chlorella miniata, Chlorella minutissima, Chlorella mutabilis, Chlorella nocturna, Chlorella parva, Chlorella photophila, Chlorella pringsheimii, Chlorella protothecoides* (including any of UTEX strains 1806, 411, 264, 256, 255, 250, 249, 31, 29, 25, and CCAP strains 211/17 and 211/8d), *Chlorella protothecoides var. acidicola, Chlorella regularis, Chlorella regularis var. minima, Chlorella regularis var. umbricata, Chlorella reisiglii, Chlorella saccharophila, Chlorella saccharophila var. ellipsoidea, Chlorella salina, Chlorella simplex, Chlorella sorokiniana, Chlorella sp., Chlorella sphaerica, Chlorella stigmatophora, Chlorella vanniellii, Chlorella vulgaris, Chlorella vulgaris, Chlorella vulgaris f. tertia, Chlorella vulgaris var. autotrophica, Chlorella vulgaris var. viridis, Chlorella vulgaris var. vulgaris, Chlorella vulgaris var. vulgaris f. tertia, Chlorella vulgaris var. vulgaris f. viridis, Chlorella xanthella, Chlorella zofingiensis, Chlorella trebouxioides, Chlorella vulgaris, Chlorococcum infusionum, Chlorococcum sp., Chlorogonium, Chroomonas sp., Chrysosphaera sp., Cricosphaera sp., Cryptomonas sp., Cyclotella cryptica, Cyclotella meneghiniana, Cyclotella sp., Dunaliella sp., Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera sp., Ellipsoidon sp., Euglena, Franceia sp., Fragilaria crotonensis, Fragilaria sp., Gleocapsa sp., Gloeothamnion sp., Hymenomonas sp., Isochrysis* aff. *galbana, Isochrysis galbana, Lepocinclis, Micractinium, Micractinium* (UTEX LB 2614), *Monoraphidium minutum, Monoraphidium sp., Nannochloris sp., Nannochloropsis salina, Nannochloropsis sp., Navicula acceptata, Navicula biskanterae, Navicula pseudotenelloides, Navicula pelliculosa, Navicula saprophila, Navicula sp., Nephrochloris sp., Nephroselmis sp., Nitschia communis, Nitzschia alexandrina, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia sp., Ochromonas sp., Oocystis parva, Oocystis pusilla, Oocystis sp., Oscillatoria limnetica, Oscillatoria sp., Oscillatoria subbrevis, Pascheria acidophila,*

TABLE 1-continued

Examples of algae.

*Pavlova* sp., *Phagus*, *Phormidium*, *Platymonas* sp., *Pleurochrysis carterae*, *Pleurochrysis dentate*, *Pleurochrysis* sp., *Prototheca wickerhamii*, *Prototheca stagnora*, *Prototheca portoricensis*, *Prototheca moriformis*, *Prototheca zopfii*, *Pyramimonas* sp., *Pyrobotrys*, *Sarcinoid chrysophyte*, *Scenedesmus armatus*, *Spirogyra*, *Spirulina platensis*, *Stichococcus* sp., *Synechococcus* sp., *Tetraedron*, *Tetraselmis* sp., *Tetraselmis suecica*, *Thalassiosira weissflogii*, and *Viridiella fridericiana*

1. *Chlorella* and *Prototheca*

In a preferred embodiment of the present invention, the microorganism producing a lipid or a microorganism from which a lipid can be extracted, recovered, or obtained, is of the genus *Chlorella*, preferably, *Chlorella prototheco ides*.

*Chlorella* is a genus of single-celled green algae, belonging to the phylum Chlorophyta. It is spherical in sh ape, about 2 to 10 μm in diameter, and is without flagella. Some species of *Chlorella* are naturally heterotrophic.

*Chlorella*, particularly *Chlorella prototheco ides*, is a preferred microorganism for use in the invention because of its high composition (at least about 55% by weight) of lipid, particularly long-chain lipid suitable for biodiesel. In addition, this microalgae grows heterotrophically, can be genetically engineered as demonstrated in the Examples herein, and can be lysed by *Chlorella* virus.

In a preferred embodiment of the present invention, the microorganism used for expression of a transgene is of the genus *Chlorella*, preferably, *Chlorella prototheco ides*. Examples of expression of transgenes in, e.g., *Chlorella*, can be found in the literature (see for example *Current Microbiology* Vol. 35 (1997), pp. 356-362; Sheng Wu Gong Cheng Xue Bao. 2000 July; 16(4):443-6; *Current Microbiology* Vol. 38 (1999), pp. 335-341; *Appl Microbiol Biotechnol* (2006) 72: 197-205; *Marine Biotechnology* 4, 63-73, 2002; *Current Genetics* 39:5, 365-370 (2001); *Plant Cell Reports* 18:9, 778-780, (1999); *Biologia Plantarium* 42(2): 209-216, (1999); *Plant Pathol.* J 21(1): 13-20, (2005)). Also see Examples herein. Other lipid-producing microbes can be engineered as well, including prokaryotic microbes (see Kalscheuer et al., Applied Microbiology and Biotechnology, volume 52, number 4/October, 1999).

In another preferred embodiment of the present invention, the microorganism producing a lipid or a microorganism from which a lipid can be extracted, recovered, or obtained, is of the genus *Prototheca*, preferably, *Prototheca moriformis*. Species of the genus *Prototheca* are suited for the production of lipid because they can produce high levels of lipids, particularly lipids suitable for fuel and chemical production. The lipid produced by *Prototheca* has fatty acid chains of shorter chain length and a higher degree of saturation than the lipid produced by most microalgae. Moreover, *Prototheca* lipid is generally free of pigment (low to undetectable levels of chlorophyll and certain carotenoids) and in any event contains much less pigment than lipid from other microalgae. Illustrative *Prototheca* strains for use in the methods of the invention include *Prototheca wickerhamii*, *Prototheca stagnora* (including UTEX 327), *Prototheca portoricensis*, *Prototheca moriformis* (including UTEX strains 1441, 1435), and *Prototheca zopfii*. Species of the genus *Prototheca* are obligate heterotrophs.

2. Identification of Microalgal Species

Species of microalgae, including *Chlorella* and *Prototheca*, for use in the invention can be identified by amplification of certain target regions of the genome. For example, identification of a specific *Chlorella* species can be achieved through amplification and sequencing of nuclear and/or chloroplast DNA using primers and methodology described in Wu et al., Identification of *Chlorella* spp. isolates using any region of the genome. Examples include ribosomal DNA sequences, *Bot. Bull. Acad. Sin.* (2001) 42:115-121. Well established methods of phylogenetic analysis, such as amplification and sequencing of ribosomal internal transcribed spacer (ITS1 and ITS2 rDNA), 18S rRNA, and other conserved genomic regions can be used by those skilled in the art to identify species of not only *Chlorella* or *Prototheca*, but other hydrocarbon and lipid producing organisms capable of using the methods disclosed herein. For examples of methods of identification and classification of algae also see for example *Genetics*, 2005 August; 170(4):1601-10 and RNA, 2005 Apr. 11(4):361-4.

Genomic DNA comparison can be used to identify species of microalgae to be used in the present invention. Regions of conserved genomic DNA, such as but not limited to DNA encoding 23S rRNA, can be amplied from microalgal species and compared to consensus sequences in order to screen for microalgal species that are taxonomically related to the preferred microalgae used in the present invention. Examples of such DNA sequence comparison for species within the *Chlorella* genus are shown below.

Genomic DNA comparison can also be useful to identify microalgal species that have been misidentified in a strain collection. Often a strain collection will identify species of microalgae based on phenotypic and morphological characteristics. The use of these characteristics may lead to miscategorization of the species or the genus of a microalgae. The use of genomic DNA comparison can be a better method of categorizing microalgae species based on their phylogenetic relationship. Specific examples of using genotyping data to establish phyogenetic relationships of possibly misidentified microalgal strains are described below in the Examples.

In some cases, microalgae that are preferred for use in the present invention have genomic DNA sequences encoding for 23S rRNA that have at least 99%, at least 98%, at least 97%, at least 96%, at least 95%, at least 94%, at least 93%, at least 92%, at least 91%, at least 90%, at least 89%, at least 88%, at least 87%, or at least 86% nucleotide identity to at least one of the sequences listed in SEQ ID NOs: 7-31. In other cases, microalgae that are preferred for use in the present invention have genomic DNA sequences encoding for 23S rRNA that have at least 85%, at least 80%, at least 75% at least 70% at least 65% or at least 60% nucleotide identity to at least one of the sequences listed in SEQ ID NOs. 7-31, 32, 33, 34, 35, 36, 37, 38, and 39.

B. Oleaginous Yeast

In a preferred embodiment of the present invention, a microorganism producing a lipid or a microorganism from which a lipid can be extracted, recovered, or obtained, is an oleaginous yeast.

Examples of oleaginous yeast that can be used to practice the present invention include, but are not limited to the following oleaginous yeast listed in Table 2.

TABLE 2

Examples of oleaginous yeast.

*Candida apicola, Candida* sp., *Cryptococcus curvatus, Cryptococcus terricolus, Debaromyces hansenii, Endomycopsis vernalis, Geotrichum carabidarum, Geotrichum cucujoidarum, Geotrichum histeridarum, Geotrichum silvicola, Geotrichum vulgare, Hyphopichia burtonii, Lipomyces lipofer, Lypomyces orentalis, Lipomyces starkeyi, Lipomyces tetrasporous, Pichia mexicana, Rodosporidium sphaerocarpum, Rhodosporidium toruloides Rhodotorula aurantiaca, Rhodotorula dairenensis, Rhodotorula diffluens, Rhodotorula glutinus, Rhodotorula glutinis* var. *glutinis, Rhodotorula gracilis, Rhodotorula graminis Rhodotorula minuta, Rhodotorula mucilaginosa, Rhodotorula mucilaginosa* var. *mucilaginosa, Rhodotorula terpenoidalis, Rhodotorula toruloides, Sporobolomyces alborubescens, Starmerella bombicola, Torulaspora delbruekii, Torulaspora pretoriensis, Trichosporon behrend, Trichosporon brassicae , Trichosporon domesticum, Trichosporon laibachii, Trichosporon loubieri, Trichosporon loubieri* var. *loubieri, Trichosporon montevideense, Trichosporon pullulans, Trichosporon* sp., *Wickerhamomyces Canadensis, Yarrowia lipolytica,* and *Zygoascus meyerae.*

In a preferred embodiment of the present invention, the microorganism used for expression of a transgene is an oleaginous yeast. Examples of expression of transgenes in oleaginous yeast (e.g., *Yarrowia lipolytica*) can be found in the literature (see, for example, Bordes et al., *J Microbiol Methods,* June 27 (2007)).

C. Other Fungi

In a preferred embodiment of the present invention, a microorganism producing a lipid or a microorganism from which a lipid can be extracted, recovered, or obtained, is a fungus.

Examples of fungi that can be used to practice the present invention include, but are not limited to the following fungi listed in Table 3.

TABLE 3

Examples of non-yeast fungi.

*Mortierella, Mortierrla vinacea, Mortierella alpine, Pythium debaryanum, Mucor circinelloides, Aspergillus ochraceus, Aspergillus terreus, Pennicillium iilacinum, Hensenulo, Chaetomium, Cladosporium, Malbranchea, Rhizopus,* and *Pythium*

In a preferred embodiment of the present invention, the microorganism used for expression of a transgene is a fungus. Examples of expression of transgenes in fungi (e.g., *Mortierella alpine, Mucor circinelloides,* and *Aspergillus ochraceus*) can also be found in the literature (see, for example, *Microbiology,* July; 153(Pt. 7):2013-25 (2007); *Mol Genet Genomics,* June; 271(5):595-602 (2004); *Curr Genet,* March; 21(3): 215-23 (1992); *Current Microbiology,* 30(2):83-86 (1995); Sakuradani, NISR Research Grant, "Studies of Metabolic Engineering of Useful Lipid-producing Microorganisms" (2004); and PCT/JP2004/012021).

D. Bacteria

In a preferred embodiment of the present invention, a microorganism producing a lipid or a microorganism from which a lipid can be extracted, recovered, or obtained, is a bacterium.

Examples of expression of exogenous genes in bacteria, such as *E. coli,* are well known; see for example *Molecular Cloning: A Laboratory Manual,* Sambrook et al. (3d edition, 2001, Cold Spring Harbor Press).

IV. Microbe Engineering

In certain embodiments of the present invention, it is desirous to genetically modify a microorganism. Thus, the present application describes genetically engineering strains of microalgae, oleaginous yeast, bacteria, or fungi with one or more exogenous genes to produce various hydrocarbon compounds.

Promoters, cDNAs, and 3'UTRs, as well as other elements of expression vectors, can be generated through cloning techniques using fragments isolated from native sources (see for example *Molecular Cloning: A Laboratory Manual,* Sambrook et al. (3d edition, 2001, Cold Spring Harbor Press; and U.S. Pat. No. 4,683,202). Alternatively, elements can be generated synthetically using known methods (see for example *Gene,* 1995 Oct. 16; 164(1):49-53).

A. Codon-Optimization for Expression

DNA encoding a polypeptide to be expressed in a microorganism, e.g., a lipase and selectable marker are preferably codon-optimized cDNA. Methods of recoding genes for expression in microalgae are described in U.S. Pat. No. 7,135, 290. Additional information for codon optimization is available, e.g., at the codon usage database of GenBank. As non-limiting examples, codon usage in *Prototheca* species, *Dunaliella salina,* and *Chlorella protothecoides* are shown in Tables 4, 5, and 6, respectively.

TABLE 4

| Codon usage in *Prototheca* species | | |
|---|---|---|
| Ala | GCG | 345 (0.36) |
|  | GCA | 66 (0.07) |
|  | GCT | 101 (0.11) |
|  | GCC | 442 (0.46) |
| Cys | TGT | 12 (0.10) |
|  | TGC | 105 (0.90) |
| Asp | GAT | 43 (0.12) |
|  | GAC | 316 (0.88) |
| Glu | GAG | 377 (0.96) |
|  | GAA | 14 (0.04) |
| Phe | TTT | 89 (0.29) |
|  | TTC | 216 (0.71) |
| Gly | GGG | 92 (0.12) |
|  | GGA | 56 (0.07) |
|  | GGT | 76 (0.10) |
|  | GGC | 559 (0.71) |
|  | TCA | 31 (0.06) |
| His | CAT | 42 (0.21) |
|  | CAC | 154 (0.79) |
| Ile | ATA | 4 (0.01) |
|  | ATT | 30 (0.08) |
|  | ATC | 338 (0.91) |
| Lys | AAG | 284 (0.98) |
|  | AAA | 7 (0.02) |

TABLE 4-continued

Codon usage in Prototheca species

| | | | |
|---|---|---|---|
| Leu | TTG | 26 | (0.04) |
| | TTA | 3 | (0.00) |
| | CTG | 447 | (0.61) |
| | CTA | 20 | (0.03) |
| | CTT | 45 | (0.06) |
| | CTC | 190 | (0.26) |
| Met | ATG | 191 | (1.00) |
| Asn | AAT | 8 | (0.04) |
| | AAC | 201 | (0.96) |
| Pro | CCG | 161 | (0.29) |
| | CCA | 49 | (0.09) |
| | CCT | 71 | (0.13) |
| | CCC | 267 | (0.49) |
| Gln | CAG | 226 | (0.82) |
| | CAA | 48 | (0.18) |
| Arg | AGG | 33 | (0.06) |
| | AGA | 14 | (0.02) |
| | CGG | 102 | (0.18) |
| | CGA | 49 | (0.08) |
| | CGT | 51 | (0.09) |
| | CGC | 331 | (0.57) |
| Ser | AGT | 16 | (0.03) |
| | AGC | 123 | (0.22) |
| | TCG | 152 | (0.28) |
| | TCT | 55 | (0.10) |
| | TCC | 173 | (0.31) |
| Thr | ACG | 184 | (0.38) |
| | ACA | 24 | (0.05) |
| | ACT | 21 | (0.05) |
| | ACC | 249 | (0.52) |
| Val | GTG | 308 | (0.50) |
| | GTA | 9 | (0.01) |
| | GTT | 35 | (0.06) |
| | GTC | 262 | (0.43) |
| Trp | TGG | 107 | (1.00) |
| Tyr | TAT | 10 | (0.05) |
| | TAC | 180 | (0.95) |
| Stop | TGA/TAG/TAA | | |

TABLE 5

Preferred codon usage in *Dunaliella salina*.

| | | | |
|---|---|---|---|
| TTC (Phe) | TAC (Tyr) | TGC (Cys) | TAA (Stop) |
| TGG (Trp) | CCC (Pro) | CAC (His) | CGC (Arg) |
| CTG (Leu) | CAG (Gln) | ATC (Ile) | ACC (Thr) |
| AAC (Asn) | AGC (Ser) | ATG (Met) | AAG (Lys) |
| GCC (Ala) | GAC (Asp) | GGC (Gly) | GTG (Val) |
| GAG (Glu) | | | |

TABLE 6

Preferred codon usage in *Chlorella protothecoides*.

| | | | |
|---|---|---|---|
| TTC (Phe) | TAC (Tyr) | TGC (Cys) | TGA (Stop) |
| TGG (Trp) | CCC (Pro) | CAC (His) | CGC (Arg) |
| CTG (Leu) | CAG (Gln) | ATC (Ile) | ACC (Thr) |
| GAC (Asp) | TCC (Ser) | ATG (Met) | AAG (Lys) |
| GCC (Ala) | AAC (Asn) | GGC (Gly) | GTG (Val) |
| GAG (Glu) | | | |

B. Promoters

Many promoters are active in microalgae, including promoters that are endogenous to the algae being transformed, as well as promoters that are not endogenous to the algae being transformed (i.e., promoters from other algae, promoters from higher plants, and promoters from plant viruses or algae viruses). Exogenous and/or endogenous promoters that are active in microalgae, and antibiotic resistance genes functional in microalgae are described by e.g., *Curr Microbiol.* 1997 December; 35(6):356-62 (*Chlorella vulgaris*); *Mar Biotechnol* (NY). 2002 January; 4(1):63-73 (*Chlorella ellipsoidea*); *Mol Gen Genet.* 1996 Oct. 16; 252(5):572-9 (*Phaeodactylum tricornutum*); *Plant Mol Biol.* 1996 April; 31(1):1-12 (*Volvox carteri*); *Proc Natl Acad Sci USA.* 1994 Nov. 22; 91(24):11562-6 (*Volvox carteri*); Falciatore A, Casotti R, Leblanc C, Abrescia C, Bowler C, PMID: 10383998, 1999 May; 1(3):239-251 (Laboratory of Molecular Plant Biology, Stazione Zoologica, ViIla Comunale, 1-80121 Naples, Italy) (*Phaeodactylum tricornutum* and *Thalassiosira weissflogii*); *Plant Physiol.* 2002 May; 129(1):7-12. (*Porphyridium* sp.); *Proc Natl Acad Sci USA.* 2003 Jan. 21; 100(2):438-42. (*Chlamydomonas reinhardtii*); *Proc Natl Acad Sci USA.* 1990 February; 87(3):1228-32. (*Chlamydomonas reinhardtii*); *Nucleic Acids Res.* 1992 Jun. 25; 20(12):2959-65; *Mar Biotechnol* (NY). 2002 January; 4(1):63-73 (*Chlorella*); *Biochem Mol Biol Int.* 1995 August; 36(5):1025-35 (*Chlamydomonas reinhardtii*); *J. Microbiol.* 2005 August; 43(4):361-5 (*Dunaliella*); Yi Chuan Xue Bao. 2005 April; 32(4):424-33 (*Dunaliella*); *Mar Biotechnol* (NY). 1999 May; 1(3):239-251. (*Thalassiosira* and *Phaedactylum*); Koksharova, *Appl Microbiol Biotechnol* 2002 February; 58(2):123-37 (various species); *Mol Genet Genomics* 2004 February; 271(1):50-9 (*Thermosynechococcus elongates*); *J. Bacteriol.* (2000), 182, 211-215; *FEMS Microbiol Lett.* 2003 Apr. 25; 221(2):155-9; *Plant Physiol.* 1994 June; 105(2):635-41; *Plant Mol Biol.* 1995 December; 29(5):897-907 (*Synechococcus* PCC 7942); *Mar Pollut Bull.* 2002; 45(1-12):163-7 (*Anabaena* PCC 7120); *Proc Natl Acad Sci USA.* 1984 March; 81(5):1561-5 (*Anabaena* (various strains)); *Proc Natl Acad Sci USA.* 2001 Mar. 27; 98(7):4243-8 (*Synechocystis*); Wirth, *Mol Gen Genet* 1989 March; 216(1):175-7 (various species); *Mol Microbiol,* 2002 June; 44(6):1517-31; *Plasmid,* 1993 September; 30(2):90-105 (*Fremyella diplosiphon*); Hall et al. (1993) *Gene* 124: 75-81 (*Chlamydomonas reinhardtii*); Gruber et al. (1991). *Current Micro.* 22: 15-20; Jarvis et al. (1991) *Current Genet.* 19: 317-322 (*Chlorella*); for additional promoters see also Table 1 from U.S. Pat. No. 6,027,900).

The promoter used to express an exogenous gene can be the promoter naturally linked to that gene or can be a heterologous gene. Some promoters are active in more than one species of microalgae. Other promoters are species-specific. Preferred promoters include promoters such as RBCS2 from

*Chlamydomonas reinhardtii* and viral promoters, such as cauliflower mosaic virus (CMV) and *chlorella* virus, which have been shown to be active in multiple species of microalgae (see for example *Plant Cell Rep.* 2005 March; 23(10-11):727-35; *J. Microbiol.* 2005 August; 43(4):361-5; *Mar Biotechnol* (NY). 2002 January; 4(1):63-73). In other embodiments, the *Botryococcus* malate dehydrogenase promoter, such a nucleic acid comprising any part of SEQ ID NO:3, or the *Chlamydomonas reinhardtii* RBCS2 promoter (SEQ ID NO:4) can be used. Optionally, at least 10, 20, 30, 40, 50, or 60 nucleotides or more of these sequences containing a promoter are used. Preferred promoters endogenous to species of the genus *Chlorella* are SEQ ID NOs: 1 and 2.

Preferred promoters useful for expression of exogenous genes in *Chlorella* are listed in the sequence listing of this application, such as the promoter of the *Chlorella* HUP1 gene (SEQ ID NO:1) and the *Chlorella ellipsoidea* nitrate reductase promoter (SEQ ID NO:2). *Chlorella* virus promoters can also be used to express genes in *Chlorella*, such as SEQ ID NOs: 1-7 of U.S. Pat. No. 6,395,965. Additional promoters active in *Chlorella* can be found, for example, in *Biochem Biophys Res Commun*, 1994 Oct. 14; 204(1):187-94; *Plant Mol Biol*, 1994 October; 26(1):85-93; *Virology*, 2004 Aug. 15; 326(1):150-9; and *Virology*, 2004 Jan. 5; 318(1):214-23.

C. Selectable Markers

Any of a wide variety of selectable markers can be employed in a transgene construct useful for transforming a microorganism, e.g., *Chlorella*. Examples of suitable selectable markers include the nitrate reductase gene, the hygromycin phosphotransferase gene (HPT), the neomycin phosphotransferase gene, and the ble gene, which confers resistance to phleomycin. Methods of determining sensitivity of microalgae to antibiotics are well known. For example, *Mol Gen Genet*, 1996 Oct. 16; 252(5):572-9.

More specifically, Dawson et al. (1997), *Current Microbiology* 35:356-362 (incorporated by reference herein in its entirety), described the use of the nitrate reductase (NR) gene from *Chlorella vulgaris* as a selectable marker for NR-deficient *Chlorella sorokiniana* mutants. Kim et al. (2002), *Mar. Biotechnol.* 4:63-73 (incorporated by reference herein in its entirety), disclosed the use of the HPT gene as a selectable marker for transforming *Chorella ellipsoidea*. Huang et al. (2007), *Appl. Microbiol. Biotechnol.* 72: 197-205 (incorporated by reference herein in its entirety), reported on the use of Sh ble as a selectable marker for *Chlorella* sp. DT.

D. Inducible Expression

The present invention also provides for the use of an inducible promoter to express a gene of interest. In particular, the use of an inducible promoter to express a lipase gene permits production of the lipase after growth of the microorganism when conditions have been adjusted, if necessary, to enhance transesterification, for example, after disruption of the cells, reduction of the water content of the reaction mixture, and/or addition sufficient alcohol to drive conversion of TAGs to fatty acid esters.

Inducible promoters useful in the invention include those that mediate transcription of an operably linked gene in response to a stimulus, such as an exogenously provided small molecule (e.g., glucose, as in SEQ ID NO:1), temperature (heat or cold), light, etc. Suitable promoters can activate transcription of an essentially silent gene or upregulate, preferably substantially, transcription of an operably linked gene that is transcribed at a low level. In the latter case, the level of transcription of the gene of interest, e.g., the lipase gene, preferably does not significantly interfere with the growth of the microorganism in which it is expressed.

Expression of a transgene in *Chlorella* can be performed under inducible conditions, e.g., using promoters such as the promoter for the *Chlorella* hexose transporter gene (SEQ ID NO:1). This promoter is strongly activated by the presence of glucose in the culture media.

E. Expression of Two or More Exogenous Genes

Further, a genetically engineered microorganism, such as a microalgae, may comprise and express two or more exogenous genes, such as, for example, a lipase and a lytic gene, e.g., one encoding a polysaccharide-degrading enzyme. One or both genes can be expressed using an inducible promoter, which allows the relative timing of expression of these genes to be controlled to enhance the lipid yield and conversion to fatty acid esters. Expression of the two or more exogenous genes may be under control of the same inducible promoter or under control of a different inducible promoters. In the latter situation, expression of a first exogenous gene can be induced for a first period of time (during which expression of a second exogenous gene may or may not be induced) and expression of a second exogenous gene can be induced for a second period of time (during which expression of a first exogenous gene may or may not be induced). Provided herein are vectors and methods for engineering lipid-producing microbes to metabolize sucrose, which is an advantageous trait because it allows the engineered cells to convert sugar cane feedstocks into lipids appropriate for biodiesel production.

Also provided herein are genetically engineered strains of microbes (e.g., microalgae, oleaginous yeast, bacteria, or fungi) that express two or more exogenous genes, such as, for example, a fatty acyl-ACP thioesterase and a fatty acyl-CoA/aldehyde reductase, the combined action of which yields an alcohol product. Further provided are other combinations of exogenous genes, including without limitation, a fatty acyl-ACP thioesterase and a fatty acyl-CoA reductase to generate aldehydes. In addition, this application provides for the combination of a fatty acyl-ACP thioesterase, a fatty acyl-CoA reductase, and a fatty aldehyde decarbonylase to generate alkanes. One or more of the exogenous genes can be expressed using an inducible promoter.

Examples of further modifications suitable for use in the present invention are described in co-pending, commonly owned Application No. 60/837,839, which is incorporated herein by reference. This application discloses genetically engineering strains of microalgae to express two or more exogenous genes, one encoding a transporter of a fixed carbon source (such as sucrose) and a second encoding a sucrose invertase enzyme. The resulting fermentable organisms produce hydrocarbons at lower manufacturing cost than what has been obtainable by previously known methods of biological hydrocarbon production. This co-pending application also teaches that the insertion of the two exogenous genes described above can be combined with the disruption of polysaccharide biosynthesis through directed and/or random mutagenesis, which steers ever greater carbon flux into hydrocarbon production. Individually and in combination, trophic conversion, engineering to alter hydrocarbon production and treatment with exogenous enzymes alter the hydrocarbon composition produced by a microorganism. The alteration can be a change in the amount of hydrocarbons produced, the amount of one or more hydrocarbon species produced relative to other hydrocarbons, and/or the types of hydrocarbon species produced in the microorganism. For example, microalgae can be engineered to produce a higher amount and/or percentage of TAGs.

F. Compartmentalized Expression

The present invention also provides for compartmentalized expression a gene of interest. In particular, it can be advantageous, in particular embodiments, to target expression of a lipase gene, to one or more cellular compartments, where it is sequestered from the majority of cellular lipids until initiation of the transesterification reaction. Preferred organelles for targeting are chloroplasts, mitochondria, and endoplasmic reticulum.

1. Expression in Chloroplasts

In a preferred embodiment of the present invention, the expression of a polypeptide in a microorganism is targeted to chloroplasts. Methods for targeting expression of a heterologous gene to the chloroplast are known and can be employed in the present invention. Methods for targeting foreign gene products into chloroplasts are described in Shrier et al., *EMBO J.* (1985) 4:25 32. See also Tomai et al., *Gen. Biol. Chem.* (1988) 263:15104 15109 and U.S. Pat. No. 4,940,835 for the use of transit peptides for translocating nuclear gene products into the chloroplast. Methods for directing the transport of proteins to the chloroplast are also reviewed in Kenauf *TIBTECH* (1987) 5:40 47. Chloroplast targeting sequences endogenous to *Chlorella* are known, such as genes in the *Chlorella* nuclear genome that encode proteins that are targeted to the chloroplast; see for example GenBank Accession numbers AY646197 and AF499684.

Wageningen UR-Plant Research International sells an IMPACTVECTOR1.4 vector, which uses the secretion signal of the *Chrysanthemum morifolium* small subunit protein to deliver a heterologous protein into the chloroplast stroma (cytoplasmic) environment, shuttling across a double membrane system. The protein is fused to the first 11 amino acids of the mature rubisco protein in order to allow proper processing of the signal peptide (Wong et al., *Plant Molecular Biology* 20: 81-93 (1992)). The signal peptide contains a natural intron from the RbcS gene.

In another approach, the chloroplast genome is genetically engineered to express the heterologous protein. Stable transformation of chloroplasts of *Chlamydomonas reinhardtii* (a green alga) using bombardment of recipient cells with high-velocity tungsten microprojectiles coated with foreign DNA has been described. See, for example, Boynton et al., *Science* (1988) 240: 1534 1538; Blowers et al. *Plant Cell* (1989) 1:123 132 and Debuchy et al., *EMBO J.* (1989) 8: 2803 2809. The transformation technique, using tungsten microprojectiles, is described by Klein et al., *Nature* (London) (1987) 7:70 73. Other methods of chloroplast transformation for both plants and microalgae are known. See for example U.S. Pat. Nos. 5,693,507; 6,680,426; *Plant Physiol.* 2002 May; 129(1):7-12; and *Plant Biotechnol J.* 2007 May; 5(3):402-12.

As described in U.S. Pat. No. 6,320,101 (issued Nov. 20, 2001 to Kaplan et al.; which is incorporated herein by reference), cells can be chemically treated so as to reduce the number of chloroplasts per cell to about one. Then, the heterologous nucleic acid can be introduced into the cells via particle bombardment with the aim of introducing at least one heterologous nucleic acid molecule into the chloroplasts. The heterologous nucleic acid is selected such that it is integratable into the chloroplast's genome via homologous recombination which is readily effected by enzymes inherent to the chloroplast. To this end, the heterologous nucleic acid includes, in addition to a gene of interest, at least one nucleic acid sequence that is derived from the chloroplast's genome. In addition, the heterologous nucleic acid typically includes a selectable marker. Further details relating to this technique are found in U.S. Pat. Nos. 4,945,050 and 5,693,507, which are incorporated herein by reference. A polypeptide can thus be produced by the protein expression system of the chloroplast.

U.S. Pat. No. 7,135,620 (issued Nov. 14, 2006 to Daniell et al.; incorporated herein by reference) describes chloroplast expression vectors and related methods. Expression cassettes are DNA constructs including a coding sequence and appropriate control sequences to provide for proper expression of the coding sequence in the chloroplast. Typical expression cassettes include the following components: the 5' untranslated region from a microorganism gene or chloroplast gene such as psbA which will provide for transcription and translation of a DNA sequence encoding a polypeptide of interest in the chloroplast; a DNA sequence encoding a polypeptide of interest; and a translational and transcriptional termination region, such as a 3' inverted repeat region of a chloroplast gene that can stabilize RNA of introduced genes, thereby enhancing foreign gene expression. The cassette can optionally include an antibiotic resistance gene.

Typically, the expression cassette is flanked by convenient restriction sites for insertion into an appropriate genome. The expression cassette can be flanked by DNA sequences from chloroplast DNA to facilitate stable integration of the expression cassette into the chloroplast genome, particularly by homologous recombination. Alternatively, the expression cassette may remain unintegrated, in which case, the expression cassette typically includes a chloroplast origin of replication, which is capable of providing for replication of the heterologous DNA in the chloroplast.

The expression cassette generally includes a promoter region from a gene capable of expression in the chloroplast. The promoter region may include promoters obtainable from chloroplast genes, such as the psbA gene from spinach or pea, or the rbcL and atpB promoter region from maize and rRNA promoters. Examples of promoters are described in Hanley-Bowdoin and Chua, *TIBS* (1987) 12:67 70; Mullet et al., *Plant Molec Biol*. (1985) 4: 39 54; Hanley-Bowdoin (1986) PhD. Dissertation, the Rockefeller University; Krebbers et al., *Nucleic Acids Res*. (1982) 10: 4985 5002; Zurawaki et al., *Nucleic Acids Res*. (1981) 9:3251 3270; and Zurawski et al., *Proc. Natl. Acad. Sci. U.S.A.* (1982) 79: 7699 7703. Other promoters can be identified and the relative strength of promoters so identified evaluated, by placing a promoter of interest 5' to a promoterless marker gene and observing its effectiveness relative to transcription obtained from, for example, the promoter from the psbA gene, a relatively strong chloroplast promoter. The efficiency of heterologous gene expression additionally can be enhanced by any of a variety of techniques. These include the use of multiple promoters inserted in tandem 5' to the heterologous gene, for example a double psbA promoter, the addition of enhancer sequences and the like.

Numerous promoters active in the *Chlorella* chloroplast can be used for expression of exogenous genes in the *Chlorella* chloroplast, such as those found in GenBank accession number NC_001865 (*Chlorella vulgaris* chloroplast, complete genome).

Where it is desired to provide for inducible expression of the heterologous gene, an inducible promoter and/or a 5' untranslated region containing sequences which provide for regulation at the level of transcription and/or translation (at the 3' end) may be included in the expression cassette. For example, the 5' untranslated region can be from a gene wherein expression is regulatable by light. Similarly, 3' inverted repeat regions could be used to stabilize RNA of heterologous genes. Inducible genes may be identified by enhanced expression in response to a particular stimulus of interest and low or absent expression in the absence of the stimulus. For example, a light-inducible gene can be identified where enhanced expression occurs during irradiation with light, while substantially reduced expression or no expression occurs in low or no light. Light regulated promoters from green microalgae are known (see for example *Mol Genet Genomics*, 2005 December; 274(6):625-36).

The termination region which is employed will be primarily one of convenience, since the termination region appears to be relatively interchangeable among chloroplasts and bacteria. The termination region may be native to the transcriptional initiation region, may be native to the DNA sequence of interest, or may be obtainable from another source. See, for example, Chen and Orozco, *Nucleic Acids Res*. (1988) 16:8411.

The expression cassettes may be transformed into a plant cell of interest by any of a number of methods. These methods include, for example, biolistic methods (See, for example, Sanford, *Trends In Biotech*. (1988) 6:299 302, U.S. Pat. No. 4,945,050; electroporation (Fromm et al., *Proc. Natl. Acad. Sci*. (USA) (1985) 82:5824 5828); use of a laser beam, microinjection or any other method capable of introducing DNA into a chloroplast.

Additional descriptions of chloroplast expression vectors suitable for use in microorganisms such as microalgae are found in U.S. Pat. No. 7,081,567 (issued Jul. 25, 2006 to Xue et al.); U.S. Pat. No. 6,680,426 (issued Jan. 20, 2004 to Daniell et al.); and U.S. Pat. No. 5,693,507 (issued Dec. 2, 1997 to Daniell et al.).

Proteins expressed in the nuclear genome of *Chlorella* can be targeted to the chloroplast using chloroplast targeting signals. Chloroplast targeting sequences endogenous to *Chlorella* are known, such as genes in the *Chlorella* nuclear genome that encode proteins that are targeted to the chloroplast; see for example GenBank Accession numbers AY646197 and AF499684. Proteins can also be expressed in the *Chlorella* chloroplast by insertion of genes directly into the chloroplast genome. Chloroplast transformation typically occurs through homologous recombination, and can be performed if chloroplast genome sequences are known for creation of targeting vectors (see for example the complete genome sequence of a *Chlorella* chloroplast; Genbank accession number NC_001865). See previous sections herein for details of chloroplast transformation.

2. Expression in Mitochondria

In another preferred embodiment of the present invention, the expression of a polypeptide in a microorganism is targeted to mitochondria. Methods for targeting foreign gene products into mitochondria (Boutry et al., *Nature* (London) (1987) 328:340 342) have been described, including in green microalgae (see for example *Mol Gen Genet.,* 1993 January; 236(2-3):235-44).

For example, an expression vector encoding a suitable secretion signal can target a heterologous protein to the mitochondria. An exemplary expression vector for mitochondria targeting is the IMPACTVECTOR1.5 vector, from Wageningen UR-Plant Research International, which uses the yeast CoxIV secretion signal. This expression vector was shown to deliver proteins in the mitochondrial matrix. The protein is fused to the first 4 amino acids of the yeast CoxIV protein in order to allow proper processing of the signal peptide (Kohler et al., *Plant J.* 11: 613-621 (1997)). Other mitochondrial targeting sequences are known, including those functional in green microalgae. For example, see *FEBS Lett*. 1990 Jan. 29; 260(2):165-8; and *J. Biol. Chem*. 2002 Feb. 22; 277(8):6051-8.

Proteins expressed in the nuclear genome of *Chlorella* can be targeted to the mitochondria using mitochondrial targeting signals. Details of mitochondrial protein targeting and transformation are provided herein.

3. Expression in Endoplasmic Reticulum

In another preferred embodiment of the present invention, the expression of a polypeptide in a microorganism is targeted to the endoplasmic reticulum (ER). The inclusion of an appropriate retention or sorting signal in an expression vector ensure that proteins are retained in the endoplasmic reticulum (ER) and do not go downstream into Golgi. For example, the IMPACTVECTOR1.3 vector, from Wageningen UR-Plant Research International, includes the well known KDEL (SEQ ID NO:96) retention or sorting signal. With this vector, ER retention has a practical advantage in that it has been reported to improve expression levels 5-fold or more. The main reason for this appears to be that the ER contains lower concentrations and/or different proteases responsible for post-translational degradation of expressed proteins than are present in the cytoplasm. ER retention signals functional in green microalgae are known. For example, see *Proc. Nat.l Acad. Sci. USA*. 2005 Apr. 26; 102(17):6225-30.

G. Transformation

Cells can be transformed by any suitable technique including, e.g., biolistics, electroporation (see Maruyama et al., (2004) *Biotechnology Techniques* 8:821-826), glass bead transformation and silicon carbide whisker transformation. Another method that can be used involves forming protoplasts and using $CaCl_2$ and polyethylene glycol (PEG) to introduce recombinant DNA into microalgal cells (see Kim et al., (2002), *Mar. Biotechnol*. 4:63-73, which reports the use of this method for the transformation of *Chlorella ellipsoidea*). Co-transformation of microalgae can be used to introduce two distinct vector molecules into a cell simultaneously (see for example, *Protist* (2004) December; 155(4):381-93).

Biolistic methods (see for example, Sanford, *Trends in Biotech*. (1988) 6:299-302, U.S. Pat. No. 4,945,050; electroporation (Fromm et al., *PNAS* (1985) 82:5824-5828), use of a laser beam, microinjection, or any other method capable of introducing DNA into a microalgae can also be used for transformation.

H. Lipid Pathway Engineering

In certain embodiments of the present invention, it is preferred to further modify a microorganism, such as a microalgae, for example, to provide desired growth characteristics and/or to enhance the amount and/or quality of lipids produced. For example, microalgae can be engineered to increase carbon flux into the lipid pathway and/or modify the lipid pathway to beneficially alter the proportions or properties of lipid produced by the cells. The pathway is further, or alternatively, modified to alter the properties and/or proportions of various hydrocarbon molecules produced through enzymatic processing of lipids.

1. Alteration of Properties or Portions of Lipids or Hydrocarbons Produced

In some embodiments of the present invention, it can be desirable to alter characteristics, such as lipid yield per unit volume and/or per unit time, carbon chain length (e.g., for biodiesel production or for industrial applications requiring hydrocarbon feedstock), reducing the number of double or triple bonds, optionally to zero, removing or eliminating rings and cyclic structures, and increasing the hydrogen:carbon ratio of a particular species of lipid or of a population of distinct lipid. In addition, microalgae that produce appropriate hydrocarbons can also be engineered to have even more desirable hydrocarbon outputs. Examples of such microalgae include species of the genus *Chlorella*.

a) Regulation of Enzymes Controlling Branch Points in Fatty Acid Synthesis

In particular embodiments of the present invention, one or more key enzymes that control branch points in metabolism to fatty acid synthesis is up-regulated or down-regulated to improve lipid production. Up-regulation is achieved, for example, by transforming cells with expression constructs in which a gene encoding the enzyme of interest is expressed, e.g., using a strong promoter and/or enhancer elements that increase transcription. Such expression constructs can include a selectable marker such that the transformants can be subjected to selection, which can result in amplification of the construct and an increase in the expression level of the encoded enzyme. Examples of enzymes suitable for up-regulation according to the methods of the invention include pyruvate dehydrogenase, which plays a role in converting pyruvate to acetyl-CoA (examples, some from microalgae, include GenBank accession numbers NP_415392; AAA53047; Q1XDM1; and CAF05587). Up-regulation of pyruvate dehydrogenase can increase production of acetyl-CoA, and thereby increase fatty acid synthesis. Acetyl-CoA carboxylase catalyzes the initial step in fatty acid synthesis. Accordingly, in certain embodiments of the present invention, this enzyme is up-regulated to increase production of fatty acids (examples, some from microalgae, include GenBank accession numbers BAA94752; AAA75528; AAA81471; YP_537052; YP_536879; NP_045833; and BAA57908). In another embodiment, fatty acid production is increased by up-regulation of acyl carrier protein (ACP), which carries the growing acyl chains during fatty acid synthesis (examples, some from microalgae, include GenBank accession numbers A0T0F8; P51280; NP_849041; YP_874433). Glycerol-3-phosphate acyltransferase catalyzes the rate-limiting step of fatty acid synthesis. Up-regulation of this enzyme is desired to increase fatty acid production (examples, some from microalgae, include GenBank accession numbers AAA74319; AAA33122; AAA37647; P44857; and ABO94442). In some embodiments, two or more of these polypeptides (pyruvate dehydrogenase, Acetyl-CoA carboxylase, acyl carrier protein (ACP), Glycerol-3-phosphate acyltransferase) are up-regulated. In that case, the two or more genes encoding the respective polypeptides may reside on a single expression construct or, alternatively, on two or more expression constructs. The preceding proteins are candidates for expression in microalgae, including species of the genus *Chlorella* and/or *Prototheca*.

Down-regulation of an enzyme of interest can achieved using, e.g., antisense, catalytic RNA/DNA, RNA interference (RNAi), "knock-out," "knock-down," or other mutagenesis techniques. Enzyme expression/function can also be inhibited using intrabodies. Examples of enzymes suitable for down-regulation according to the methods of the invention include citrate synthase, which consumes acetyl-CoA as part of the tricarboxylic acid (TCA) cycle. Down-regulation of citrate synthase can force more acetyl-CoA into the fatty acid synthetic pathway.

b) Modulation of Global Regulators of Fatty Acid Synthetic Genes

Global regulators modulate the expression of the genes of the fatty acid biosynthetic pathways. Accordingly, one or more global regulators of fatty acid synthesis can be up- or down-regulated, as appropriate, to inhibit or enhance, respectively, the expression of a plurality of fatty acid synthetic genes and, ultimately, to increase lipid production. Examples include sterol regulatory element binding proteins (SREBPs), such as SREBP-1a and SREBP-1c (for examples see GenBank accession numbers NP_035610 and Q9WTN3). Global regulators can be up- or down-regulated, for example, as described above with respect to regulation of control point enzymes.

c) Regulation of Hydrocarbon Modification Enzymes

The present application describes genetically engineering strains of microalgae, oleaginous yeast, bacteria, or fungi with one or more exogenous genes to produce various hydrocarbon compounds. Thus, in certain embodiments of the present invention, the methods of the invention also comprise transforming cells with one or more genes encoding hydrocarbon modification enzymes, such as, for example, a fatty acyl-ACP thioesterase (see examples in Table 7 with accession numbers), a fatty acyl-CoA/aldehyde reductase (see examples in Table 8 with accession numbers), a fatty acyl-CoA reductase (see examples in Table 9 with accession numbers), a fatty aldehyde decarbonylase (see examples in Table 10 with accession numbers), a fatty aldehyde reductase, or a squalene synthase gene (e.g., see GenBank Accession number AF205791). Stearoyl-ACP desaturase, for example, catalyzes the conversion of stearoyl-ACP to oleoyl-ACP. Up-regulation of this gene can increase the proportion of monounsaturated fatty acids produced by a cell; whereas down-regulation can reduce the proportion of monounsaturates. Similarly, the expression of one or more glycerolipid desaturases can be controlled to alter the ratio of unsaturated to saturated fatty acids such as ω-6 fatty acid desaturase, ω-3 fatty acid desaturase, or ω-6-oleate desaturase.

For example, microalgae that would naturally, or through genetic modification, produce high levels of lipids can be engineered (or further engineered) to express an exogenous fatty acyl-ACP thioesterase, which can facilitate the cleavage of fatty acids from the acyl carrier protein (ACP) during lipid synthesis. These fatty acids can be recovered or, through further enzymatic processing within the cell, yield other hydrocarbon compounds. Optionally, the fatty acyl-ACP thioesterase can be expressed from a gene operably linked to an inducible promoter, and/or can be expressed in an intracellular compartment.

Thus, in a preferred embodiment of the present invention, the hydrocarbon modification enzyme suitable for use with the microorganisms and methods of the invention is a fatty acyl-ACP thioesterase. Fatty acyl-ACP thioesterases include, without limitation, those listed in Table 7, each of which is hereby incorporated by reference.

TABLE 7

Fatty acyl-ACP thioesterases and GenBank accession numbers.

*Umbellularia californica* fatty acyl-ACP thioesterase (GenBank #AAC49001)
*Cinnamomum camphora* fatty acyl-ACP thioesterase (GenBank #Q39473)
*Umbellularia californica* fatty acyl-ACP thioesterase (GenBank #Q41635)
*Myristica fragrans* fatty acyl-ACP thioesterase (GenBank #AAB71729)
*Myristica fragrans* fatty acyl-ACP thioesterase (GenBank #AAB71730)
*Elaeis guineensis* fatty acyl-ACP thioesterase (GenBank #ABD83939)
*Elaeis guineensis* fatty acyl-ACP thioesterase (GenBank #AAD42220)
*Populus tomentosa* fatty acyl-ACP thioesterase (GenBank #ABC47311)
*Arabidopsis thaliana* fatty acyl-ACP thioesterase (GenBank #NP_172327)
*Arabidopsis thaliana* fatty acyl-ACP thioesterase (GenBank #CAA85387)
*Arabidopsis thaliana* fatty acyl-ACP thioesterase (GenBank #CAA85388)
*Gossypium hirsutum* fatty acyl-ACP thioesterase (GenBank #Q9SQI3)
*Cuphea lanceolata* fatty acyl-ACP thioesterase (GenBank #CAA54060)
*Cuphea hookeriana* fatty acyl-ACP thioesterase (GenBank #AAC72882)
*Cuphea calophylla* subsp. *mesostemon* fatty acyl-ACP thioesterase (GenBank #ABB71581)
*Cuphea lanceolata* fatty acyl-ACP thioesterase (GenBank #CAC19933)
*Elaeis guineensis* fatty acyl-ACP thioesterase (GenBank #AAL15645)
*Cuphea hookeriana* fatty acyl-ACP thioesterase (GenBank #Q39513)
*Gossypium hirsutum* fatty acyl-ACP thioesterase (GenBank #AAD01982)
*Vitis vinifera* fatty acyl-ACP thioesterase (GenBank #CAN81819)
*Garcinia mangostana* fatty acyl-ACP thioesterase (GenBank #AAB51525)
*Brassica juncea* fatty acyl-ACP thioesterase (GenBank #ABI18986)
*Madhuca longifolia* fatty acyl-ACP thioesterase (GenBank #AAX51637)

TABLE 7-continued

Fatty acyl-ACP thioesterases and GenBank accession numbers.

*Brassica napus* fatty acyl-ACP thioesterase (GenBank #ABH11710)
*Oryza sativa* (indica cultivar-group) fatty acyl-ACP thioesterase (GenBank #EAY86877)
*Oryza sativa* (japonica cultivar-group) fatty acyl-ACP thioesterase (GenBank #NP_001068400)
*Oryza sativa* (indica cultivar-group) fatty acyl-ACP thioesterase (GenBank #EAY99617)
*Cuphea hookeriana* fatty acyl-ACP thioesterase (GenBank #AAC49269)

A fatty acyl-ACP thioesterase can be chosen based on its specificity for a growing (during fatty acid synthesis) fatty acid having a particular carbon chain length. For example, the fatty acyl-ACP thioesterase can have a specificity for a carbon chain length ranging from 8 to 34 carbon atoms, preferably from 8 to 18 carbon atoms, and more preferably from 10 to 14 carbon atoms. A specificity for a fatty acid with 12 carbon atoms is most preferred. A specificity for a fatty acid with 14 carbon atoms is also preferred.

In another preferred embodiment of the present invention, the hydrocarbon modification enzyme suitable for use with the microorganisms and methods of the invention is a fatty acyl-CoA/aldehyde reductase. Fatty acyl-CoA/aldehyde reductases include, without limitation, those listed in Table 8.

TABLE 8

Fatty acyl-CoA/aldehyde reductases listed by GenBank accession numbers.

AAC45217, YP_047869, BAB85476, YP_001086217, YP_580344,
YP_001280274, YP_264583, YP_436109, YP_959769, ZP_01736962,
ZP_01900335, ZP_01892096, ZP_01103974, ZP_01915077,
YP_924106, YP_130411, ZP_01222731, YP_550815, YP_983712,
YP_001019688, YP_524762, YP_856798, ZP_01115500,
YP_001141848, NP_336047, NP_216059, YP_882409, YP_706156,
YP_001136150, YP_952365, ZP_01221833, YP_130076, NP_567936,
AAR88762, ABK28586, NP_197634, CAD30694, NP_001063962,
BAD46254, NP_001030809, EAZ10132, EAZ43639, EAZ07989,
NP_001062488, CAB88537, NP_001052541, CAH66597, CAE02214,
CAH66590, CAB88538, EAZ39844, AAZ06658, CAA68190,
CAA52019, and BAC84377

In another preferred embodiment of the present invention, the hydrocarbon modification enzyme suitable for use with the microorganisms and methods of the invention is a fatty acyl-CoA reductase. Fatty acyl-CoA reductases include, without limitation, those listed in Table 9.

TABLE 9

Fatty acyl-CoA reductases listed by GenBank accession numbers.

NP_187805, ABO14927, NP_001049083, CAN83375, NP_191229,
EAZ42242, EAZ06453, CAD30696, BAD31814, NP_190040,
AAD38039, CAD30692, CAN81280, NP_197642, NP_190041,
AAL15288, and NP_190042

In another preferred embodiment of the present invention, the hydrocarbon modification enzyme suitable for use with the microorganisms and methods of the invention is a fatty aldehyde decarbonylase. Fatty aldehyde decarbonylases include, without limitation, those listed in Table 10.

TABLE 10

Fatty aldehyde decarbonylases listed by GenBank accession numbers.

NP_850932, ABN07985, CAN60676, AAC23640, CAA65199,
AAC24373, CAE03390, ABD28319, NP_181306, EAZ31322,
CAN63491, EAY94825, EAY86731, CAL55686, XP_001420263,
EAZ23849, NP_200588, NP_001063227, CAN83072, AAR90847,
and AAR97643

Additional examples of amino acid sequences for hydrocarbon modification enzymes or nucleic acids encoding them are described in U.S. Pat. Nos. 6,610,527, 6,451,576, 6,429,014, 6,342,380, 6,265,639, 6,194,185, 6,114,160, 6,083,731, 6,043,072, 5,994,114, 5,891,697, 5,871,988, and 6,265,639, and further described in GenBank Accession numbers AAO18435, ZP_00513891, Q38710, AAK60613, AAK60610, AAK60611, NP_113747, CAB75874, AAK60612, AAF20201, BAA11024, AF205791, and CAA03710.

In particular embodiments, microorganisms of the present invention are genetically engineered to express one or more exogenous genes selected from a fatty acyl-ACP thioesterase, a fatty acyl-CoA/aldehyde reductase, a fatty acyl-CoA reductase, a fatty aldehyde reductase, or a fatty aldehyde decarbonylase. Suitable expression methods are described above with respect to the expression of a lipase gene, including, among other methods, inducible expression and compartmentalized expression.

Other suitable enzymes for use with the microrganisms and the methods of the invention include those that have at least 70% amino acid identity with one of the proteins listed in Tables 7-10, and that exhibit the corresponding desired enzymatic activity (e.g., cleavage of a fatty acid from an acyl carrier protein, reduction of an acyl-CoA to an aldehyde or an alcohol, or conversion of an aldehyde to an alkane). In additional embodiments, the enzymatic activity is present in a sequence that has at least about 75%, at least about 80%, at least about 85%, at least about 90%, at least about 95%, or at least about 99% identity with one of the above described sequences, all of which are hereby incorporated by reference as if fully set forth.

The hydrocarbon modification enzymes described herein are useful in the production of various hydrocarbons from a microorganism (e.g., a microalgae, an oleaginous yeast, or a fungus) or population of microorganisms, whereby a fatty acyl-ACP thioesterase cleaves a fatty acid from an acyl carrier protein (ACP) during lipid synthesis. Through further enzymatic processing, the cleaved fatty acid is then combined with a coenzyme to yield an acyl-CoA molecule. This acyl-CoA is the substrate for the enzymatic activity of a fatty acyl-CoA reductase to yield an aldehyde, as well as for a fatty acyl-CoA/aldehyde reductase to yield an alcohol. The aldehyde produced by the action of the fatty acyl-CoA reductase identified above is the substrate for further enzymatic activity by either a fatty aldehyde reductase to yield an alcohol, or a fatty aldehyde decarbonylase to yield an alkane.

The hydrocarbon modification enzymes have a specificity for acting on a substrate which includes a specific number of carbon atoms. For example, a fatty acyl-ACP thioesterase may have a specificity for cleaving a fatty acid having 12 carbon atoms from the ACP. Therefore, in various embodiments, the microorganism can contain an exogenous gene that encodes a protein with specificity for catalyzing an enzymatic activity (e.g., cleavage of a fatty acid from an ACP, reduction of an acyl-CoA to an aldehyde or an alcohol, or conversion of an aldehyde to an alkane) with regard to the number of carbon atoms contained in the substrate. The enzymatic specificity can, in various embodiments, be for a substrate having from 8 to 34 carbon atoms, preferably from 8 to 18 carbon atoms, and more preferably from 10 to 14 carbon atoms. The most preferred specificity is for a substrate having 12 carbon atoms. In yet another embodiment, the preferred specificity is for a substrate having 14 carbon atoms. In other embodiments the specificity can be for 20 to 30 carbon atoms.

By selecting the desired combination of exogenous genes to be expressed, one can tailor the product generated by the microorganism, which may then be extracted from the aqueous biomass. For example, in certain embodiments, the microorganism contains: (i) an exogenous gene encoding a fatty acyl-ACP thioesterase; and, optionally, (ii) an exogenous gene encoding a fatty acyl-CoA/aldehyde reductase or a fatty acyl-CoA reductase; and, optionally, (iii) an exogenous gene encoding a fatty aldehyde reductase or a fatty aldehyde decarbonylase. The microorganism, when cultured as described herein, synthesizes a fatty acid linked to an ACP and the fatty acyl-ACP thioesterase catalyzes the cleavage of the fatty acid from the ACP to yield, through further enzymatic processing, a fatty acyl-CoA molecule. When present, the fatty acyl-CoA/aldehyde reductase catalyzes the reduction of the acyl-CoA to an alcohol. Similarly, the fatty acyl-CoA reductase, when present, catalyzes the reduction of the acyl CoA to an aldehyde. In those embodiments in which an exogenous gene encoding a fatty acyl-CoA reductase is present and expressed to yield an aldehyde product, a fatty aldehyde reductase, encoded by the third exogenous gene, catalyzes the reduction of the aldehyde to an alcohol. Similarly, a fatty aldehyde decarbonylase catalyzes the conversion of the aldehyde to an alkane, when present in the microrganism.

Genes encoding such enzymes can be obtained from cells already known to exhibit significant lipid production such as *Chlorella protothecoides*. Genes already known to have a role in lipid production, e.g., a gene encoding an enzyme that saturates double bonds, can be transformed individually into recipient cells. However, to practice the invention it is not necessary to make a priori ansumptions as to which genes are required. A library of DNA containing different genes, such as cDNAs from a good lipid-production organism, can be transformed into recipient cells. The cDNA is preferably in operable linkage with a promoter active in microalgae. Different recipient microalgae cells transformed by a library receive different genes from the library. Transformants having improved lipid production are identified though screening methods known in the art, such as, for example, HPLC, gas chromatography, and mass spectrometry methods of hydrocarbon analysis (for examples of such analysis, see *Biomass and Bioenergy* Vol. 6. No. 4. pp. 269-274 (1994); *Experientia* 38; 47-49 (1982); and *Phytochemistry* 65 (2004) 3159-3165). These transformants are then subjected to further transformation with the original library and/or optionally interbred to generate a further round of organisms having improved lipid production. General procedures for evolving whole organisms to acquire a desired property are described in, e.g., U.S. Pat. No. 6,716,631. Such methods entail, e.g., introducing a library of DNA fragments into a plurality of cells, whereby at least one of the fragments undergoes recombination with a segment in the genome or an episome of the cells to produce modified cells. The modified cells are then screened for modified cells that have evolved toward acquisition of the desired function. Vectors and methods for transformation are analogous to those discussed in connection with expression of lipase genes.

Furthermore, subtractive libraries can be used to identify genes whose transcription is induced under different conditions, especially conditions employed in culturing microorganisms for biodiesel production, or for the production of hydrocarbons useful as a feedstock for industrial applications. Subtractive libraries contain nucleotide sequences reflecting the differences between two different samples. Such libraries are prepared by procedures that include the steps of denaturing and hybridizing populations of polynucleotides (e.g., mRNA, cDNA, amplified sequences) from each sample. Sequences common to both samples hybridize and are removed, leaving the sequences that differ between the samples. In this manner, sequences that are induced under particular conditions can be identified. This technique can be employed, for example, to identify genes useful for increasing lipid (e.g., fatty acid) production and, in particular, lipid production under any desired culture conditions. The subtractive hybridization technique can also be employed to identify promoters, e.g., inducible promoters, useful in expression constructs according to the invention.

Thus, for example, subtractive libraries can be prepared from microorganism cultures grown autotrophically (in the light without a fixed carbon source) or heterotrophically (in the dark in the presence of a fixed carbon source). In particular, heterotrophic genes may be induced during dark growth in the presence of a fixed carbon source and may therefore be present in a library generated by subtracting sequences from autotrophic cells from sequences from dark heterotrophic cells. Subtractive libraries can also be prepared from cultures to which a particular carbon substrate, such as glucose, has been added to identify genes that play a role in metabolizing the substrate. Subtractive libraries prepared from cultures grown in the presence of excess versus limited nitrogen can be used to identify genes that control cell division as opposed to hydrocarbon accumulation production. The preparation of a subtractive library from a culture to which lipids (e.g., fatty acids) have been added can help identify genes whose overexpression increases fatty acid production. More specifically, the addition of fatty acids to a culture of cells that can use the added fatty acids will lead to the down-regulation of fatty acid synthetic genes to down-regulate fatty acid production. The overexpression of one or more such genes will have the opposite effect.

2. Increased Carbon Flux into Lipid Pathway

Some microalgae produce significant quantities of non-lipid metabolites, such as, for example, polysaccharides. Because polysaccharide biosynthesis can use a significant proportion of the total metabolic energy available to cells, mutagenesis of lipid-producing cells followed by screening for reduced or eliminated polysaccharide production generates novel strains that are capable of producing higher yields of lipids.

The phenol: sulfuric acid assay detects carbohydrates (see Hellebust, *Handbook of Phycological Methods*, Cambridge University Press, 1978; and Cuesta G., et al., *J. Microbiol. Methods*, 2003 Jan. 52(1):69-73). The 1,6 dimethylmethylene blue assay detects anionic polysaccharides. (see for example *Braz. j . Med. Biol. Res.* 1999 May; 32(5):545-50; *Clin. Chem.* 1986 Nov. 32(11):2073-6).

Polysaccharides can also be analyzed through methods such as HPLC, size exclusion chromatography, and anion exchange chromatography (see for example Prosky L, Asp N, Schweizer T F, DeVries J W & Furda I (1988) Determination of insoluble, soluble and total dietary fiber in food and food products: Interlaboratory study. *Journal of the Association* of Official Analytical Chemists 71, 1017±1023; *Int J Biol Macromol.* 2003 Nov. 33(1-3):9-18). Polysaccharides can also be detected using gel electrophoresis (see for example, *Anal Biochem.* 2003 Oct. 15; 321(2):174-82; *Anal Biochem* . 2002 Jan. 1; 300(1):53-68).

V. Methods of Culturing Microorganisms

A. Bioreactor

Microorganisms are cultured both for purposes of conducting genetic manipulations and for subsequent production of hydrocarbons (e.g., lipids, fatty acids, aldehydes, alcohols, and alkanes). The former type of culture is conducted on a small scale and initially, at least, under conditions in which the starting microorganism can grow. For example, if the starting microorganism is a photoautotroph the initial culture is conducted in the presence of light. The culture conditions can be changed if the microorganism is evolved or engineered to grow independently of light. Culture for purposes of hydrocarbon production is preferentially conducted on a large scale (e.g., 10,000, 40,000, 100,000or larger bioreactors) in a bioreactor. Microorganisms (e.g., microalgae) of the invention are typically cultured in the methods of the invention in liquid media within a bioreactor, typically in the absence of light (heterotrophic growth).

The bioreactor or fermentor is used to culture microalgal cells through various phases of their physiological cycle. Bioreactors offer many advantages for use in the heterotrophic growth and propagation. To produce biomass for lipid production, microalgae are preferably grown in large quantities in liquid, such as in suspension cultures as an example. Bioreactors such as stainless steel fermentors can accommodate very large culture volumes (40,000 liter and greater capacity bioreactors are used in various embodiments of the invention). Bioreactors also typically allow for the control of culture conditions such as temperature, pH, oxygen tension, and carbon dioxide levels. For example, bioreactors are typically configurable, for example, using ports attached to tubing, to allow gaseous components, like oxygen or nitrogen, to be bubbled through a liquid culture. Other culture parameters, such as pH of the culture media, the identity and concentration of trace elements, and other media constituents can also be more readily manipulated using a bioreactor.

Bioreactors can be configured to flow culture media through the bioreactor throughout the time period during which the microalgae reproduce and increase in number. In some embodiments, for example, media can be infused into the bioreactor after inoculation but before the cells reach a desired density. In other instances, a bioreactor is filled with culture media at the beginning of a culture, and no more culture media is infused after the culture is inoculated. In other words, the microalgal biomass is cultured in an aqueous medium for a period of time during which the microalgae reproduce and increase in number; however, quantities of aqueous culture medium are not flowed through the bioreactor throughout the time period. Thus, in some embodiments, aqueous culture medium is not flowed through the bioreactor after inoculation.

Bioreactor ports can be used to introduce, or extract gases, solids, semisolids, and liquids, into the bioreactor chamber containing microalgae. While many bioreactors have more than one port (for example, one for media entry, and another for sampling), it is not necessary that only one substance enter or leave a port. For example, a port can be used to flow culture media or additional carbon source into the bioreactor and later be used for sampling, gas entry, gas exit, or other purposes. Preferably, a sampling port can be used repeatedly without altering or compromising the axenic nature of the culture. A sampling port can be configured with a valve or other device that allows the flow of sample to be stopped or started or to provide a means of continuos sampling. Bioreactors typically have at least one port that allows inoculation of a culture, and such a port can also be used for other purposes such as media or gas entry.

Bioreactors allow the gas content of the culture of microorganism (e.g., microalgae) to be manipulated. To illustrate, part of the volume of a bioreactor can be gas rather than liquid, and the gas inlets of the bioreactor allow pumping of gases into the bioreactor. Gases that can be beneficially pumped into a bioreactor include air, air/$CO_2$ mixtures, noble gases, such as argon, and other gases. Bioreactors are typically equipped to enable the user to control the rate of entry of a gas into the bioreactor. As noted above, increasing gas flow into a bioreactor can be used to increase mixing of the culture.

Increased gas flow affects the turbidity of the culture as well. Turbulence can be achieved by placing a gas entry port below the level of the aqueous culture media so that gas entering the bioreactor bubbles to the surface of the culture. One or more gas exit ports allow gas to escape, thereby preventing pressure buildup in the bioreactor. Preferably a gas exit port leads to a "one-way" valve that prevents contaminating microorganisms from entering the bioreactor.

B. Media

Culture media for the cultivation of microorganisms, including microalgae, typically contains components such as a fixed nitrogen source, a fixed carbon source, trace elements, optionally a buffer for pH maintenance, and phosphate (typically provided as a phosphate salt). Other components can include salts such as sodium chloride, particularly for seawater microalgae. Nitrogen sources include organic and inorganic nitrogen sources, including, for example, but without limitation, molecular nitrogen, nitrate, nitrate salts, ammonia (pure or in salt form, such as $(NH_4)_2SO_4$ and $NH_4OH$), protein (and amino acids), soybean meal, cornsteep liquor, and yeast extract. Examples of trace elements include zinc, boron, cobalt, copper, manganese, and molybdenum, in for example, the respective forms of $ZnCl_2$, $H_3BO_3$, $CoCl_2 \cdot 6H_2O$, $CuCl_2 \cdot 2H_2O$, $MnCl_2 \cdot 4H_2O$ and $(NH_4)_6Mo_7O_{24} \cdot 4H_2O$.

Solid and liquid growth media are generally available from a wide variety of sources, and instructions for the preparation of particular media that is suitable for a wide variety of strains of microorganisms can be found, for example, online at http://www.utex.org/, a site maintained by the University of Texas at Austin, 1 University Station A6700, Austin, Tex. 78712-0183, for its culture collection of algae (UTEX). For example, various fresh water and salt water media include those described in PCT Pub No. 2008/151149, incorporated herein by reference.

In a particular example, Proteose Medium is suitable for axenic cultures, and a 1 liter volume of Proteose Medium (pH ~6.8) can be prepared by the addition of 1 g proteose peptone to 1 liter of Bristol Medium. Bristol Medium comprises 2.94 mM $NaNO_3$, 0.17 mM $CaCl_2 \cdot 2H_2O$, 0.3 mM $MgSO_4 \cdot 7H_2O$, 0.43 mM $K_2HPO_4$, 1.29 mM $KH_2PO_4$ and 1.43 mM NaCl in an aqueous solution. The solution is covered and autoclaved, and the stored at a refrigerated temperature prior to use. Another example is the *Prototheca* isolation medium (PIM), which comprises 10 g/L postassium hydrogen phthalate (KHP), 0.9 g/L sodium hydroxide, 0.1 g/L magnesium sulfate, 0.2 g/L potassium hydrogen phosphate, 0.3 g/L ammonium chloride, 10 g/L glucose, 0.001 g/L thiamine hydrochloride, 20 g/L agar, 0.25 g/L 5-fluorocytosine, at a pH in the range of 5.0 to 5.2 (see Pore (1973) *App. Microbiology*, 26:648-649). Other suitable media for use with the methods of the invention can be readily identified by consulting the URL identified above, or by consulting other organizations that maintain cultures of microorganisms, such as SAG, CCAP or CCALA. SAG refers to the Culture Collection of Algae at the University of Göttingen (Göttingen, Germany), CCAP refers to the culture collection of algae and protozoa managed by the Scottish Association for Marine Science (Scotland, United Kingdom), and CCLA refers to the culture collection of algal laboratory at the Institute of Botany (Třeboň, Czech Republic). Additionally, U.S. Pat. No. 5,900,370 describes media formulations and conditions suitable for heterotrophic fermentation of *Prototheca* species.

For oil (lipid) production, selection of fixed carbon source is important, as the cost of the fixed carbon source must be sufficiently low to make oil production economical. Thus, while suitable carbon sources include, for example, acetate, floidoside, fructose, galactose, glucuronic acid, glucose, glycerol, lactose, mannose, N-acetylglucosamine, rhamnose, sucrose, glucose, and/or xylose, selection of feedstocks containing these compounds is an important aspect of the methods of the invention. Some microorganism (e.g., microalgae) species can grow by utilizing a fixed carbon source such as glucose or acetate in the absence of light. Such growth is known as heterotrophic growth. For *Chlorella protothecoides*, for example, heterotrophic growth results in high production of biomass and accumulation of high lipid content in cells. Other suitable feedstocks include, for example, black liquor, corn starch, depolymerized cellulosic material, milk whey, molasses, thick cane juice, potato, sorghum, sucrose, sugar beet, sugar cane, rice and wheat. Carbon sources can also be provided as a mixture, such as a mixture of sucrose and depolymerized sugar beet pulp. The one or more carbon source(s) can be supplied at a concentration of at least about 50 µM, at least about 100 µM, at least about 500 µM, at least about 5 mM, at least about 50 µM, at least about 500 mM, of one or more exogenously provided fixed carbon source(s). Carbon sources of particular interest for purposes of the present invention include cellulose (in a depolymerized form), glycerol, sucrose (in the form of cane juice or molasses) and sorghum.

Some microorganisms naturally grow on or can be engineered to grow on a fixed carbon source that is a heterogeneous source of compounds such as municipal waste, secondarily treated sewage, wastewater, and other sources of fixed carbon and other nutrients such as sulfates, phosphates, and nitrates. The sewage component serves as a nutrient source in the production of hydrocarbons, and the culture provides an inexpensive source of hydrocarbons.

In some heterotrophic growth methods, microorganisms can be cultured using cellulosic biomass as a feedstock. Cellulosic biomass (e.g., stover, such as corn stover) is inexpensive and readily available; however, attempts to use this material as a feedstock for yeast have failed. In particular, such feedstock have been found to be inhibitory to yeast growth, and yeast cannot use the 5-carbon sugars produced from cellulosic materials (e.g., xylose from hemi-cellulose). By contrast, microalgae can grow on processed cellulosic material. Accordingly, heterotrophic growth methods include a method of culturing a microalgae in the presence of a cellulosic material and/or a 5-carbon sugar. Cellulosic materials generally include:

| Component | Percent Dry Weight |
| --- | --- |
| Cellulose | 40-60% |
| Hemicellulose | 20-40% |
| Lignin | 10-30% |

Suitable cellulosic materials include residues from herbaceous and woody energy crops, as well as agricultural crops, i.e., the plant parts, primarily stalks and leaves, not removed from the fields with the primary food or fiber product. Examples include corn stover (stalks, leaves, husks, and cobs), wheat straw, and rice straw. Five-carbon sugars that are produced from such materials include xylose.

*Chlorella protothecoides*, for example, has been shown to exhibit higher levels of productivity when cultured on a combination of glucose and xylose than when cultured on either glucose or xylose alone. This synergistic effect provides a significant advantage in that it allows cultivation of *Chlorella* on combinations of xylose and glucose, such as cellulosic material.

In another embodiment of the methods of the invention, the carbon source is sucrose, including a complex feedstock containing sucrose, such as thick cane juice from sugar cane processing or molasses. In one embodiment, the culture medium further includes at least one sucrose utilization enzyme. In some cases, the culture medium includes a sucrose invertase. In one embodiment, the sucrose invertase enzyme is a secretable sucrose invertase enzyme encoded by an exogenous sucrose invertase gene expressed by the population of microorganisms. Thus, in some cases, the microalgae has been genetically engineered to express a sucrose utilization enzyme, such as a sucrose transporter, a sucrose invertase, a hexokinase, a glucokinase, or a fructokinase.

Complex feedstocks containing sucrose include waste molasses from sugar cane processing; the use of this low-value product of sugar cane processing can provide significant cost savings in the production of lipids/oil. Another complex feedstock containing sucrose that is useful in the methods of the invention is sorghum, including sorghum syrup and pure sorghum. *Sorghum* syrup is produced from the juice of sweet sorghum cane; its sugar profile consists of mainly glucose (dextrose), fructose, and sucrose.

C. Increasing Yield of Lipids

For the production of lipids/oil in accordance with the methods of the invention, it is preferable to culture cells in the dark, as is the case, for example, when using extremely large (40,000 liter or greater capacity) fermentors that do not allow light to strike the culture. As an example, an inoculum of lipid-producing microalgal cells are introduced into the medium; there is a lag period (lag phase) before the cells begin to propagate. Following the lag phase, the propagation rate increases steadily and enters the log, or exponential phase. The exponential phase is in turn followed by a slowing of propagation due to decreases in nutrients such as nitrogen, increases in toxic substances, and quorum sensing mechanisms. After this slowing, propagation stops, and cells enter a stationary phase or steady growth state, depending on the particular environment provided to the cells. For obtaining lipid-rich biomass, the culture is typically harvested well after the end of the exponential phase, which may be terminated early by allowing nitrogen or another key nutrient (other than carbon) to become depleted, forcing the cells to convert the carbon sources, which are present in excess, to lipid. Culture parameters can be manipulated to optimize total oil production, the combination of lipid species produced, and/or production of a specific oil.

Process conditions can be adjusted to increase the yield of lipids suitable for use as biodiesel or other target molecules, and/or to reduce production cost. For example, in certain embodiments, a microbe (e.g., a microalgae) is cultured in the presence of a limiting concentration of one or more nutrients, such as, for example, nitrogen. This condition tends to increase microbial lipid yield over microbial lipid yield in a culture in which nitrogen is provided in excess. In particular embodiments, the increase in lipid yield is at least about:

10%, 20%, 30%, 40%, 50%, 75%, 100%, 200%, 300%, 400%, or 500%. The microbe can be cultured in the presence of a limiting amount of the nutrient for a portion of the total culture period or for the entire period. In particular embodiments, the nutrient concentration is cycled between a limiting concentration and a non-limiting concentration at least twice during the total culture period. In addition, as described above, certain fixed carbon feedstocks, such as glycerol, can be employed to increase the percentage of cell weight that is lipid, in relation to comparable quantities of other fixed carbon feedstocks.

To increase lipid yield, acetic acid can be employed in the feedstock for a lipid-producing microbe (e.g., a microalgae). Acetic acid feeds directly into the point of metabolism that initiates fatty acid synthesis (i.e., acetyl-CoA); thus providing acetic acid in the culture can increase fatty acid production. Generally, the microbe is cultured in the presence of a sufficient amount of acetic acid to increase microbial lipid yield, and/or microbial fatty acid yield, specifically, over microbial lipid (e.g., fatty acid) yield in the absence of acetic acid.

In another embodiment, lipid yield is increased by culturing a lipid-producing microbe (e.g., microalgae) in the presence of one or more cofactor(s) for a lipid pathway enzyme (e.g., a fatty acid synthetic enzyme). Generally, the concentration of the cofactor(s) is sufficient to increase microbial lipid (e.g., fatty acid) yield over microbial lipid yield in the absence of the cofactor(s). In a particular embodiment, the cofactor(s) are provided to the culture by including in the culture a microbe (e.g., microalgae) containing an exogenous gene encoding the cofactor(s). Alternatively, cofactor(s) may be provided to a culture by including a microbe (e.g., microalgae) containing an exogenous gene that encodes a protein that participates in the synthesis of the cofactor. In certain embodiments, suitable cofactors include any vitamin required by a lipid pathway enzyme, such as, for example: biotin, pantothenate. Genes encoding cofactors suitable for use in the invention or that participate in the synthesis of such cofactors are well known and can be introduced into microbes (e.g., microalgae), using constructs and techniques such as those described above.

D. Microalgal Biomass with High Oil Content

Microalgal biomass with a high percentage of oil/lipid accumulation by dry cell weight has been generated using different methods of culture, which are known in the art. Microalgal biomass with a higher percentage of accumulated oil/lipid is useful in accordance with the present invention. Li et al. describe *Chlorella vulgaris* cultures with up to 56.6% lipid by dry cell weight (DCW) in stationary cultures grown under autotrophic conditions using high iron concentrations (Li et al., *Bioresource Technology* 99(11):4717-22 (2008)). Rodolfi et al., describe *Nanochloropsis* sp. and *Chaetoceros calcitrans* cultures with 60% lipid by DCW and 39.8% lipid by DCW, respectively, grown in a photobioreactor under nitrogen starvation conditions (Rodolfi et al., *Biotechnology & Bioengineering* (2008) [June 18 Epub ahead of print]). Solovchenko et al., describe *Parietochloris incise* cultures with approximately 30% lipid accumulation (by DCW) when grown phototrophically and under low nitrogen conditions (Solovchenko et al., *Journal of Applied Phycology* 20:245-251 (2008)). *Chlorella protothecoides* can produce up to 55% lipid (DCW) grown under certain heterotrophic conditions with nitrogen starvation (Miao and Wu, *Bioresource Technology* 97:841-846 (2006)). Other *Chlorella* species including *Chlorella emersonii, Chlorella sorokiniana* and *Chlorella minutissima* have been described to have accumulated up to 63% oil (DCW) when grown in stirred tank bioreactors under low-nitrogen media conditions (Illman et al., *Enzyme and Microbial Technology* 27:631-635 (2000)). Still higher percent lipid accumulation by dry cell weight has been reported, including 70% lipid (DCW) accumulation in *Dumaliella tertiolecta* cultures grown in increased NaCl conditions (Takagi et al., *Journal of Bioscience and Bioengineering* 101(3): 223-226 (2006)) and 75% lipid accumulation in *Botryococcus braunii* cultures (Banerjee et al., *Critical Reviews in Biotechnology* 22(3): 245-279 (2002)).

Microalgal biomass generated by the culture methods described herein and useful in accordance with the present invention comprises at least 10% microalgal oil by dry weight. In some embodiments, the microalgal biomass comprises at least 15%, at least 25%, at least 35%, at least 45%, at least 55%, or at least 60% microalgal oil by dry weight. In some embodiments, the microalgal biomass contains from 10-90% microalgal oil, from 25-75% microalgal oil, form 40-75% microalgal oil, or from 50-70% microalgal oil by dry weight.

E. Culturing Microorganisms Under Induced Conditions

As described herein, in certain embodiments of the present invention, microorganisms are cultured under induced conditions, i.e., by providing a stimulus. Generally, this is carried out as follows: The microorganism is cultured for a first period of time sufficient to increase the cell density. Then, the stimulus is provided and the microorganisms are cultured for a second period of time. During the second period of time the desired effect of the stimulus takes place, e.g., induction of an exogenous gene or increased lipid production. Culturing the microorganisms for the second period of time can be in the continued presence of the stimulus. Alternatively, the stimulus may not be provided or may only partially provided (i.e., for a limited time) during the culturing of the microorganism for the second period of time.

F. Storing Microorganisms Prior to Extraction of Lipid

In some cases it is desirable to store cultured microorganisms for a period of time prior to subjecting them to the extraction processes described below. In some methods of the invention, the microorganisms, produced via a culturing process as described herein are optionally stored for a period of time between termination of the culturing process and lysing the microorganism. In some cases, the microorganism is stored for at least one hour between termination of the culturing process and lysing the cultured microorganism. In other cases, the microorganism is stored for at least two hours, at least three hours, at least four hours, at least five hours, at least six hours, at least seven hours, at least eight hours, at least nine hours, at least ten hours, at least eleven hours, at least twelve hours, at least thirteen hours, at least fourteen hours, at least fifteen hours, at least sixteen hours, at least seventeen hours, at least eighteen hours, at least nineteen hours, at least twenty hours, at least twenty-one hours, at least twenty-two hours, at least twenty-three hours, or for at least twenty-four hours between termination of the culturing process and lysing the cultured microorganism. In some cases, the microorganism is stored for at least thirty-six hours between termination of the culturing process and lysing the cultured microorganism. In some cases, the microorganism is stored for at least forty-eight hours between termination of the culturing process and lysing the cultured microorganism, or for longer periods of time. In other cases, the microorganism is stored for at least sixty or seventy-two hours, or longer, between termination of the culturing process and lysing the cultured microorgansim.

Microorganisms prepared in a culture process are optionally stored at a temperature below 15 degrees Celsius between termination of the culturing process and lysing the cultured microorganism. In some cases the microorganisms are stored at a temperature below 14° C., below 13° C., below 12° C., below 11° C., below 10° C., below 9° C., below 8° C., below 7° C., below 6° C., below 5° C., below 4° C., below 3° C., below 2° C., or below 1° C. between termination of the culturing process and lysing the cultured microorganism. In some cases, the microorganism is stored at a temperature above 30 degrees Celsius between termination of the culturing process and lysing the cultured microorganism. In some cases, the microorganism is stored at a temperature above 40 degrees Celsius between termination of the culturing process and lysing the cultured microorganism. In other cases, the microorganism is stored at a temperature above 31° C., above 32° C., above 33° C., above 34° C., above 35° C., above 36° C., above 37° C., above 38° C., above 39° C., above 41° C., above 42° C., above 43° C., above 44° C., above 45° C., above 46° C., above 47° C., above 48° C., above 49° C., or above 50° C. between termination of the culturing process and lysing the cultured microorganism.

In some cases, storage or ageing of the cultured microorganisms is used to disrupt the cells to facilitate oil extraction. With storage, the cell structure may weaken sufficiently to cause the contents of the cells to begin leaking, or to permit passage of reagents or other materials into the cells to facilitate extraction of the lipid contents. Storage can be used in this context in combination with other lysing methods described below.

In some cases, the microorganism is subjected to agitation during storage. Agitation can be in addition to any combination of storage conditions set forth above. Agitation can be done on a shaker, vortexer, or the like. Agitation can also result from the shear forces present during high g force centrifugation. Alternatively, the microorganism is not agitated during storage. The microorganisms can be stored in a bioreactor or other culture vessel, or optionally transferred to a separate storage container.

VI. Methods of Extraction of Lipid from Microorganism

In one aspect, the present invention is directed to a process for extracting, recovering, isolating or obtaining lipids from microorganisms. The process of the present invention is applicable to extracting a variety of lipids from a variety of microorganisms.

A. Lysing Cells

Intracellular lipids produced in microorganisms are extracted after lysing the cells of the microorganism. Once extracted, the lipids can be further refined to produce a high purity lipids.

After completion of culturing, the microorganisms can be separated from the fermentation broth, preferably without a drying step such as drum drying, spray drying, tray drying, vacuum drying and other steps that remove substantially all of the extracellular and intracellular water from the broth. Optionally, the separation is effected by centrifugation to generate a concentrated paste. Centrifugation does not remove significant amounts of intracellular water from the microorganisms and is not a drying step. The biomass can then be washed with a washing solution (e.g., DI water) to get rid of the fermentation broth and debris. Optionally, the washed microbial biomass may also be dried (oven dried, lyophilized, etc.) prior to cell disruption. Alternatively, cells can be lysed without separation from some or all of the fermentation broth when the fermentation is complete. For example, the cells can be at a ratio of less than 1:1 v:v cells to extracellular liquid when the cells are lysed.

Microorganism containing a lipid can be lysed to produce a lysate. As detailed herein, the step of lysing a microorganism (also referred to as cell lysis) can be achieved by any convenient means, including heat-induced lysis, adding a base, adding an acid, using enzymes such as proteases and polysaccharide degradation enzymes such as amylases, using ultrasound, mechanical lysis, using osmotic shock, infection with a lytic virus, and/or expression of one or more lytic genes. Lysis is performed to release intracellular molecules which have been produced by the microorganism. Each of these methods for lysing a microorganism can be used as a single method or in combination.

The extent of cell disruption can be observed by microscopic analysis. Using one or more of the methods described herein, typically more than 70% cell breakage is observed. Preferably, cell breakage is more than 80%, more preferably more than 90% and most preferred about 100%.

In particular embodiments, the microorganism is lysed after growth, for example to increase the exposure of cellular lipid to a catalyst for transesterification such as a lipase or a chemical catalyst, expressed as described above. The timing of lipase expression (e.g., via an inducible promoter), cell lysis, and the adjustment of transesterification reaction conditions (e.g., removal of water, addition of alcohol, etc.) can be adjusted to optimize the yield of fatty acid esters from lipase-mediated transesterification. Below are described a number of lysis techniques. These techniques can be used individually or in combination.

1. Heat-Induced Lysis

In a preferred embodiment of the present invention, the step of lysing a microorganism comprises heating of a cellular suspension containing the microorganism. In this embodiment, the fermentation broth containing the microorganisms (or a suspension of microorganisms isolated from the fermentation broth) is heated until the microorganisms, i.e., the cell walls and membranes of microorganisms degrade or breakdown. Typically, temperatures applied are at least 50° C. Higher temperatures, such as, at least 60° C., at least 70° C., at least 80° C., at least 90° C., at least 100° C., at least 110° C., at least 120° C., at least 130° C. or higher are used for more efficient cell lysis. Example 7 describes an embodiment of lysis using heat treatment.

Lysing cells by heat treatment can be performed by boiling the microorganism. Alternatively, heat treatment (without boiling) can be performed in an autoclave (see Example 6). The heat treated lysate may be cooled for further treatment.

Cell disruption can also be performed by steam treatment, i.e., through addition of pressurized steam. Steam treatment of microalgae for cell disruption is described, for example, in U.S. Pat. No. 6,750,048.

2. Lysis Using a Base

In another preferred embodiment of the present invention, the step of lysing a microorganism comprises adding a base to a cellular suspension containing the microorganism.

The base should be strong enough to hydrolyze at least a portion of the proteinaceous compounds of the microorganisms used. Bases which are useful for solubilizing proteins are known in the art of chemistry. Exemplary bases which are useful in the methods of the present invention include, but are not limited to, hydroxides, carbonates and bicarbonates of lithium, sodium, potassium, calcium, and mixtures thereof. A preferred base is KOH. Examples 6 and 7 describe embodiments of cell lysis using KOH.

3. Acidic Lysis

In another preferred embodiment of the present invention, the step of lysing a microorganism comprises adding an acid to a cellular suspension containing the microorganism. Acid lysis can be effected using an acid at a concentration of 10-500 mN or preferably 40-160 nM. Acid lysis is preferably performed at above room temperature (e.g., at 40-160°, and preferably a temperature of 50-130°. For moderate temperatures (e.g., room temperature to 100° C. and particularly room temperature to 65°, acid treatment can usefully be combined with sonication or other cell disruption methods. Example 7 describes embodiments of cell lysis using acidic lysis.

4. Lysing Cells Using Enzymes

In another preferred embodiment of the present invention, the step of lysing a microorganism comprises lysing the microorganism by using an enzyme. Preferred enzymes for lysing a microorganism are proteases and polysaccharide-degrading enzymes such as hemicellulase (e.g., hemicellulase from *Aspergillus niger*; Sigma Aldrich, St. Louis, Mo.; #H2125), pectinase (e.g., pectinase from *Rhizopus* sp.; Sigma Aldrich, St. Louis, Mo.; #P2401), Mannaway 4.0 (Novozymes), cellulase (e.g., cellulose from *Trichoderma viride*; Sigma Aldrich, St. Louis, Mo.; #C9422), and driselase (e.g., driselase from *Basidiomycetes* sp.; Sigma Aldrich, St. Louis, Mo.; #D9515. Example 7 describes embodiments of cell lysis using enzymes.

a) Cellulases

In a preferred embodiment of the present invention, a cellulase for lysing a microorganism is a polysaccharide-degrading enzyme, optionally from *Chlorella* or a *Chlorella* virus. Example 7 describes embodiments of cell lysis using a cellulase. Another example of a polysaccharide-degrading enzyme that can be used is mannaway, as described in the Examples.

b) Proteases

Proteases such as *Streptomyces griseus* protease, chymotrypsin, proteinase K, proteases listed in Degradation of Polylactide by Commercial Proteases, Oda Y et al., Journal of Polymers and the Environment, Volume 8, Number 1, January 2000, pp. 29-32(4), and other proteases can be used to lyse microorganisms. Other proteases that can be used include Alcalase 2.4 FG (Novozymes) and Flavourzyme 100 (Novozymes), as described in the Examples.

c) Combinations

Any combination of a protease and a polysaccharide-degrading enzyme can also be used, including any combination of the preceding proteases and polysaccharide-degrading enzymes.

5. Lysis Cells Using Ultrasound

In another preferred embodiment of the present invention, the step of lysing a microorganism is performed by using ultrasound, i.e., sonication. Thus, cells can also by lysed with high frequency sound. The sound can be produced electronically and transported through a metallic tip to an appropriately concentrated cellular suspension. This sonication (or ultrasonication) disrupts cellular integrity based on the creation of cavities in cell suspension. Example 6 describes a method for cell lysis using ultrasound. Example 7 describes embodiments of cell lysis using sonication.

6. Mechanical Lysis

In another preferred embodiment of the present invention, the step of lysing a microorganism is performed by mechanical lysis. Cells can be lysed mechanically and optionally homogenized to facilitate hydrocarbon (e.g., lipid) collection. For example, a pressure disrupter can be used to pump a cell containing slurry through a restricted orifice valve. High pressure (up to 1500 bar) is applied, followed by an instant expansion through an exiting nozzle. Cell disruption is accomplished by three different mechanisms: impingement on the valve, high liquid shear in the orifice, and sudden pressure drop upon discharge, causing an explosion of the cell. The method releases intracellular molecules.

Alternatively, a ball mill can be used. In a ball mill, cells are agitated in suspension with small abrasive particles, such as beads. Cells break because of shear forces, grinding between beads, and collisions with beads. The beads disrupt the cells to release cellular contents. Cells can also be disrupted by shear forces, such as with the use of blending (such as with a high speed or Waring blender as examples), the french press, or even centrifugation in case of weak cell walls, to disrupt cells.

7. Lysing Cells by Osmotic Shock (Cytolysis)

In another preferred embodiment of the present invention, the step of lysing a microorganism is performed by applying an osmotic shock. This can be achieved, for example, by centrifuging fermentation broth and resuspending the cell paste in deionized water.

8. Infection with a Lytic Virus

In a preferred embodiment of the present invention, the step of lysing a microorganism comprises infection of the microorganism with a lytic virus. A wide variety of viruses are known to lyse microorganisms suitable for use in the present invention, and the selection and use of a particular lytic virus for a particular microorganism is within the level of skill in the art.

For example, *paramecium bursaria chlorella* virus (PBCV-1) is the prototype of a group (family Phycodnaviridae, genus *Chlorovirus*) of large, icosahedral, plaque-forming, double-stranded DNA viruses that replicate in, and lyse, certain unicellular, eukaryotic *chlorella*-like green algae. Accordingly, any susceptible microalgae, such as *C. protothecoides*, can be lysed by infecting the culture with a suitable *chlorella* virus. Methods of infecting species of *Chlorella* with a *chlorella* virus are known. See for example *Adv. Virus Res.* 2006; 66:293-336; *Virology,* 1999 Apr. 25; 257(1):15-23; *Virology,* 2004 Jan. 5; 318(1):214-23; *Nucleic Acids Symp. Ser.* 2000; (44):161-2; *J. Virol.* 2006 March; 80(5): 2437-44; and *Annu. Rev. Microbiol.* 1999; 53:447-94.

9. Autolysis (Expression of a Lytic Gene)

In another preferred embodiment of the present invention, the step of lysing a microorganism comprises autolysis. In this embodiment, a microorganism according to the invention is genetically engineered to produce a lytic gene that will lyse the microorganism. This lytic gene can be expressed using an inducible promoter, so that the cells can first be grown to a desirable density in a fermentor and then harvested, followed by induction of the promoter to express the lytic gene to lyse the cells. In one embodiment, the lytic gene encodes a polysaccharide-degrading enzyme.

In certain other embodiments, the lytic gene is a gene from a lytic virus. Thus, for example, a lytic gene from a *Chlorella* virus can be expressed in a *Chlorella*, such as *C. protothecoides*.

Suitable expression methods are described herein with respect to the expression of a lipase gene. Expression of lytic genes is preferably done using an inducible promoter, such as a promoter active in microalgae that is induced by a stimulus such as the presence of a small molecule, light, heat, and other stimuli. Lytic genes from *chlorella* viruses are known. For example, see *Virology* 260, 308-315 (1999); *FEMS Microbiology Letters* 180 (1999) 45-53; *Virology* 263, 376-387 (1999); and *Virology* 230, 361-368 (1997).

10. Pressure Oscillation

In another preferred embodiment of the present invention, the step of lysing a microorganism comprises subjecting the microorganism to rapid increases and decreases in pressure. Such rapid increases and decreases are preferably performed across a wide enough differential in pressure that the cells are not able to self-regulate, and burst as a result.

11. Additional Consideration

When lipids are not extracted immediately after isolating the microorganism, the isolated microorganisms are typically dried. Drying a microorganism can be done, e.g., on a drum dryer. Dried microorganisms can be packaged in vacuum-sealed containers to prevent degradation of lipids.

B. Treatment of Cell Lysate with Organic Solvent

A lipid produced by a microorganism is also referred herein as a "first lipid." A first lipid may comprise one or more lipids produced by the microorganism.

A lipid used to extract a first lipid from a microorganism is referred to as a "second lipid." A preferred second lipid is an oil. An organic solvent of the present invention comprises a second lipid.

Some methods of the present invention comprise the step of treating a lysate with an organic solvent. Typically, the organic solvent is added directly to the lysate without prior separation of the lysate components. After addition of the solvent, the lysate separates either of its own accord or as a result of centrifugation or the like into different layers. The layers can include in order of decreasing density: a pellet of heavy solids, an aqueous phase, an emulsion phase, and an oil phase. The emulsion phase is an emulsion of lipids and aqueous phase. Depending on the percentage of organic solvent added with respect to the lysate (w/w or v/v), the force of centrifugation if any, volume of aqueous media and other factors, either or both of the emulsion and oil phases can be present.

Incubation or treatment of the cell lysate or the emulsion phase with the organic solvent is performed for a time sufficient to allow the lipid produced by the microorganism to become solubilized in the organic solvent to form a heterogeneous mixture.

1. Oils

In a preferred embodiment of the present invention, an organic solvent is an oil selected from the group consisting of oil from soy, rapeseed, canola, palm, palm kernel, coconut, corn, waste vegetable oil, Chinese tallow, olive, sunflower, cotton seed, chicken fat, beef tallow, porcine tallow, microalgae, macroalgae, *Cuphea*, flax, peanut, choice white grease (lard), *Camelina sativa* mustard seedcashew nut, oats, lupine, kenaf, *calendula*, hemp, coffee, linseed, hazelnut, *euphorbia*, pumpkin seed, coriander, camellia, sesame, safflower, rice, tung oil tree, cocoa, copra, pium poppy, castor beans, pecan, jojoba, jatropha, *macadamia*, Brazil nuts, and avocado. Also included are fossil oils such as crude oil or a distillate fraction of a fossil oil.

The amount of organic solvent added to the lysate is typically greater than 5% (measured by v/v and/or w/w) of the lysate with which the solvent is being combined. Thus, a preferred v/v or w/w of the organic solvent is greater than 5%, at least 6%, at least 7%, at least 10%, at least 20%, at least 25%, at least 30%. at least 40%, at least 50%, at least 60%, at least 70%, at least 80%, at least 90%, and at least 95% of the cell lysate.

2. Other Organic Solvents

Other non-limiting examples of organic solvents which can be used to practice the methods of the present invention include hexane, isohexane, methanol, dodecane, fossil-derived crude oil and distillate fractions thereof, and supercritical carbon dioxide. Methanol can be an advantageous organic solvent to use in biodiesel manufacturing because it can be used in the transesterification process as well as extraction of oil.

C. Solventless Extraction

Lipids can also be extracted from a lysate without substantial or any use of organic solvents by cooling the lysate. In such methods, the lysate is preferably produced by acid treatment in combination with above room temperature. Sonication can also be used, particularly if the temperature is between room temperature and 65° C. Such a lysate on centrifugation or settling can be separated into layers, one of which is an aqueous:lipid layer. Other layers can include a solid pellet, an aqueous layer, and a lipid layer. Lipid can be extracted from the emulsion layer by freeze thawing or otherwise cooling the emulsion as described further below. In such methods, it is not necessary to add any organic solvent. If any organic solvent is added, the organic solvent can be below 5% v/v or w/w of the lysate.

D. Agitation or No Agitation of the Heterogeneous Mixture

In a preferred embodiment of the present invention, after producing a cell lysate and optionally adding the organic solvent to the cell lysate or to the emulsion phase as described above, the heterogeneous mixture is agitated. Agitation can be done on a shaker, vortexer, or the like. Agitation can also result from the shear forces present during high g force centrifugation. Alternatively, the heterogeneous mixture is not agitated.

E. Separation of the Heterogeneous Mixture into a Lipid: Organic Solvent Composition and an Aqueous Composition and, Optionally an Emulsified Composition or Cell Pellet Composition The cell lysate, optionally treated with an organic solvent, produced by the above methods is a heterogeneous mixture including lipids, aqueous solutions, cell debris and the organic solvent (if added). The heterogeneous mixture can be separated into multiple layers as described below. The multiple layers can include in order of descending density, a pellet of cell debris, an aqueous layer, a lipid:aqueous emulsion layer and a lipid layer. The presence and relative proportions of the different layers depends on the lysis technique, the separation technique including centrifugal force, concentration of lipid in the microorganism and whether an organic solvent is used. The desired lipid can occur both in a separate lipid layer and in a lipid: aqueous layer. The use of an organic solvent favors formation of a separate lipid layer. The higher the concentration of the organic solvent relative to the lysis, the more lipid is likely to be found in a separate lipid layer rather than in an aqueous:lipid emulsion layer. The organic solvent, if present, associates with the lipid either in the lipid layer or the emulsion or both. The lipid can be obtained both from a separate lipid layer and from an emulsion layer, as described below.

Cell lysates can be separated into different layers as described above by techniques, such as, centrifugation and settling, i.e., allowing the layers to form spontaneously with time.

F. Separation of Lipid

The separation of lipid from other components present in the lysate depends on which layers are formed as a result of the separation. If a separate lipid layer is formed, this layer forms on top of other layers and can be suctioned off, pipetted or decanted or the like from the top of the vessel containing the separated layers. This lipid layer can then be used in various applications described below. Likewise solid and/or aqueous layers can be drained off and discarded from the bottom of the vessel. If an emulsion layer is formed, the emulsion can be subjected to further extraction to separate lipids in the emulsion from aqueous fluid. In such a circumstance, separate aqueous and/or pellet layers, if present, can be drained off before separating the emulsion. A separate lipid layer if present can also be decanted off; however, such is not necessary, and the separate lipid layer can facilitate separation of the emulsion into its components.

The emulsion can be separated into its components by washing with a further volume of organic solvent to extract lipids from the emulsion. Alternatively, the emulsion can be washed with an aqueous solution to remove aqueous fluids from the emulsion. Alternatively, the emulsion can be subject to cooling below room temperature. Preferably, the emulsion is frozen and rethawed. Freezing is preferably to a temperature of −5° C. to −30° C., and is maintained for at least one hour.

After any of the above treatments, the emulsion is re-separated into component layers by the same techniques as previously described. The component layers can include a cell pellet, aqueous layer, emulsion layer and lipid layer as previously described. The component layers can be separated as previously described. If an emulsion layer is present, the emulsion layer can be subjected to a further round of extraction using the same procedures described above.

After one or more rounds of separation, the lysate eventually yields a lipid layer. The lipid layer can be used in various applications as described below. When any of the rounds of extraction is performed with an organic solvent, that organic solvent remains associated with the lipid layer. Typically, it is not necessary to separate the lipid layer from the organic solvent. For example, when the organic solvent is an oil or lipid, the lipid present in the microorganisms can be referred to as a first lipid and the lipid or oil used for extraction can be referred to as a second lipid. For example, the first lipid can be triacylglycerol from a microalgae and the second lipid can be soy oil. After separation of a lipid:organic solvent layer, (in this case microalgal lipid:soy oil) the mixture can for example be transesterified or hydrotreated to yield biodiesel or renewable diesel, respectively.

One method of separation that can be used on a lysate, including a lysate that contains an emulsion, is the application of shear forces. Following cell lysis, oil may be present as an oil-in-water emulsion with a small (<5 or <10 micron) droplet size. The emulsion may be stabilized by any number of ampipathic emulsifiers (e.g. oleosins, denatured proteins, phospholipids, fatty acids etc.). All else being equal, the stability of an emulsion is inversely related to the droplet size of the included phase. There are a number of procedures provided herein that may be applied to cause oil droplets to coalesce and increase in size, thus rendering the emulsion more amenable to breakage (e.g. gentle agitation in the presence of certain detergents, or acid or base). Once an oil-in-water emulsion has been treated so as to weaken the emulsion (by an increase in droplet size, as described above, and/or by some chemical or physical treatment that decreases the efficacy of the emulsifying agent(s)), the droplets need to be physically forced together in order that they may coalesce and phase separation may occur.

One method of forcing the included oil droplets together is by centrifugation that causes physical crowding by forcing the emulsion through a thin film and introducing concomitant shear that may be required to break the emulsion. A device that can be used in the methods provided herein to introduce g-force, thin film and shear is a stacked disk centrifuge in which the light phase is ejected as a thin film between rapidly rotating disks. The film is preferably between 1 micrometer and 1000 micrometers. The film is preferably less than or similar to the diameter of the included oil droplets.

In one embodiment, microbial oil-bearing cells in fermentation broth are centrifuged to reduce the water content of the composition. Cells are ruptured by homogenization and/or chemical/enzymatic treatment. Optionally, the oil droplets are forced to coalesce by gentle agitation of the lysate. Phase separation of the composition is then achieved by stacked disk centrifugation.

Another method of separation that can be used alone or in combination with other methods described herein is the use of one or more surfactants to destabilize an emulsion. Destabilization results in coalescence of oil globules into larger clusters and eventually into a phase separated composition of a light layer of oil, and a heavier aqueous phase. Preferred surfactants for destabilizing emulsions of oil-bearing microbial biomass is oleamide DEA (diethanolamine) (Stepan Chemical Co.) including but not limited to NINOL 201, laurelamide DEA including but not limited to NINOL 96L and NINOL 55L and cocoamide DEA including but not limited to NINOL 4000. Methods of oil recovery from a lipid emulsion using surfactants are provided in the Examples below.

The lipid composition obtained can be analyzed by a number of methods, including HPLC as described in Example 6.

VII. Method of Producing Fuels Suitable for Use in Diesel Vehicles and Jet Engines Increasing interest is directed to the use of hydrocarbon components of biological origin in fuels, such as biodiesel, renewable diesel, and jet fuel, since renewable biological starting materials that may replace fossil ones are available, and the use thereof is desirable. There is an urgent need for methods for producing hydrocarbon components from biological materials. The present invention fulfills this need by providing methods for production of biodiesel, renewable diesel, and jet fuel using the lipid:organic solvent composition or the lipids described herein as a biological material to produce biodiesel, renewable diesel, and jet fuel.

After extraction, the present invention provides the advantage that the microbial oil and the organic solvent (preferably a plant oil) can together be subjected to chemical treatment to manufacture a fuel for use in diesel vehicles and jet engines. The ability to avoid separation of the organic solvent used for extraction from the microbial oil provides a significant advantage over traditional methods of oil extraction such as hexane extraction in which hexane must be distilled away from the microbial oil prior to any further processing steps.

Traditional diesel fuels are petroleum distillates rich in paraffinic hydrocarbons. They have boiling ranges as broad as 370° to 780° F., which are suitable for combustion in a compression ignition engine, such as a diesel engine vehicle. The American Society of Testing and Materials (ASTM) establishes the grade of diesel according to the boiling range, along with allowable ranges of other fuel properties, such as cetane number, cloud point, flash point, viscosity, aniline point, sulfur content, water content, ash content, copper strip corrosion, and carbon residue. Technically, any hydrocarbon distillate material derived from biomass that meets the appropriate ASTM specification can be defined as diesel, or as biodiesel.

Diesel fuel can be produced from biomass via several types of technologies. Feedstocks for diesel fuels derived from biomass include, but are not limited to, soybean, rape seed, canola, palm, and waste cooking oils, along with animal fats. Starting oils can also be of algal origin. The lipid:organic solvent layer produced by the method of the present invention can serve as feedstock to produce biodiesel and renewable diesel.

A. Biodiesel

Biodiesel is a liquid which varies in color—between golden and dark brown—depending on the production feedstock. It is practically immiscible with water, has a high boiling point and low vapor pressure. Biodiesel refers to a diesel-equivalent processed fuel for use in diesel-engine vehicles. Biodiesel is biodegradable and non-toxic. An additional benefit of biodiesel over conventional diesel fuel is lower engine wear.

Typically, biodiesel comprises short chain alkyl esters. Various processes convert biomass or a lipid produced and isolated as described herein to diesel fuels. A preferred method to produce biodiesel is by transesterification of a lipid as described herein. A preferred short chain alkyl ester for use as biodiesel is a methyl ester or ethyl ester.

Biodiesel produced by a method described herein can be used alone or blended with conventional diesel fuel at any concentration in most modern diesel-engine vehicles. When blended with conventional diesel fuel (petroleum diesel), biodiesel may be present from about 0.1% to about 99.9%. Much of the world uses a system known as the "B" factor to state the amount of biodiesel in any fuel mix. For example, fuel containing 20% biodiesel is labeled B20. Pure biodiesel is referred to as B100.

Biodiesel can also be used as a heating fuel in domestic and commercial boilers. Existing oil boilers may contain rubber parts and may require conversion to run on biodiesel. The conversion process is usually relatively simple, involving the exchange of rubber parts for synthetic parts due to biodiesel being a strong solvent. Due to its strong solvent power, burning biodiesel will increase the efficiency of boilers.

Biodiesel can be used as an additive in formulations of diesel to increase the lubricity of pure Ulta-Low Sulfur Diesel (ULSD) fuel, which is advantageous because it has virtually no sulfur content.

Biodiesel is a better solvent than petrodiesel and can be used to break down deposits of residues in the fuel lines of vehicles that have previously been run on petrodiesel.

1. Production of Biodiesel

Biodiesel can be produced by transesterification of triglycerides contained in oil-rich biomass and animal fats. The lipid:organic solvent layer or lipids produced by the method of the present invention can serve as feedstock to produce biodiesel. Thus, in another aspect of the present invention a method for producing biodiesel is provided. In a preferred embodiment, the method for producing biodiesel comprises the steps of (a) lysing a lipid-containing microorganism to produce a lysate; (b) treating the lysate with an organic solvent for a period of time sufficient to allow the lipid from the microorganism to become solubilized in the organic solvent, whereinby the organic solvent-treated lysate forms a heterogeneous mixture; (c) separating the heterogeneous mixture into layers comprising a lipid:organic solvent layer and an aqueous layer; (d) removing the lipid:organic solvent composition from the aqueous composition, emulsion composition, or cell pellet composition; and (e) transesterifying the lipid:organic solvent composition, whereby biodiesel is produced. The lipid:organic solvent composition comprises the organic solvent and the microbial lipids.

Methods for growth of a microorganism, lysing a microorganism to produce a lysate, treating the lysate in a medium comprising an organic solvent to form a heterogeneous mixture and separating the treated lysate into a lipid:organic solvent composition and an aqueous or emulsified composition have been described above and can also be used in the method of producing biodiesel.

Lipids and lipid:organic solvent composition, where the organic solvent is a triacylglyceride selected as described above can be subjected to transesterification to yield long-chain fatty acid esters useful as biodiesel. Preferred transesterification reactions are outlined below and include base catalyzed transesterification and transesterification using recombinant lipases.

In a base-catalyzed transesterification process, the triacylglycerides are reacted with an alcohol, such as methanol or ethanol, in the presence of an alkaline catalyst, typically potassium hydroxide. This reaction forms methyl or ethyl esters and glycerin (glycerol) as a byproduct.

a) General Chemical Process

Animal and plant oils are typically made of triglycerides which are esters of free fatty acids with the trihydric alcohol, glycerol. In transesterification, the glycerol in a triacylglyceride (TAG) is replaced with a short-chain alcohol such as methanol or ethanol. A typical reaction scheme is as follows:

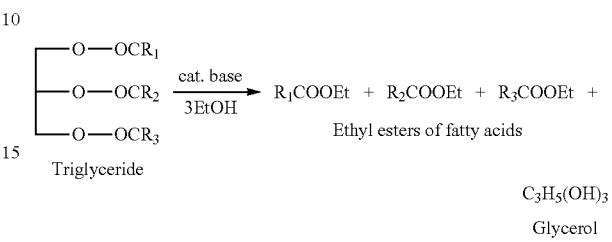

Triglyceride $C_3H_5(OH)_3$

Glycerol

In this scheme, the alcohol is deprotonated with a base to make it a stronger nucleophile. Commonly, ethanol or methanol is used in vast excess (up to 50-fold). Normally, this reaction will proceed either exceedingly slowly or not at all. Heat, as well as an acid or base can be used to help the reaction proceed more quickly. The acid or base are not consumed by the transesterification reaction, thus they are not reactants but catalysts. Almost all biodiesel has been produced using the base-catalyzed technique as it requires only low temperatures and pressures and produces over 98% conversion yield (provided the starting oil is low in moisture and free fatty acids).

Any free fatty acids in the base oil are either converted to soap and removed from the process, or they are esterified (yielding more biodiesel) using an acidic catalyst.

The most common form of transesterification uses methanol to produce methyl esters as it is the cheapest alcohol available. Ethanol is used to produce ethyl ester biodiesel. Higher alcohols, such as isopropanol and butanol can also be used.

A byproduct of the transesterification process is the production of glycerol. Approximately for every ton of biodiesel produced, 100 kg of glycerol are produced. This glycerol may be used as a chemical building block, and may also be used as a carbon source to ferment microorganisms.

b) Using Recombinant Lipases

Transesterification has also been carried out using an enzyme, such as a lipase instead of a base. Lipase-catalyzed transesterification can be carried out, for example, at a temperature between the room temperature and 80° C., and a mole ratio of the TAG to the lower alcohol of greater than 1:1, preferably 2:1, more preferably 3:1, and most preferably about 3:1.

Lipases suitable for use in transesterification include, but are not limited to, those listed in Table 11 below. Other examples of lipases useful for transesterification are found in, e.g. U.S. Pat. Nos. 4,798,793; 4,940,845 5,156,963; 5,342,768; 5,776,741 and WO89/01032.

TABLE 11

Lipases suitable for use in transesterification.

*Aspergillus niger* lipase ABG73614, *Candida antarctica* lipase B (novozym-435) CAA83122, *Candida cylindracea* lipase AAR24090, *Candida lipolytica* lipase (Lipase L; Amano Pharmaceutical Co., Ltd.), *Candida rugosa* lipase (e.g., Lipase-OF; Meito Sangyo Co., Ltd.), *Mucor miehei* lipase (Lipozyme IM 20), *Pseudomonas fluorescens* lipase AAA25882, *Rhizopus japonicas* lipase (Lilipase A-10FG)

TABLE 11-continued

Lipases suitable for use in transesterification.

Q7M4U7_1, *Rhizomucor miehei* lipase B34959, *Rhizopus oryzae* lipase (Lipase F) AAF32408, *Serratia marcescens* lipase (SM Enzyme) ABI13521, *Thermomyces lanuginosa* lipase CAB58509, Lipase P (Nagase ChemteX Corporation), and Lipase QLM (Meito Sangyo Co., Ltd., Nagoya, Japan)

One challenge to using a lipase for the production of fatty acid esters suitable for biodiesel is that the price of lipase is much higher than the price of sodium hydroxide (NaOH) used by the strong base process. This challenge has been addressed by using an immobilized lipase, which can be recycled. However, the activity of the immobilized lipase must be maintained after being recycled for a minimum number of cycles to allow a lipase-based process to compete with the strong base process in terms of the production cost. Immobilized lipases are subject to poisoning by the lower alcohols typically used in transesterification. U.S. Pat. No. 6,398,707 (issued Jun. 4, 2002 to Wu et al.) describes methods for enhancing the activity of immobilized lipases and regenerating immobilized lipases having reduced activity.

2. Standards

The common international standard for biodiesel is EN 14214. ASTM D6751 is the most common biodiesel standard referenced in the United States and Canada. Germany uses DIN EN 14214 and the UK requires compliance with BS EN 14214.

Basic industrial tests to determine whether the products conform to these standards typically include gas chromatography, HPLC, and others. Biodiesel meeting the quality standards is very non-toxic, with a toxicity rating ($LD_{50}$) of greater than 50 mL/kg.

B. Renewable Diesel

Renewable diesel comprises a mixture of alkanes, such as C10:0, C12:0, C14:0, C16:0 and C18:0 and thus, are distinguishable from biodiesel. High quality renewable diesel conforms to the ASTM D 975 standard.

The lipid:organic solvent layer or lipids produced by the method of the present invention can serve as feedstock to produce renewable diesel. Thus, in another aspect of the present invention, a method for producing renewable diesel is provided. Renewable diesel can be produced by at least three processes, hydrothermal processing (hydrotreating), hydroprocessing, and indirect liquefaction. These processes yield non-ester distillates. During these processes, triacylglycerides produced and isolated as described herein, are broken down to alkenes of C16 and C18.

Thus, in another aspect of the present invention a method for producing renewable diesel is provided. In a preferred embodiment, the method for producing renewable diesel comprises the steps of A method of producing renewable diesel comprising the steps of: (a) lysing a lipid-containing microorganism to produce a lysate; (b) treating the lysate with an organic solvent for a period of time sufficient to allow the lipid from the microorganism to become solubilized in the organic solvent to form a heterogeneous mixture; (c) separating the heterogeneous mixture into a lipid:organic solvent composition and an aqueous composition and, optionally, an emulsified composition or cell pellet composition; (d) removing the lipid:organic solvent composition from the aqueous composition, emulsion composition, or cell pellet composition; and (e) treating the lipid:organic to produce a straight chain alkane, whereby renewable diesel is produced. The lipid:organic solvent composition comprises the organic solvent and the cellular lipids.

1. Hydrotreating

In a preferred embodiment of the method for producing renewable diesel, treating the lipid:organic solvent composition or the lipids produced and isolated to produce a straight chain alkane, is performed by hydrotreating of the lipid:organic solvent composition. In hydrothermal processing, typically, biomass is reacted in water at an elevated temperature and pressure to form oils and residual solids. Conversion temperatures are typically 570° to 660° F., with pressure sufficient to keep the water primarily as a liquid, 100 to 170 standard atmosphere (atm). Reaction times are on the order of 15 to 30 minutes. After the reaction is completed, the organics are separated from the water. Thereby a distillate suitable for diesel is produced.

2. Hydroprocessing

A renewable diesel, referred to as "green diesel" can be produced from fatty acids by traditional hydroprocessing technology. The triglyceride-containing oils can be hydroprocessed either as co-feed with petroleum or as a dedicated feed. The product is a premium diesel fuel containing no sulfur and having a cetane number of 90-100. Thus, in another preferred embodiment of the method for producing renewable diesel, treating the lipid:organic solvent composition or the lipids produced and isolated to produce a straight chain alkane, is performed by hydroprocessing of the lipid:organic solvent composition.

Petroleum refiners use hydroprocessing to remove impurities by treating feeds with hydrogen. Hydroprocessing conversion temperatures are typically 600° to 700° F. Pressures are typically 40 to 100 atm. The reaction times are on the order of 10 to 60 minutes.

Solid catalysts are employed to increase certain reaction rates, improve selectivity for certain products, and optimize hydrogen consumption.

Hydrotreating and hydroprocessing can ultimately lead to a reduction in the molecular weight of the feed. In the case of triglyceride-containing oils, the triglyceride molecule is reduced to four hydrocarbon molecules under hydroprocessing conditions: a propane molecule and three hydrocarbon molecules, typically in the C12 to C18 range. In some methods, the first step of treating a triglyceride is hydroprocessing to saturate double bonds, followed by deoxygenation at elevated temperature in the presence of hydrogen and a catalyst. In some methods, hydrogenation and deoxygenation occur in the same reaction. In other methods deoxygenation occurs before hydrogenation. Isomerization is then optionally performed, also in the presence of hydrogen and a catalyst. Finally, gases and naphtha components can be removed if desired. For example, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

3. Indirect Liquefaction

A traditional ultra-low sulfur diesel can be produced from any form of biomass by a two-step process. First, the biomass is converted to a syngas, a gaseous mixture rich in hydrogen and carbon monoxide. Then, the syngas is catalytically converted to liquids. Typically, the production of liquids is accomplished using Fischer-Tropsch (FT) synthesis. This technology applies to coal, natural gas, and heavy oils. Thus, in yet another preferred embodiment of the method for producing renewable diesel, treating the lipid:organic solvent composition or the lipids produced and isolated to produce a straight chain alkane, is performed by indirect liquefaction of the lipid:organic solvent composition.

C. Jet Fuel

The annual U.S. usage of jet fuel in 2006 was about 21 billion gallons (about 80 billion liters). Aeroplane fuel is clear to straw colored. The most common fuel is an unleaded/paraffin oil-based fuel classified as Aeroplane A-1, which is produced to an internationally standardized set of specifications. Aeroplane fuel is a mixture of a large number of different hydrocarbons, possibly as many as a thousand or more. The range of their sizes (molecular weighs or carbon numbers) is restricted by the requirements for the product, for example, freezing point or smoke point. Kerosone-type Aeroplane fuel (including Jet A and Jet A-1) has a carbon number distribution between about 8 and 16 carbon numbers. Wide-cut or naphta-type Aeroplane fuel (including Jet B) has a carbon number distribution between about 5 and 15 carbon numbers.

Both Aeroplanes (Jet A and jet B) may contain a number of additives. Useful additives include, but are not limited to, antioxidants, antistatic agents, corrosion inhibitors, and fuel system icing inhibitor (FSII) agents. Antioxidants prevent gumming and usually, are based on alkylated phenols, for example, AO-30, AO-31, or AO-37. Antistatic agents dissipate static electricity and prevent sparking. Stadis 450 with dinonylnaphthylsulfonic acid (DINNSA) as the active ingredient, is an example. Corrosion inhibitors, e.g., DCI-4A is used for civilian and military fuels and DCI-6A is used for military fuels. FSII agents, include, e.g., Di-EGME.

A solution is blending algae fuels with existing jet fuel. The present invention provides such a solution. The lipid:organic solvent layer or lipids produced by the method of the present invention can serve as feedstock to produce jet fuel. Thus, in another aspect of the present invention, a method for producing jet fuel is provided. Herewith two methods for producing jet fuel from the lipid:organic solvent layer or lipids produced by the method of the present invention are provided, fluid catalytic cracking (FCC) and hydrodeoxygenation (HDO).

1. Fluid Catalytic Cracking

Fluid Catalytic Cracking (FCC) is one method which is used to produce olefins, especially propylene from heavy crude fractions. There are reports in the literature that vegetable oils such as canola oil could be processed using FCC to give a hydrocarbon stream useful as a gasoline fuel.

The lipid:organic solvent layer or lipids produced by the method of the present invention can be converted to $C_2$-$C_5$ olefins. The process involves flowing the lipid:organic solvent layer or lipids produced through an FCC zone and collecting a product stream comprised of olefins, which is useful as a jet fuel. The lipid:organic solvent layer or lipids produced are contacted with a cracking catalyst at cracking conditions to provide a product stream comprising $C_2$-$C_5$ olefins and hydrocarbons useful as jet fuel.

Thus, in yet another aspect of the present invention a method for producing jet fuel is provided. In a preferred embodiment, the method for producing jet fuel comprises the steps of (a) lysing a lipid-containing microorganism to produce a lysate; (b) treating the lysate with anorganic solvent for a period of time sufficient to allow the lipid from the microorganism to become solubilized in the organic solvent to form a heterogeneous mixture; (c) separating the heterogeneous mixture into a lipid:organic solvent composition and an aqueous composition and, optionally, an emulsified composition or cell pellet composition; (d) removing the lipid:organic solvent composition from the aqueous composition, emulsion composition, or cell pellet composition; and (e) treating the lipid:organic solvent composition to produce a C2-C5 olefine, whereby jet fuel is produced. The lipid:organic solvent composition comprises the organic solvent and cellular lipids.

In a preferred embodiment of the method for producing a jet fuel, step (f) is performed by flowing the lipid:organic solvent composition through a fluid catalytic cracking zone. Step (f) may further comprise contacting the lipid:organic solvent composition with a cracking catalyst at cracking conditions to provide a product stream comprising $C_2$-$C_5$ olefins.

In certain embodiments of this method it may be desirable to remove any contaminants that may be present in the lipid:organic solvent composition. Thus, prior to step (f) flowing the lipid:organic solvent composition through a fluid catalytic cracking zone, the lipid:organic solvent composition is pretreated. Pretreatment may involve contacting the lipid:organic solvent composition with an ion-exchange resin. The ion exchange resin is an acidic ion exchange resin, such as Amberlyst™-15 and can be used as a bed in a reactor through which the lipid:organic solvent composition is flowed through, either upflow or downflow. Other pretreatments may include mild acid washes by contacting the lipid:organic solvent composition with an acid, such as sulfuric, acetic, nitric, or hydrochloric acid. Contacting is done with a dilute acid solution usually at ambient temperature and atmospheric pressure.

The lipid:organic solvent composition, optionally pretreated, is flowed to an FCC zone where the hydrocarbonaceous components are cracked to olefins. Catalytic cracking is accomplished by contacting the lipid:organic solvent composition in a reaction zone with a catalyst composed of finely divided particulate material. The reaction is catalytic cracking, as opposed to hydrocracking, and is carried out in the absence of added hydrogen or the consumption of hydrogen. As the cracking reaction proceeds, substantial amounts of coke are deposited on the catalyst. The catalyst is regenerated at high temperatures by burning coke from the catalyst in a regeneration zone. Coke-containing catalyst, referred to herein as "coked catalyst", is continually transported from the reaction zone to the regeneration zone to be regenerated and replaced by essentially coke-free regenerated catalyst from the regeneration zone. Fluidization of the catalyst particles by various gaseous streams allows the transport of catalyst between the reaction zone and regeneration zone. Methods for cracking hydrocarbons, such as those of the lipid:organic solvent composition described herein, in a fluidized stream of catalyst, transporting catalyst between reaction and regeneration zones, and combusting coke in the regenerator are well known by those skilled in the art of FCC processes. Exemplary FCC applications and catalysts useful for cracking the lipid:organic solvent composition to produce $C_2$-$C_5$ olefins are described in U.S. Pat. Nos. 6,538,169, 7,288,685, which are incorporated in their entirety by reference.

In one embodiment, cracking the lipid:organic solvent composition of the present invention, takes place in the riser section or, alternatively, the lift section, of the FCC zone. The lipid:organic solvent composition is introduced into the riser by a nozzle resulting in the rapid vaporization of the lipid:organic solvent composition. Before contacting the catalyst, the lipid:organic solvent composition will ordinarily have a temperature of about 149° C. to about 316° C. (300° F. to 600° F.). The catalyst is flowed from a blending vessel to the riser where it contacts the lipid:organic solvent composition for a time of abort 2 seconds or less.

The blended catalyst and reacted lipid:organic solvent composition vapors are then discharged from the top of the riser through an outlet and separated into a cracked product vapor stream including olefins and a collection of catalyst particles covered with substantial quantities of coke and generally referred to as "coked catalyst." In an effort to minimize the contact time of the lipid:organic solvent composition and the catalyst which may promote further conversion of desired products to undesirable other products, any arrangement of separators such as a swirl arm arrangement can be used to remove coked catalyst from the product stream quickly. The separator, e.g. swirl arm separator, is located in an upper portion of a chamber with a stripping zone situated in the lower portion of the chamber. Catalyst separated by the swirl arm arrangement drops down into the stripping zone. The cracked product vapor stream comprising cracked hydrocarbons including light olefins and some catalyst exit the chamber via a conduit which is in communication with cyclones. The cyclones remove remaining catalyst particles from the product vapor stream to reduce particle concentrations to very low levels. The product vapor stream then exits the top of the separating vessel. Catalyst separated by the cyclones is returned to the separating vessel and then to the stripping zone. The stripping zone removes adsorbed hydrocarbons from the surface of the catalyst by counter-current contact with steam.

Low hydrocarbon partial pressure operates to favor the production of light olefins. Accordingly, the riser pressure is set at about 172 to 241 kPa (25 to 35 psia) with a hydrocarbon partial pressure of about 35 to 172 kPa (5 to 25 psia), with a preferred hydrocarbon partial pressure of about 69 to 138 kPa (10 to 20 psia). This relatively low partial pressure for hydrocarbon is achieved by using steam as a diluent to the extent that the diluent is 10 to 55 wt-% of lipid:organic solvent composition and preferably about 15 wt-% of lipid:organic solvent composition. Other diluents such as dry gas can be used to reach equivalent hydrocarbon partial pressures.

The temperature of the cracked stream at the riser outlet will be about 510° C. to 621° C. (950° F. to 1150° F.). However, riser outlet temperatures above 566° C. (1050° F.) make more dry gas and more olefins. Whereas, riser outlet temperatures below 566° C. (1050° F.) make less ethylene and propylene. Accordingly, it is preferred to run the FCC process at a preferred temperature of about 566° C. to about 630° C., preferred pressure of about 138 kPa to about 240 kPa (20 to 35 psia). Another condition for the process is the catalyst to lipid:organic solvent composition ratio which can vary from about 5 to about 20 and preferably from about 10 to about 15.

In one embodiment of the method for producing a jet fuel, the lipid:organic solvent composition is introduced into the lift section of an FCC reactor. The temperature in the lift section will be very hot and range from about 700° C. (1292° F.) to about 760° C. (1400° F.) with a catalyst to lipid:organic solvent composition ratio of about 100 to about 150. It is anticipated that introducing the lipid:organic solvent composition into the lift section will produce considerable amounts of propylene and ethylene.

Gas and liquid hydrocarbon products produced can be analyzed by gas chromatography, HPLC, etc.

2. Hydrodeoxygenation

In another embodiment of the method for producing a jet fuel using the lipid:organic solvent composition or the lipids produced as described herein, the structure of the lipid:organic solvent composition or the lipids is broken by a process referred to as hydrodeoxygenation (HDO). As such step (f) is performed by hydrodeoxygenating the lipid:organic solvent composition.

HDO means removal of oxygen by means of hydrogen, that is, oxygen is removed while breaking the structure of the material. Olefinic double bonds are hydrogenated and any sulphur and nitrogen compounds are removed. Sulphur removal is called hydrodesulphurization (HDS). Pretreatment and purity of the raw materials (lipid:organic solvent composition or the lipids) contribute to the service life of the catalyst.

Generally in the HDO/HDS step, hydrogen is mixed with the feed stock (lipid:organic solvent composition or the lipids) and then the mixture is passed through a catalyst bed as a co-current flow, either as a single phase or a two phase feed stock. After the HDO/MDS step, the product fraction is separated and passed to a separate isomerzation reactor. An isomerization reactor for biological starting material is described in the literature (FI 100 248) as a co-current reactor.

The process for producing a fuel by hydrogenating a hydrocarbon feed, e.g., the lipid:organic solvent composition or the lipids herein, can also be performed by passing the lipid:organic solvent composition or the lipids as a co-current flow with hydrogen gas through a first hydrogenation zone, and thereafter the hydrocarbon effluent is further hydrogenated in a second hydrogenation zone by passing hydrogen gas to the second hydrogenation zone as a counter-current flow relative to the hydrocarbon effluent. Exemplary HDO applications and catalysts useful for cracking the lipid:organic solvent composition to produce $C_2$-$C_5$ olefins are described in U.S. Pat. No. 7,232,935 which is incorporated in its entirety by reference.

Typically, in the hydrodeoxygenation step, the structure of the biological component, such as the lipid:organic solvent composition or lipids herein, is decomposed, oxygen, nitrogen, phosphorus and sulphur compounds, and light hydrocarbons as gas are removed, and the olefinic bonds are hydrogenated. In the second step of the process, i.e. in the so-called isomerization step, isomerzation is carried out for branching the hydrocarbon chain and improving the performance of the paraffin at low temperatures.

In the first step i.e. HDO step of the cracking process, hydrogen gas and the lipid:organic solvent composition or lipids herein which are to be hydrogenated are passed to a HDO catalyst bed system either as co-current or counter-current flows, said catalyst bed system comprising one or more catalyst bed(s), preferably 1-3 catalyst beds. The HDO step is typically operated in a co-current manner. In case of a HDO catalyst bed system comprising two or more catalyst beds, one or more of the beds may be operated using the counter-current flow principle.

In the HDO step, the pressure varies between 20 and 150 bar, preferably between 50 and 100 bar, and the temperature varies between 200 and 500° C., preferably in the range of 300-400° C.

In the HDO step, known hydrogenation catalysts containing metals from Group VII and/or VIB of the Periodic System may be used. Preferably, the hydrogenation catalysts are supported Pd, Pt, Ni, NiMo or a CoMo catalysts, the support being alumina and/or silica. Typically, $NiMo/Al_2O_3$ and $CoMo/Al_2O_3$ catalysts are used.

Prior to the HDO step, the lipid:organic solvent composition or lipids herein may optionally be treated by prehydrogenation under milder conditions thus avoiding side reactions of the double bonds. Such prehydrogenation is carried out in the presence of a prehydrogenation catalyst at temperatures of 50 400° C. and at hydrogen pressures of 1 200 bar, preferably at a temperature between 150 and 250° C. and at a hydrogen pressure between 10 and 100 bar. The catalyst may contain metals from Group VIII and/or VIB of the Periodic System. Preferably, the prehydrogenation catalyst is a supported Pd, Pt, Ni, NiMo or a CoMo catalyst, the support being alumina and/or silica.

A gaseous stream from the HDO step containing hydrogen is cooled and then carbon monoxide, carbon dioxide, nitrogen, phosphorus and sulphur compounds, gaseous light hydrocarbons and other impurities are removed therefrom. After compressing, the purified hydrogen or recycled hydrogen is returned back to the first catalyst bed and/or between the catalyst beds to make up for the withdrawn gas stream. Water is removed from the condensed liquid. The liquid is passed to the first catalyst bed or between the catalyst beds.

After the HDO step, the product is subjected to an isomerization step. It is substantial for the process that the impurities are removed as completely as possible before the hydrocarbons are contacted with the isomerization catalyst. The isomerization step comprises an optional stripping step, wherein the reaction product from the HDO step may be purified by stripping with water vapour or a suitable gas such as light hydrocarbon, nitrogen or hydrogen. The optional stripping step is carried out in counter-current manner in a unit upstream of the isomerization catalyst, wherein the gas and liquid are contacted with each other, or before the actual isomerization reactor in a separate stripping unit utilizing counter-current principle.

After the stripping step the hydrogen gas and the hydrogenated lipid:organic solvent composition or lipids herein, and optionally an n-paraffin mixture, are passed to a reactive isomerization unit comprising one or several catalyst bed(s). The catalyst beds of the isomerization step may operate either in co-current or counter-current manner.

It is important for the process that the counter-current flow principle is applied in the isomerization step. In the isomerization step this is done by carrying out either the optional stripping step or the isomerization reaction step or both in counter-current manner.

The isomerization step and the HDO step may be carried out in the same pressure vessel or in separate pressure vessels. Optional prehydrogenation may be carried out in a separate pressure vessel or in the same pressure vessel as the HDO and isomerization steps.

In the isomerzation step, the pressure varies in the range of 20 150 bar, preferably in the range of 20 100 bar, the temperature being between 200 and 500° C., preferably between 300 and 400° C.

In the isomerization step, isomerization catalysts known in the art may be used. Suitable isomerization catalysts contain molecular sieve and/or a metal from Group VII and/or a carrier. Preferably, the isomerization catalyst contains SAPO-11 or SAPO41 or ZSM-22 or ZSM-23 or ferrierite and Pt, Pd or Ni and $Al_2O_3$ or $SiO_2$. Typical isomerization catalysts are, for example, $Pt/SAP0-11/Al_2O_3$, $Pt/ZSM-22/Al_2O_3$, $Pt/ZSM-23/Al_2O_3$ and $Pt/SAP0-11/SiO_2$.

As the product, a high quality hydrocarbon component of biological origin, useful as a diesel fuel or a component thereof, is obtained, the density, cetane number and performance at low temperate of said hydrocarbon component being excellent.

VIII. Compositions

Another object of the present invention is to provide compositions comprising lipids isolated by using the methods described herein. A preferred composition comprises (i) a first lipid isolated from a microorganism and (ii) a second lipid, wherein the second lipid is obtained from a source other than the microorganism.

The first lipid can be isolated from any of the microorganisms described herein.

A. First Lipids

Methods of the present invention are applicable to extracting a variety of lipids from a variety of microorganisms. Microorganisms described herein produce a variety of lipids, such as phospholipids, free fatty acids, esters of fatty acids, including triglycerides of fatty acids, sterols; pigments (e.g., carotenoids and oxycarotenoids) and other lipids, and lipid associated compounds such as phytosterols, ergothionine, lipoic acid and antioxidants including beta-carotene and tocopherol. Exemplary first lipids include, but are not limited to, C8, C10, C12, C14, C16 and C18 triacylglycerides, lipids containing omega-3 highly unsaturated fatty acids, such as docosahexaenoic acid (DHA), eicosapentaenoic acid (EPA), and/or docosapentaenoic acid (DPA). First lipids also include arachidonic acid, stearidonic acid, cholesterol, desmesterol, astaxanthin, canthaxanthin, and n-6 and n-3 highly unsaturated fatty acids such as eicosapentaenoic acid, docosapentaenoic acid and docosahexaenoic acid. Other lipids and microorganisms which may be suitable for use in the instant invention will be readily apparent to those skilled in the art.

Preferred first lipids are lipids containing a relatively large amount of C18 and C16 fatty acids.

1. C18:1

In a preferred embodiment of the present invention, the first lipid of a composition comprises at least 50% of a C18:1 lipid, preferably at least 60%, and more preferably at least 80%.

2. C10, C12 and C14

In another preferred embodiment of the present invention, the first lipid of a composition comprises at least 10% of a C10:0, C12:0 and C14:0 lipid combined, preferably at least 15%, more preferably at least 20%, and most preferably at least 30%.

B. Second Lipids

The second lipid can be any oil, optionally selected from the group consisting of oil from soy, rapeseed, canola, palm, coconut, corn, waste vegetable, Chinese tallow, olive, sunflower, cotton seed. chicken fat, beef tallow, porcine tallow, microalgae, macroalgae, *Cuphea*, flax, peanut, choice white grease, lard, *Camelina sativa*, mustard seed, cashew nut, oats, lupine, kenaf, *calendula*, hemp, coffee, linseed, hazelnuts, *euphorbia*, pumpkin seed, coriander, camellia, sesame, safflower, rice, tung oil tree, cocoa, copra, pium poppy, castor beans, pecan nuts, jojoba, jatropha, *macadamia* nuts, Brazil nuts, and avocado. A preferred second lipid is coconut oil. Another preferred second lipid is palm oil or soy oil. A second lipid can also be a fossil oil such as crude oil or a distillate fraction of crude oil.

C. Compositions Comprising a First Lipid and a Second Lipid

The first lipid and the second lipid can be provided at different ratios. In a preferred embodiment, the ratio of the first lipid to the second lipid is between 1 and 100. In another preferred embodiment, the ratio of the first lipid to the second lipid is between 1 and 10. In another preferred embodiment, the ratio of the first lipid to the second lipid is about 1. In another embodiment, the ratio of the second lipid to the first lipid is between 10 and 1.

Additional embodiments of the present invention include optional functional components that would allow one of ordinary skill in the art to perform any of the method variations described herein.

Although the forgoing invention has been described in some detail by way of illustration and example for clarity and understanding, it will be readily apparent to one of ordinary skill in the art in light of the teachings of this invention that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature, including accession numbers to GenBank database sequences, referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter. The publications mentioned herein are cited for the purpose of describing and disclosing reagents, methodologies and concepts that may be used in connection with the present invention. Nothing herein is to be construed as an admission that these references are prior art in relation to the inventions described herein. In particular, the following patent applications are hereby incorporated by reference in their entireties for all purposes: U.S. Provisional Application No. 61/028,493, filed Feb. 13, 2008, entitled "Extraction of Lipids from Microorganisms"; U.S. Provisional Application No. 61/036,918, filed Mar. 14, 2008, entitled "Oil Separation Methods"; U.S. Provisional Application No. 61/043,318, filed Apr. 8, 2008, entitled "Fractionation of Oil-Bearing Biomass"; PCT Patent Application No. PCT/US2009/066142, filed Nov. 30, 2009, entitled "Production of Tailored Oils in Heterotrophic Microorganisms"; and PCT Patent Application No. PCT/US2009/066141, filed Nov. 30, 2009, entitled "Manufacturing of Tailored Oils in Recombinant Heterotrophic Microorganisms".

Although this invention has been described in connection with specific embodiments thereof, it will be understood that it is capable of further modifications. The present invention also has a wide variety of applications. This application is intended to cover any variations, uses or adaptations of the invention following, in general, the principles of the invention and including such departures from the present disclosure as come within known or customary practice within the art to which the invention pertains and as may be applied to the essential features hereinbefore set forth.

IX. Examples

Example 1

Cultivation of Microalgae to Achieve High Oil Content

Microalgae strains were cultivated to achieve a high percentage of oil by dry cell weight. Cryopreserved cells were thawed at room temperature and 500 µl of cells were added to 4.5 ml of medium (4.2 g/L $K_2HPO_4$, 3.1 g/L $NaH_2PO_4$, 0.2 g/L $MgSO_4\cdot7H_2O$, 0.25 g/L citric acid monohydrate, 0.025 g/L $CaCl_2\cdot2H_2O$, 2 g/L yeast extract) plus 2% glucose and grown for 7 days at 28° C. with agitation (200 rpm) in a 6-well plate. Dry cell weights were determined by centrifuging 1 ml of culture at 14,000 rpm for 5 min in a pre-weighed Eppendorf tube. The culture supernatant was discarded and the resulting cell pellet washed with 1 ml of deionized water. The culture was again centrifuged, the supernatant discarded, and the cell pellets placed at −80° C. until frozen. Samples were then lyophilized for 24 hours and dry cell wights calculated. For determination of total lipid in cultures, 3 ml of culture was removed and subjected to analysis using an Ankom system (Ankom Inc., Macedon, N.Y.) according to the manufacturer's protocol. Samples were subjected to solvent extraction with an Ankom XT10 extractor according to manufacturer's protocol. Total lipid was determined as the difference in mass between acid hydrolyzed dried samples and solvent extracted, dried samples. Percent oil dry cell weight measurements are shown in Table 12.

TABLE 12

Percent oil dry cell weight for microalgae.

| Species | Strain | % Oil | Strain # |
|---|---|---|---|
| Chlorella kessleri | UTEX 387 | 39.42 | 4 |
| Chlorella kessleri | UTEX 2229 | 54.07 | 5 |
| Chlorella kessleri | UTEX 398 | 41.67 | 6 |
| Parachlorella kessleri | SAG 11.80 | 37.78 | 7 |
| Parachlorella kessleri | SAG 14.82 | 50.70 | 8 |
| Parachlorella kessleri | SAG 21.11 H9 | 37.92 | 9 |
| Prototheca stagnora | UTEX 327 | 13.14 | 10 |
| Prototheca moriformis | UTEX 1441 | 18.02 | 11 |
| Prototheca moriformis | UTEX 1435 | 27.17 | 12 |
| Chlorella minutissima | UTEX 2341 | 31.39 | 13 |
| Chlorella protothecoides | UTEX 250 | 34.24 | 1 |
| Chlorella protothecoides | UTEX 25 | 40.00 | 2 |
| Chlorella protothecoides | CCAP 211/8D | 47.56 | 3 |
| Chlorella sp. | UTEX 2068 | 45.32 | 14 |
| Chlorella sp. | CCAP 211/92 | 46.51 | 15 |
| Chlorella sorokiniana | SAG 211.40B | 46.67 | 16 |
| Parachlorella beijerinkii | SAG 2046 | 30.98 | 17 |
| Chlorella luteoviridis | SAG 2203 | 37.88 | 18 |
| Chlorella vulgaris | CCAP 211/11K | 35.85 | 19 |
| Chlorella reisiglii | CCAP 11/8 | 31.17 | 20 |
| Chlorella epllipsoidea | CCAP 211/42 | 32.93 | 21 |
| Chlorella saccharophila | CCAP 211/31 | 34.84 | 22 |
| Chlorella saccharophila | CCAP 211/32 | 30.51 | 23 |

Example 2

Cultivation of *Chlorella protothecoides*

Three fermentation processes were performed with three different media formulations with the goal of generating algal biomass with high oil content. The first formulation (Media 1) was based on medium described in Wu et al. (1994 *Science in China*, vol. 37, No. 3, pp. 326-335) and consisted of per liter: $KH_2PO_4$, 0.7 g; $K_2HPO_4$, 0.3 g; $MgSO_4\cdot7H_2O$, 0.3 g; $FeSO_4\cdot7H_2O$, 3 mg; thiamine hydrochloride, 10 µg; glucose, 20 g; glycine, 0.1 g; $H_3BO_3$, 2.9 mg; $MnCl_2\cdot4H_2O$, 1.8 mg; $ZnSO_4\cdot7H_2O$, 220 µg; $CuSO_4\cdot5H_2O$, 80 µg; and $NaMoO_4\cdot2H_2O$, 22.9 mg. The second medium (Media 2) was derived from the flask media described in Example 1 and consisted of per liter: $K_2HPO_4$, 4.2 g; $NaH_2PO_4$, 3.1 g; $MgSO_4\cdot7H_2O$, 0.24 g; citric acid monohydrate, 0.25 g; calcium chloride dehydrate, 25 mg; glucose, 20 g; yeast extract, 2 g. The third medium (Media 3) was a hybrid and consisted of per liter: $K_2HPO_4$, 4.2 g; $NaH_2PO_4$, 3.1 g; $MgSO_4\cdot7H_2O$, 0.24 g; citric acid monohydrate, 0.25 g; calcium chloride dehydrate, 25 mg; glucose, 20 g; yeast extract, 2 g; $H_3BO_3$, 2.9 mg; $MnCl_2\cdot4H_2O$, 1.8 mg; $ZnSO_4\cdot7H_2O$, 220 µg; $CuSO_4\cdot5H_2O$, 80 µg; and $NaMoO_4\cdot2H_2O$, 22.9 mg. All three media formulations were prepared and autoclave sterilized in lab scale fermentor vessels for 30 minutes at 121° C. Sterile glucose was added to each vessel following cool down post autoclave sterilization.

Inoculum for each fermentor was *Chlorella protothecoides* (UTEX 250), prepared in two flask stages using the medium and temperature conditions of the fermentor inoculated. Each fermentor was inoculated with 10% (v/v) mid-log culture. The three lab scale fermentors were held at 28° C. for the duration of the experiment. The microalgal cell growth in Media 1 was also evaluated at a temperature of 23° C. For all fermentor evaluations, pH was maintained at 6.6-6.8, agitations at 500 rpm, and airflow at 1 vvm. Fermentation cultures were cultivated for 11 days. Biomass accumulation was measured by optical density at 750 nm and dry cell weight.

Lipid/oil concentration was determined using direct transesterification with standard gas chromatography methods. Briefly, samples of fermentation broth with biomass was blotted onto blotting paper and transferred to centrifuge tubes and dried in a vacuum oven at 65-70° C. for 1 hour. When the samples were dried, 2 mL of 5% $H_2SO_4$ in methanol was added to the tubes. The tubes were then heated on a heat block at 65-70° C. for 3.5 hours, while being vortexed and sonicated intermittently. 2 ml of heptane was then added and the tubes were shaken vigorously. 2Ml of 6% $K_2CO_3$ was added and the tubes were shaken vigorously to mix and then centrifuged at 800 rpm for 2 minutes. The supernatant was then transferred to GC vials containing $Na_2SO_4$ drying agent and ran using standard gas chromatography methods. Percent oil/lipid was based on a dry cell weight basis. The dry cell weights for cells grown using: Media 1 at 23° C. was 9.4 g/L; Media 1 at 28° C. was 1.0 g/L, Media 2 at 28° C. was 21.2 g/L; and Media 3 at 28° C. was 21.5 g/L. The lipid/oil concentration for cells grown using: Media 1 at 23° C. was 3 g/L; Media 1 at 28° C. was 0.4 g/L; Media 2 at 28° C. was 18 g/L; and Media 3 at 28° C. was 19 g/L. The percent oil based on dry cell weight for cells grown using: Media 1 at 23° C. was 32%; Media 1 at 28° C. was 40%; Media 2 at 28° C. was 85%; and Media 3 at 28° C. was 88%. The lipid profiles (in area %, after normalizing to the internal standard) for algal biomass generated using the three different media formulations at 28° C. are summarized below in Table 13.

TABLE 13

Lipid profiles for *Chlorella protothecoides* grown under different media conditions.

|  | Media 1 28° C. (in Area %) | Media 2 28° C. (in Area %) | Media 3 28° C. (in Area %) |
|---|---|---|---|
| C14:0 | 1.40 | 0.85 | 0.72 |
| C16:0 | 8.71 | 7.75 | 7.43 |
| C16:1 | — | 0.18 | 0.17 |
| C17:0 | — | 0.16 | 0.15 |
| C17:1 | — | 0.15 | 0.15 |
| C18:0 | 3.77 | 3.66 | 4.25 |
| C18:1 | 73.39 | 72.72 | 73.83 |
| C18:2 | 11.23 | 12.82 | 11.41 |
| C18:3 alpha | 1.50 | 0.90 | 1.02 |
| C20:0 | — | 0.33 | 0.37 |
| C20:1 | — | 0.10 | 0.39 |
| C20:1 | — | 0.25 | — |
| C22:0 | — | 0.13 | 0.11 |

Example 3

Genotyping of Microalgae with High Oil Content

Microalgae samples from the 23 strains listed in Table 12 above were genotyped. Genomic DNA was isolated from algal biomass as follows. Cells (approximately 200 mg) were centrifuged from liquid cultures for 5 minutes at 14,000×g. Cells were then resuspended in sterile distilled water, centrigured for 5 minutes at 14,000×g and the supernatant discarded. A single glass bead ~2 mm in diameter was added to the biomass and tubes were placed at −80° C. for at least 15 minutes. Samples were removed and 150 μl of grinding buffer (1% Sarkosyl, 0.25 M sucrose, 50 mM NaCl, 20 mM EDTA, 100 mM Tris-HCl, pH 8.0, RNase A 0.5 μg/μl) was added. Pellets were resuspended by vortexing briefly, followed by the addition of 40 μl of 5M NaCl. Samples were vortexed briefly, followed by the addition of 66 μl of 5% CTAB (Cetyl trimethylammonium bromide) and a final brief vortex. Samples were next incubated at 65° C. for 10 minutes after which they were centrifuged at 14,000×g for 10 minutes. The supernatant was transferred to a fresh tube and extracted once with 300 μl Phenol: Chloroform:Isoamyl alcohol 12:12:1, followed by centrifugation for 5 minutes at 14,000×g. The resulting aqueous phase was transferred to a fresh tube containing 0.7 vol of isoproanol (~190 μl), mixed by inversion and incubated at room temperature for 30 minutes or overnight at 4° C. DNA was recovered via centrifugation at 14,000×g for 10 minutes. The resulting pellet was then washed twice with 70% ethanol, followed by a final wash with 100% ethanol. Pellets were air dried for 20-30 minutes at room temperature followed by resuspension in 50 μl of 10 mM TrisCl, 1 mM EDTA (pH 8.0).

Five μl of total algal DNA, prepared as described above, was diluted 1:50 in 10 mM Tris, pH 8.0. PCR reactions, final volume 20 μl, were set up as follows. Ten μl of 2×iProof HF master mix (BIO-RAD) was added to 0.4 μl primer SZ02613 (5'-TGTTGAAGAATGAGCCGGCGAC-3' (SEQ ID NO:5) at 10 mM stock concentration). This primer sequence runs from position 567-588 in Gen Bank accession no. L43357 and is highly conserved in higher plants and algal plastid genomes. This was followed by the addition of 0.4 μl primer SZ02615 (5'-CAGTGAGCTATTACGCACTC-3' (SEQ ID NO:6) at 10 mM stock concentration). This primer sequence is complementary to position 1112-1093 in Gen Bank accession no. L43357 and is highly conserved in higher plants and algal plastid genomes. Next, 5 μl of diluted total DNA and 3.2 μl $dH_2O$ were added. PCR reactions were run as follows: 98° C., 45"; 98° C., 8"; 53° C., 12"; 72° C., 20" for 35 cycles followed by 72° C. for 1 min and holding at 25° C. For purification of PCR products, 20 μl of 10 mM Tris, pH 8.0, was added to each reaction, followed by extraction with 40 μl of Phenol:Chloroform:isoamyl alcohol 12:12:1, vortexing and centrifuging at 14,000×g for 5 minutes. PCR reactions were applied to S-400 columns (GE Healthcare) and centrifuged for 2 minutes at 3,000×g. Purified PCR products were subsequently TOPO cloned into PCR8/GW/TOPO and positive clones selected for on LB/Spec plates. Purified plasmid DNA was sequenced in both directions using M13 forward and reverse primers. Sequences from strains 1-23 (designated in Example 1, Table 12) are listed as SEQ ID NOs: 7-29 in the attached Sequence Listing.

Example 4

Genomic DNA Analysis of 23S rRNA from *Chlorella protothecoides* and *Prototheca*

Genomic DNA from 8 strains of *Chlorella protothecoides* (UTEX 25, UTEX 249, UTEX 250, UTEX 256, UTEX 264, UTEX 411, CCAP 211/17 and CCAP 211/8d) was isolated and genomic DNA analysis of 23S rRNA was performed according to the methods described above in Example 3. All strains of *Chlorella protothecoides* tested were identical in sequence except for UTEX 25. Sequences for all eight strains are listed as SEQ ID NOs: 30 and 31 in the attached Sequence Listing.

The 23s rRNA genomic sequence for *Prototheca moriformis* UTEX 1436 (SEQ ID NO: 32) was also compared to other *Prototheca* species (UTEX 1435, UTEX 1437, and UTEX 1439) and the above described *Chlorella protothecoides* strains. The comparison showed that the 23s rRNA genomic sequence for *Prototheca moriformis* UTEX 1436 was dissimilar to the other *Prototheca* genotypes (SEQ ID NO: 33).

Example 5

Diversity of Lipid Chains in Microalgal Species

Lipid samples from a subset of strains grown in Example 1, Table 12 were analyzed for lipid profile using HPLC. Results are shown below in Table 14.

TABLE 14

Diversity of lipid chains in microalgal species.

| Strain # from Table 12 | C:14:0 | C:16:0 | C:16:1 | C:18:0 | C:18:1 | C:18:2 | C:18:3 | C:20:0 | C:20:1 |
|---|---|---|---|---|---|---|---|---|---|
| 1 | 0.57 | 10.30 | 0 | 3.77 | 70.52 | 14.24 | 1.45 | 0.27 | 0 |
| 2 | 0.61 | 8.70 | 0.30 | 2.42 | 71.98 | 14.21 | 1.15 | 0.20 | 0.24 |
| 4 | 0.68 | 9.82 | 0 | 2.83 | 65.78 | 12.94 | 1.46 | 0 | 0 |
| 5 | 1.47 | 21.96 | 0 | 4.35 | 22.64 | 9.58 | 5.2 | 3.88 | 3.3 |
| 10 | 0 | 12.01 | 0 | 0 | 50.33 | 17.14 | 0 | 0 | 0 |
| 11 | 1.41 | 29.44 | 0.70 | 3.05 | 57.72 | 12.37 | 0.97 | 0.33 | 0 |
| 12 | 1.09 | 25.77 | 0 | 2.75 | 54.01 | 11.90 | 2.44 | 0 | 0 |

Example 6

Extraction of Lipids from Microalgae Using Coconut Oil

1. Cell Production

An F-Tank batch of *Chlorella protothecoides* (about 1,200 gallons) was used to generate biomass for extraction processes. The batch (#ZA07126) was allowed to run for 100 hours, while controlling the glucose levels at 16 g/L, after which time the corn syrup feed was terminated. Residual glucose levels dropped to <0 g/L two hours later. This resulted in a final age of 102 hours. The final broth volume was 1,120 gallons. Both in-process contamination checks and a thorough analysis of a final broth sample failed to show any signs of contamination.

2. Cell Disruption

Lyophilized *Chlorella protothecoides* cells were resuspended to 200 g/L with DI water containing 20 g/L KOH. This cell suspension was autoclaved at 130° C. for 30 minutes and cooled to room temperature. A 10 ml sample of this material was sonicated using a Misonix 3000 sonicator equipped with a micro-tip on level 7. The suspension was sonicated for 6 minutes on a 30 sec on/off cycle for a total of 3 cycles. More than 70% breakage was observed by microscope analysis. An aliquot of this suspension (1 ml sample) was centrifuged at 14 K rpm for 15 min. Three layers were observed: a pellet of heavy solids, an aqueous phase and an emulsion phase. No oil layer was observed.

A second set of experiments were performed looking at cell breakage efficiency at a variety of times of sonication to achieve maximal cell breakage. 6 ml samples of *Chlorella protothecoides* cells prepared as described above were sonicated using a Misonix 3000 sonicator equipped with a micro-tip on level 8 with interval times of 20 seconds on and 20 seconds off. The sonication times ranged from 10 minutes, 20 minutes and 30 minutes and were all performed with the samples on ice. The samples were then centrifuged at 4300 rpm for 30 minutes. Three layers were observed: a pellet of heavy solids, an aqueous phase and an emulsion phase. No oil layer was observed. Each time point sample was also analyzed qualitatively for total cell breakage by looking for whole cells in the lysate under 100× magnification. No whole cells were observed in any of the time point samples, indicating that 10 minutes of sonication was sufficient to achieve maximal cell breakage. Micrographs of the lysate under magnification showed oil droplets and cell debris consisting of organelles and disrupted cell membranes. To further inspection of the cell pellets from each of the samples showed no whole cells were observed, only cell debris.

*Chlorella protothecoides* oil was obtained from dried biomass via hexane extraction using standard methods known in the art (see for example U.S. Pat. Nos. 5,567,732; 6,255,505; and Yamada et al., Industrial applications of single cell oils, Eds. Kyle and Ratledge, 118-138 (1992)).

4. HPLC Analysis of Fatty Acid Profiles

The fatty acid concentrations and profiles of (i) *Chlorella* cells, (ii) pure algal oil, (iii) pure coconut oil, and (iv) the extracted oil samples were determined by HPLC.

A 50 µl sample of the (200 g/L) washed *Chlorella* cell suspension (before caustic and heat treatment; see above) was hydrolyzed by incubation at 80° C. in an isopropanol/KOH saturated solution for 4 hours. The cells were then centrifuged at 14 K rpm for 10 min and the hydrolysate was loaded onto an HPLC column. Samples were analyzed using an Aligent 1100 HPLC using the following method. The samples were derivatized with bromophenacyl bromide (60 mg/ml) and loaded onto a Luna 5u C8(2) 100 A 150×2 mm column (Phenomenex). The samples were eluted from the column using a gradient of water to 100% Acetonitrile:tetrahydrofuran (95:5). Signals were detected using DAD array detector at a wavelength of 254 nm. The result of such an analysis detailing the lipid profiles for pure oils (algal and coconut oil), established separately (i.e., not mixed with each other), is shown in FIG. 1. This result demonstrated that the lipid profiles of pure algal oil and coconut oil are different. As such, coconut oil can be used as an organic solvent to extract lipids from microalgae and the percent of lipids extracted can be determined (see below).

5. Construction and Validation of Theoretical Curves

The fatty acids from mixtures of pure algal oil extracted from *Chlorella* and coconut oil were measured as percentages of the total lipid and are shown in Table 15.

TABLE 15

Fatty acid content as percentage of total lipid.

| % Coconut Oil | % Algal Oil | C18:1 | C12 | C14 | C18:1/C12 | C18:1/C14 |
|---|---|---|---|---|---|---|
| 0 | 100 | 59 | 0.01 | 1.00 | 5,900 | 59.00 |
| 2 | 98 | 57.9 | 1.09 | 8.14 | 53.13 | 7.12 |
| 5 | 95 | 56.3 | 2.71 | 8.39 | 20.76 | 6.71 |
| 10 | 90 | 53.5 | 5.41 | 8.81 | 9.89 | 6.08 |
| 20 | 80 | 48.0 | 10.81 | 9.64 | 4.44 | 4.98 |
| 25 | 75 | 45.3 | 13.51 | 10.06 | 3.35 | 4.5 |
| 40 | 60 | 37.0 | 21.61 | 11.31 | 1.71 | 3.27 |
| 50 | 50 | 31.5 | 27.01 | 12.15 | 1.17 | 2.59 |
| 60 | 40 | 26.0 | 32.40 | 12.98 | 0.80 | 2.00 |
| 27 | 25 | 17.8 | 40.5 | 14.23 | 0.44 | 1.25 |
| 80 | 20 | 15.0 | 43.2 | 14.65 | 0.35 | 1.02 |
| 89.75 | 10.25 | 9.6 | 48.47 | 15.46 | 0.20 | 0.62 |
| 94.75 | 5.25 | 6.9 | 51.17 | 15.88 | 0.13 | 0.43 |
| 100 | 0 | 4 | 54 | 17.00 | 0.07 | 0.24 |

In pure algal oil, 59% of the total fatty acids are of the C18:1 type, 0.01% are of the C12 type, and 1% are of the C14 type. The remaining 39.99% of algal fatty acids are C10:1, C10, C18:3, C18:2, C16 or C18 fatty acids, the majority being C18:2 fatty acids (see FIG. 1). In pure coconut oil, 4% of the fatty acids are of the C18:1 type, 54% are of the C12 type, and 17% are of the C14 type. The remaining 25% are C10:1, C10, C18:3, C18:2, C16 or C18 fatty acids (see FIG. 1). Upon mixing algal oil with coconut oil, the ratio of the respective fatty acids changes. For example, in a 1:1 mixture of pure algal oil and pure coconut oil, 31.5% of the total fatty acids are of the C18:1 type (where the majority is from algal oil), 27.01% are of the C12 type (which are almost exclusively from coconut oil), and 12.15% are of the C14 type (where the majority is from coconut oil). This reference table is useful for determining the percent of algal fatty acids and the percent of coconut fatty acids upon HPLC analysis of a lipid:organic solvent composition obtained from the lightest layer of a microalgal biomass lysate that has been subjected to centrifugation.

Figure 2:
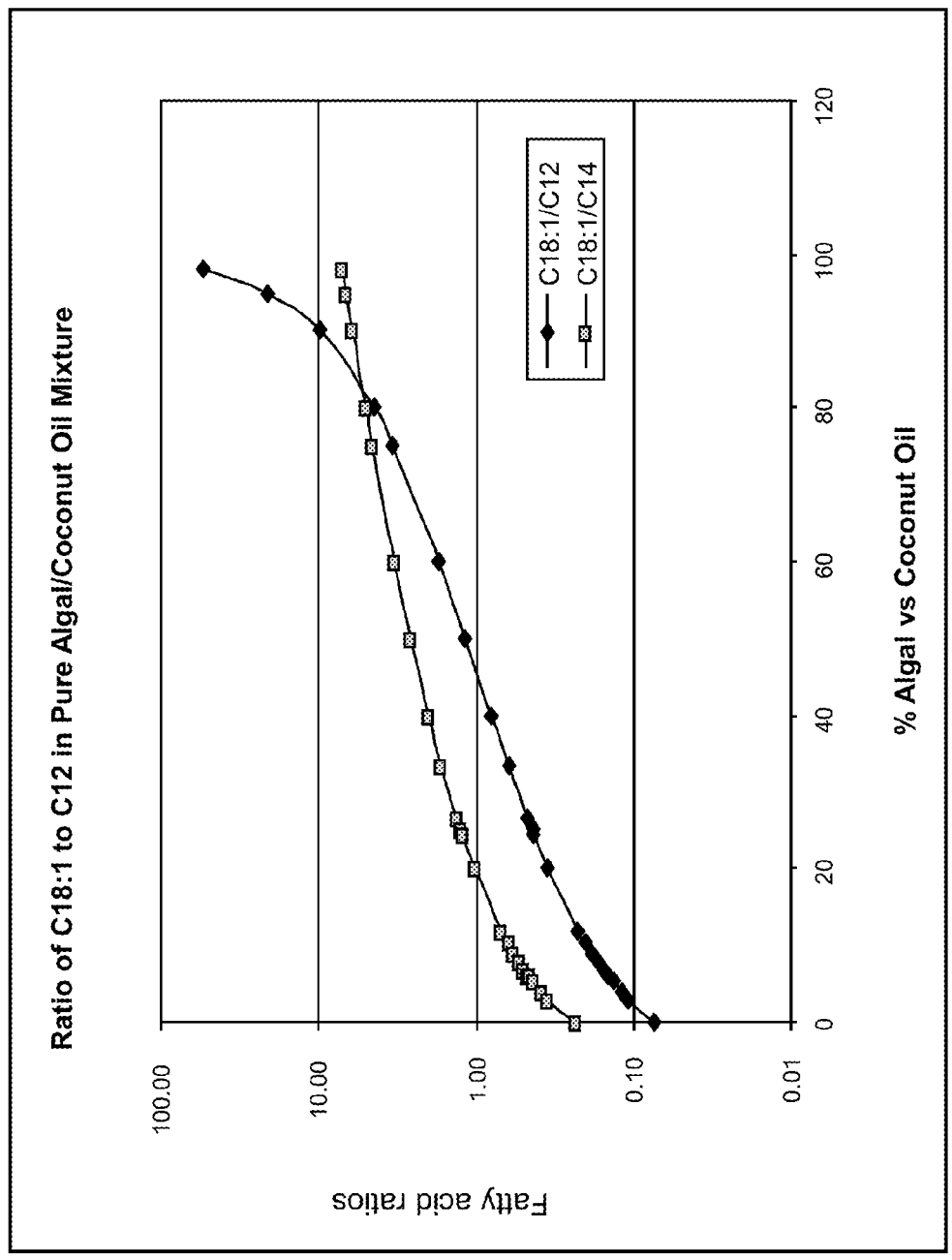
FIG. 2 depicts the ratio of C18:1 to C12 fatty acids and C18:1 to C14 fatty acids in pure algal/coconut oil mixture. Details are described in Example 6.

A curve was constructed based on the expected total C18:1 vs C12 or C14 in a mixture of the two pure oils, i.e., algal oil and coconut oil. The theoretical measurements for both curves were validated by HPLC analysis of a 1:1 mixture of pure algal to pure coconut oil which should result in 50% of each ratio. The measured value from the C18:1 to C12 and C14 was 51% and 65% respectively when fitted to the corresponding curve (FIG. 2).

6. Separating Microbial Oil from an Emulsion Using an Organic Solvent (Coconut Oil Example)

In order to free the oil from the *Chlorella* lysate, coconut oil was added to 1 ml of disrupted *Chlorella* cell material at ratios of 3:1, 1:1, 1:3 and 1:10 (algal oil to coconut oil), mixed well and heated for 15 min at 70° C. and then centrifuged for 15 min at 14 K rpm in a microcentrifuge. Upon centrifugation 4 layers were observed: a pellet of heavy solids, an aqueous phase, an emulsion phase an oil phase. Then the oil phase was separated from the other layers by pipetting. The oil phase included a mixture of algal oil and coconut oil of which an aliquot as subjected to HPLC analysis. The measurement of algal oil in the suspension was based on oil content of cells. Controls included (i) 3 mg of pure algal oil, (ii) 3 mg of pure coconut oil; and (iii) a 1:1 mixture of pure algal oil and pure coconut oil. A 5 µl sample from each was analyzed by HPLC.

7. Results

The oil content of the starting cell mass (CM) was approximately 30% as determined by HPLC. Coconut oil was used to extract lipids from a disrupted cell suspension of *Chlorella* (200 g/L was suspension) in mixtures of 3:1, 1:1, 1:3 and 1:10 (algal to coconut oil). The samples in this experiment included: (1) 3 mg pure algal oil (control); (2) 3 mg pure coconut oil (control); (3) 1:1 mix of 3 mg of each pure oil (control); (4) CM (1 ml)+coconut oil (3:1); (5) CM (1 ml)+coconut oil (1:1); (6) CM (1 ml)+coconut oil (1:3); (7) CM (1 ml)+coconut oil (1:10); and (8) CM (1 ml).

No oil layer was present in the sample without coconut oil (8). The fatty acid composition (expressed as % fatty acid of total lipid) of the pure oil controls and each of the extraction mixtures (experiments (1)-(7)) is shown in Table 16.

TABLE 16

Fatty acid composition of pure oil controls and extraction mixtures.

| % Fatty Acid of Total | Algal Oil (1) | Coconut Oil (2) | 1:1 Mix of Algal Oil and Coconut Oil (3) | C.p./C. oil (3:1) (4) | C.p./C. oil (1:1) (5) | C.p./C. oil (1:3) (6) | C.p./C. oil (1:10) (7) |
|---|---|---|---|---|---|---|---|
| C10:1 | 0% | 1% | 0% | 0% | 0% | 0% | 0% |
| C10 | 0% | 10% | 5% | 9% | 10% | 9% | 10% |
| C12 | 0% | 56% | 27% | 50% | 53% | 53% | 54% |
| C18:3 | 4% | 0% | 1% | 0% | 0% | 0% | 0% |
| C14 | 1% | 18% | 9% | 18% | 17% | 18% | 18% |
| C18:2 | 25% | 1% | 11% | 1% | 1% | 1% | 1% |
| C16 | 11% | 8% | 9% | 8% | 8% | 8% | 8% |
| C18:1 | 59% | 4% | 33% | 11% | 8% | 8% | 6% |
| C18:0 | 0% | 2% | 4% | 3% | 3% | 3% | 2% |

C.p., *Chlorella protothecoides*; C. oil, coconut oil

The ratios of C18:1 to C12 and to C14 were calculated and fitted into the theoretical graph (see above and FIG. 2). The extraction efficiency of the coconut oil was determined by dividing the calculated percent of algal oil (from theoretical curve) by the expected percent (oil content in starting material). The extraction efficiency ranged from 44% in the 1:10 (algal oil to coconut oil) mixture (see experiment (7) above) to 16% in the 3:1 mixture (see experiment (4) above) as determined from the C18:1 to C12 data (Table 17). Thus, the higher the percent of coconut oil in the extraction procedure, the higher the yield of extracting lipids from Chorella.

TABLE 17

Extraction efficiency as a function of coconut oil fraction.

| % Algal Oil in Extraction | Measured C18:1 to C12 | % Measured | % Extraction (C18:1/C12) |
|---|---|---|---|
| 9 (7) | 0.12 | 4.0 | 44% |
| 25 (6) | 0.14 | 6.0 | 24% |
| 50 (5) | 0.16 | 7.0 | 14% |
| 75 (4) | 0.22 | 12.0 | 16% |

The range of the extraction efficiency was 33% (see experiment (7) above) to 14% (see experiment (4) above) as determined from the C18:1 to C14 data (Table 18). Thus, the higher the percent of coconut oil in the extraction procedure, the higher the yield of extracting lipids from Chorella.

TABLE 18

Extraction efficiency as a function of coconut oil fraction.

| % Algal Oil in Extraction | Measured C18:1 to C14 | % Measured | % Extraction (C18:1/C14) |
|---|---|---|---|
| 9 (7) | 0.35 | 3.0 | 33% |
| 25 (6) | 0.43 | 5.3 | 21% |
| 50 (5) | 0.47 | 6.3 | 13% |
| 75 (4) | 0.62 | 10.3 | 14% |

The above experiments demonstrated that an organic solvent (in this case coconut oil) efficiently extracted lipids from an algal cell mass to yield a lipid:organic solvent composition.

An additional set of experiments were performed to look at the efficiency of extracting lipids from a disrupted cell suspension of Chlorella protothecoides (sonication) using four emulsion breaking surfactants. The surfactants that were used in this study were: oleamide DEA (NINOL 201), laurelamide DEA (NINOL 55LL), laurelamide DEA (NINOL 96L) and cocoamide DEA (NINOL 40CO). Each surfactant was added in the concentrations of 0.2%, 0.5% and 1.0% to the cell lysate suspensions and were placed in a oven at 55° C. for 15 hours. Each tube was then centrifuged at 4200 rpm for 20 minutes. In each sample, four phases could be seen: a solid phase, an aqueous phase, and emulsion layer and an oil layer on the top. Negative control samples with no added surfactant produced no visible oil phase, but produced only the solid, aqueous and emulsion layers. The oil layers from each of the surfactant treated samples were carefully pipetted off and were weighed to determine overall oil yields. The results are summarized below in Table 19. These results show that an organic solvent, such as a surfactant, efficiently extracted lipids from lipid-containing algae biomass to yield a lipid:organic solvent composition.

TABLE 19

Use of surfactants to extract lipids from algae biomass.

| | Surfactant Name | | | | | | | | | | | |
|---|---|---|---|---|---|---|---|---|---|---|---|---|
| | NINOL 201 | NINOL 201 | NINOL 201 | NINOL 55LL | NINOL 55LL | NINOL 55LL | NINOL 40C0 | NINOL 40C0 | NINOL 40C0 | NINOL 96SL | NINOL 96SL | NINOL 96SL |
| Surfactant | Ole-amide DEA | Ole-amide DEA | Ole-amide DEA | Laurel-amid DEA | Laurel-amid DEA | Laurel-amid DEA | Coco-amide DEA | Coco-amide DEA | Coco-amide DEA | Laurel-amid DEA | Laurel-amid DEA | Laurel-amid DEA |
| Percent v/v | 1.0% | 0.5% | 0.2% | 1.0% | 0.5% | 0.2% | 1.0% | 0.5% | 0.2% | 1.0% | 0.5% | 0.2% |
| Oil in Ferm g/L | 62 | 62 | 62 | 62 | 62 | 62 | 62 | 62 | 62 | 62 | 62 | 62 |
| (g) Oil in 5 mL sample (theoretical) | 0.31 | 0.31 | 0.31 | 0.31 | 0.31 | 0.31 | 0.31 | 0.31 | 0.31 | 0.31 | 0.31 | 0.31 |
| Temperature (C.) | 55 | 55 | 55 | 55 | 55 | 55 | 55 | 55 | 55 | 55 | 55 | 55 |
| Time (hrs) | 15 | 15 | 15 | 15 | 15 | 15 | 15 | 15 | 15 | 15 | 15 | 15 |
| TOTAL | | | | | | | | | | | | |
| Oil in sample (g) | 0.183 | 0.237 | 0.041 | 0.262 | 0.012 | 0.026 | 0.276 | 0.082 | 0.000 | 0.286 | 0.035 | 0.000 |
| % of theoretical | 59.07% | 76.55% | 13.11% | 84.44% | 4.03% | 8.40% | 89.01% | 26.45% | 0.00% | 92.30% | 11.41% | 0.00% |

Example 7

Lysing of Chlorella Protothecoides

1. Biomass Production

An F-Tank batch of *Chlorella protothecoides* (about 1,200 gallons) was used to generate biomass for extraction processes. The batch (#ZA07126) was allowed to run for 100 hours, while controlling the glucose levels at 16 g/L, after which time the corn syrup feed was terminated. Residual glucose levels dropped to <0 g/L two hours later. This resulted in a final age of 102 hours. The final broth volume was 1,120 gallons. Both in-process contamination checks and a thorough analysis of a final broth sample failed to show any signs of contamination.

2. Heat and Chemical Treatment

Cells were resuspended in water to a biomass concentration of 150 g/L and aliquoted into 27×5 mL tubes. Each tube was conditioned per the matrix below in Table 20.

TABLE 20

Chemical/heat treatment matrix.

| Tube | Condition | [KOH] mN | [H$_2$SO$_4$] mN | Temp, 30 min |
|---|---|---|---|---|
| 1 | Control | 0 | 0 | 25° C. |
| 2 | 40 mN KOH | 40 | 0 | 25° C. |
| 3 | 80 mN KOH | 80 | 0 | 25° C. |
| 4 | 120 mN KOH | 120 | 0 | 25° C. |
| 5 | 160 mN KOH | 160 | 0 | 25° C. |
| 6 | 40 mN H$_2$SO$_4$ | 0 | 40 | 25° C. |
| 7 | 80 mN H$_2$SO$_4$ | 0 | 80 | 25° C. |
| 8 | 120 mN H$_2$SO$_4$ | 0 | 120 | 25° C. |
| 9 | 160 mN H$_2$SO$_4$ | 0 | 160 | 25° C. |
| 10 | Control | 0 | 0 | 65° C. |
| 11 | 40 mN KOH | 40 | 0 | 65° C. |
| 12 | 80 mN KOH | 80 | 0 | 65° C. |
| 13 | 120 mN KOH | 120 | 0 | 65° C. |
| 14 | 160 mN KOH | 160 | 0 | 65° C. |
| 15 | 40 mN H$_2$SO$_4$ | 0 | 40 | 65° C. |
| 16 | 80 mN H$_2$SO$_4$ | 0 | 80 | 65° C. |
| 17 | 120 mN H$_2$SO$_4$ | 0 | 120 | 65° C. |
| 18 | 160 mN H$_2$SO$_4$ | 0 | 160 | 65° C. |
| 19 | Control | 0 | 0 | 130° C. |
| 20 | 40 mN KOH | 40 | 0 | 130° C. |
| 21 | 80 mN KOH | 80 | 0 | 130° C. |
| 22 | 120 mN KOH | 120 | 0 | 130° C. |
| 23 | 160 mN KOH | 160 | 0 | 130° C. |
| 24 | 40 mN H$_2$SO$_4$ | 0 | 40 | 130° C. |
| 25 | 80 mN H$_2$SO$_4$ | 0 | 80 | 130° C. |
| 26 | 120 mN H$_2$SO$_4$ | 0 | 120 | 130° C. |
| 27 | 160 mN H$_2$SO$_4$ | 0 | 160 | 130° C. |

After treatment, a 1.5 ml sample was centrifuged at 14 K rpm for 15 min, and the size of each of the resulting layers was measured.

3. Emulsion Water Washing

A fresh set of samples were generated under conditions for samples 21-27 using a total of 10 mL cell suspension, and aliquoted into 3×3 mL samples. The resulting emulsions were isolated in new 15 mL tubes, and subjected to the following water wash scheme according to Table 21.

TABLE 21

Emulsion water washing matrix.

| Sample | Wash 1 Ratio of water wash volume:emulsion | Wash 2 Ratio of water wash volume:emulsion |
|---|---|---|
| 21 | 1 to 1 | 1 to 1 |
| 22 | 1 to 1 | 1 to 1 |
| 23 | 1 to 1 | 1 to 1 |
| 24 | 1 to 1 | 1 to 1 |
| 25 | 1 to 1 | 1 to 1 |
| 26 | 1 to 1 | 1 to 1 |
| 27 | 1 to 1 | 1 to 1 |
| 21 | 5 to 1 | 5 to 1 |
| 22 | 5 to 1 | 5 to 1 |
| 23 | 5 to 1 | 5 to 1 |
| 24 | 5 to 1 | 5 to 1 |
| 25 | 5 to 1 | 5 to 1 |
| 26 | 5 to 1 | 5 to 1 |
| 27 | 5 to 1 | 5 to 1 |
| 21 | 10 to 1 | 10 to 1 |
| 22 | 10 to 1 | 10 to 1 |
| 23 | 10 to 1 | 10 to 1 |
| 24 | 10 to 1 | 10 to 1 |
| 25 | 10 to 1 | 10 to 1 |
| 26 | 10 to 1 | 10 to 1 |
| 27 | 10 to 1 | 10 to 1 |

The water was added to the emulsion, vortexed, and centrifuged at 4,400 rpm for 10 minutes. Following the 1st wash, the aqueous phase was removed, and a 2nd water wash performed at the same ratio, vortexed, and centrifuged at 4,400 rpm for 10 minutes. Following treatment, the emulsions were observed for the appearance of a visible oil layer.

4. Sonication

A sampling of conditions (samples #1, 9, 10, 14, 18, 19, 23, 27) from the chemical/heat treatment matrix were sonicated using a Misonix 3000 sonicator equipped with a micro-tip on level 7. The suspension was sonicated for 3 minutes on a 30 sec on/20 sec off cycle. After treatment, a 1.5 ml sample was centrifuged at 14 K rpm for 15 min and the size of each of the resulting layers was measured.

5. Emulsion Freezing

Samples which generated emulsions were subjected to freezing at −20° C. for >24 hours. Following freezing, the samples were thawed at room temperature, vortexed, and centrifuged at 4,400 rpm for 10 minutes. The samples studied are listed in Table 22.

TABLE 22

Emulsions used in freezing cycle.

| Sample | Sonicated |
|---|---|
| 160 mN HCl, 130° C. for 30 min | Yes, 30 min cycle |
| 120 mN HCl, 130° C. for 30 min | No |
| 160 mN KOH 130° C. for 30 min | Yes, 30 min cycle |
| No chemical, 130° C. for 30 min | Yes, 30 min cycle |
| No chemical, no heat | Yes, 30 min cycle |

Following treatment, the emulsions were observed for the appearance of a visible oil layer.

6. Enzyme Treatment Experiments #1

Several enzymes were evaluated as an alternative method of cell breakage. These enzymes, all obtained from Sigma Aldrich, were Hemicellulase (P/N H2125), Pectinase (P/N P2401), Cellulase (C9422), and Driselase (D9515). 5 mL of cell material was prepared to various biomass concentrations, and exchanged into buffer. The enzyme concentrations were then prepared as described in Table 23.

TABLE 23

Enzyme treatment matrix.

| Enzyme | Enzyme conc. (%) | Incubation temp, °C. | Incubation time, hrs | Incubation buffer | [BM] g/L |
|---|---|---|---|---|---|
| Hemicellulase | 1% | 25° C. | 12 | 100 mM Acetate, pH 4.6 | 150 |
| Pectinase | 1% | 25° C. | 12 | 100 mM Acetate, pH 4.6 | 150 |
| Cellulase | 1% | 25° C. | 12 | 100 mM Acetate, pH 4.6 | 150 |
| Driselase | 1% | 25° C. | 12 | 100 mM Acetate, pH 4.6 | 150 |
| Cocktail of all 4 enzymes | 1% of each | 25° C. | 12 | 100 mM Acetate, pH 4.6 | 150 |
| Hemicellulase | 1% | 37° C. | 1 | 100 mM Acetate, pH 4.6 | 150 |
| Pectinase | 1% | 37° C. | 1 | 100 mM Acetate, pH 4.6 | 150 |
| Cellulase | 1% | 37° C. | 1 | 100 mM Acetate, pH 4.6 | 150 |
| Driselase | 1% | 37° C. | 1 | 100 mM Acetate, pH 4.6 | 150 |
| Cocktail of all 4 enzymes | 1% of each | 37° C. | 1 | 100 mM Acetate, pH 4.6 | 150 |
| Hemicellulase/Driselase | 4%/2% | 37° C. | 12 | 50 mM Citrate, pH 4.5 | 150 |
| Hemicellulase/Driselase | 4%/2% | 50° C. | 12 | 50 mM Citrate, pH 4.5 | 150 |
| Hemicellulase/Driselase | 4%/2% | 37° C. | 12 | 50 mM Citrate, pH 4.5 | 100 |
| Hemicellulase/Driselase | 4%/2% | 50° C. | 12 | 50 mM Citrate, pH 4.5 | 100 |
| Hemicellulase/Driselase | 4%/2% | 37° C. | 12 | 50 mM Citrate, pH 4.5 | 50 |
| Hemicellulase/Driselase | 4%/2% | 50° C. | 12 | 50 mM Citrate, pH 4.5 | 50 |
| Hemicellulase/Driselase | 4%/2% | 37° C. | 12 | 50 mM Citrate, pH 4.5 | 25 |
| Hemicellulase/Driselase | 4%/2% | 50° C. | 12 | 50 mM Citrate, pH 4.5 | 25 |

7. Enzyme Treatment Experiments #2

Additional enzymes were evaluated alone, and in combination with one another, and compared against disruption of cells by storing and aging the cells with or without enzyme treatment. A polysaccharide-degrading enzyme mannose and a protease were evaluated for their ability to disrupt cells of *Chlorella protothecoides*. Also, the effect of storing and aging a sample of cultured cells on the weakening of the cell structure to facilitate oil extraction was evaluated.

Three experiments were conducted. *Chlorella protothecoides* cells were generated via heterotrophic growth using glucose as the sole carbon source. In experiments in which dried cells were used, fermentation broth was centrifuged and the cell paste was subjected to drum drying. In experiments in which cells were stored for 7 days, storage was at 4° C. A polysaccharide-degrading enzyme (Mannaway 4.0L) and protease (Alcalase 2.4 FG) (both from Novozymes) were used in the experiments, as indicated. Enzymes were added at a concentration of 0.2% weight/volume.

In the first experiment, dried cells were reconstituted in deionized water to a dry cell weight of 155 grams/liter in flasks, and maintained at pH 7.5. Flasks were placed in an incubating shaker for 22 hours at 50° C. Enzymatic cell lysis for sample 1 in Experiment 1 was very effective when combining enzymes, as evidenced by 90.4% of total oil being found in the emulsion and not in the pellet. Neither enzyme individually was as effective as the combination of both, nor was the control without enzyme treatment. The results are shown in Table 27 below.

In the second experiment, fresh fermentation broth was separated into two aliquots for fresh and 7 day broth experiments. The fresh cells were concentrated by centrifugation and reconstituted in deionized water to 170 g/l in flasks. Resuspended cell samples were then subdivided into two sets of 4 flasks, half of which were stored for 7 days at 4° C. before further treatment. For experimental treatment, 3 flasks contained combinations of a protease and a polysaccharide-degrading mannase while the 4$^{th}$ contained no enzymes (see Table 27 for experimental conditions). Flasks were placed in an incubating shaker for 22 hours at 50° C. This second experiment indicated extensive cell lysis with dual enzyme treatment at day 0 and day 7, as well as lysis in the absence of enzymes after 7 days. The results are shown in Table 28 below.

In the third experiment, fermentation broth was collected from fresh fermentations, concentrated by centrifugation and re-suspended in deionized water at two different concentrations of 71 and 115 g/l and agitated at 150 rpm in Applikon fermentors for 22 hours at 50° C. pH was maintained at 7.5 by feedback acid/base control. The results of this third experiment indicated that cell disruption and/or emulsion formation is facilitated by addition of enzymes and aging of the cells. The results are shown in Table 29 below.

8. Oil Analysis and Characterization

TLC was performed on aluminum backed silica TLC plates (Sigma#60805). The developing solvent (mobile phase) was hexane/diethyleter/acetic acid (80:20:1, by vol). Spots were visualized by spraying with 10% sulfuric acid and charring on a hotplate. Recovered oil samples from control, acidic, and basic conditions were analyzed to determine if any significant product degradation and/or modification occurred due to the processing conditions.

9. Results (a) Heat and Chemical Treatment

Figure 3:
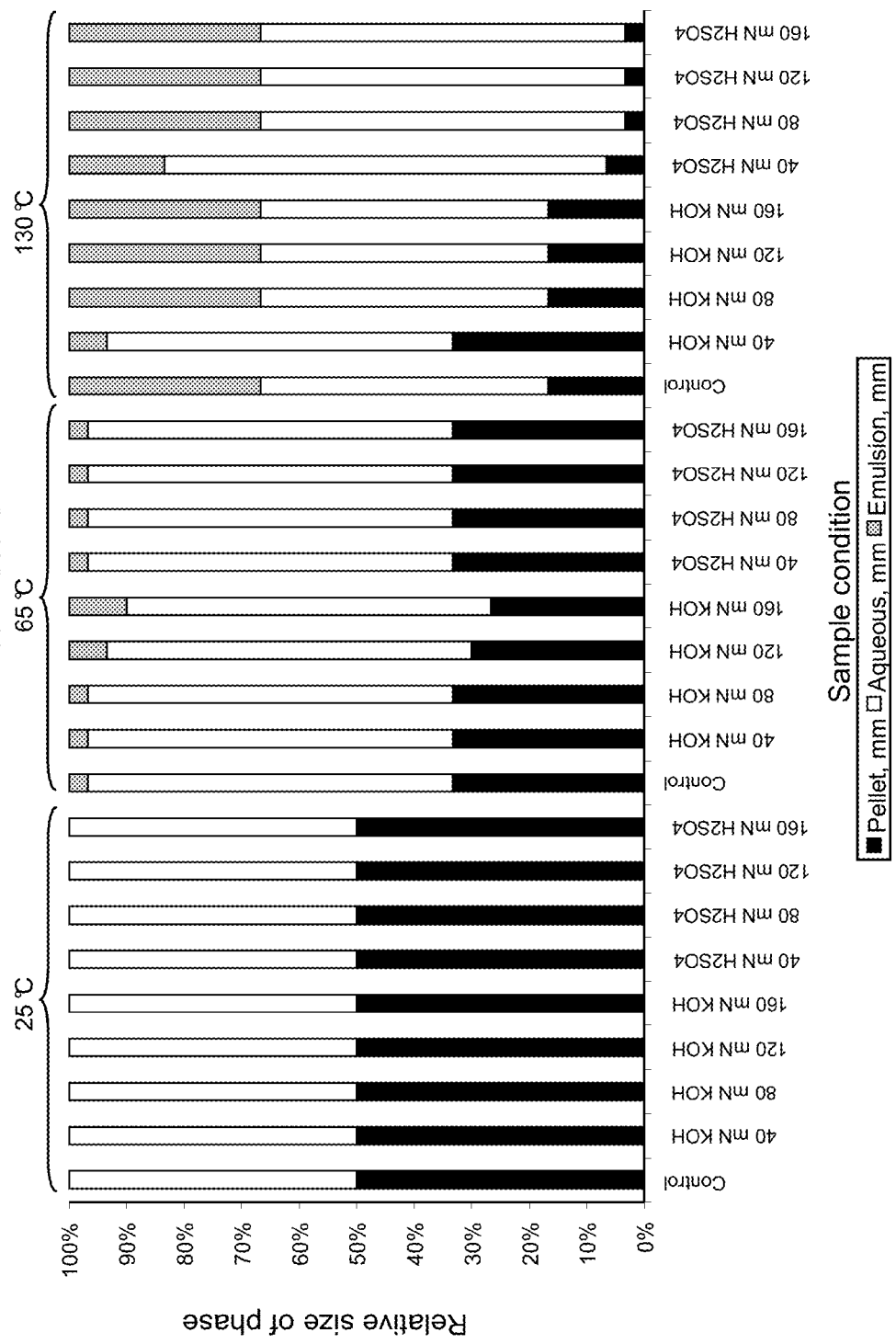
FIG. 3 depicts results of chemical/heat treatment of *Chlorella protothecoides*. Details are described in Example 7.

The results from the chemical/heat treatment matrix are reported in FIG. 3 and Table 24 below.

TABLE 24

Measurement of layers from chemical/heat treatment matrix.

| Tube | Condition | [KOH] mN | [H$_2$SO$_4$] mN | Temp, 30 min | Pellet, mm | Aqueous, mm | Emulsion, mm |
|---|---|---|---|---|---|---|---|
| 1 | Control | 0 | 0 | 25° C. | 15 | 15 | 0 |
| 2 | 40 mN KOH | 40 | 0 | 25° C. | 15 | 15 | 0 |
| 3 | 80 mN KOH | 80 | 0 | 25° C. | 15 | 15 | 0 |
| 4 | 120 mN KOH | 120 | 0 | 25° C. | 15 | 15 | 0 |
| 5 | 160 mN KOH | 160 | 0 | 25° C. | 15 | 15 | 0 |

TABLE 24-continued

Measurement of layers from chemical/heat treatment matrix.

| Tube | Condition | [KOH] mN | [H$_2$SO$_4$] mN | Temp, 30 min | Pellet, mm | Aqueous, mm | Emulsion, mm |
|---|---|---|---|---|---|---|---|
| 6 | 40 mN H$_2$SO$_4$ | 0 | 40 | 25° C. | 15 | 15 | 0 |
| 7 | 80 mN H$_2$SO$_4$ | 0 | 80 | 25° C. | 15 | 15 | 0 |
| 8 | 120 mN H$_2$SO$_4$ | 0 | 120 | 25° C. | 15 | 15 | 0 |
| 9 | 160 mN H$_2$SO$_4$ | 0 | 160 | 25° C. | 15 | 15 | 0 |
| 10 | Control | 0 | 0 | 65° C. | 10 | 19 | 1 |
| 11 | 40 mN KOH | 40 | 0 | 65° C. | 10 | 19 | 1 |
| 12 | 80 mN KOH | 80 | 0 | 65° C. | 10 | 19 | 1 |
| 13 | 120 mN KOH | 120 | 0 | 65° C. | 9 | 19 | 2 |
| 14 | 160 mN KOH | 160 | 0 | 65° C. | 8 | 19 | 3 |
| 15 | 40 mN H$_2$SO$_4$ | 0 | 40 | 65° C. | 10 | 19 | 1 |
| 16 | 80 mN H$_2$SO$_4$ | 0 | 80 | 65° C. | 10 | 19 | 1 |
| 17 | 120 mN H$_2$SO$_4$ | 0 | 120 | 65° C. | 10 | 19 | 1 |
| 18 | 160 mN H$_2$SO$_4$ | 0 | 160 | 65° C. | 10 | 19 | 1 |
| 19 | Control | 0 | 0 | 65° C. | 5 | 15 | 10 |
| 20 | 40 mN KOH | 40 | 0 | 130° C. | 10 | 18 | 2 |
| 21 | 80 mN KOH | 80 | 0 | 130° C. | 5 | 15 | 10 |
| 22 | 120 mN KOH | 120 | 0 | 130° C. | 5 | 15 | 10 |
| 23 | 160 mN KOH | 160 | 0 | 130° C. | 5 | 15 | 10 |
| 24 | 40 mN H$_2$SO$_4$ | 0 | 40 | 130° C. | 2 | 23 | 5 |
| 25 | 80 mN H$_2$SO$_4$ | 0 | 80 | 130° C. | 1 | 19 | 10 |
| 26 | 120 mN H$_2$SO$_4$ | 0 | 120 | 130° C. | 1 | 19 | 10 |
| 27 | 160 mN H$_2$SO$_4$ | 0 | 160 | 130° C. | 1 | 19 | 10 |

At 25° C., no difference was observed between the chemically treated samples and the control, and no emulsion formed.

At 65° C., an emulsion began to appear for the KOH treated samples, increasing in size with higher concentrations of caustic. The aqueous phase also became more turbid with increasing concentrations of KOH. There appeared to be a proportional decrease in the size of the pellet as the emulsion size increased. For the acidic treated samples at 65° C., a smaller emulsion formed relative to the caustic treated samples, and no increase in the size of the emulsion was observed with increasing level of acid, and the aqueous phase was clear and uncolored.

Samples heated to 130° C. all showed significantly larger emulsions compared to 65° C., and comprised roughly ⅓ of the total sample volume. The aqueous phase of the caustic treated samples showed increasing dark color with increasing concentration of KOH.

In the acidic treated samples, the aqueous phase remained clear for all samples. In contrast to the base treated materials, the pellet virtually disappeared for the acid treated preparations, indicating that the cells and cell debris had partitioned to the emulsion and aqueous phase. In none of the 27 conditions tested was a visible oil layer observed.

(b) Emulsion Water Washing

The emulsion of the caustic treated samples was poorly defined and difficult to separate from the aqueous phase to prepare the emulsion for water washing. In contrast, the acidic emulsion was firm and partitioned easily from the aqueous phase. Under all washing conditions for the KOH treated samples, the emulsion became thinner and thinner until it was nearly gone. No visible oil layer was observed during either wash.

The acidic emulsions were easier to manipulate and separate from the aqueous phase. The emulsion size remained essentially unchanged during both washes. However, no visible oil layer was observed during either wash.

(c) Sonication

The results of the sonication are recorded in Table 25 below.

TABLE 25

Impact of sonication compared to corresponding pre-sonicated samples.

| Tube | [KOH] mN | [H$_2$SO$_4$] mN | Temp, 30 min | Pellet, mm | Emulsion, mm |
|---|---|---|---|---|---|
| 1 | 0 | 0 | 25° C. | −5 | +1 |
| 9 | 0 | 160 | 25° C. | −5 | +1 |
| 10 | 0 | 0 | 65° C. | −5 | +1 |
| 14 | 160 | 0 | 65° C. | −3 | +2 |
| 18 | 0 | 160 | 65° C. | −5 | +1 |
| 19 | 0 | 0 | 130° C. | −2 | −7 |
| 23 | 160 | 0 | 130° C. | −3 | −7 |
| 27 | 0 | 160 | 130° C. | +1 | −7 |

The 25° C. and 65° C. sample emulsions increased in size while the pellet decreased relative to their pre-sonicated counterparts. For the 130° C. samples, the emulsion decreased in size substantially, and the pellet of the control and base treated samples decreased, while the pellet increased for the acid treated preparation. There was some oil layer formation for the sonicated samples, particularly at the elevated temperatures.

(d) Temperature Reduction of Emulsion

The results of the emulsion freezing are recorded in Table 26 below.

TABLE 26

Results of emulsion freezing.

| Sample | Sonicated | Visible oil layer |
|---|---|---|
| 160 mN HCl, 130° C. for 30 min | Yes, 30 min cycle | Yes |
| 120 mN HCl, 130° C. for 30 min | No | No |
| 160 mN KOH 130° C. for 30 min | Yes, 30 min cycle | Yes |
| No chemical, 130° C. for 30 min | Yes, 30 min cycle | Yes |
| No chemical, no heat | Yes, 30 min cycle | Yes |

Figure 4:
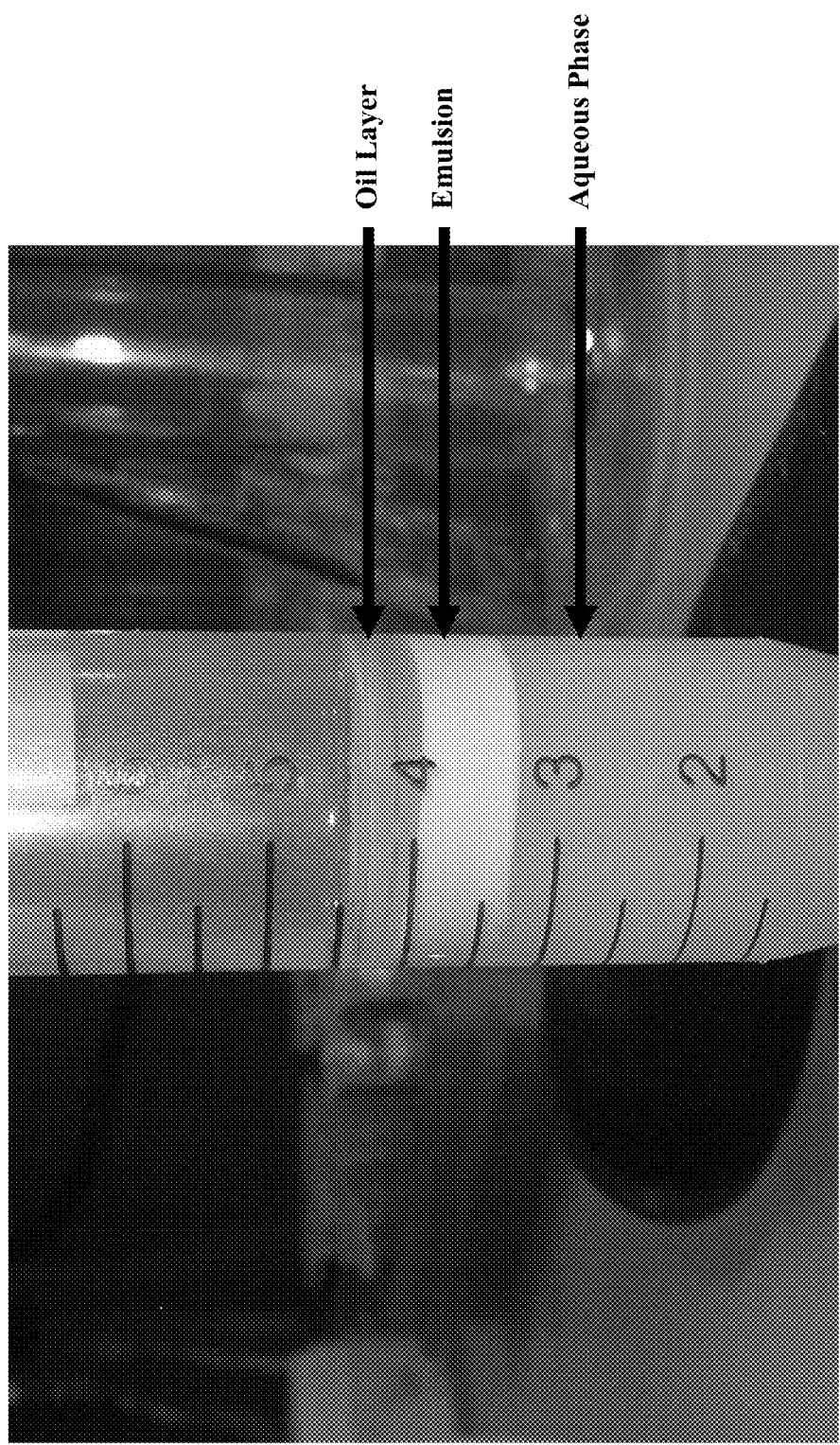
FIG. 4 depicts an image of oil layer recovered from a frozen, heat treated emulsion. Details are described in Example 7 (Enzyme Treatment #1).

Reducing the temperature of the emulsion to −20° C. proved to be an effective emulsion breaker. In all samples where the emulsion was sonicated, a large oil layer was observed. A representative result is shown in FIG. 4. When compared to the lipid content of the cell material by HPLC, the oil layer constituted the majority of the oil from the emulsion.

(e) Enzymatic Treatment #1

Samples incubated at 25° C. and 37° C. at 1% enzyme levels showed minimal emulsion formation. Considerably larger emulsions formed at the higher enzyme concentrations of 4%/2% Hemicellulase/Driselase combination, with the 50° C. producing a larger emulsion compared to the 37° C. sample. No oil layer was observed with enzyme treatment alone. Enzyme-generated emulsions subjected to sonication and then −20° C., generated an oil layer.

(f) Enzymatic Treatment #2

Figure 6:
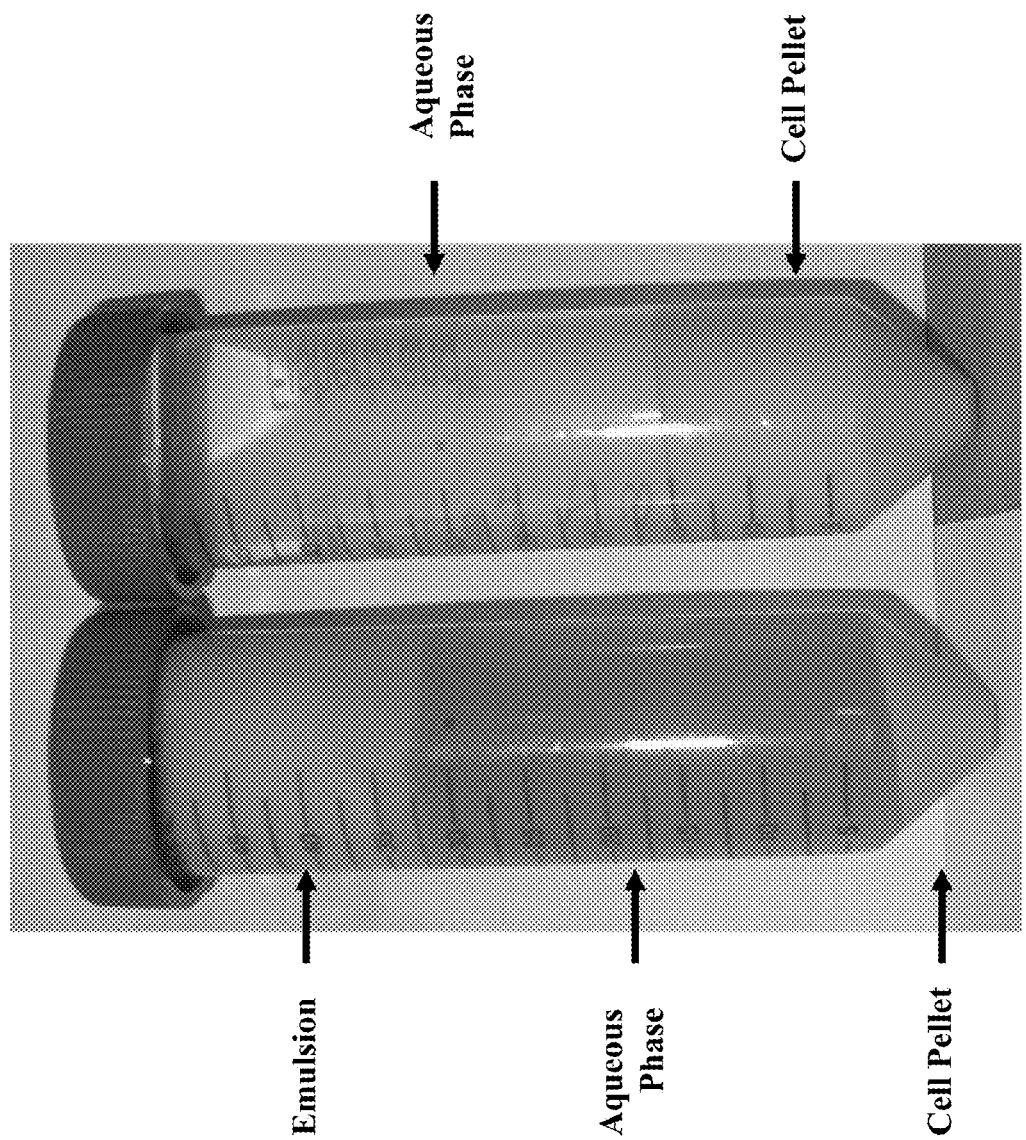
FIG. 6 depicts an image of layers recovered from enzyme treated (left tube) versus untreated (right tube) cell culture material. Details are described in Example 7 (Enzyme Treatment #2).

Enzyme treatment combining a polysaccharide-degrading mannase and a protease was found effective to disrupt cells from *Chlorella protothecoides*. Another technique found effective in weakening cell structure enough to facilitate oil extraction was storing/aging the cells. Tables 27, 28 and 29 show the results of the three experiments described above, and FIG. 6 illustrates the resulting layers from enzyme-treated (left tube) vs. untreated (right tube) biomass. In the untreated tube, the cell pellet is considerably larger in size because it comprises a large lipid component. In neither case was lipid found in the aqueous phase.

TABLE 27

Enzymatic treatment #2, experiment 1 results.

| | Sample Number | | | |
|---|---|---|---|---|
| | 1 | 2 | 3 | 4 |
| ALCALASE 2.4 FG | + | + | − | − |
| MANNAWAY 4.0 L | + | − | + | − |
| % of oil in cell pellet | 9.6% | 30.7% | 50.3% | 97.8% |
| % of oil in emulsion | 90.4% | 69.3% | 49.7% | 2.2% |

TABLE 28

Enzymatic treatment #2, experiment 2 results.

| | | Sample Number | | | |
|---|---|---|---|---|---|
| | AGE | 1 | 2 | 3 | 4 |
| ALCALASE 2.4 FG | | + | + | − | − |
| MANNAWAY 4.0 L | | + | − | + | − |
| DCW G/L | | 170.0 | 170.0 | 170.0 | 170.0 |
| | DAYS | W/W % | W/W % | W/W % | W/W % |
| % of oil in cell pellet | 0 | 28.8% | 48.2% | 67.8% | 100.0% |
| % of oil in emulsion | 0 | 71.2% | 51.8% | 32.2% | 0% |
| % of oil in cell pellet | 7 | 47.8% | 81.3% | 80.7% | 81.8% |
| % of oil in emulsion | 7 | 52.2% | 18.7% | 19.3% | 18.2% |

TABLE 29

Enzymatic treatment #2, experiment 3 results.

| | Sample Number | | | | |
|---|---|---|---|---|---|
| | 1 | 2 | 3 | 4 | 5 |
| ALCALASE 2.4 FG | − | − | + | − | − |
| MANNAWAY 4.0 L | − | − | + | − | − |

TABLE 29-continued

Enzymatic treatment #2, experiment 3 results.

| | | | | | |
|---|---|---|---|---|---|
| DCW G/L | 71.7 | 115.1 | 115.1 | 71.7 | 115.1 |
| TEMPERATURE | 50 | 50 | 50 | 50 | 50 |
| PH | 7.5 | 7.5 | 7.5 | 7.5 | 7.5 |
| | W/W % | W/W % | W/W % | W/W % | W/W % |
| % of oil in cell pellet | 81.8% | 63.0% | 12.0% | 49.1% | 42.0% |
| % of oil in emulsion | 18.2% | 37.0% | 88.0% | 50.9% | 58.0% |
| age | 0 | 0 | 0 | 7 | 7 |

(g) Oil Analysis and Characterization

Figure 5:
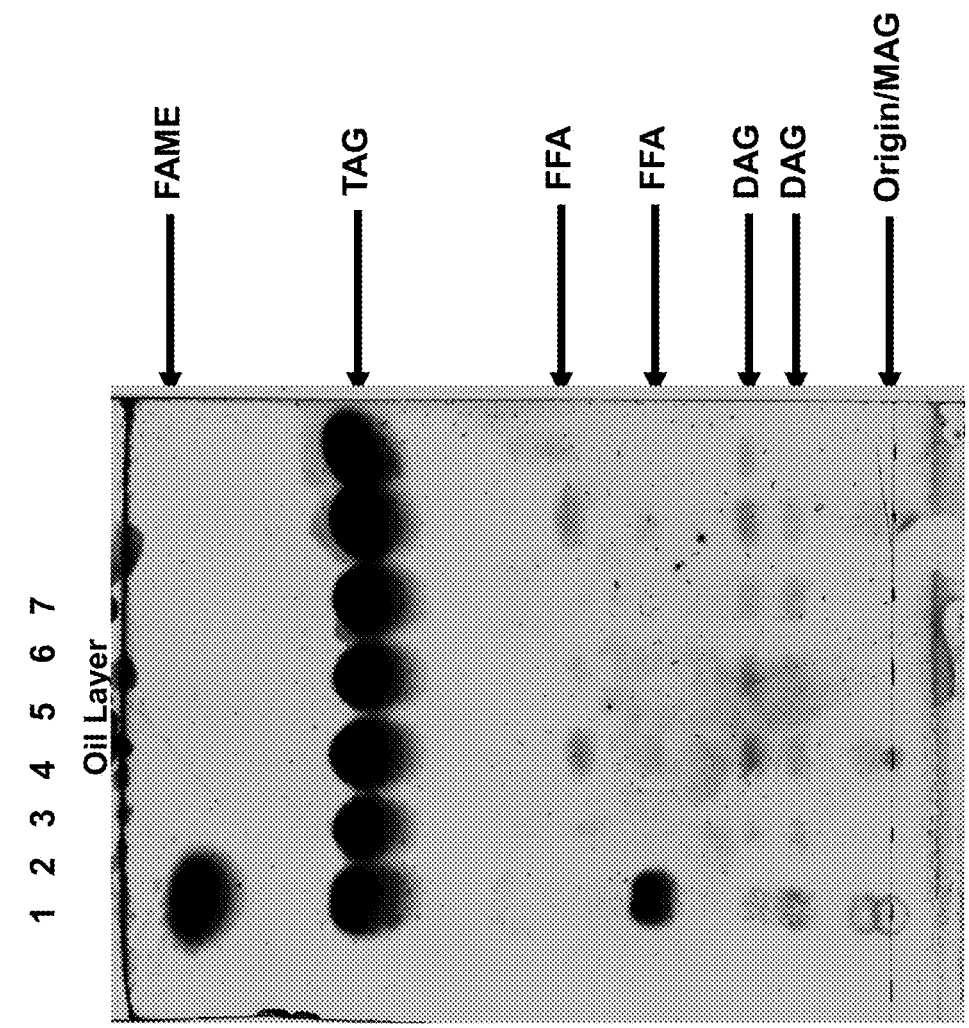
FIG. 5 depicts a result of a thin layer chromatography (TLC) analysis of control, basic, and acid generated oil samples. Lane 1, Reference @ 100 μg/each (FAME/TAG/FFA); Lane 2, No chemical treatment; Lane 3, treatment with 120 mN H2SO4; Lane 4, treatment with 160 mN KOH; Lane 5, no chemical treatment; Lane 6, treatment with 120 mN H2SO4; Lane 7, treatment with 160 mN KOH. FAME, fatty acid methyl ester; TAG, triacylglycerides; FFA, free fatty acid; DAG, diacylglycerol (1,3-diolein); MAG, monoacylglycerol (1-monoolein) Details are described in Example 7.

An oil sample was isolated from each of the chemically treated conditions and analyzed via TLC to determine if product degradation was occurring at the extreme pHs compared the control condition. TLC analysis is shown in FIG. 5. The pattern showed a minor generation of free fatty acids (FFA's) under acidic conditions compared to the base treated and control sample.

Example 8

Methods for Culturing *Prototheca*

*Prototheca* strains were cultivated to achieve a high percentage of oil by dry cell weight. Cryopreserved cells were thawed at room temperature and 500 ul of cells were added to 4.5 ml of medium (4.2 g/L $K_2HPO_4$, 3.1 g/L $NaH_2PO_4$, 0.24 g/L $MgSO_4.7H_2O$, 0.25 g/L Citric Acid monohydrate, 0.025 g/L $CaCl_2$ $2H_2O$, 2 g/L yeast extract) plus 2% glucose and grown for 7 days at 28° C. with agitation (200 rpm) in a 6-well plate. Dry cell weights were determined by centrifuging 1 ml of culture at 14,000 rpm for 5 min in a pre-weighed Eppendorf tube. The culture supernatant was discarded and the resulting cell pellet washed with 1 ml of deionized water. The culture was again centrifuged, the supernatant discarded, and the cell pellets placed at −80° C. until frozen. Samples were then lyophilized for 24 hrs and dry cell weights calculated. For determination of total lipid in cultures, 3 ml of culture was removed and subjected to analysis using an Ankom system (Ankom Inc., Macedon, N.Y.) according to the manufacturer's protocol. Samples were subjected to solvent extraction with an Amkom XT10 extractor according to the manufacturer's protocol. Total lipid was determined as the difference in mass between acid hydrolyzed dried samples and solvent extracted, dried samples. Percent oil dry cell weight measurements are shown in Table 30.

TABLE 30

Percent oil by dry cell weight

| Species | Strain | % Oil |
|---|---|---|
| *Prototheca stagnora* | UTEX 327 | 13.14 |
| *Prototheca moriformis* | UTEX 1441 | 18.02 |
| *Prototheca moriformis* | UTEX 1435 | 27.17 |

Microalgae samples from the strains listed in Table 30, above, were genotyped. Genomic DNA was isolated from algal biomass as follows. Cells (approximately 200 mg) were centrifuged from liquid cultures 5 minutes at 14,000×g. Cells were then resuspended in sterile distilled water, centrifuged 5 minutes at 14,000×g and the supernatant discarded. A single glass bead ~2 mm in diameter was added to the biomass and tubes were placed at −80° C. for at least 15 minutes. Samples were removed and 150 µl of grinding buffer (1% Sarkosyl, 0.25 M Sucrose, 50 mM NaCl, 20 mM EDTA, 100 mM Tris-HCl, pH 8.0, RNase A 0.5 ug/ul) was added. Pellets were resuspended by vortexing briefly, followed by the addition of 40 ul of 5M NaCl. Samples were vortexed briefly, followed by the addition of 66 µl of 5% CTAB (Cetyl trimethylammonium bromide) and a final brief vortex. Samples were next incubated at 65° C. for 10 minutes after which they were centrifuged at 14,000×g for 10 minutes. The supernatant was transferred to a fresh tube and extracted once with 300 µl of Phenol:Chloroform:Isoamyl alcohol 12:12:1, followed by centrifugation for 5 minutes at 14,000×g. The resulting aqueous phase was transferred to a fresh tube containing 0.7 vol of isopropanol (~190 µl), mixed by inversion and incubated at The resulting pellet was then washed twice with 70% ethanol, followed by a final wash with 100% ethanol. Pellets were air dried for 20-30 minutes at room temperature followed by resuspension in 50 µl of 10 mM TrisCl, 1 mM EDTA (pH 8.0).

Five µl of total algal DNA, prepared as described above, was diluted 1:50 in 10 mM Tris, pH 8.0. PCR reactions, final volume 20 µl, were set up as follows. Ten µl of 2×iProof HF master mix (BIO-RAD) was added to 0.4 µl primer SZ02613 (5'-TGTTGAAGAATGAGCCGGCGAC-3' (SEQ ID NO:5) at 10 mM stock concentration). This primer sequence runs from position 567-588 in Gen Bank accession no. L43357 and is highly conserved in higher plants and algal plastid genomes. This was followed by the addition of 0.4 µl primer SZ02615 (5'-CAGTGAGCTATTACGCACTC-3' (SEQ ID NO:6) at 10 mM stock concentration). This primer sequence is complementary to position 1112-1093 in Gen Bank accession no. L43357 and is highly conserved in higher plants and algal plastid genomes. Next, 5 µl of diluted total DNA and 3.2 µl dH$_2$O were added. PCR reactions were run as follows: 98° C., 45"; 98° C., 8"; 53° C., 12"; 72° C., 20" for 35 cycles followed by 72° C. for 1 min and holding at 25° C. For purification of PCR products, 20 µl of 10 mM Tris, pH 8.0, was added to each reaction, followed by extraction with 40 µl of Phenol:Chloroform:isoamyl alcohol 12:12:1, vortexing and centrifuging at 14,000×g for 5 minutes. PCR reactions were applied to S-400 columns (GE Healthcare) and centrifuged for 2 minutes at 3,000×g. Purified PCR products were subsequently TOPO cloned into PCR8/GW/TOPO and positive clones selected for on LB/Spec plates. Purified plasmid DNA was sequenced in both directions using M13 forward and reverse primers. In total, twelve *Prototheca* strains were selected to have their 23S rRNA DNA sequenced and the sequences are listed in the Sequence Listing. A summary of the strains and Sequence Listing Numbers is included below in Table 31. The sequences were analyzed for overall divergence from the UTEX 1435 (SEQ ID NO: 17) sequence. Two pairs emerged (UTEX 329/UTEX 1533 and UTEX 329/UTEX 1440) as the most divergent. In both cases, pairwise alignment resulted in 75.0% pairwise sequence identity. The percent sequence identity to UTEX 1435 is also included below in Table 31.

TABLE 31

Genotyped *Prototheca* strains.

| Species | Strain | % nt identity | SEQ ID NO. |
|---|---|---|---|
| *Prototheca kruegani* | UTEX 329 | 75.2 | SEQ ID NO: 34 |
| *Prototheca wickerhamii* | UTEX 1440 | 99 | SEQ ID NO: 35 |
| *Prototheca stagnora* | UTEX 1442 | 75.7 | SEQ ID NO: 16 |
| *Prototheca moriformis* | UTEX 288 | 75.4 | SEQ ID NO: 36 |
| *Prototheca moriformis* | UTEX 1439; 1441; 1435; 1437 | 100 | SEQ ID NO: 17 |
| *Prototheca wikerhamii* | UTEX 1533 | 99.8 | SEQ ID NO: 37 |
| *Prototheca moriformis* | UTEX 1434 | 75.9 | SEQ ID NO: 38 |
| *Prototheca zopfii* | UTEX 1438 | 75.7 | SEQ ID NO: 39 |
| *Prototheca moriformis* | UTEX 1436 | 88.9 | SEQ ID NO: 32 |

Lipid samples from a subset of the above-listed strains were analyzed for lipid profile using HPLC. Results are shown below in Table 32.

TABLE 32

Diversity of lipid chains in *Prototheca* species.

| Strain | C14:0 | C16:0 | C16:1 | C18:0 | C18:1 | C18:2 | C18:3 | C20:0 | C20:1 |
|---|---|---|---|---|---|---|---|---|---|
| UTEX 327 | 0 | 12.01 | 0 | 0 | 50.33 | 17.14 | 0 | 0 | 0 |
| UTEX 1441 | 1.41 | 29.44 | 0.70 | 3.05 | 57.72 | 12.37 | 0.97 | 0.33 | 0 |
| UTEX 1435 | 1.09 | 25.77 | 0 | 2.75 | 54.01 | 11.90 | 2.44 | 0 | 0 |

Algal plastid transit peptides were identified through the analysis of UTEX 1435 (*Prototheca moriformis*) or UTEX 250 (*Chlorella prototheoides*) cDNA libraries. cDNAs encoding potentially plastid targeted proteins based upon BLAST hit homology to other known plastid targeted proteins were subjected to further analysis by the software programs PSORT, ChloroP and TargetP. Candidate plastid transit peptides identified through at least one of these three programs were then PCR amplified from the appropriate genomic DNA. Below, in Table 33, is a summary of the algal plastid targeting amino acid sequences (PTS) that were identified from this screen. Also included are the amino acid sequences of plant fatty acyl-ACP thioesterases that are used in the heterologous expression Examples below.

TABLE 33

Summary of algal plastic targeting amino acid sequences.

| cDNA | SEQ ID NO. |
|---|---|
| *P. moriformis* isopentenyl diphosphate synthase PTS | SEQ ID NO: 40 |
| *P. moriformis* delta 12 fatty acid desaturase PTS | SEQ ID NO: 41 |
| *P. moriformis* stearoyl ACP desaturase PTS | SEQ ID NO: 42 |
| *C. prototheoides* stearoyl ACP desaturase PTS | SEQ ID NO: 43 |
| *Cuphea hookeriana* fatty acyl-ACP thioesterase (C8-10) | SEQ ID NO: 44 |
| *Umbellularia californica* fatty acyl-ACP thioesterase | SEQ ID NO: 45 |

TABLE 33-continued

Summary of algal plastic targeting amino acid sequences.

| cDNA | SEQ ID NO. |
|---|---|
| (C12) | |
| *Cinnamomum camphora* fatty acyl-ACP thioesterase (C14) | SEQ ID NO: 46 |

Example 9

Methods for Transforming *Prototheca*

1. General Method for Biolistic Transformation of *Prototheca*

S550d gold carriers from Seashell Technology were prepared according to the protocol from manufacturer. Linearized plasmid (20 µg) was mixed with 50 µl of binding buffer and 60 µl (30 mg) of S550d gold carriers and incubated in ice for 1 min. Precipitation buffer (100 µl) was added, and the mixture was incubated in ice for another 1 min. After vortexing, DNA-coated particles were pelleted by spinning at 10,000 rpm in an Eppendorf 5415C microfuge for 10 seconds. The gold pellet was washed once with 500 µl of cold 100% ethanol, pelleted by brief spinning in the microfuge, and resuspended with 50 µl of ice-cold ethanol. After a brief (1-2 sec) sonication, 10 µl of DNA-coated particles were immediately transferred to the carrier membrane.

*Prototheca* strains were grown in proteose medium (2 g/L yeast extract, 2.94 mM NaNO3, 0.17 mM CaCl2.2H2O, 0.3 mM MgSO4.7H2O, 0.4 mM K2HPO4, 1.28 mM KH2PO4, 0.43 mM NaCl) on a gyratory shaker until it reaches a cell density of $2 \times 10^6$ cells/ml. The cells were harvested, washed once with sterile distilled water, and resuspended in 50 µl of medium. $1 \times 10^7$ cells were spread in the center third of a non-selective proteose media plate. The cells were bombarded with the PDS-1000/He Biolistic Particle Delivery System (Bio-Rad). Rupture disks (1100 and 1350 psi) were used, and the plates are placed 9 and 12 cm below the screen/macrocarrier assembly. The cells were allowed to recover at 25° C. for 12-24 h. Upon recovery, the cells were scraped from the plates with a rubber spatula, mixed with 100 µl of medium and spread on plates containing the appropriate antibiotic selection. After 7-10 days of incubation at 25° C., colonies representing transformed cells were visible on the plates from 1100 and 1350 psi rupture discs and from 9 and 12 cm distances. Colonies were picked and spotted on selective agar plates for a second round of selection.

2. Transformation of *Prototheca* with G418 Resistance Gene

*Prototheca moriformis* and other *Prototheca* strains sensitive to G418 can be transformed using the methods described below. G418 is an aminoglycoside antibiotic that inhibits the function of 80S ribosomes and thereby inhibits protein synthesis. The corresponding resistance gene functions through phosphorylation, resulting in inactivation of G418. *Prototheca* strains UTEX 1435, UTEX 1439 and UTEX 1437 were selected for transformation. All three *Prototheca* strains were genotyped using the methods described above. All three *Prototheca* strains had identical 23s rRNA genomic sequences (SEQ ID NO:17).

All transformation cassettes were cloned as EcoRI-SacI fragments into pUC19. Standard molecular biology techniques were used in the construction of all vectors according to Sambrook and Russell, 2001. The *C. reinhardtii* beta-tubulin promoter/5'UTR was obtained from plasmid pHyg3 (Berthold et al., (2002) Protist: 153(4), pp 401-412) by PCR as an EcoRI-AscI fragment. The *Chlorella vulgaris* nitrate reductase 3'UTR was obtained from genomic DNA isolated from UTEX strain 1803 via PCR using the following primer pairs:

```
Forward:
                                    (SEQ ID NO: 47)
5' TGACCTAGGTGATTAATTAACTCGAGGCAGCAGCAGCTCGGATAG

TATCG 3'

Reverse:
                                    (SEQ ID NO: 48)
5' CTACGAGCTCAAGCTTTCCATTTGTGTTC CCATCCCACTACTTC

C 3'
```

The *Chlorella sorokiniana* glutamate dehydrogenase promoter/UTR was obtained via PCR of genomic DNA isolated from UTEX strain 1230 via PCR using the following primer pairs:

```
Forward:
                                    (SEQ ID NO: 94)
5' GATCAGAATTCCGCCTGCAACGCAAGG GCAGC 3'

Reverse:
                                    (SEQ ID NO: 95)
5' GCATACTAGTGGCGGGACGGAGAGA GGGCG 3'
```

Codon optimization was based on the codons for *Prototheca moriformis*. The sequence of the non-codon optimized neomycin phosphotransferase (nptII) cassette was synthesized as an AscI-XhoI fragment and was based on upon the sequence of Genbank Accession No. YP_788126. The codon optimized nptII cassette was also based on this Genbank Accession number.

The three *Prototheca* strains were transformed using biolistic methods described above. Briefly, the *Prototheca* strains were grown heterophically in liquid medium containing 2% glucose until they reached the desired cell density ($1 \times 10^7$ cells/mL to $5 \times 10^7$ cells/mL). The cells were harvested, washed once with sterile distilled water and resuspended at $1 \times 10^8$ cells/mL. 0.5 mL of cells were then spread out on a non-selective solid media plate and allowed to dry in a sterile hood. The cells were bombarded with the PDS-1000/He Biolistic Particle Delivery System (BioRad). The cells were allowed to recover at 25° C. for 24 hours. Upon recovery, the cells were removed by washing plates with 1 mL of sterile media and transferring to fresh plates containing 100 µg/mL G418. Cells were allowed to dry in a sterile hood and colonies were allowed to form on the plate at room temperature for up to three weeks. Colonies of UTEX 1435, UTEX 1439 and UTEX 1437 were picked and spotted on selective agar plates for a second round of selection.

Figure 7:
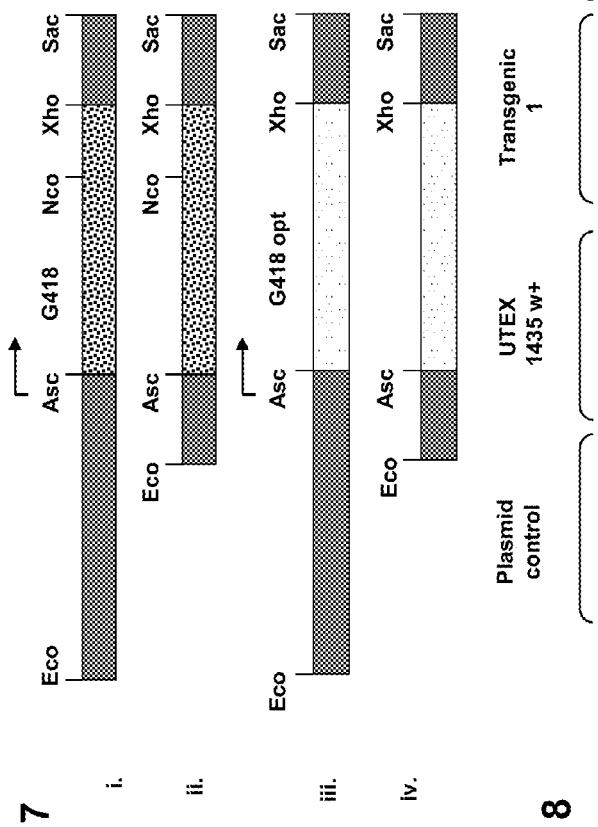
FIG. 7 shows maps of the cassettes used in *Prototheca* transformations, as described in Example 9.
Figure 8:
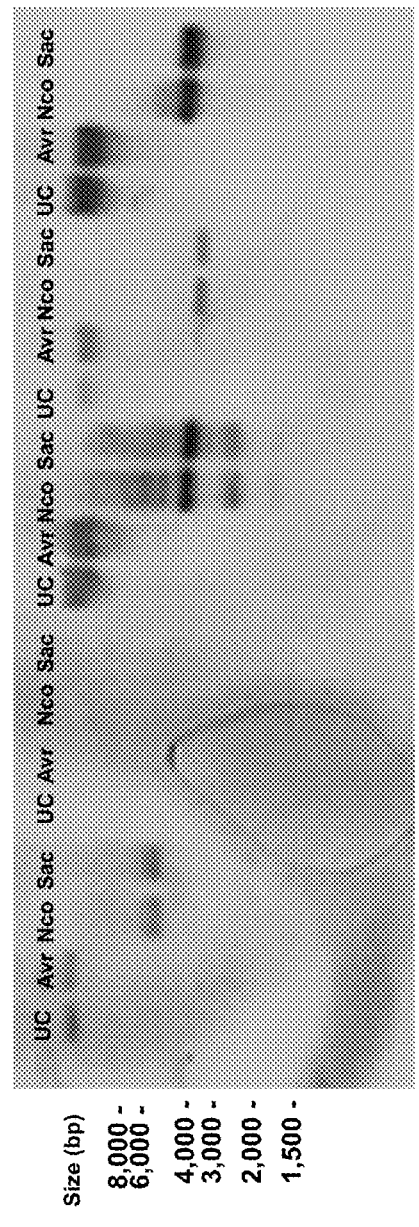
FIG. 8 shows the results of Southern blot analysis on three transformants of UTEX strain 1435, as described in Example 9.

A subset of colonies that survived a second round of selection described above, were cultured in small volume and genomic DNA and RNA were extracted using standard molecular biology methods. Southern blots were done on genomic DNA extracted from untransformed (WT), the transformants and plasmid DNA. DNA from each sample was run on 0.8% agarose gels after the following treatments: undigested (U), digested with AvrII (A), digested with NcoI (N), digested with SacI (S). DNA from these gels was blotted on Nylon+membranes (Amersham). These membranes were probed with a fragment corresponding to the entire coding region of the nptII gene (NeoR probe). FIG. 7 shows maps of the cassettes used in the transformations. FIG. 8 shows the results of Southern blot analysis on three transformants (all generated in UTEX strain 1435) (1, 2, and 3) transformed with either the beta-tubulin::neo::nit (SEQ ID NO: 49) (transformants 1 and 2) or glutamate dehydrogenase:neo:nit (SEQ ID NO: 50) (transformant 3). The glutamate dehydrogenase:neo:nit transforming plasmid was run as a control and cut with both NcoI and SacI. AvrII does not cut in this plasmid. Genomic DNA isolated from untransformed UTEX strain 1435 shows no hybridization to the NeoR probe.

Additional transformants containing the codon-optimized glutamate dehydrogenase:neo:nit (SEQ ID NO: 51) and codon-optimized β-tubulin::neo::nit (SEQ ID NO:52) constructs were picked and analyzed by Southern blot analysis. As expected, only digests with SacI show linearization of the transforming DNA. These transformation events are consistent with integration events that occur in the form of oligomers of the transforming plasmid. Only upon digestion with restriction enzymes that cut within the transforming plasmid DNA do these molecules collapse down the size of the transforming plasmid.

Southern blot analysis was also performed on transformants generated upon transformation of *Prototheca* strains UTEX 1437 and UTEX 1439 with the glutamate dehydrogenase::neo::nit cassette. The blot was probed with the NeoR probe probe and the results are similar to the UTEX 1435 transformants. The results are indicative of integration events characterized by oligomerization and integration of the transforming plasmid. This type of integration event is known to occur quite commonly in *Dictyostelium discoideum* (see, for example, Kuspa, A. and Loomis, W. (1992) *PNAS*, 89:8803-8807 and Morio et al., (1995) *J. Plant Res.* 108:111-114).

To further confirm expression of the transforming plasmid, Northern blot analysis and RT-PCR analysis were performed on selected transformants. RNA extraction was performed using Trizol Reagent according to manufacturer's instructions. Northern blot analysis were run according to methods published in Sambrook and Russel, 2001. Total RNA (15 µg) isolated from five UTEX 1435 transformants and untransformed UTEX 1435 (control lanes) was separated on 1% agarose-formaldehyde gel and blotted on nylon membrane. The blot was hybridized to the neo-non-optimized probe specific for transgene sequences in transformants 1 and 3. The two other transformants RNAs express the codon-optimized version of the neo-transgene and, as expected, based on the sequence homology between the optimized and non-optimized neo genes, showed significantly lower hybridization signal.

RNA (1 µg) was extracted from untransformed *Prototheca* strain UTEX 1435 and two representative UTEX 1435 transformants and reverse transcribed using an oligio dT primer or a gene specific primer. Subsequently these cDNAs (in duplicate) were subjected to qPCR analysis on ABI Veriti Thermocycler using SYBR-Green qPCR chemistry using the following primers (nptII):

```
Forward:
                                       (SEQ ID NO: 53)
5' GCCGCGACTGGCTGCTGCTGG 3'

Reverse:
                                       (SEQ ID NO: 54)
5' AGGTCCTCGCCGTCGGGCATG 3'
```

Possible genomic DNA contamination was ruled out by a no reverse transcriptase negative control sample. The results indicated that the NeoR genes used to transform these strains is actively transcribed in the transformants.

3. Transformation of *Prototheca* with Secreted Heterologous Sucrose Invertase

All of the following experiments were performed using liquid medium/agar plates based on the basal medium described in Ueno et al., (2002) *J Bioscience and Bioengineering* 94(2):160-65, with the addition of trace minerals described in U.S. Pat. No. 5,900,370, and 1×DAS Vitamin Cocktail (1000× solution): tricine: 9 g, thiamine HCL: 0.67 g, biotin: 0.01 g, cyannocobalamin (vitamin B 12): 0.008 g, calcium pantothenate: 0.02 g and p-aminobenzoic acid: 0.04 g).

Figure 9:
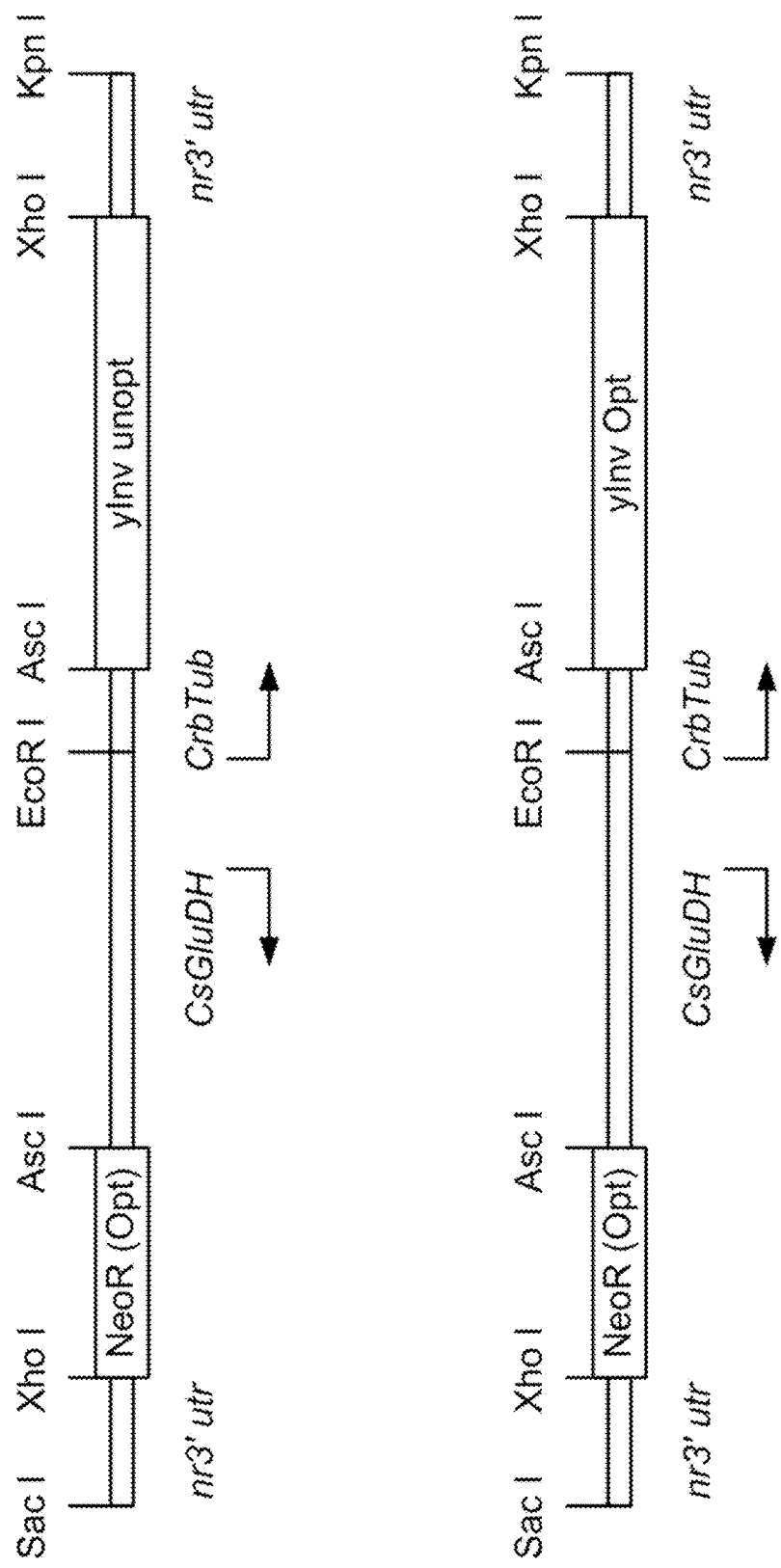
FIG. 9 shows a schematic of the codon optimized and non-codon optimized suc2 (yeast sucrose invertase (yInv)) transgene construct. The relevant restriction cloning sites are indicated and arrows indicate the direction of transcription.

Two plasmid constructs were assembled using standard recombinant DNA techniques. The yeast sucrose invertase genes (one codon optimized and one non-codon optimized), suc2, were under the control of the *Chlorella reinhardtii* beta-tubulin promoter/5'UTR and had the *Chlorella vulgaris* nitrate reductase 3'UTR. The sequences (including the 5'UTR and 3'UTR sequences) for the non-codon optimized (Crβ-tub::NCO-suc2::CvNitRed) construct, SEQ ID NO: 55, and codon optimized (Crβ-tub::CO-suc2::CvNitRed) construct, SEQ ID NO: 56, are listed in the Sequence Listing. Codon optimization was based on *Prototheca* sp (see Table 4). FIG. 9 shows a schematic of the two constructs with the relevant restriction cloning sites and arrows indicating the direction of transcription. Selection was provided by Neo R. Codon optimization was based on preferred codon usage in *Prototheca* strains in Table 4.

Preparation of the DNA/gold microcarrier: DNA/gold microcarriers were prepared immediately before use and stored on ice until applied to macrocarriers. The plasmid DNA (in TE buffer) was added to 50 µA of binding buffer. Saturation of the gold beads was achieved at 15 µg plasmid DNA for 3 mg gold carrier. The binding buffer and DNA were mixed well via vortexing. The DNA and binding buffer should be pre-mix prior to gold addition to ensure uniformed plasmid binding to gold carrier particles. 60 µA of S550d (Seashell Technologies, San Diego, Calif.) gold carrier was added to the DNA/binding buffer mixture. For a gold stock at 50 mg/ml, addition of 60 µA results in an optimal ratio of 15 µg DNA/3 mg gold carrier. The gold carrier/DNA mixture was allowed to incubate on ice for 1 minute and then 100 µA of precipitation buffer was added. The mixture was allowed to incubate again on ice for 1 minute and then briefly vortexed and centrifuged at 10,000 rpm at room temperature for 10 seconds to pellet the gold carrier. The supernatant was carefully removed with a pipette and the pellet was washed with 500 µA of ice cold 100% ethanol. The gold particles were re-pelleted by centrifuging again at 10,000 rpm for 10 seconds. The ethanol was removed and 50 µA of ice cold ethanol was added to the gold mixture. Immediately prior to applying the gold to macrocarriers, the gold/ethanol was resuspended with a brief 1-2 second pulse at level 2 on a MISONIX sonicator using the micro tip. Immediately after resuspension, 10 µl of the dispersed gold particles was transferred to the macrocarrier and allowed to dry in a sterile hood.

The two *Prototheca moriformis* strains (UTEX 1435 and 1441) were grown heterotrophically in liquid medium containing 2% glucose from cryopreserved vials. Each strain was grown to a density of $10^7$ cells/ml. This seed culture was then diluted with fresh media to a density of $10^5$ cells/ml and allowed to grow for 12-15 hours to achieve a final cell density of approximately $10^6$ cells/ml. The microalgae were aliquoted into 50 ml conical tubes and centrifuged for 10 minutes at 3500 rpm. The cells were washed with fresh medium and centrifuged again for 10 minutes at 3500 rpm. The cells were then resuspended at a density of $1.25 \times 10^8$ cells/ml in fresh medium.

In a sterile hood, 0.4 ml of the above-prepared cells were removed and placed directly in the center of an agar plate (without selection agent). The plate was gently swirled with a level circular motion to evenly distribute the cells to a diameter of no more than 3 cm. The cells were allowed to dry onto the plates in the sterile hood for approximately 30-40 minutes and then were bombarded at a rupture disk pressure of 1350 psi and a plate to macrocarrier distance of 6 cm. The plates were then covered and wrapped with parafilm and allowed to incubate under low light for 24 hours.

After the 24 hour recovery, 1 ml of sterile medium (with no glucose) was added to the lawn of cells. The cells were resuspended using a sterile loop, applied in a circular motion to the lawn of cells and the resuspended cells were collected using a sterile pipette. The cells were then plated onto a fresh agar plate with 2% glucose and 100 µg/ml G418. The appearance of colonies occurred 7-12 days after plating. Individual colonies were picked and grown in selective medium with 2% glucose and 100 µg/ml G418. The wildtype (untransformed) and transgenic cells were then analyzed for successful introduction, integration and expression of the transgene.

Genomic DNA from transformed *Prototheca moriformis* UTEX 1435 and 1441 and their wildtype (untransformed) counterparts were isolated using standard methods. Briefly, the cells were centrifuged for 5 minutes at 14,000 rpm in a standard table top Eppendorf centrifuge (model 5418) and flash frozen prior to DNA extraction. Cell pellets were lysed by adding 200 uL of Lysis buffer (100 mM Tris HCl, pH 8.0, 1% Lauryl Sarcosine, 50 mM NaCl, 20 mM EDTA, 0.25 M sucrose, 0.5 mg/ml RNase A) for every 100-200 mg of cells (wet weight) and vortexing for 30-60 seconds. Cetyl trimethyammonium bromide (CTAB) and NaCl were brought to 1% and 1 M, respectively, and cell extracts were incubated at 60-65° C. for 10 minutes. Subsequently, extracts were clarified via centrifugation at 14,000 rpm for 10 minutes and the resulting supernatant was extracted with an equal volume of phenol/chloroform/isoamyl alcohol (25:24:1). Samples were then centrifuged for 5 minutes at 14,000 rpm and the aqueous phase removed. DNA was precipitated with 0.7 volumes of isopropanol. DNA was pelleted via centrifugation at 14,000 rpm for 10 minutes and washed twice with 80% ethanol, and once with ethanol. After drying, DNA was resuspended in 10 mM Tris HCl, pH 8.0 and DNA concentrations were determined by using PicoGreen fluorescence quantification assay (Molecular Probes).

RNA from transformed *Prototheca moriformis* UTEX 1435 and 1441 and their wildtype (untransformed) counterparts were isolated using standard methods. Briefly, the cells were centrifuged for 5 minutes at 14,000 rpm in a standard table top Eppendorf centrifuge (model 5418) and flash frozen before RNA extraction. Cell pellets were lysed by addition of 1 mL of Trizol reagent (Sigma) for every 100 mg of cells (wet weight) and by vortexing for 1-2 minutes. Samples were incubated at room temperature for 5 minutes and subsequently adjusted with 200 uL of chloroform per 1 mL of Trizol reagent. After extensive shaking, cells were incubated at room temperature for 15 minutes and then subjected to centrifugation at 14000 rpm for 15 minutes in a refrigerated table top microcentrifuge. RNA partitioning to the upper aqueous phase was removed and precipitated by addition of isopropanol (500 uL per 1 ml of Trizol reagent). RNA was collected by centrifugation for 10 minutes and the resulting pellet washed twice with 1 mL of 80% ethanol, dried, and resuspended in RNAse free water. RNA concentration was estimated by RiboGreen fluorescence quantification assay (Molecular Probes).

Expression of neomycin phophotransferase gene conferring G418 antibiotic resistance and yeast invertase was assayed in non-transformed *Prototheca moriformis* UTEX 1435 and 1441 and transformants T98 (UTEX 1435 transformant) and T97 (UTEX 1441 transformant) using reverse transcription quantitative PCR analysis (RT-qPCR). 20 ng total RNA (isolated as described above) was subjected to one step RT-qPCR analysis using iScript SYBR Green RT-PCR kit (BioRad Laboratories) and primer pairs targeting the neomycin resistance gene (forward primer 5' CCGCCGTGCTGGACGTGGTG 3' and reverse primer 5' GGTGGCGGGGTCCAGGGTGT 3'; SEQ ID NOs: 57 and 58, respectively) and suc2 invertase transcripts (forward primer 5' CGGCCGGCGGCTCCTTCAAC 3' and reverse primer 5' GGCGCTCCCGTAGGTCGGGT 3'; SEQ ID NO: 59 and 60, respectively). Endogenous beta-tubulin transcripts served as an internal positive control for PCR amplification and as a normalization reference to estimate relative transcript levels.

Both codon optimized and non-codon optimized constructs were transformed into UTEX 1435 and 1441 *Prototheca moriformis* cells as described above. Initially, transformants were obtained with both constructs and the presence of the transgene was verified by Southern blot analysis followed by RTPCR to confirm the presence of the DNA and mRNA from the transgene. For the Southern blot analysis, genomic DNA isolated as described above was electrophoresed on 0.7% agarose gels in 1×TAE buffer. Gels were processed as described in Sambrook et al. (Molecular Cloning; A Laboratory Manual, $2^{nd}$ Edition. Cold Spring Harbor Laboratory Press, 1989). Probes were prepared by random priming and hybridizations carried out as described in Sambrook et al. Transformants from both the codon optimized and the non-codon optimized constructs showed the presence of the invertase cassette, while the non-transformed control was negative. Invertase mRNA was also detected in transformants with both the codon optimized and non-codon optimized constructs.

To confirm that the transformants were expressing an active invertase protein, the transformants were plated on sucrose plates. The transformants containing the non-codon optimized cassette failed to grow on the sucrose containing plates, indicating that, while the gene and the mRNA encoding the SUC2 protein were present, the protein was either (1) not being translated, or (2) being translated, but not accumulating to levels sufficient to allow for growth on sucrose as the sole carbon source. The transformants with the codon optimized cassette grew on the sucrose containing plates. To assess the levels of invertase being expressed by these transformants, two clones (T98 and T97) were subjected to an invertase assay of whole cells scraped from solid medium and direct sampling and quantitation of sugars in the culture supernatants after 48 hours of growth in liquid medium containing 2% sucrose as the sole carbon source.

For the invertase assay, the cells (T98 and T97) were grown on plates containing 2% sucrose, scraped off and assayed for invertase activity. 10 µl of the scraped cells was mixed with 40 µl of 50 mM NaOAc pH 5.1. 12.5 µl of 0.5M sucrose was added to the cell mixture and incubated at 37° C. for 10-30 minutes. To stop the reaction, 75 µl of 0.2M $K_2HPO_4$ was added. To assay for glucose liberated, 500 µl of reconstituted reagent (glucose oxidase/peroxidase+o-Dianisidine) from Sigma (GAGO-20 assay kit) was added to each tube and incubated at 37° C. for 30 minutes. A glucose standard curve was also created at this time (range: 25 µg to 0.3 µg glucose). After incubation, 500 µl of 6N HCl was added to stop the reaction and to develop the color. The samples were read at 540 nm. The amount of glucose liberated was calculated from the glucose standard curve using the formula y=mx+c, where y is the 540 nm reading, and x is μg of glucose. Weight of glucose was converted to moles of glucose, and given the equimolar relationship between moles of sucrose hydrolyzed to moles of glucose generated, the data was expressed as nmoles of sucrose hydrolyzed per unit time. The assay showed that both T98 and T97 clones were able to hydrolyze sucrose, indicating that a functional sucrose invertase was being produced and secreted by the cells.

For the sugar analysis on liquid culture media after 48 hours of algal growth, T97 and T98 cells were grown in 2% sucrose containing medium for 48 hours and the culture media were processed for sugar analysis. Culture broths from each transformant (and negative non-transformed cell control) were centrifuged at 14,000 rpm for 5 minutes. The resulting supernatant was removed and subjected to HPLC/ELSD (evaporative light scattering detection). The amount of sugar in each sample was determined using external standards and liner regression analysis. The sucrose levels in the culture media of the transformants were very low (less than 1.2 g/L, and in most cases 0 g/L). In the negative controls, the sucrose levels remained high, at approximately 19 g/L after 48 hours of growth.

These results were consistant with the invertase activity results, and taken together, indicated that the codon optimized transformants, T97 and T98, secreted an active sucrose invertase that allowed the microalgae to utilize sucrose as the sole carbon source in contrast to (1) the non-codon optimized transformants and (2) the non-transformed wildtype microalgae, both of which could not utilize sucrose as the sole carbon source in the culture medium.

*Prototheca moriformis* strains, T98 and T97, expressing a functional, secreted sucrose invertase (SUC2) transgene were assayed for growth and lipid production using sucrose as the sole carbon source.

Wild type (untransformed), T98 and T97 strains were grown in growth media (as described above) containing either 4% glucose or 4% sucrose as the sole carbon source under heterotrophic conditions for approximately 6 days. Growth, as determined by A750 optical density readings were taken of all four samples every 24 hours and the dry cell weight of the cultures and lipid profiles were determined after the 6 days of growth. The optical density readings of the transgenic strains grown in both the glucose and sucrose conditions were comparable to the wildtype strains grown in the glucose conditions. These results indicate that the transgenic strains were able to grow on either glucose or sucrose as the sole carbon source at a rate equal to wildtype strains in glucose conditions. The non-transformed, wildtype strains did not grow in the sucrose-only condition.

The biomass for the wildtype strain grown on glucose and T98 strain grown on sucrose was analyzed for lipid profile. Lipid samples were prepared from dried biomass (lyophilized) using an Acid Hydrolysis System (Ankom Technology, NY) according to manufacturer's instructions. Lipid profile determinations were carried as described in Example 6. The lipid profile for the non-transformed *Prototheca moriformis* UTEX 1435 strain, grown on glucose as the sole carbon source and two colonal T98 strains (UTEX 1435 transformed with a sucrose invertase transgene), grown on sucrose as the sole carbon source, are disclosed in Table 34 (wildtype UTEX 1435 and T98 clone 8 and clone 11 below. C:19:0 lipid was used as an internal calibration control.

TABLE 34

Lipid profile of wildtype UTEX 1435 and UTEX 1435 clones with suc2 transgene.

| Name | wildtype (Area % - ISTD) | T98 clone 11 (Area % - ISTD) | T98 clone 8 (Area % - ISTD) |
|---|---|---|---|
| C 12:0 | 0.05 | 0.05 | 0.05 |
| C 14:0 | 1.66 | 1.51 | 1.48 |
| C 14:1 | 0.04 | nd | nd |
| C 15:0 | 0.05 | 0.05 | 0.04 |
| C 16:0 | 27.27 | 26.39 | 26.50 |
| C 16:1 | 0.86 | 0.80 | 0.84 |
| C 17:0 | 0.15 | 0.18 | 0.14 |
| C 17:1 | 0.05 | 0.07 | 0.05 |
| C 18:0 | 3.35 | 4.37 | 4.50 |
| C 18:1 | 53.05 | 54.48 | 54.50 |
| C 18:2 | 11.79 | 10.33 | 10.24 |
| C 19:0 (ISTD) | — | — | — |
| C 18:3 alpha | 0.90 | 0.84 | 0.81 |
| C 20:0 | 0.32 | 0.40 | 0.38 |
| C 20:1 | 0.10 | 0.13 | 0.12 |
| C 20:1 | 0.04 | 0.05 | 0.04 |
| C 22:0 | 0.12 | 0.16 | 0.12 |
| C 20:3 | 0.07 | 0.08 | 0.07 |
| C 24:0 | 0.12 | 0.11 | 0.10 | nd - denotes none detected

Oil extracted from wildtype *Prototheca moriformis* UTEX 1435 (via solvent extraction or using an expeller press) was analyzed for carotenoids, chlorophyll, tocopherols, other sterols and tocotrienols. The results are summarized below in Table 35.

TABLE 35

Carotenoid, chlorophyll, tocopherol/sterols and tocotrienol analysis in oil extracted from *Prototheca moriformis* (UTEX 1435).

| | Pressed oil (mcg/ml) | Solvent extracted oil (mcg/ml) |
|---|---|---|
| cis-Lutein | 0.041 | 0.042 |
| trans-Lutein | 0.140 | 0.112 |
| trans-Zeaxanthin | 0.045 | 0.039 |
| cis-Zeaxanthin | 0.007 | 0.013 |
| t-alpha-Crytoxanthin | 0.007 | 0.010 |
| t-beta-Crytoxanthin | 0.009 | 0.010 |
| t-alpha-Carotene | 0.003 | 0.001 |
| c-alpha-Carotene | none detected | none detected |
| t-beta-Carotene | 0.010 | 0.009 |
| 9-cis-beta-Carotene | 0.004 | 0.002 |
| Lycopene | none detected | none detected |
| Total Carotenoids | 0.267 | 0.238 |
| Chlorophyll | <0.01 mg/kg | <0.01 mg/kg |

| Tocopherols and Sterols | | |
|---|---|---|
| | Pressed oil (mg/100 g) | Solvent extracted oil (mg/100 g) |
| gamma Tocopherol | 0.49 | 0.49 |
| Campesterol | 6.09 | 6.05 |
| Stigmasterol | 47.6 | 47.8 |
| Beta-sitosterol | 11.6 | 11.5 |
| Other sterols | 445 | 446 |

| Tocotrienols | | |
|---|---|---|
| | Pressed oil (mg/g) | Solvent extracted oil (mg/g) |
| alpha Tocotrienol | 0.26 | 0.26 |
| beta Tocotrienol | <0.01 | <0.01 |

TABLE 35-continued

Carotenoid, chlorophyll, tocopherol/sterols and tocotrienol analysis
in oil extracted from *Prototheca moriformis* (UTEX 1435).

| gamma Tocotrienol | 0.10 | 0.10 |
| detal Tocotrienol | <0.01 | <0.01 |
| Total Tocotrienols | 0.36 | 0.36 |

The ability of using sucrose as the sole carbon source as the selection factor for clones containing the suc2 transgene construct instead of G418 (or another antibiotic) was assessed using the positive suc2 gene transformants. A subset of the positive transformants was grown on plates containing sucrose as the sole carbon source and without antibiotic selection for 24 doublings. The clones were then challenged with plates containing glucose as the sole carbon source and G418. There was a subset of clones that did not grow on the glucose+ G418 condition, indicating a loss of expression of the transgene. An additional experiment was performed using a plate containing sucrose as the sole carbon source and no G418 and streaking out a suc2 transgene expressing clone on one half of the plate and wild-type *Prototheca moriformis* on the other half of the plate. Growth was seen with both the wild-type and transgene-containing *Prototheca moriformis* cells. Wild-type *Prototheca moriformis* has not demonstrated the ability to grow on sucrose, therefore, this result shows that unlike antibiotic resistance, the use of sucrose/invertase selection is not cell-autonomous. It is very likely that the transformants were secreting enough sucrose invertase into the plate/media to support wildtype growth as the sucrose was hydrolyzed into fructose and glucose.

Example 10

Recombinant *Prototheca* with Exogenous TE Gene

As described above, *Prototheca* strains can be transformed with exogenous genes. *Prototheca moriformis* (UTEX 1435) was transformed, using methods described above, with either *Umbellularia californica* C12 thioesterase gene or *Cinnamomum camphora* C14 thiotesterase gene (both codon optimized according to Table 4). Each of the transformation constructs contained a *Chlorella sorokiniana* glutamate dehydrogenase promoter/5'UTR region (SEQ ID NO: 61) to drive expression of the thioesterase transgene. The thioesterase transgenes coding regions of *Umbellularia californica* C12 thioesterase (SEQ ID NO: 62) or *Cinnamomum camphora* C14 thioesterase (SEQ ID NO: 63), each with the native putative plastid targeting sequence. Immediately following the thioesterase coding sequence is the coding sequence for a c-terminal 3x-FLAG tag (SEQ ID NO: 64), followed by the *Chlorella vulgaris* nitrate reductase 3'UTR (SEQ ID NO: 65).

Preparation of the DNA, gold microcarrier and *Prototheca moriformis* (UTEX 1435) cells were performed using the methods described above in Example 9. The microalgae were bombarded using the gold microcarrier-DNA mixture and plated on selection plates containing 2% glucose and 100 µg/ml G418. The colonies were allowed to develop for 7 to 12 days and colonies were picked from each transformation plate and screened for DNA construct incorporation using Southern blots assays and expression of the thioesterase constructs were screened using RT-PCR.

Positive clones were picked from both the C12 and C14 thioesterase transformation plates and screened for construct incorporation using Southern blot assays. Southern blot assays were carried out using standard methods (and described above in Example 9) using an optimized c probes, based on the sequence in SEQ ID NO: 62 and SEQ ID NO: 63. Transforming plasmid DNA was run as a positive control. Out of the clones that were positive for construct incorporation, a subset was selected for reverse transcription quantitative PCR (RT-qPCR) analysis for C12 thioesterase and C14 thioesterase expression.

RNA isolation was performed using methods described in Example 9 above and RT-qPCR of the positive clones were performed using 20 ng of total RNA from each clone using the below-described primer pair and iScript SYBR Green RT-PCR kit (Bio-Rad Laboratories) according to manufacturer's protocol. Wildtype (non-transformed) *Prototheca moriformis* total RNA was included as a negative control. mRNA expression was expressed as relative fold expression (RFE) as compared to negative control. The primers that were used in the C12 thioesterase transformation RT-qPCR screening were:

*U. californica* C12 thioesterase PCR primers:

```
Forward:
                                     (SEQ ID NO: 66)
   5' CTGGGCGACGGCTTCGGCAC 3'

Reverse:
                                     (SEQ ID NO: 67)
   5' AAGTCGCGGCGCATGCCGTT 3'
```

The primers that were used in the C14 thioesterase transformation RT-qPCR screening were:
*Cinnamomum camphora* C14 thioesterase PCR primers:

```
Forward:
                                     (SEQ ID NO: 68)
   5' TACCCCGCCTGGGGCGACAC 3'

Reverse:
                                     (SEQ ID NO: 69)
   5' CTTGCTCAGGCGGCGGGTGC 3'
```

RT-qPCR results for C12 thioesterase expression in the positive clones showed an increased RFE of about 40 fold to over 2000 fold increased expression as compared to negative control. Similar results were seen with C14 thioesterase expression in the positive clones with an increase RFE of about 60-fold to over 1200 fold increased expression as compared to negative control.

A subset of the positive clones from each transformation (as screened by Southern blotting and RT-qPCR assays) were selected and grown under nitrogen-replete conditions and analyzed for total lipid production and profile. Lipid samples were prepared from dried biomass from each clone. 20-40 mg of dried biomass from each transgenic clone was resuspended in 2 mL of 3% $H_2SO_4$ in MeOH, and 200 ul of toluene containing an appropriate amount of a suitable internal standard (C19:0) was added. The mixture was sonicated briefly to disperse the biomass, then heated at 65-70° C. for two hours. 2 mL of heptane was added to extract the fatty acid methyl esters, followed by addition of 2 mL of 6% $K_2CO_3$ (aq) to neutralize the acid. The mixture was agitated vigorously, and a portion of the upper layer was transferred to a vial containing $Na_2SO_4$ (anhydrous) for gas chromatography analysis using standard FAME GC/FID (fatty acid methyl ester gas chromatography flame ionization detection) methods. Lipid profile (expressed as Area %) of the positive clones as compared to wildtype negative control are summarized in Tables 36 and 37 below. As shown in Table 36, the fold increase of C12 production in the C12 transformants ranged from about a 5-fold increase (clone C12-5) to over 11-fold increase (clone C12-1). Fold increase of C14 production in the C14 transformants ranged from about a 1.5 fold increase to about a 2.5 fold increase.

TABLE 36

Summary of total lipid profile of the *Prototheca moriformis* C12 thioesterase transformants.

|  | Wildtype | C12-1 | C12-2 | C12-3 | C12-4 | C12-5 | C12-6 | C12-7 | C12-8 |
|---|---|---|---|---|---|---|---|---|---|
| C6:0 | 0.03 | nd | nd | nd | nd | nd | nd | nd | nd |
| C8:0 | 0.11 | 0.09 | nd | 0.11 | nd | nd | nd | nd | nd |
| C10:0 | nd | nd | nd | 0.01 | 0.01 | nd | nd | 0.01 | nd |
| C12:0 | 0.09 | 1.04 | 0.27 | 0.72 | 0.71 | 0.50 | 0.67 | 0.61 | 0.92 |
| C14:0 | 2.77 | 2.68 | 2.84 | 2.68 | 2.65 | 2.79 | 2.73 | 2.56 | 2.69 |
| C14:1 | 0.01 | nd | nd | 0.02 | nd | nd | nd | 0.01 | nd |
| C15:0 | 0.30 | 0.09 | 0.10 | 0.54 | 0.19 | 0.09 | 0.13 | 0.97 | 0.09 |
| C15:1 | 0.05 | nd | nd | 0.02 | nd | nd | nd | nd | nd |
| C16:0 | 24.13 | 23.12 | 24.06 | 22.91 | 22.85 | 23.61 | 23.14 | 21.90 | 23.18 |
| C16:1 | 0.57 | 0.62 | 0.10 | 0.52 | 0.69 | 0.63 | 0.69 | 0.49 | 0.63 |
| C17:0 | 0.47 | 0.24 | 0.27 | 1.02 | 0.36 | 0.17 | 0.26 | 2.21 | 0.19 |
| C17:1 | 0.08 | nd | 0.09 | 0.27 | 0.10 | 0.05 | 0.09 | 0.80 | 0.05 |
| C18:0 | nd | nd | 2.14 | 1.75 | 2.23 | 2.16 | 2.38 | 1.62 | 2.47 |
| C18:1 | 22.10 | 23.15 | 24.61 | 21.90 | 23.52 | 19.30 | 22.95 | 20.22 | 22.85 |
| C18:1 | nd | 0.33 | 0.24 | nd | nd | 0.09 | 0.09 | nd | 0.11 |
| C18:2 | 37.16 | 34.71 | 35.29 | 35.44 | 35.24 | 36.29 | 35.54 | 36.01 | 35.31 |
| C18:3 alpha | 11.68 | 11.29 | 9.26 | 11.62 | 10.76 | 13.61 | 10.64 | 11.97 | 10.81 |
| C20:0 | 0.15 | 0.16 | 0.19 | 0.16 | 0.16 | 0.14 | 0.18 | 0.14 | 0.18 |
| C20:1 | 0.22 | 0.17 | 0.19 | 0.20 | 0.21 | 0.19 | 0.21 | 0.20 | 0.21 |
| C20:2 | 0.05 | nd | 0.04 | 0.05 | 0.05 | 0.05 | 0.04 | 0.05 | 0.04 |
| C22:0 | nd | nd | nd | 0.01 | nd | nd | nd | 0.02 | nd |
| C22:1 | nd | nd | nd | nd | nd | 0.01 | nd | 0.01 | nd |
| C20:3 | 0.05 | nd | 0.07 | 0.06 | 0.06 | 0.10 | 0.07 | 0.05 | 0.06 |
| C20:4 | nd | nd | nd | nd | nd | 0.02 | nd | nd | nd |
| C24:0 | nd | nd | 0.24 | 0.01 | 0.20 | 0.19 | 0.19 | 0.14 | 0.20 |

TABLE 37

Summary or total lipid profile or the *Prototheca moriformis* C14 thioesterase transformants.

|  | Wildtype | C14-1 | C14-2 | C14-3 | C14-4 | C14-5 | C14-6 | C14-7 |
|---|---|---|---|---|---|---|---|---|
| C6:0 | 0.03 | nd | nd | nd | nd | nd | nd | nd |
| C8:0 | 0.11 | nd | nd | nd | nd | nd | nd | nd |
| C10:0 | nd | 0.01 | nd | 0.01 | nd | 0.01 | nd | nd |
| C12:0 | 0.09 | 0.20 | 0.16 | 0.25 | 0.21 | 0.19 | 0.40 | 0.17 |
| C14:0 | 2.77 | 4.31 | 4.76 | 4.94 | 4.66 | 4.30 | 6.75 | 4.02 |
| C14:1 | 0.01 | nd | 0.01 | nd | nd | 0.01 | nd | nd |
| C15:0 | 0.30 | 0.43 | 0.45 | 0.12 | 0.09 | 0.67 | 0.10 | 0.33 |
| C15:1 | 0.05 | nd | nd | nd | nd | nd | nd | nd |
| C16:0 | 24.13 | 22.85 | 23.20 | 23.83 | 23.84 | 23.48 | 24.04 | 23.34 |
| C16:1 | 0.57 | 0.65 | 0.61 | 0.60 | 0.60 | 0.47 | 0.56 | 0.67 |
| C17:0 | 0.47 | 0.77 | 0.76 | 0.21 | 0.19 | 1.11 | 0.18 | 0.54 |
| C17:1 | 0.08 | 0.23 | 0.15 | 0.06 | 0.05 | 0.24 | 0.05 | 0.12 |
| C18:0 | nd | 1.96 | 1.46 | 2.48 | 2.34 | 1.84 | 2.50 | 2.06 |
| C18:1 | 22.10 | 22.25 | 19.92 | 22.36 | 20.57 | 19.50 | 20.63 | 22.03 |
| C18:1 | nd | nd | nd | nd | nd | nd | 0.10 | nd |
| C18:2 | 37.16 | 34.97 | 36.11 | 34.35 | 35.70 | 35.49 | 34.03 | 35.60 |
| C18:3 alpha | 11.68 | 10.71 | 12.00 | 10.15 | 11.03 | 12.08 | 9.98 | 10.47 |
| C20:0 | 0.15 | 0.16 | 0.19 | 0.17 | 0.17 | 0.14 | 0.18 | 0.16 |
| C20:1 | 0.22 | 0.20 | 0.12 | .019 | 0.19 | 0.19 | 0.17 | 0.20 |
| C20:2 | 0.05 | 0.04 | 0.02 | 0.03 | 0.04 | 0.05 | 0.03 | 0.04 |
| C22:0 | nd | nd | nd | nd | 0.02 | 0.01 | nd | nd |
| C22:1 | nd | 0.01 | nd | nd | nd | nd | nd | 0.01 |
| C20:3 | 0.05 | 0.08 | 0.03 | 0.06 | 0.09 | 0.05 | 0.05 | 0.07 |
| C20:4 | nd | 0.01 | nd | nd | nd | nd | 0.02 | nd |
| C24:0 | nd | 0.17 | 0.14 | 0.19 | 0.20 | 0.16 | 0.22 | 0.17 |

The above-described experiments indicate the successful transformation of *Prototheca moriformis* (UTEX 1435) with transgene constructs of two different thioesterases (C12 and C14), which involved not only the successful expression of the transgene, but also the correct targeting of the expressed protein to the plastid and a functional effect (the expected change in lipid profile) as a result of the transformation. The same transformation experiment was performed using an expression construct containing a codon-optimized (according to Table 4) *Cuphea hookeriana* C8-10 thioesterase coding region with the native plastid targeting sequence (SEQ ID NO: 70) yielded no change in lipid profile. While the introduction of the *Cuphea hookeriana* C8-10 transgene into *Prototheca moriformis* (UTEX 1435) was successful and confirmed by Southern blot analysis, no change in C8 or C10 fatty acid production was detected in the transformants compared to the wildtype strain.

Example 11

Generation of *Prototheca moriformis* Strain with Exogenous Plant TE with Algal Plastid Targeting Sequence In order to investigate whether the use of algal chloroplast/plastid targeting sequences would improve medium chain (C8-C14) thioesterase expression and subsequent medium chain lipid production in *Prototheca moriformis* (UTEX 1435), several putative algal plastid targeting sequences were cloned from *Chlorella protothecoides* and *Prototheca moriformis*. Thioesterase constructs based on *Cuphea hookeriana* C8-10 thioesterase, *Umbellularia californica* C12 thioesterase, and *Cinnamomum camphora* C14 thioesterase were made using made with a *Chlorella sorokiniana* glutamate dehydrogenase promoter/5'UTR and a *Chlorella vulgaris* nitrate reductase 3'UTR. The thioesterase coding sequences were modified by removing the native plastid targeting sequences and replacing them with plastid targeting sequences from the *Chlorella protothecoides* and the *Prototheca moriformis* genomes. The thioesterase expression constructs and their corresponding sequence identification numbers are listed below. Each transformation plasmid also contained a Neo resistance construct that was identical to the ones described in Example 9 above. Additionally, another algal-derived promoter, the *Chlamydomonas reinhardtii* β-tubulin promoter, was also tested in conjunction with the thioesterase constructs. "Native" plastid targeting sequence refers to the higher plant thioesterase plastid targeting sequence. A summary of the constructs used in these experiments is provided below:

| Construct Name | Promoter/ 5'UTR | Plastid targeting seq | Gene | 3'UTR | SEQ ID NO. |
|---|---|---|---|---|---|
| Construct 1 | *C. sorokiniana* glutamate dehydrogenase | *C. protothecoides* stearoyl ACP desaturase | *Cuphea hookeriana* C8-10 TE | *C. vulgaris* nitrate reductase | SEQ ID NO: 71 |
| Construct 2 | *C. sorokiniana* glutamate dehydrogenase | *P. moriformis* delta 12 fatty acid desaturase | *Cuphea hookeriana* C8-10 TE | *C. vulgaris* nitrate reductase | SEQ ID NO: 72 |
| Construct 3 | *C. sorokiniana* glutamate dehydrogenase | *P. moriformis* isopentenyl diphosphate synthase | *Cuphea hookeriana* C8-10 TE | *C. vulgaris* nitrate reductase | SEQ ID NO: 73 |
| Construct 4 | *C. sorokiniana* glutamate dehydrogenase | *P. moriformis* isopentenyl diphosphate synthase | *Umbellularia californica* C12 TE | *C. vulgaris* nitrate reductase | SEQ ID NO: 74 |
| Construct 5 | *C. sorokiniana* glutamate dehydrogenase | *P. moriformis* stearoyl ACP desaturase | *Umbellularia californica* C12 TE | *C. vulgaris* nitrate reductase | SEQ ID NO: 75 |
| Construct 6 | *C. sorokiniana* glutamate dehydrogenase | *C. protothecoides* stearoyl ACP desaturase | *Umbellularia californica* C12 TE | *C. vulgaris* nitrate reductase | SEQ ID NO: 76 |
| Construct 7 | *C. sorokiniana* glutamate dehydrogenase | *P. moriformis* delta 12 fatty acid desaturase | *Umbellularia californica* C12 TE | *C. vulgaris* nitrate reductase | SEQ ID NO: 77 |
| Construct 8 | *C. sorokiniana* glutamate dehydrogenase | *C. protothecoides* stearoyl ACP desaturase | *Cinnamomum camphora* C14 TE | *C. vulgaris* nitrate reductase | SEQ ID NO: 78 |
| Construct 9 | *Chlamydomonas reinhardtii* β-tubulin | Native | *Cuphea hookeriana* C8-10 TE | *C. vulgaris* nitrate reductase | SEQ ID NO: 79 |
| Construct 10 | *Chlamydomonas reinhardtii* β-tubulin | *P. moriformis* isopentenyl diphosphate synthase | *Cuphea hookeriana* C8-10 TE | *C. vulgaris* nitrate reductase | SEQ ID NO: 80 |
| Construct 11 | *Chlamydomonas reinhardtii* β-tubulin | *P. moriformis* delta 12 fatty acid desaturase | *Cuphea hookeriana* C8-10 TE | *C. vulgaris* nitrate reductase | SEQ ID NO: 81 |
| Construct 12 | *Chlamydomonas reinhardtii* β-tubulin | *C. protothecoides* stearoyl ACP desaturase | *Cuphea hookeriana* C8-10 TE | *C. vulgaris* nitrate reductase | SEQ ID NO: 82 |
| Construct 13 | *Chlamydomonas reinhardtii* β-tubulin | *P. moriformis* stearoyl ACP desaturase | *Cuphea hookeriana* C8-10 TE | *C. vulgaris* nitrate reductase | SEQ ID NO: 83 |
| Construct 14 | *Chlamydomonas reinhardtii* β-tubulin | Native | *Umbellularia californica* C12 TE | *C. vulgaris* nitrate reductase | SEQ ID NO: 84 |
| Construct 15 | *Chlamydomonas reinhardtii* β-tubulin | *P. moriformis* isopentenyl diphosphate | *Umbellularia californica* C12 TE | *C. vulgaris* nitrate reductase | SEQ ID NO: 85 |
| Construct 16 | *Chlamydomonas reinhardtii* β-tubulin | *P. moriformis* delta 12 fatty acid desaturase | *Umbellularia californica* C12 TE | *C. vulgaris* nitrate reductase | SEQ ID NO: 86 |
| Construct 17 | *Chlamydomonas reinhardtii* β-tubulin | *C. protothecoides* stearoyl ACP desaturase | *Umbellularia californica* C12 TE | *C. vulgaris* nitrate reductase | SEQ ID NO: 87 |

| Construct Name | Promoter/ 5'UTR | Plastid targeting seq | Gene | 3'UTR | SEQ ID NO. |
|---|---|---|---|---|---|
| Construct 18 | Chlamydomonas reinhardtii β-tubulin | P. moriformis stearoyl ACP desaturase | Umbellularia californica C12 TE | C. vulgaris nitrate reductase | SEQ ID NO: 88 |
| Construct 19 | Chlamydomonas reinhardtii β-tubulin | Native | Cinnamomum camphora C14 TE | C. vulgaris nitrate reductase | SEQ ID NO: 89 |
| Construct 20 | Chlamydomonas reinhardtii β-tubulin | P. moriformis isopentenyl diphosphate synthase | Cinnamomum camphora C14 TE | C. vulgaris nitrate reductase | SEQ ID NO: 90 |
| Construct 21 | Chlamydomonas reinhardtii β-tubulin | P. moriformis delta 12 fatty acid desaturase | Cinnamomum camphora C14 TE | C. vulgaris nitrate reductase | SEQ ID NO: 91 |
| Construct 22 | Chlamydomonas reinhardtii β-tubulin | C. prototheocoides stearoyl ACP desaturase | Cinnamomum camphora C14 TE | C. vulgaris nitrate reductase | SEQ ID NO: 92 |
| Construct 23 | Chlamydomonas reinhardtii β-tubulin | P. moriformis stearoyl ACP desaturase | Cinnamomum camphora C14 TE | C. vulgaris nitrate reductase | SEQ ID NO: 93 |

Each construct was transformed into *Prototheca moriformis* (UTEX 1435) and selection was performed using G418 using the methods described in Example 9 above. Several positive clones from each transformation were picked and screened for the presence thioesterase transgene using Southern blotting analysis. Expression of the thioesterase transgene was confirmed using RT-PCR. A subset of the positive clones (as confirmed by Southern blotting analysis and RT-PCR) from each transformation was selected and grown for lipid profile analysis. Lipid samples were prepared from dried biomass samples of each clone and lipid profile analysis was performed using acid hydrolysis methods described in Example 9. Changes in area percent of the fatty acid corresponding to the thioesterase transgene were compared to wildtype levels, and clones transformed with a thioesterase with the native plastid targeting sequence.

The clones transformed with *Cuphea hookeriana* C8-10 thioesterase constructs with the native plastid targeting sequence had the same level of C8 and C10 fatty acids as wildtype. The clones transformed with *Cuphea hookeriana* C8-10 thioesterase constructs (Constructs 1-3) with algal plastid targeting sequences had over a 10-fold increase in C10 fatty acids for Construct 3 and over 40-fold increase in C10 fatty acids for Constructs 1 and 2 (as compared to wildtype). The clones transformed with *Umbellularia californica* C12 thioesterase constructs with the native plastid targeting sequence had a modest 6-8 fold increase in C12 fatty acid levels as compared to wildtype. The clones transformed with the *Umbellularia californica* C12 thioesterase constructs with the algal plasmid targeting constructs (Constructs 4-7) had over an 80-fold increase in C12 fatty acid level for Construct 4, about an 20-fold increase in C12 fatty acid level for Construct 6, about a 10-fold increase in C12 fatty acid level for Construct 7 and about a 3-fold increase in C12 fatty acid level for Construct 5 (all compared to wildtype). The clones transformed with *Cinnamomum camphora* C14 thioesterase with either the native plastid targeting sequence or the construct 8 (with the *Chlorella prototheocoides* stearoyl ACP desaturase plastid targeting sequence) had about a 2-3 fold increase in C14 fatty acid levels as compared to wildtype. In general clones transformed with an algal plastid targeting sequence thioesterase constructs had a higher fold increase in the corresponding chain-length fatty acid levels than when using the native higher plant targeting sequence.

1. *Clamydomonas reinhartii* β-Tubulin Promoter

Additional heterologous thioesterase expression constructs were prepared using the *Chlamydomonas reinhardtii* β-tubulin promoter instead of the *C. sorokinana* glutamate dehydrogenase promoter. The construct elements and sequence of the expression constructs are listed above. Each construct was transformed into *Prototheca moriformis* UTEX 1435 host cells using the methods described above. Lipid profiles were generated from a subset of positive clones for each construct in order to assess the success and productivity of each construct. The lipid profiles compare the fatty acid levels (expressed in area %) to wildtype host cells. The "Mean" column represents the numerical average of the subset of positive clones. The "Sample" column represents the best positive clone that was screened (best being defined as the sample that produced the greatest change in area % of the corresponding chain-length fatty acid production). The "low-high" column represents the lowest area % and the highest area % of the fatty acid from the clones that were screened. The lipid profile results of Constructs 9-12 and 14-23 are summarized below.

| Fatty Acid | wildtype | Mean | Sample | low/high |
|---|---|---|---|---|
| Construct 9. *Cuphea hookeriana* C8-10 TE | | | | |
| C 8:0 | 0 | 0.05 | 0.30 | 0-0.29 |
| C 10:0 | 0.01 | 0.63 | 2.19 | 0-2.19 |
| C 12:0 | 0.03 | 0.06 | 0.10 | 0-0.10 |
| C 14:0 | 1.40 | 1.50 | 1.41 | 1.36-3.59 |
| C 16:0 | 24.01 | 24.96 | 24.20 | |
| C 16:1 | 0.67 | 0.80 | 0.85 | |
| C 17:0 | 0 | 0.16 | 0.16 | |
| C 17:1 | 0 | 0.91 | 0 | |
| C 18:0 | 4.15 | 17.52 | 3.19 | |
| C 18:1 | 55.83 | 44.81 | 57.54 | |
| C 18:2 | 10.14 | 7.58 | 8.83 | |
| C 18:3α | 0.93 | 0.68 | 0.76 | |
| C 20:0 | 0.33 | 0.21 | 0.29 | |
| C 24:0 | 0 | 0.05 | 0.11 | |
| Construct 10. *Cuphea hookeriana* C8-10 TE | | | | |
| C 8:0 | 0 | 0.01 | 0.02 | 0-0.03 |
| C 10:0 | 0 | 0.16 | 0.35 | 0-0.35 |
| C 12:0 | 0.04 | 0.05 | 0.07 | 0-0.07 |
| C 14:0 | 1.13 | 1.62 | 1.81 | 0-0.05 |
| C 14:1 | 0 | 0.04 | 0.04 | |
| C 15:0 | 0.06 | 0.05 | 0.05 | |

| Fatty Acid | wildtype | Mean | Sample | low/high |
|---|---|---|---|---|
| C 16:0 | 19.94 | 26.42 | 28.08 | |
| C 16:1 | 0.84 | 0.96 | 0.96 | |
| C 17:0 | 0.19 | 0.14 | 0.13 | |
| C 17:1 | 0.10 | 0.06 | 0.05 | |
| C 18:0 | 2.68 | 3.62 | 3.43 | |
| C 18:1 | 63.96 | 54.90 | 53.91 | |
| C 18:2 | 9.62 | 9.83 | 9.11 | |
| C 18:3 γ | 0 | 0.01 | 0 | |
| C 18:3 α | 0.63 | 0.79 | 0.73 | |
| C 20:0 | 0.26 | 0.35 | 0.33 | |
| C 20:1 | 0.06 | 0.08 | 0.09 | |
| C 20:1 | 0.08 | 0.06 | 0.07 | |
| C 22:0 | 0 | 0.08 | 0.09 | |
| C 24:0 | 0.13 | 0.13 | 0.11 | |

Construct 11. *Cuphea hookeriana* C8-10 TE

| Fatty Acid | wildtype | Mean | Sample | low/high |
|---|---|---|---|---|
| C 8:0 | 0 | 0.82 | 1.57 | 0-1.87 |
| C 10:0 | 0 | 3.86 | 6.76 | 0-6.76 |
| C 12:0 | 0.04 | 0.13 | 0.20 | 0.03-0.20 |
| C 14:0 | 1.13 | 1.80 | 1.98 | 1.64-2.05 |
| C 14:1 | 0 | 0.04 | 0.04 | |
| C 15:0 | 0.06 | 0.06 | 0.06 | |
| C 16:0 | 19.94 | 25.60 | 25.44 | |
| C 16:1 | 0.84 | 1.01 | 1.02 | |
| C 17:0 | 0.19 | 0.13 | 0.11 | |
| C 17:1 | 0.10 | 0.06 | 0.05 | |
| C 18:0 | 2.68 | 2.98 | 2.38 | |
| C 18:1 | 63.96 | 51.59 | 48.85 | |
| C 18:2 | 9.62 | 9.85 | 9.62 | |
| C 18:3 γ | 0 | 0.01 | 0 | |
| C 18:3 α | 0.63 | 0.91 | 0.92 | |
| C 20:0 | 0.26 | 0.29 | 0.26 | |
| C 20:1 | 0.06 | 0.06 | 0 | |
| C 20:1 | 0.08 | 0.06 | 0.03 | |
| C 22:0 | 0 | 0.08 | 0.08 | |
| C 24:0 | 0.13 | 0.06 | 0 | |

Construct 12. *Cuphea hookeriana* C8-10 TE

| Fatty Acid | wildtype | Mean | Sample | low/high |
|---|---|---|---|---|
| C 8:0 | 0 | 0.31 | 0.85 | 0-0.85 |
| C 10:0 | 0 | 2.16 | 4.35 | 0.20-4.35 |
| C 12:0 | 0.04 | 0.10 | 0.15 | 0-0.18 |
| C 14:0 | 1.13 | 1.96 | 1.82 | 1.66-2.97 |
| C 14:1 | 0 | 0.03 | 0.04 | |
| C 15:0 | 0.06 | 0.07 | 0.07 | |
| C 16:0 | 19.94 | 26.08 | 25.00 | |
| C 16:1 | 0.84 | 1.04 | 0.88 | |
| C 17:0 | 0.19 | 0.16 | 0.16 | |
| C 17:1 | 0.10 | 0.05 | 0.07 | |
| C 18:0 | 2.68 | 3.02 | 3.19 | |
| C 18:1 | 63.96 | 51.08 | 52.15 | |
| C 18:2 | 9.62 | 11.44 | 9.47 | |
| C 18:3 γ | 0 | 0.01 | 0 | |
| C 18:3 α | 0.63 | 0.98 | 0.90 | |
| C 20:0 | 0.26 | 0.30 | 0.28 | |
| C 20:1 | 0.06 | 0.06 | 0.05 | |
| C 20:1 | 0.08 | 0.04 | 0 | |
| C 22:0 | 0 | 0.07 | 0 | |
| C 24:0 | 0.13 | 0.05 | 0 | |

Construct 14. *Umbellularia californica* C12 TE

| Fatty Acid | wildtype | Mean | Sample | low/high |
|---|---|---|---|---|
| C 10:0 | 0.01 | 0.02 | 0.03 | 0.02-0.03 |
| C 12:0 | 0.03 | 2.62 | 3.91 | 0.04-3.91 |
| C 14:0 | 1.40 | 1.99 | 2.11 | 1.83-2.19 |
| C 16:0 | 24.01 | 27.64 | 27.01 | |
| C 16:1 | 0.67 | 0.92 | 0.92 | |
| C 18:0 | 4.15 | 2.99 | 2.87 | |
| C 18:1 | 55.83 | 53.22 | 52.89 | |
| C 18:2 | 10.14 | 8.68 | 8.41 | |
| C 18:3 α | 0.93 | 0.78 | 0.74 | |
| C 20:0 | 0.33 | 0.29 | 0.27 | |

Construct 15. *Umbellularia californica* C12 TE

| Fatty Acid | wildtype | Mean | Sample | low/high |
|---|---|---|---|---|
| C 10:0 | 0 | 0.05 | 0.08 | 0-0.08 |
| C 12:0 | 0.04 | 8.12 | 12.80 | 4.35-12.80 |
| C 13:0 | 0 | 0.02 | 0.03 | 0-0.03 |
| C 14:0 | 1.13 | 2.67 | 3.02 | 2.18-3.37 |
| C 14:1 | 0 | 0.04 | 0.03 | 0.03-0.10 |

| Fatty Acid | wildtype | Mean | Sample | low/high |
|---|---|---|---|---|
| C 15:0 | 0.06 | 0.07 | 0.06 | |
| C 16:0 | 19.94 | 25.26 | 23.15 | |
| C 16:1 | 0.84 | 0.99 | 0.86 | |
| C 17:0 | 0.19 | 0.14 | 0.14 | |
| C 17:1 | 0.10 | 0.05 | 0.05 | |
| C 18:0 | 2.68 | 2.59 | 2.84 | |
| C 18:1 | 63.96 | 46.91 | 44.93 | |
| C 18:2 | 9.62 | 10.59 | 10.01 | |
| C 18:3 α | 0.63 | 0.92 | 0.83 | |
| C 20:0 | 0.26 | 0.27 | 0.24 | |
| C 20:1 | 0.06 | 0.06 | 0.06 | |
| C 20:1 | 0.08 | 0.05 | 0.04 | |
| C 22:0 | 0 | 0.07 | 0.09 | |
| C 24:0 | 0.13 | 0.13 | 0.12 | |

Construct 16. *Umbellularia californica* C12 TE

| Fatty Acid | wildtype | Mean | Sample | low/high |
|---|---|---|---|---|
| C 10:0 | 0 | 0.03 | 0.04 | 0.02-0.04 |
| C 12:0 | 0.04 | 2.43 | 5.32 | 0.98-5.32 |
| C 13:0 | 0 | 0.01 | 0.02 | 0-0.02 |
| C 14:0 | 1.13 | 1.77 | 1.93 | 1.62-1.93 |
| C 14:1 | 0 | 0.03 | 0.02 | 0.02-0.04 |
| C 15:0 | 0.06 | 0.06 | 0.05 | |
| C 16:0 | 19.94 | 24.89 | 22.29 | |
| C 16:1 | 0.84 | 0.91 | 0.82 | |
| C 17:0 | 0.19 | 0.16 | 0.15 | |
| C 17:1 | 0.10 | 0.06 | 0.06 | |
| C 18:0 | 2.68 | 3.81 | 3.67 | |
| C 18:1 | 63.96 | 53.19 | 52.82 | |
| C 18:2 | 9.62 | 10.38 | 10.57 | |
| C 18:3 α | 0.63 | 0.80 | 0.77 | |
| C 20:0 | 0.26 | 0.35 | 0.32 | |
| C 20:1 | 0.06 | 0.06 | 0.07 | |
| C 20:1 | 0.08 | 0.07 | 0.08 | |
| C 22:0 | 0 | 0.08 | 0.07 | |
| C 24:0 | 0.13 | 0.15 | 0.14 | |

Construct 17. *Umbellularia californica* C12 TE

| Fatty Acid | wildtype | Mean | Sample | low/high |
|---|---|---|---|---|
| C 10:0 | 0 | 0.04 | 0.07 | 0.03-0.08 |
| C 12:0 | 0.04 | 7.02 | 14.11 | 4.32-14.11 |
| C 13:0 | 0 | 0.03 | 0.04 | 0.01-0.04 |
| C 14:0 | 1.13 | 2.25 | 3.01 | 1.95-3.01 |
| C 14:1 | 0 | 0.03 | 0.03 | 0.02-0.03 |
| C 15:0 | 0.06 | 0.06 | 0.06 | |
| C 16:0 | 19.94 | 23.20 | 21.46 | |
| C 16:1 | 0.84 | 0.82 | 0.77 | |
| C 17:0 | 0.19 | 0.15 | 0.14 | |
| C 17:1 | 0.10 | 0.06 | 0.06 | |
| C 18:0 | 2.68 | 3.47 | 2.93 | |
| C 18:1 | 63.96 | 50.30 | 45.17 | |
| C 18:2 | 9.62 | 10.33 | 9.98 | |
| C 18:3 γ | 0 | 0.01 | 0 | |
| C 18:3 α | 0.63 | 0.84 | 0.86 | |
| C 20:0 | 0.26 | 0.32 | 0.27 | |
| C 20:1 | 0.06 | 0.07 | 0.06 | |
| C 20:1 | 0.08 | 0.06 | 0.06 | |
| C 22:0 | 0 | 0.08 | 0.09 | |
| C 24:0 | 0.13 | 0.14 | 0.13 | |

Construct 18. *Umbellularia californica* C12 TE

| Fatty Acid | wildtype | Mean | Sample | low/high |
|---|---|---|---|---|
| C 10:0 | 0 | 0.03 | 0.05 | 0.01-0.05 |
| C 12:0 | 0.04 | 5.06 | 7.77 | 0.37-7.77 |
| C 13:0 | 0 | 0.02 | 0 | 0-0.03 |
| C 14:0 | 1.13 | 2.11 | 2.39 | 1.82-2.39 |
| C 14:1 | 0 | 0.03 | 0.03 | 0.02-0.05 |
| C 15:0 | 0.06 | 0.06 | 0.06 | |
| C 16:0 | 19.94 | 24.60 | 23.95 | |
| C 16:1 | 0.84 | 0.86 | 0.83 | |
| C 17:0 | 0.19 | 0.15 | 0.14 | |
| C 17:1 | 0.10 | 0.06 | 0.05 | |
| C 18:0 | 2.68 | 3.31 | 2.96 | |
| C 18:1 | 63.96 | 51.26 | 49.70 | |
| C 18:2 | 9.62 | 10.18 | 10.02 | |
| C 18:3 γ | 0 | 0.01 | 0.02 | |
| C 18:3 α | 0.63 | 0.86 | 0.86 | |
| C 20:0 | 0.26 | 0.32 | 0.29 | |
| C 20:1 | 0.06 | 0.05 | 0.05 | |
| C 20:1 | 0.08 | 0.07 | 0.04 | |

| Fatty Acid | wildtype | Mean | Sample | low/high |
|---|---|---|---|---|
| C 22:0 | 0 | 0.08 | 0.08 | |
| C 24:0 | 0.13 | 0.13 | 0.13 | |
| Construct 19. *Cinnamomum camphora* C14 TE | | | | |
| C 10:0 | 0.02 | 0.01 | 0.01 | 0.01-0.02 |
| C 12:0 | 0.05 | 0.27 | 0.40 | 0.08-0.41 |
| C 14:0 | 1.52 | 4.47 | 5.81 | 2.10-5.81 |
| C 16:0 | 25.16 | 28.14 | 28.55 | |
| C 16:1 | 0.72 | 0.84 | 0.82 | |
| C 18:0 | 3.70 | 3.17 | 2.87 | |
| C 18:1 | 54.28 | 51.89 | 51.01 | |
| C 18:2 | 12.24 | 9.36 | 8.62 | |
| C 18:3α | 0.87 | 0.74 | 0.75 | |
| C 20:0 | 0.33 | 0.33 | 0.31 | |
| Construct 20. *Cinnamomum camphora* C14 TE | | | | |
| C 10:0 | 0.01 | 0.01 | 0.02 | 0.01-0.02 |
| C 12:0 | 0.03 | 0.39 | 0.65 | 0.08-0.65 |
| C 13:0 | 0 | 0.01 | 0.01 | 0.01-0.02 |
| C 14:0 | 1.40 | 5.61 | 8.4 | 2.1-8.4 |
| C 14:1 | 0 | 0.03 | 0.03 | 0.02-0.03 |
| C 15:0 | 0 | 0.06 | 0.07 | |
| C 16:0 | 24.01 | 25.93 | 25.57 | |
| C 16:1 | 0.67 | 0.75 | 0.71 | |
| C 17:0 | 0 | 0.13 | 0.12 | |
| C 17:1 | 0 | 0.05 | 0.05 | |
| C 18:0 | 4.15 | 3.30 | 3.23 | |
| C 18:1 | 55.83 | 51.00 | 48.48 | |
| C 18:2 | 10.14 | 10.38 | 10.35 | |
| C 18:3α | 0.93 | 0.91 | 0.88 | |
| C 20:0 | 0.33 | 0.35 | 0.32 | |
| C 20:1 | 0 | 0.08 | 0.08 | |
| C 20:1 | 0 | 0.07 | 0.07 | |
| C 22:0 | 0 | 0.08 | 0.08 | |
| C 24:0 | 0 | 0.14 | 0.13 | |
| Construct 21. *Cinnamomum camphora* C14 TE | | | | |
| C 10:0 | 0.01 | 0.01 | 0.01 | 0-0.01 |
| C 12:0 | 0.03 | 0.10 | 0.27 | 0.04-0.27 |
| C 14:0 | 1.40 | 2.28 | 4.40 | 1.47-4.40 |
| C 16:0 | 24.01 | 26.10 | 26.38 | |
| C 16:1 | 0.67 | 0.79 | 0.73 | |
| C 17:0 | 0 | 0.15 | 0.16 | |
| C 17:1 | 0 | 0.06 | 0.06 | |
| C 18:0 | 4.15 | 3.59 | 3.51 | |
| C 18:1 | 55.83 | 53.53 | 50.86 | |
| C 18:2 | 10.14 | 10.83 | 11.11 | |
| C 18:3α | 0.93 | 0.97 | 0.87 | |
| C 20:0 | 0.33 | 0.36 | 0.37 | |
| C 20:1 | 0 | 0.09 | 0.08 | |
| C 20:1 | 0 | 0.07 | 0.07 | |
| C 22:0 | 0 | 0.09 | 0.09 | |
| Construct 22. *Cinnamomum camphora* C14 TE | | | | |
| C 10:0 | 0.01 | 0.02 | 0.02 | 0.02-0.02 |
| C 12:0 | 0.03 | 1.22 | 1.83 | 0.59-1.83 |
| C 13:0 | 0 | 0.02 | 0.03 | 0.01-0.03 |
| C 14:0 | 1.40 | 12.77 | 17.33 | 7.97-17.33 |
| C 14:1 | 0 | 0.02 | 0.02 | 0.02-0.04 |
| C 15:0 | 0 | 0.07 | 0.08 | |
| C 16:0 | 24.01 | 24.79 | 24.22 | |
| C 16:1 | 0.67 | 0.64 | 0.58 | |
| C 17:0 | 0 | 0.11 | 0.10 | |
| C 17:1 | 0 | 0.04 | 0.04 | |
| C 18:0 | 4.15 | 2.85 | 2.75 | |
| C 18:1 | 55.83 | 45.16 | 41.23 | |
| C 18:2 | 10.14 | 9.96 | 9.65 | |
| C 18:3α | 0.93 | 0.91 | 0.85 | |
| C 20:0 | 0.33 | 0.30 | 0.30 | |
| C 20:1 | 0 | 0.07 | 0.06 | |
| C 20:1 | 0 | 0.06 | 0.05 | |
| C 22:0 | 0 | 0.08 | 0.08 | |
| Construct 23. *Cinnamomum camphora* C14 TE | | | | |
| C 10:0 | 0.01 | 0.01 | 0.02 | 0-0.02 |
| C 12:0 | 0.05 | 0.57 | 1.08 | 0.16-1.08 |
| C 13:0 | 0 | 0.02 | 0.02 | 0-0.02 |
| C 14:0 | 1.45 | 7.18 | 11.24 | 2.96-11.24 |
| C 14:1 | 0.02 | 0.03 | 0.03 | 0.02-0.03 |
| C 15:0 | 0.06 | 0.07 | 0.07 | |
| C 16:0 | 24.13 | 25.78 | 25.21 | |
| C 16:1 | 0.77 | 0.72 | 0.66 | |
| C 17:0 | 0.19 | 0.13 | 0.11 | |
| C 17:1 | 0.08 | 0.05 | 0.04 | |
| C 18:0 | 3.53 | 3.35 | 3.12 | |
| C 18:1 | 56.15 | 49.65 | 46.35 | |
| C 18:2 | 11.26 | 10.17 | 9.72 | |
| C 18:3α | 0.84 | 0.95 | 0.83 | |
| C 20:0 | 0.32 | 0.34 | 0.32 | |
| C 20:1 | 0.09 | 0.08 | 0.09 | |
| C 20:1 | 0.07 | 0.05 | 0.06 | |
| C 22:0 | 0.07 | 0.08 | 0.08 | |
| C 24:0 | 0.13 | 0.13 | 0.12 | |

Constructs 9-12 were expression vectors containing the *Cuphea hookeriana* C8-10 thioesterase construct. As can be seen in the data summaries above, the best results were seen with Construct 11, with the Sample C8 fatty acid being 1.57 Area % (as compared to 0 in wildtype) and C10 fatty acid being 6.76 Area % (as compared to 0 in wildtype). There was also a modest increase in C12 fatty acids (approximately 2-5 fold increase). While the native plastid targeting sequence produced no change when under the control of the *C. sorokinana* glutamate dehydrogenase promoter, the same expression construct driven by the *C. reinhardtii* β-tubulin promoter produced significant changes in C8-10 fatty acids in the host cell. This is further evidence of the idiosyncrasies of heterologous expression of thioesterases in *Prototheca* species. All of the clones containing the *C. reinhardtii* β-tubulin promoter C8-10 thioesterase construct had greater increases in C8-10 fatty acids than the clones containing the *C. sorokinana* glutamate dehydrogenase promoter C8-10 thioesterase construct. Lipid profile data for Construct 13 was not obtained and therefore, not included above.

Constructs 14-18 were expression vectors containing the *Umbellularia californica* C12 thioesterase construct. As can be seen in the data summaries above, the best results were seen with Constructs 15 (*P. moriformis* isopentenyl diphosphate synthase plastid targeting sequence) and 17 (*C. protothecoides* stearoyl ACP desaturase plastid targeting sequence). The greatest change in C12 fatty acid production was seen with Construct 17, with C12 fatty acids levels of up to 14.11 area %, as compared to 0.04 area % in wildtype. Modest changes (about 2-fold) were also seen with C14 fatty acid levels. When compared to the same constructs with the *C. sorokinana* glutamate dehydrogenase promoter, the same trends were true with the *C. reinhardtii* β-tubulin promoter—the *C. protothecoides* stearoyl ACP desaturase and *P. moriformis* isopentenyl diphosphate synthase plastid targeting sequences produced the greatest change in C12 fatty acid levels with both promoters.

Constructs 19-23 were expression vectors containing the *Cinnamomum camphora* C14 thioesterase construct. As can be seen in the data summaries above, the best results were seen with Constructs 22 and Construct 23. The greatest change in C14 fatty acid production was seen with Construct 22, with C14 fatty acid levels of up to 17.35 area % (when the values for C140 and C141 are combined), as compared to 1.40% in wildtype. Changes in C12 fatty acids were also seen (5-60 fold). When compared to the same constructs with the *C. sorokinana* glutamate dehydrogenase promoter, the same trends were true with the *C. reinhardtii* β-tubulin promoter— the *C. protothecoides* stearoyl ACP desaturase and *P. moriformis* stearoyl ACP desaturase plastid targeting sequences produced the greatest change in C14 fatty acid levels with both promoters. Consistently with all thioesterase expression constructs, the *C. reinhardtii* β-tubulin promoter constructs produced greater changes in C8-14 fatty acid levels than the *C. sorokiniana* glutamate dehydrogenase Two positive clones from the Construct 22 were selected and grown under high selective pressure (50 mg/L G418). After 6 days in culture, the clones were harvested and their lipid profile was determined using the methods described above. The lipid profile data is summarized below and is expressed in area %.

| Construct 22 clones + 50 mg/L G418 | | |
| --- | --- | --- |
| Fatty Acid | Construct 22 A | Construct 22 B |
| C 12:0 | 3.21 | 3.37 |
| C 14:0 | 27.55 | 26.99 |
| C 16:0 | 25.68 | 24.37 |
| C 16:1 | 0.99 | 0.92 |
| C 18:0 | 1.37 | 1.23 |
| C 18:1 | 28.35 | 31.07 |
| C 18:2 | 11.73 | 11.05 |
| C 18:3α | 0.92 | 0.81 |
| C 20:0 | 0.16 | 0.17 |

Both clones, when grown under constant, high selective pressure, produced an increased amount of C14 and C12 fatty acids, about double the levels seen with Construct 22 above. These clones yielded over 30 area % of C12-14 fatty acids, as compared to 1.5 area % of C12-14 fatty acids seen in wildtype cells.

What is claimed is:

1. A method of extracting a lipid from recombinant *Prototheca* cells, the method comprising the steps of:
   (a) lysing recombinant *Prototheca* cells to produce a lysate, wherein the recombinant *Prototheca* cells:
      (i) have not been subjected to a drying step between culturing and lysing; and
      (ii) comprise at least 10% lipid by dry weight, and wherein the fatty acid profile of the lipid is at least 10% C8-C14;
   (b) treating the lysate with an organic solvent for a period of time, wherein the organic solvent is an alcohol selected from ethanol, isopropanol or butanol;
   (c) separating the treated lysate into layers comprising a lipid layer and an aqueous layer and, optionally, a lipid:aqueous emulsion layer, and/or a cell pellet; and
   (d) removing the lipid from the other layer(s).

2. The method of claim 1, wherein step (d) further comprises reducing the temperature of the mixture to below 25° C.

3. The method of claim 1, wherein the recombinant *Prototheca* cells comprise lipid that is at least 10% C14 triacylglycerols, at least 10% C12 triacylglycerols, or at least 10% C10 triacylglycerols.

4. The method of claim 1, wherein the lysing is accomplished by subjecting the recombinant *Prototheca* cells to heating, sonication, mechanical lysis, osmotic shock, expression of an autolysis gene, exposure to pH above 8, exposure to an acidic pH, heating and exposure to an acidic pH, or digestion with an enzyme.

5. The method of claim 1, wherein the lysing is accomplished by subjecting the recombinant *Prototheca* cells to sonication.

6. The method of claim 1, wherein the recombinant *Prototheca* cells comprise a polynucleotide encoding a sucrose invertase or a lipid pathway enzyme.

7. The method of claim 6, wherein the polynucleotide encodes a lipid pathway enzyme.

8. The method of claim 6, wherein the recombinant *Prototheca* cells comprise one or more polynucleotides encoding a sucrose invertase and a lipid pathway enzyme.

9. The method of claim 8, wherein the lipid pathway enzyme is a fatty acyl-ACP thioesterase.

10. The method of claim 7, wherein the lipid pathway enzyme is a fatty acyl-ACP thioesterase.

11. The method of claim 1, wherein the *Prototheca* cells are *Prototheca wickerhamii*, *Prototheca stagnora*, *Prototheca portoricensis*, *Prototheca moriformis*, or *Prototheca zopfii*.

12. A method of extracting a lipid from recombinant Prototheca cells, the method comprising the steps of:
   (a) lysing recombinant *Prototheca* cells to produce a lysate, wherein the recombinant *Prototheca* cells:
      (i) have not been subjected to a drying step between culturing and lysing; and
      (ii) comprise at least 10% lipid by dry weight, and wherein the fatty acid profile of the lipid is at least 4% C8-C14;
   (b) treating the lysate with an organic solvent for a period of time, wherein the organic solvent is an alcohol selected from ethanol, isopropanol or butanol;
   (c) separating the treated lysate into layers comprising a lipid layer and an aqueous layer and, optionally, a lipid:aqueous emulsion layer, and/or a cell pellet; and
   (d) removing the lipid from the other layer(s).

13. The method of claim 12, wherein the recombinant *Prototheca* cells comprise one or more polynucleotides encoding a sucrose invertase and/or a lipid pathway enzyme.

14. The method of claim 13, wherein the lipid pathway enzyme is a fatty acyl-ACP thioesterase.

15. The method of claim 12, wherein the *Prototheca* cells are *Prototheca wickerhamii*, *Prototheca stagnora*, *Prototheca portoricensis*, *Prototheca moriformis*, or *Prototheca zopfii*.

16. A method of extracting a lipid from recombinant *Prototheca* cells, the method comprising the steps of:
   (a) lysing recombinant *Prototheca* cells to produce a lysate, wherein the recombinant *Prototheca* cells:
      (i) have not been subjected to a drying step between culturing and lysing; and
      (ii) comprise at least 10% lipid by dry weight, and wherein the fatty acid profile of the lipid is at least 60% C18:1;
   (b) treating the lysate with an organic solvent for a period of time, wherein the organic solvent is an alcohol selected from ethanol, isopropanol or butanol;
   (c) separating the treated lysate into layers comprising a lipid layer and an aqueous layer and, optionally, a lipid:aqueous emulsion layer, and/or a cell pellet; and
   (d) removing the lipid from the other layer(s).

17. The method of claim 16, wherein the fatty acid profile of the lipid is at least 80% C18:1.

18. The method of claim 16, wherein the recombinant *Prototheca* cells comprise one or more polynucleotides encoding a sucrose invertase and/or a lipid pathway enzyme.

19. The method of claim 18, wherein the lipid pathway enzyme is a fatty acyl-ACP thioesterase.

20. The method of claim 16, wherein the *Prototheca* cells are *Prototheca wickerhamii*, *Prototheca stagnora*, *Prototheca portoricensis*, *Prototheca moriformis*, or *Prototheca zopfii*.

* * * * *